US008084442B2

(12) United States Patent
Kurimura et al.

(10) Patent No.: US 8,084,442 B2
(45) Date of Patent: Dec. 27, 2011

(54) N,N-SUBSTITUTED 3-AMINOPYRROLIDINE COMPOUNDS USEFUL AS MONOAMINES REUPTAKE INHIBITORS

(75) Inventors: Muneaki Kurimura, Tokushima (JP); Shinichi Taira, Tokushima (JP); Takahiro Tomoyasu, Tokushima (JP); Nobuaki Ito, Tokushima (JP); Kuninori Tai, Tokushima (JP); Noriaki Takemura, Tokushima (JP); Takayuki Matsuzaki, Tokushima (JP); Yasuhiro Menjo, Tokushima (JP); Shin Miyamura, Tokushima (JP); Yohji Sakurai, Tokushima (JP); Akihito Watanabe, Tokushima (JP); Yasuyo Sakata, Tokushima (JP); Takumi Masumoto, Tokushima (JP); Kohei Akazawa, Tokushima (JP); Haruhiko Sugino, Tokushima (JP); Naoki Amada, Tokushima (JP); Satoshi Ohashi, Tokushima (JP); Tomoichi Shinohara, Tokushima (JP); Hirofumi Sasaki, Tokushima (JP); Chisako Morita, Tokushima (JP); Junko Yamashita, Tokushima (JP); Satoko Nakajima, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 242 days.

(21) Appl. No.: 11/914,183

(22) PCT Filed: May 12, 2006

(86) PCT No.: PCT/JP2006/309988
§ 371 (c)(1),
(2), (4) Date: Sep. 29, 2008

(87) PCT Pub. No.: WO2006/121218
PCT Pub. Date: Nov. 16, 2006

(65) Prior Publication Data
US 2009/0088406 A1   Apr. 2, 2009

(30) Foreign Application Priority Data
May 13, 2005 (JP) ................ 2005-141230

(51) Int. Cl.
A61K 31/40 (2006.01)
A61K 31/497 (2006.01)
A61K 31/538 (2006.01)
A61K 31/695 (2006.01)
A61K 31/501 (2006.01)
C07D 207/12 (2006.01)
C07D 241/20 (2006.01)
C07D 403/12 (2006.01)
C07D 498/04 (2006.01)
A61P 25/00 (2006.01)

(52) U.S. Cl. ............... 514/63; 514/230.5; 514/252.05; 514/255.05; 514/423; 544/105; 544/238; 544/336; 548/531

(58) Field of Classification Search .............. None
See application file for complete search history.

(56) References Cited

U.S. PATENT DOCUMENTS

| 3,433,802 A | 3/1969 | Dawson et al. |
| 3,509,171 A | 4/1970 | Welstead, Jr. et al. |
| 3,577,440 A | 5/1971 | Lunsford et al. |
| 4,254,135 A | 3/1981 | Walsh et al. |

FOREIGN PATENT DOCUMENTS

| GB | 1164828 | 9/1969 |
| GB | 1 173 373 | 12/1969 |
| GB | 1523631 | 9/1976 |
| GB | 2 295 387 A | 5/1996 |
| WO | 98/28270 A1 | 7/1998 |
| WO | 01/83434 A2 | 11/2001 |
| WO | 02/94794 A1 | 11/2002 |
| WO | 2004/110995 A1 | 12/2004 |
| WO | 2004/111003 A1 | 12/2004 |
| WO | 2005/000305 A1 | 1/2005 |
| WO | 2005/000811 A1 | 1/2005 |
| WO | 2005/047251 A1 | 5/2005 |

OTHER PUBLICATIONS

Pelcman et al., caplus an 1998:479507.*
Alzheimer's Disease Treatment Phases, http://www.alzheimerstreatment.org/treatment/disease-treatment.htm (2008).*
Alzheimer's Drugs, Consumer Reports Best Buy Drugs (p. 1-5) (2006).*
Kurimura et al., caplus an 2008:733525.* Office Action dated Oct. 19, 2009 as issued in European Patent Application No. 06756356.9.
Sadanori Miura, "Rinshoseishinyakuri", Japanese Journal of Clinical Psychopharmacology, 2000, vol. 3, pp. 311-318.
Phil Skolnick, "Antidepressants for the new millennium", European Jounal of Pharmacology 375, 1999, pp. 31-40.
Office Action dated Oct. 16, 2009 as issued in European Patent Application No. 06756356.9.
Examination Report for Australian Patent Application No. 2010201952, dated Jun. 2, 2011.

* cited by examiner

*Primary Examiner* — Sun Jae Loewe
(74) *Attorney, Agent, or Firm* — Sughrue Mion, PLLC

(57) ABSTRACT

The present invention provides a pyrrolidine compound of General Formula (1)

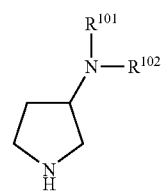

(1)

or a salt thereof, wherein $R^{101}$ and $R^{102}$ are each independently a phenyl group or a pyridyl group, the phenyl group or the pyridyl group may have one or more substituents selected from halogen atoms and lower alkyl groups optionally substituted with one or more halogen atoms, etc. The pyrrolidine compound or a salt thereof of the present invention is usable to produce a pharmaceutical preparation having a wider therapeutic spectrum and being capable of exhibiting sufficient therapeutic effects after short-term administration.

9 Claims, No Drawings

N,N-SUBSTITUTED 3-AMINOPYRROLIDINE COMPOUNDS USEFUL AS MONOAMINES REUPTAKE INHIBITORS

CROSS REFERENCE TO RELATED APPLICATIONS

This application is a National Stage of International Application No. PCT/JP2006/309988 filed on May 12, 2006, claiming priority based on Japanese Patent Application No. 2005-141230, filed May 13, 2005, the contents of all of which are incorporated herein by reference in their entirety.

TECHNICAL FIELD

The present invention relates to a pyrrolidine compound.

BACKGROUND OF THE INVENTION

Three types of monoamines, known as serotonin, norepinephrine and dopamine, act as neurotransmitters in organisms. Therefore, pharmaceuticals having a monoamine reuptake inhibitory effect are widely used as therapeutic pharmaceuticals for diseases of the central and peripheral nervous systems.

Many of the pharmaceuticals used to date for treating depression selectively inhibit norepinephrine or serotonin reuptake. Examples of such pharmaceuticals include imipramine (a first-generation antidepressant), maprotiline (a second-generation antidepressant), selective serotonin-uptake inhibitors such as fluoxetine (SSRI, third-generation antidepressants), serotonin and/or norepinephrine reuptake inhibitors such as venlafaxine (SNRI, fourth-generation antidepressants), and the like (see Sadanori Miura, Rinshoseishinyakuri (Japanese Journal of Clinical Psychopharmacology), 2000, 3: 311-318).

However, it takes at least three weeks for these pharmaceuticals to exhibit their therapeutic effects and furthermore, these pharmaceuticals fail to exhibit sufficient effects in about 30% of patients suffering from depression (see Phil Skolnick, European Journal of Pharmacology, 2001, 375: 31-40).

DISCLOSURE OF THE INVENTION

An object of the invention is to provide a pharmaceutical preparation having a wider therapeutic spectrum than known antidepressants, and being capable of exhibiting sufficient therapeutic effects after short-term administration.

The present inventors carried out extensive research to achieve the above object and found that a pyrrolidine compound represented by formula (1) below can be used to produce such a desired pharmaceutical preparation. The present invention has been accomplished based on this finding.

The present invention provides a pyrrolidine compound, a composition comprising said compound, an agent comprising said compound, a use of said compound, a method for treating a disorder, and a process for producing said compound, as described in Items 1 to 14 below.

Item 1. A pyrrolidine compound of General Formula (1)

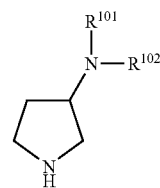

or a salt thereof,
wherein $R^{101}$ and $R^{102}$ are each independently one of the following groups (1) to (86):
(1) a phenyl group,
(2) a pyridyl group,
(3) a benzothienyl group,
(4) an indolyl group,
(5) a 2,3-dihydro-1H-indenyl group,
(6) a naphthyl group,
(7) a benzofuryl group,
(8) a quinolyl group,
(9) a thiazolyl group,
(10) a pyrimidinyl group,
(11) a pyrazinyl group,
(12) a benzothiazolyl group,
(13) a thieno[3,2-b]pyridyl group,
(14) a thienyl group,
(15) a cycloalkyl group,
(16) a tetrahydropyranyl group,
(17) a pyrrolyl group,
(18) a 2,4-dihydro-1,3-benzodioxinyl group,
(19) a 2,3-dihydrobenzofuryl group,
(20) a 9H-fluorenyl group,
(21) a pyrazolyl group,
(22) a pyridazinyl group,
(23) an indolinyl group,
(24) a thieno[2,3-b]pyridyl group,
(25) a thieno[3,2-d]pyrimidinyl group,
(26) a thieno[3,2-e]pyrimidinyl group,
(27) a 1H-pyrazolo[3,4-b]pyridyl group,
(28) an isoquinolyl group,
(29) a 2,3-dihydro-1,4-benzoxadinyl group,
(30) a quinoxalinyl group,
(31) a quinazolinyl group,
(32) a 1,2,3,4-tetrahydroquinolyl group,
(33) a cycloalkyl lower alkyl group,
(34) a lower alkylthio lower alkyl group,
(35) an amino-substituted lower alkyl group optionally substituted with one or two lower alkyl groups on the amino group,
(36) a phenoxy lower alkyl group,
(37) a pyridyloxy lower alkyl group,
(38) a lower alkynyl group,
(39) a phenyl lower alkenyl group,
(40) a 1,3-benzodioxolyl group,
(41) a 2,3-dihydro-1,4-benzodioxinyl group,
(42) a 3,4-dihydro-1,5-benzodioxepinyl group,
(43) a dihydropyridyl group,
(44) a 1,2-dihydroquinolyl group,
(45) a 1,2,3,4-tetrahydroisoquinolyl group,
(46) a benzoxazolyl group,
(47) a benzoisothiazolyl group,
(48) an indazolyl group,
(49) a benzoimidazolyl group,
(50) an imidazolyl group,
(51) a 1,2,3,4-tetrahydronaphthyl lower alkyl group,

(52) an imidazo[1,2-a]pyridyl lower alkyl group,
(53) a thiazolyl lower alkyl group,
(54) a tetrahydropyranyl lower alkyl group,
(55) a piperidyl lower alkyl group,
(56) a diphenyl lower alkoxy-substituted lower alkyl group,
(57) a lower alkoxycarbonyl-substituted lower alkyl group,
(58) a phenyl lower alkoxycarbonyl-substituted lower alkyl group,
(59) a hydroxy-substituted lower alkyl group,
(60) a lower alkoxy lower alkyl group,
(61) a carboxy lower alkyl group,
(62) a carbamoyl-substituted lower alkyl group optionally substituted with one or two lower alkyl groups on the carbamoyl group,
(63) a lower alkenyl group,
(64) a morpholinylcarbonyl lower alkyl group,
(65) a benzoyl lower alkyl group,
(66) a phenylthio lower alkyl group,
(67) a naphthylthio lower alkyl group,
(68) a cycloalkylthio lower alkyl group,
(69) a pyridylthio lower alkyl group,
(70) a pyrimidinylthio lower alkyl group,
(71) a furylthio lower alkyl group,
(72) a thienylthio lower alkyl group,
(73) a 1,3,4-thiadiazolylthio lower alkyl group,
(74) a benzimidazolylthio lower alkyl group,
(75) a benzthiazolylthio lower alkyl group,
(76) a tetrazolylthio lower alkyl group,
(77) a benzoxazolylthio lower alkyl group,
(78) a thiazolylthio lower alkyl group,
(79) an imidazolylthio lower alkyl group,
(80) an amino-substituted lower alkylthio lower alkyl group optionally substituted with one or two lower alkyl groups on the amino group,
(81) a phenyl-substituted lower alkylthio lower alkyl group,
(82) a furyl-substituted lower alkylthio lower alkyl group,
(83) a pyridyl-substituted lower alkylthio lower alkyl group,
(84) a hydroxy-substituted lower alkylthio lower alkyl group,
(85) a phenoxy-substituted lower alkylthio lower alkyl group, and
(86) a lower alkoxycarbonyl-substituted lower alkylthio lower alkyl group,
and each of the groups (1) to (32), (37), (39) to (56), (64) to (79), (81) to (83) and (85) may have one or more substituents selected from the following (1-1) to (1-37) on the cycloalkyl, aromatic or heterocyclic ring:
(1-1) halogen atoms,
(1-2) lower alkylthio groups optionally substituted with one or more halogen atoms,
(1-3) lower alkyl groups optionally substituted with one or more halogen atoms,
(1-4) lower alkoxy groups optionally substituted with one or more halogen atoms,
(1-5) nitro group,
(1-6) lower alkoxycarbonyl groups,
(1-7) amino groups optionally substituted with one or two lower alkyl groups,
(1-8) lower alkylsulfonyl groups,
(1-9) cyano group,
(1-10) carboxy group,
(1-11) hydroxy group,
(1-12) thienyl groups,
(1-13) oxazolyl groups,
(1-14) naphthyl groups,
(1-15) benzoyl group,
(1-16) phenoxy groups optionally substituted with one to three halogen atoms on the phenyl ring,
(1-17) phenyl lower alkoxy groups,
(1-18) lower alkanoyl groups,
(1-19) phenyl groups optionally substituted on the phenyl ring with one to five substituents selected from the group consisting of halogen atoms, lower alkoxy groups, cyano group, lower alkanoyl groups and lower alkyl groups,
(1-20) phenyl lower alkyl groups,
(1-21) cyano lower alkyl groups,
(1-22) 5 to 7-membered saturated heterocyclic group-substituted sulfonyl groups, the heterocyclic group containing on the heterocyclic ring one or two heteroatoms selected from the group consisting of nitrogen, oxygen and sulfur,
(1-23) thiazolyl groups optionally substituted with one or two lower alkyl groups on the thiazole ring,
(1-24) imidazolyl groups,
(1-25) amino lower alkyl groups optionally substituted with one or two lower alkyl groups on the amino group,
(1-26) pyrrolidinyl lower alkoxy groups,
(1-27) isoxazolyl groups,
(1-28) cycloalkylcarbonyl groups,
(1-29) naphthyloxy groups,
(1-30) pyridyl groups,
(1-31) furyl groups,
(1-32) phenylthio group,
(1-33) oxo group,
(1-34) carbamoyl group,
(1-35) 5 to 7-membered saturated heterocyclic groups containing one or two heteroatoms selected from the group consisting of nitrogen, oxygen and sulfur, the heterocyclic group optionally being substituted with one to three substituents selected from the group consisting of oxo group; lower alkyl groups; lower alkanoyl groups; phenyl lower alkyl groups; phenyl groups optionally substituted on the phenyl ring with one to three members selected from the group consisting of halogen atoms and lower alkoxy groups; and pyridyl groups,
(1-36) oxido group and
(1-37) lower alkoxido groups, with the proviso that $R^{101}$ and $R^{102}$ are not simultaneously unsubstituted phenyl.

Item 2. A pyrrolidine compound of General Formula (1) or a salt thereof according to Item 1, wherein
$R^{101}$ is
(1) a phenyl group,
(3) a benzothienyl group,
(4) an indolyl group,
(5) a 2,3-dihydro-1H-indenyl group,
(6) a naphthyl group,
(7) a benzofuryl group,
(8) a quinolyl group,
(12) a benzothiazolyl group,
(18) a 2,4-dihydro-1,3-benzodioxinyl group,
(19) a 2,3-dihydrobenzofuryl group,
(20) a 9H-fluorenyl group,
(23) an indolinyl group,
(28) an isoquinolyl group,
(29) a 2,3-dihydro-1,4-benzoxadinyl group,
(30) a quinoxalinyl group,
(31) a quinazolinyl group,
(32) a 1,2,3,4-tetrahydroquinolyl groups
(40) a 1,3-benzodioxolyl group,
(41) a 2,3-dihydro-1,4-benzodioxinyl group,
(42) a 3,4-dihydro-1,5-benzodioxepinyl group,
(44) a 1,2-dihydroquinolyl group,
(45) a 1,2,3,4-tetrahydroisoquinolyl group,
(46) a benzoxazolyl group,
(47) a benzoisothiazolyl group,
(48) an indazolyl group or

(49) a benzoimidazolyl group, and each of which may have on the aromatic or heterocyclic ring one to three substituents selected from the groups (1-1) to (1-37) as defined in Item 1.

Item 3. A pyrrolidine compound of General Formula (1) or a salt thereof according to Item 2, wherein
$R^{101}$ is
(1) a phenyl group or
(3) a benzothienyl group,
and each of which may have on the aromatic or heterocyclic ring one to three substituents selected from the group consisting of (1-1) halogen atoms and (1-3) lower alkyl groups optionally substituted with one to three halogen atoms.

Item 4. A pyrrolidine compound of General Formula (1) or a salt thereof according to Item 3, wherein
$R^{102}$ is
(1) a phenyl group,
(2) a pyridyl group,
(9) a thiazolyl group,
(10) a pyrimidinyl group,
(11) a pyrazinyl group
(14) a thienyl group,
(48) an indazolyl group,
(59) a hydroxy-substituted lower alkyl group or
(60) a lower alkoxy lower alkyl group,
and each of the groups (1), (2), (9), (10), (11), (14) and (48) may have on the aromatic or heterocyclic ring one to three substituents selected from the groups (1-1) to (1-37) as defined in Item 1.

Item 5. A pyrrolidine compound of General Formula (1) or a salt thereof according to Item 4, wherein
$R^{101}$ is
a monohalophenyl group, a dihalophenyl group or a phenyl group substituted with one halogen atom and one lower alkyl group,
$R^{102}$ is
(1) a phenyl group,
(2) a pyridyl group,
(9) a thiazolyl group,
(10) a pyrimidinyl group,
(11) a pyrazinyl group,
(14) a thienyl group,
(48) an indazolyl group,
(59) a hydroxy-substituted lower alkyl group or
(60) a lower alkoxy lower alkyl group,
and each of the groups (1), (2), (9), (10), (11), (14) and (48) may have on the aromatic or heterocyclic ring one or two substituents selected from the group consisting of (1-1) halogen atoms, (1-3) lower alkyl groups optionally substituted with one or more halogen atoms, and (1-9) cyano group.

Item 6. A pyrrolidine compound of General Formula (1) or a salt thereof according to Item 5 selected from the group consisting of:
(4-chlorophenyl)phenyl-(S)-pyrrolidin-3-ylamine,
(4-fluorophenyl)phenyl-(S)-pyrrolidin-3-ylamine,
(3,4-difluorophenyl)phenyl-(S)-pyrrolidin-3-ylamine,
bis-(4-fluorophenyl)-(S)-pyrrolidin-3-ylamine,
(3,4-difluorophenyl)-(4-fluorophenyl)-(S)-pyrrolidin-3-ylamine,
(3-chloro-4-fluorophenyl)-(S)-pyrrolidin-3-yl-p-tolylamine,
4-[(S)-(4-fluoro-3-methylphenyl)pyrrolidin-3-ylamino]-benzonitrile,
bis-(3-fluorophenyl)-(S)-pyrrolidin-3-ylamine,
(3-chloro-4-fluorophenyl)-(S)-pyrrolidin-3-ylthiazol-2-ylamine,
(4-fluorophenyl)-(S)-pyrrolidin-3-ylthiazol-2-ylamine,
(3,4-dichlorophenyl)-(S)-pyrrolidin-3-ylthiazol-2-ylamine,
(3,4-dichlorophenyl)pyrimidin-5-yl-(S)-pyrrolidin-3-ylamine,
(3-chloro-4-fluorophenyl)pyrazin-2-yl-(S)-pyrrolidin-3-ylamine,
(3-chloro-4-fluorophenyl)-(5-chloropyridin-2-yl)-(S)-pyrrolidin-3-ylamine,
(3-chloro-4-fluorophenyl)pyridin-2-yl-(S)-pyrrolidin-3-ylamine,
(3-chloro-4-fluorophenyl)pyridin-3-yl-(S)-pyrrolidin-3-ylamine,
(3-chloro-4-fluorophenyl)-(6-fluoropyridin-3-yl)-(S)-pyrrolidin-3-ylamine,
(3,4-dichlorophenyl)pyridin-3-yl-(S)-pyrrolidin-3-ylamine,
(3-chloro-4-fluorophenyl)-(S)-pyrrolidin-3-ylthiophen-3-ylamine,
(3-chloro-4-fluorophenyl)-(5-fluoropyridin-3-yl)-(S)-pyrrolidin-3-ylamine,
(4-fluoro-3-methylphenyl)-(5-fluoropyridin-3-yl)-(S)-pyrrolidin-3-ylamine,
2-[(S)-(3-chloro-4-fluorophenyl)pyrrolidin-3-ylamino]ethanol,
1-[(S)-(3-chloro-4-fluorophenyl)pyrrolidin-3-ylamino]-2-methyl-propan-2-ol,
(3-chloro-4-fluorophenyl)-(2-methoxyethyl)-(S)-pyrrolidin-3-ylamine,
3-[(S)-(3-chloro-4-fluorophenyl)pyrrolidin-3-ylamino]-propan-1-ol,
(3-chloro-4-fluorophenyl)-(3-methoxypropyl)-(S)-pyrrolidin-3-ylamine,
(3-chloro-4-fluorophenyl)-(1-methyl-1H-indazol-5-yl)-(S)-pyrrolidin-3-ylamine,
benzo[b]thiophen-6-yl-(S)-pyrrolidin-3-ylthiophen-3-ylamine, and benzo[b]thiophen-5-yl-(S)-pyrrolidin-3-ylthiophen-3-ylamine.

Item 7. A pharmaceutical composition comprising a pyrrolidine compound of General Formula (1) or a salt thereof according to Item 1 as an active ingredient and a pharmaceutically acceptable carrier.

Item 8. A prophylactic and/or therapeutic agent for disorders caused by reduced neurotransmission of serotonin, norepinephrine or dopamine, comprising as an active ingredient a pyrrolidine compound of General Formula (1) or a salt thereof according to Item 1.

Item 9. A prophylactic and/or therapeutic agent according to Item 8, wherein the disorder is selected from the group consisting of hypertension; depression; anxiety disorders; fear; posttraumatic stress syndrome; acute stress syndrome; avoidant personality disorders; body dysmorphic disorder; precocious ejaculation; eating disorders; obesity; chemical dependencies to alcohol, cocaine, heroin, phenobarbital, nicotine and benzodiazepines; cluster headache; migraine; pain disorder; Alzheimer's disease; obsessive-compulsive disorders; panic disorders; memory disorders; Parkinson's disease; endocrine disorders; vascular spasm; cerebellar ataxia; gastrointestinal tract disorders; negative syndrome of schizophrenia; premenstrual syndrome; fibromyalgia syndrome; stress incontinence; Tourette's syndrome; trichotillomania; kleptomania; male impotence; attention deficit hyperactivity disorder (ADHD); chronic paroxysmal hemicrania; chronic fatigue; cataplexy; sleep apnea syndrome and headache.

Item 10. A prophylactic and/or therapeutic agent according to Item 8, wherein the disorder is selected from the group consisting of:
depressions selected from the group consisting of major depression; bipolar 1 disorder; bipolar 2 disorder; mixed episode; dysthymic disorders; rapid cycler; atypical depression;

seasonal affective disorders; postpartum depression; minor depression; recurrent brief depressive disorder; intractable depression/chronic depression; double depression; alcohol-induced mood disorders; mixed anxiety & depressive disorders; depressions induced by various physical disorders selected from the group consisting of Cushing's disease, hypothyroidism, hyperparathyroidism syndrome, Addison's disease, amenorrhea and lactation syndrome, Parkinson's disease, Alzheimer's disease, intracerebral bleeding, diabetes, chronic fatigue syndrome and cancers; depression of the middle-aged; senile depression; depression of children and adolescents; depression induced by interferons; depression induced by adjustment disorder; and anxieties selected from the group consisting of anxiety induced by adjustment disorder and anxiety induced by neuropathy selected from the group consisting of head trauma, brain infection and inner ear injury.

Item 11. Use of a pyrrolidine compound of General Formula (1) or a salt thereof according to any one of Items 1 to 6 as a drug.

Item 12. Use of a pyrrolidine compound of General Formula (1) or a salt thereof according to any one of Items 1 to 6 as a serotonin reuptake inhibitor and/or a norepinephrine reuptake inhibitor and/or a dopamine reuptake inhibitor.

Item 13. A method for treating or preventing disorders caused by reduced neurotransmission of serotonin, norepinephrine or dopamine, comprising administering a pyrrolidine compound of General Formula (1) or a salt thereof according to any one of Items 1 to 6 to human or animal.

Item 14. A process for producing a pyrrolidine compound of General Formula (1):

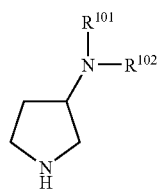

(1)

or a salt thereof, wherein $R^{101}$ and $R^{102}$ are defined above in Item 1, the process comprising (1) subjecting a compound of General Formula (2)

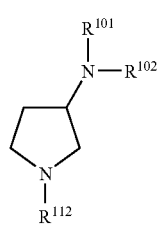

(2)

wherein $R^{101}$ and $R^{102}$ are as defined above in Item 1, and $R^{112}$ is an amino-protecting group to an elimination reaction to remove the amino protecting group.

Preferred embodiments of the pyrrolidine compound (1) include compounds represented by General Formula (1)

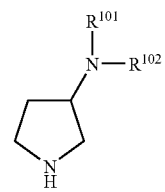

(1)

and salts thereof,
wherein $R^{101}$ is
(1) a phenyl group,
(3) a benzothienyl group,
(4) an indolyl group,
(5) a 2,3-dihydro-1H-indenyl group,
(6) a naphthyl group,
(7) a benzofuryl group,
(8) a quinolyl group,
(12) a benzothiazolyl group,
(18) a 2,4-dihydro-1,3-benzodioxinyl group,
(19) a 2,3-dihydrobenzofuryl group,
(20) a 9H-fluorenyl group,
(23) an indolinyl group,
(28) an isoquinolyl group,
(29) a 2,3-dihydro-1,4-benzoxadinyl group,
(30) a quinoxalinyl group,
(31) a quinazolinyl group,
(32) a 1,2,3,4-tetrahydroquinolyl group,
(40) a 1,3-benzodioxolyl group,
(41) a 2,3-dihydro-1,4-benzodioxinyl group,
(42) a 3,4-dihydro-1,5-benzodioxepinyl group,
(44) a 1,2-dihydroquinolyl group,
(45) a 1,2,3,4-tetrahydroisoquinolyl group,
(46) a benzoxazolyl group,
(47) a benzoisothiazolyl group,
(48) an indazolyl group or
(49) a benzoimidazolyl group,
and each of which may have on the aromatic or heterocyclic ring one to five (preferably one to three) substituents selected from the following (1-1) to (1-37):
(1-1) halogen atoms,
(1-2) lower alkylthio groups optionally substituted with one or more (preferably one to three) halogen atoms,
(1-3) lower alkyl groups optionally substituted with one or more (preferably one to three) halogen atoms,
(1-4) lower alkoxy groups optionally substituted with one or more (preferably one to four) halogen atoms,
(1-5) nitro group,
(1-6) lower alkoxycarbonyl groups,
(1-7) amino groups optionally substituted with one or two lower alkyl groups,
(1-8) lower alkylsulfonyl groups,
(1-9) cyano group,
(1-10) carboxy group,
(1-11) hydroxy group,
(1-12) thienyl groups,
(1-13) oxazolyl groups,
(1-14) naphthyl groups,
(1-15) benzoyl group,
(1-16) phenoxy groups optionally substituted with one to three halogen atoms on phenyl ring,
(1-17) phenyl lower alkoxy groups,
(1-18) lower alkanoyl groups,
(1-19) phenyl groups optionally substituted on the phenyl ring with one to five (preferably one to three) substituents selected from the group consisting of halogen atoms, lower alkoxy groups, cyano group, lower alkanoyl groups and lower alkyl groups,
(1-20) phenyl lower alkyl groups,
(1-21) cyano lower alkyl groups,
(1-22) 5 to 7-membered saturated heterocyclic group-substituted sulfonyl groups, the heterocyclic group containing on the heterocyclic ring one or two nitrogen atoms (preferably piperidylsulfonyl),
(1-23) thiazolyl groups optionally substituted with one or two lower alkyl groups on the thiazole ring,
(1-24) imidazolyl groups,
(1-25) amino lower alkyl groups optionally substituted with one or two lower alkyl groups on the amino group,
(1-26) pyrrolidinyl lower alkoxy groups,
(1-27) isoxazolyl groups,
(1-28) cycloalkylcarbonyl groups,
(1-29) naphthyloxy groups,
(1-30) pyridyl groups,
(1-31) furyl groups,
(1-32) phenylthio group,
(1-33) oxo group,
(1-34) carbamoyl group,
(1-35) 5 to 7-membered saturated heterocyclic groups containing one or two nitrogen atoms (preferably pyrrolidinyl, piperazinyl or piperidyl), the heterocyclic group optionally being substituted with one to three substituents selected from the group consisting of oxo group; lower alkyl groups; lower alkanoyl groups; phenyl lower alkyl groups; phenyl groups optionally substituted with one to three members selected from the group consisting of halogen atoms and lower alkoxy groups; and pyridyl groups,
(1-36) oxido group and
(1-37) lower alkoxido groups,
with the proviso that $R^{101}$ and $R^{102}$ are not simultaneously unsubstituted phenyl.

More preferred embodiments of the pyrrolidine compound (1) include compounds represented by General Formula (1)

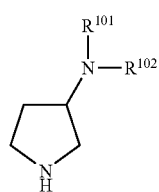

(1)

and salts thereof,
wherein $R^{101}$ is
(1) a phenyl group or
(3) a benzothienyl group,
and each of which may have on the aromatic or heterocyclic ring one or two substituents selected from the group consisting of (1-1) halogen atoms and (1-3) lower alkyl groups optionally substituted with one to three halogen atoms, and $R^{102}$ is
(1) a phenyl group,
(2) a pyridyl group,
(3) a benzothienyl group,
(4) an indolyl group,
(5) a 2,3-dihydro-1H-indenyl group,
(6) a naphthyl group,
(7) a benzofuryl group,
(8) a quinolyl group,
(9) a thiazolyl group,
(10) a pyrimidinyl group,
(11) a pyrazinyl group,
(12) a benzothiazolyl group,
(13) a thieno[3,2-b]pyridyl group,
(14) a thienyl group,
(15) a cycloalkyl group,
(16) a tetrahydropyranyl group,
(17) a pyrrolyl group,
(18) a 2,4-dihydro-1,3-benzodioxinyl group,
(19) a 2,3-dihydrobenzofuryl group,
(20) a 9H-fluorenyl group,
(21) a pyrazolyl group,
(22) a pyridazinyl group,
(23) an indolinyl group,
(24) a thieno[2,3-b]pyridyl group,
(25) a thieno[3,2-d]pyrimidinyl group,
(26) a thieno[3,2-e]pyrimidinyl group,
(27) a 1H-pyrazolo[3,4-b]pyridyl group,
(28) an isoquinolyl group,
(29) a 2,3-dihydro-1,4-benzoxadinyl group,
(30) a quinoxalinyl group,
(31) a quinazolinyl group,
(32) a 1,2,3,4-tetrahydroquinolyl group,
(40) a 1,3-benzodioxolyl group,
(41) a 2,3-dihydro-1,4-benzodioxinyl group,
(42) a 3,4-dihydro-1,5-benzodioxepinyl group,
(43) a dihydropyridyl group,
(44) a 1,2-dihydroquinolyl group,
(45) a 1,2,3,4-tetrahydroisoquinolyl group,
(46) a benzoxazolyl group,
(47) a benzoisothiazolyl group,
(48) an indazolyl group,
(49) a benzoimidazolyl group,
(50) an imidazolyl group,
(59) a hydroxy-substituted lower alkyl group or
(60) a lower alkoxy lower alkyl group
and each of groups (1) to (50) may have on the aromatic or heterocyclic ring one to five (preferably one to three) substituents selected from the following (1-1) to (1-37):
(1-1) halogen atoms,
(1-2) lower alkylthio groups optionally substituted with one or more (preferably one to three) halogen atoms,
(1-3) lower alkyl groups optionally substituted with one or more (preferably one to three) halogen atoms,
(1-4) lower alkoxy groups optionally substituted with one or more (preferably one to four) halogen atoms,
(1-5) nitro group,
(1-6) lower alkoxycarbonyl groups,
(1-7) amino groups optionally substituted with one or two lower alkyl groups,
(1-8) lower alkylsulfonyl groups,
(1-9) cyano group,
(1-10) carboxy group,
(1-11) hydroxy group,
(1-12) thienyl groups,
(1-13) oxazolyl groups,
(1-14) naphthyl groups,
(1-15) benzoyl group,
(1-16) phenoxy groups optionally substituted with one to three halogen atoms on phenyl ring,
(1-17) phenyl lower alkoxy groups,
(1-18) lower alkanoyl groups,
(1-19) phenyl groups optionally substituted on the phenyl ring with one to five (preferably one to three) substituents selected from the group consisting of halogen atoms, lower alkoxy groups, cyano group, lower alkanoyl groups and lower alkyl groups, (1-20) phenyl lower alkyl groups,
(1-21) cyano lower alkyl groups,
(1-22) 5 to 7-membered saturated heterocyclic group-substituted sulfonyl groups, the heterocyclic group containing on the heterocyclic ring one or two nitrogen atoms (preferably piperidylsulfonyl),
(1-23) thiazolyl groups optionally substituted with one or two lower alkyl groups on the thiazole ring,
(1-24) imidazolyl groups,
(1-25) amino lower alkyl groups optionally substituted with one or two lower alkyl groups on the amino group,
(1-26) pyrrolidinyl lower alkoxy groups,
(1-27) isoxazolyl groups,
(1-28) cycloalkylcarbonyl groups,
(1-29) naphthyloxy groups,
(1-30) pyridyl groups,
(1-31) furyl groups,
(1-32) phenylthio group,
(1-33) oxo group,
(1-34) carbamoyl group,
(1-35) 5 to 7-membered saturated heterocyclic groups containing one or two nitrogen atoms (preferably pyrrolidinyl, piperazinyl or piperidyl), the heterocyclic group optionally being substituted with one to three substituents selected from the group consisting of oxo group; lower alkyl groups; lower alkanoyl groups; phenyl lower alkyl groups; phenyl groups optionally substituted with one to three members selected from the group consisting of halogen atoms and lower alkoxy groups; and pyridyl groups,
(1-36) oxido group and
(1-37) lower alkoxido groups,
with the proviso that $R^{101}$ and $R^{102}$ are not simultaneously unsubstituted phenyl.

Particularly preferred embodiments of the pyrrolidine compound (1) include compounds represented by General Formula (1)

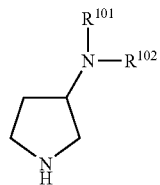

(1)

and salts thereof,
wherein $R^{101}$ is
(1) a phenyl group substituted on the phenyl ring with one or two substituents selected from the group consisting of (1-1) halogen atoms and (1-3) lower alkyl groups optionally substituted with one to three halogen atoms, and
$R^{102}$ is
(1) a phenyl group,
(2) a pyridyl group,
(9) a thiazolyl group,
(10) a pyrimidinyl group,
(11) a pyrazinyl group,
(14) a thienylgroup,
(48) an indazolyl group,
(59) a hydroxy-substituted lower alkyl group or
(60) a lower alkoxy lower alkyl group,
and each of the groups (1), (2), (9), (10), (11), (14) and (48) may have on the aromatic or heterocyclic ring one or two substituents selected from the group consisting of
(1-1) halogen atoms,
(1-3) lower alkyl groups optionally substituted with one to three halogen atoms and
(1-9) cyano group.

Examples of particularly preferable pyrrolidine compounds of the present invention are as follows:
(4-chlorophenyl)phenyl-(S)-pyrrolidin-3-ylamine,
(4-fluorophenyl)phenyl-(S)-pyrrolidin-3-ylamine,
(3,4-difluorophenyl)phenyl-(S)-pyrrolidin-3-ylamine,
bis-(4-fluorophenyl)-(S)-pyrrolidin-3-ylamine,
(3,4-difluorophenyl)-(4-fluorophenyl)-(S)-pyrrolidin-3-ylamine,
(3-chloro-4-fluorophenyl)-(S)-pyrrolidin-3-yl-p-tolylamine,
4-[(S)-(4-fluoro-3-methylphenyl)pyrrolidin-3-ylamino]-benzonitrile,
bis-(3-fluorophenyl)-(S)-pyrrolidin-3-ylamine,
(3-chloro-4-fluorophenyl)-(S)-pyrrolidin-3-ylthiazol-2-ylamine,
(4-fluorophenyl)-(S)-pyrrolidin-3-ylthiazol-2-ylamine,
(3,4-dichlorophenyl)-(S)-pyrrolidin-3-ylthiazol-2-ylamine,
(3,4-dichlorophenyl)pyrimidin-5-yl-(S)-pyrrolidin-3-ylamine,
(3-chloro-4-fluorophenyl)pyrazin-2-yl-(S)-pyrrolidin-3-ylamine,
(3-chloro-4-fluorophenyl)-(5-chloropyridin-2-yl)-(S)-pyrrolidin-3-ylamine,
(3-chloro-4-fluorophenyl)pyridin-2-yl-(S)-pyrrolidin-3-ylamine,
(3-chloro-4-fluorophenyl)pyridin-3-yl-(S)-pyrrolidin-3-ylamine,
(3-chloro-4-fluorophenyl)-(6-fluoropyridin-3-yl)-(S)-pyrrolidin-3-ylamine,
(3,4-dichlorophenyl)pyridin-3-yl-(S)-pyrrolidin-3-ylamine,
(3-chloro-4-fluorophenyl)-(S)-pyrrolidin-3-ylthiophen-3-ylamine,
(3-chloro-4-fluorophenyl)-(5-fluoropyridin-3-yl)-(S)-pyrrolidin-3-ylamine,
(4-fluoro-3-methylphenyl)-(5-fluoropyridin-3-yl)-(S)-pyrrolidin-3-ylamine,
2-[(S)-(3-chloro-4-fluorophenyl)pyrrolidin-3-ylamino]ethanol,
1-[(S)-(3-chloro-4-fluorophenyl)pyrrolidin-3-ylamino]-2-methyl-propan-2-ol,
(3-chloro-4-fluorophenyl)-(2-methoxyethyl)-(S)-pyrrolidin-3-ylamine,
3-[(S)-(3-chloro-4-fluorophenyl)pyrrolidin-3-ylamino]-propan-1-ol,
(3-chloro-4-fluorophenyl)-(3-methoxypropyl)-(S)-pyrrolidin-3-ylamine,
(3-chloro-4-fluorophenyl)-(1-methyl-1H-indazol-5-yl)-(S)-pyrrolidin-3-ylamine,
benzo[b]thiophen-6-yl-(S)-pyrrolidin-3-ylthiophen-3-ylamine, and
benzo[b]thiophen-5-yl-(S)-pyrrolidin-3-ylthiophen-3-ylamine.

Specific examples of groups in General Formula (1) are as follows.

Examples of halogen atoms include fluorine, chlorine, bromine, and iodine.

Examples of lower alkylthio groups optionally substituted with one or more halogen atoms include straight or branched $C_{1-6}$ alkylthio groups optionally substituted with one to three halogen atoms, such as methylthio, ethylthio, n-propylthio, isopropylthio, n-butylthio, isobutylthio, tert-butylthio, sec-butylthio, n-pentylthio, isopentylthio, neopentylthio, n-hexylthio, isohexylthio, 3-methylpenthylthio, trifluoromethylthio, trichloromethylthio, chloromethylthio, bromomethylthio, fluoromethylthio, iodomethylthio, difluoromethylthio, dibromomethylthio, 2-chloroethylthio, 2,2,2-trifluoroethylthio, 2,2,2-trichloroethylthio, 3-chloropropylthio, 2,3-dichloropropylthio, 4,4,4-trichlorobutylthio, 4-fluorobutylthio, 5-chloropentylthio, 3-chloro-2-methylpropylthio, 5-bromohexylthio, 5,6-dibromohexylthio, etc.

Examples of lower alkyl groups optionally substituted with one or more halogen atoms include straight or branched $C_{1-6}$ alkyl groups optionally substituted with one to four halogen atoms, such as methyl, ethyl, n-propyl, isopropyl, n-butyl, isobutyl, tert-butyl, sec-butyl, n-pentyl, isopentyl, neopentyl, n-hexyl, isohexyl, 3-methylpentyl, trifluoromethyl, trichloromethyl, chloromethyl, bromomethyl, fluoromethyl, iodomethyl, difluoromethyl, dibromomethyl, 2-chloroethyl, 2,2,2-trifluoroethyl, 2,2,2-trichloroethyl, 3-chloropropyl, 2,3-dichloropropyl, 4,4,4-trichlorobutyl, 4-fluorobutyl, 5-chloropentyl, 3-chloro-2-methylpropyl, 5-bromohexyl, 5,6-dibromohexyl, 1,1,2,2-tetrafluoroethyl, etc.

Examples of lower alkoxy groups optionally substituted with one or more halogen atoms include straight or branched $C_{1-6}$ alkoxy groups optionally substituted with one to four halogen atoms, such as methoxy, ethoxy, n-propoxy, isopropoxy, n-butoxy, isobutoxy, tert-butoxy, sec-butoxy, n-pentyloxy, isopentyloxy, neopentyloxy, n-hexyloxy, isohexyloxy, 3-methylpentyloxy, trifluoromethoxy, trichloromethoxy, chloromethoxy, bromomethoxy, fluoromethoxy, iodomethoxy, difluoromethoxy, dibromomethoxy, 2-chloroethoxy, 2,2,2-trifluoroethoxy, 2,2,2-trichloroethoxy, 3-chloropropoxy, 2,3-dichloropropoxy, 4,4,4-trichlorobutoxy, 4-fluorobutoxy, 5-chloropentyloxy, 3-chloro-2-methylpropoxy, 5-bromohexyloxy, 5,6-dibromohexyloxy, 1,1,2,2-tetrafluoroethoxy, etc.

Examples of lower alkoxycarbonyl groups include alkoxycarbonyl groups wherein the alkoxy moiety is a straight or branched $C_{1-6}$ alkoxy group, such as methoxycarbonyl, ethoxycarbonyl, n-propoxycarbonyl, isopropoxycarbonyl, n-butoxycarbonyl, isobutoxycarbonyl, tert-butoxycarbonyl, sec-butoxycarbonyl, n-pentyloxycarbonyl, neopentyloxycarbonyl, n-hexyloxycarbonyl, isohexyloxycarbonyl, 3-methylpentyloxycarbonyl, etc.

Examples of lower alkyl groups include straight or branched $C_{1-6}$ alkyl groups, such as methyl, ethyl, n-propyl, isopropyl, n-butyl, isobutyl, tert-butyl, sec-butyl, n-pentyl, isopentyl, neopentyl, n-hexyl, isohexyl, 3-methylpentyl, etc.

Examples of lower alkanoyl groups include a straight or branched $C_{1-6}$ alkanoyl group such as formyl, acetyl, propionyl, butyryl, isobutyryl, pentanoyl, tert-butylcarbonyl, hexanoyl, etc.

Examples of lower alkylsulfonyl groups include straight or branched $C_{1-6}$ alkyl sulfonyl groups, such as methylsulfonyl, ethylsulfonyl, n-propylsulfonyl, isopropylsulfonyl, n-butylsulfonyl, isobutylsulfonyl, tert-butylsulfonyl, sec-butylsulfonyl, n-pentylsulfonyl, isopentylsulfonyl, neopentylsulfonyl, n-hexylsulfonyl, isohexylsulfonyl, 3-methylpentylsulfonyl, etc.

Examples of phenoxy groups optionally substituted with one to three halogen atoms on the phenyl ring include phenoxy, 2-fluorophenoxy, 3-fluorophenoxy, 4-fluorophenoxy, 2-chlorophenoxy, 3-chlorophenoxy, 4-chlorophenoxy, 2-bromophenoxy, 3-bromophenoxy, 4-bromophenoxy, 2-iodophenoxy, 3-iodophenoxy, 4-iodophenoxy, 2,3-difluorophenoxy, 3,4-difluorophenoxy, 3,5-difluorophenoxy, 2,4-difluorophenoxy, 2,6-difluorophenoxy, 2,3-dichlorophenoxy, 3,4-dichlorophenoxy, 3,5-dichlorophenoxy, 2,4-dichlorophenoxy, 2,6-dichlorophenoxy, 3,4,5-trifluorophenoxy, 3,4,5-trichlorophenoxy, 2,4,6-trifluorophenoxy, 2,4,6-trichlorophenoxy, 2-fluoro-4-bromophenoxy, 4-chloro-3-fluorophenoxy, 2,3,4-trichlorophenoxy, etc.

Examples of phenyl lower alkoxy groups include phenylalkoxy groups wherein the alkoxy moiety is a straight or branched $C_{1-6}$ alkoxy group, such as benzyloxy, 2-phenylethoxy, 1-phenylethoxy, 3-phenylpropoxy, 4-phenylbutoxy, 5-phenylpentyloxy, 6-phenylhexyloxy, 1,1-dimethyl-2-phenylethoxy, 2-methyl-3-phenylpropoxy, etc.

Examples of phenyl lower alkyl groups include phenylalkyl groups wherein the alkyl moiety is a straight or branched $C_{1-6}$ alkyl group, such as benzyl, 1-phenethyl, 2-phenethyl, 3-phenylpropyl, 2-phenylpropyl, 4-phenylbutyl, 5-phenylpentyl, 4-phenylpentyl, 6-phenylhexyl, 2-methyl-3-phenylpropyl, 1,1-dimethyl-2-phenylethyl, etc.

Examples of cyano lower alkyl groups include cyanoalkyl groups wherein the alkyl moiety is a straight or branched $C_{1-6}$ alkyl group, such as cyanomethyl, 2-cyanoethyl, 1-cyanoethyl, 3-cyanopropyl, 4-cyanobutyl, 1,1-dimethyl-2-cyanoethyl, 5-cyanopentyl, 6-cyanohexyl, 1-cyanoisopropyl, 2-methyl-3-cyanopropyl, etc.

Examples of thiazolyl groups optionally substituted with one or two lower alkyl groups on the thiazole ring include thiazolyl groups optionally substituted with one or two straight or branched $C_{1-6}$ alkyl groups on the thiazole ring, such as (2-, 4-, or 5-)thiazolyl, 2-methyl-(4-, or 5-)thiazolyl, 4-methyl-(2- or 5-)thiazolyl, 2-ethyl-(4- or 5-)thiazolyl, 4-n-propyl-(2- or 5-)thiazolyl, 5-n-butyl-(2- or 4-)thiazolyl, 2-n-pentyl-(4- or 5-)thiazolyl, 4-n-hexyl-(2- or 5-)thiazolyl, 2,4-dimethyl-5-thiazolyl, etc.

Examples of amino lower alkyl groups optionally substituted with one or two lower alkyl groups on an amino group include aminoalkyl groups wherein the alkyl moiety is a straight or branched $C_{1-6}$ alkyl group and which are optionally substituted on an amino group with one or two straight or branched $C_{1-6}$ alkyl groups; such as aminomethyl, 2-aminoethyl, 1-aminoethyl, 3-aminopropyl, 4-aminobutyl, 5-aminopentyl, 6-aminohexyl, 1,1-dimethyl-2-aminoethyl, 2-methyl-3-aminopropyl, methylaminomethyl, 2-ethylaminoethyl, 3-propylaminopropyl, 3-isopropylaminopropyl, 4-butylaminobutyl, 5-pentylaminopentyl, 6-hexylaminohexyl, 2-dimethylaminoethyl, 2-diisopropylaminopropyl, 3-dimethylaminopropyl, diisopropylaminomethyl, 3-diisopropylaminopropyl, (N-ethyl-N-propylamino)methyl, 2-(N-methyl-N-hexylamino)methyl, etc.

Examples of pyrrolidinyl lower alkoxy groups include pyrrolidinyl alkoxy groups wherein the alkoxy moiety is a straight or branched $C_{1-6}$ alkoxy group, such as (1-, 2-, or 3-)pyrrolydinyl methoxy, 2-[(1-, 2-, or 3-)pyrrolydinyl] ethoxy, 1-[(1-, 2-, or 3-)pyrrolydinyl]ethoxy, 3-[(1-, 2-, or 3-)pyrrolydinyl]propoxy, 4-[(1-, 2-, or 3-)pyrrolydinyl]butoxy, 5-[(1-, 2-, or 3-)pyrrolydinyl]pentyloxy, 6-[(1-, 2-, or 3-)pyrrolydinyl]hexyloxy, 1,1-dimethyl-2-[(1-, 2-, or 3-)pyrrolydinyl]ethoxy, 2-methyl-3-[(1-, 2-, or 3-) pyrrolydinyl] propoxy, etc.

Examples of cycloalkyl groups include $C_{3-8}$ cycloalkyl groups, such as cyclopropyl, cycloobutyl, cyclopentyl, cyclohexyl, cycloheptyl, cyclooctyl, etc.

Examples of cycloalkylcarbonyl groups include cycloalkylcarbonyl groups wherein the cycloalkyl moiety is a $C_{3-8}$ cycloalkyl group, such as cyclopropylcarbonyl, cyclobutylcarbonyl, cyclopentylcarbonyl, cyclohexylcarbonyl, cycloheptylcarbonyl, cyclooctylcarbonyl, etc.

Examples of lower alkoxy groups include straight or branched $C_{1-6}$ alkoxy groups, such as methoxy, ethoxy, n-propoxy, isopropoxy, n-butoxy, isobutoxy, tert-butoxy, sec-butoxy, n-pentyloxy, isopentyloxy, neopentyloxy, n-hexyloxy, isohexyloxy, 3-methylpentyloxy, etc.

Examples of lower alkylthio groups include straight or branched $C_{1-6}$ alkylthio groups such as methylthio, ethylthio, n-propylthio, isopropylthio, n-butylthio, isobutylthio, tert-butylthio, sec-butylthio, n-pentylthio, isopentylthio, neopentylthio, n-hexylthio, isohexylthio, 3-methylpentylthio, etc.

Examples of phenyl groups optionally substituted on the phenyl ring with one to three members selected from the group consisting of halogen atoms and lower alkoxy groups include phenyl groups optionally substituted on the phenyl ring with one to three members selected from the group consisting of halogen atoms and straight or branched $C_{1-6}$ alkoxy groups, such as phenyl, 2-methoxyphenyl, 3-methoxyphenyl, 4-methoxylphenyl, 2-ethoxyphenyl, 3-ethoxyphenyl, 4-ethoxyphenyl, 4-isopropoxyphenyl, 3-butoxyphenyl, 4-pentyloxyphenyl, 4-hexyloxyphenyl, 3,4-dimethoxyphenyl, 3,4-diethoxyphenyl, 2,4-dimethoxyphenyl, 2,5-dimethoxyphenyl, 2,6-dimethoxyphenyl, 3,4,5-trimethoxyphenyl, 2-methoxy-4-fluorophenyl, 4-fluorophenyl, 2,5-difluorophenyl, 2,4-difluorophenyl, 3,4-difluorophenyl, 3,5-difluorophenyl, 2,6-difluorophenyl, 2-chlorophenyl, 3-chlorophenyl, 4-chlorophenyl, 2,3-dichlorophenyl, 2,4-dichlorophenyl, 2,5-dichlorophenyl, 3,4-dichlorophenyl, 2,6-dichlorophenyl, 3-fluorophenyl, 2-fluorophenyl, 3-bromophenyl, 4-iodophenyl, 2-bromophenyl, 4-bromophenyl, 3,5-dichlorophenyl, 2,4,6-trifluorophenyl, 2-chlorophenyl, 3-chlorophenyl, 4-chlorophenyl, 2-iodophenyl, 3-iodophenyl, 2,3-dibromophenyl, 2,4-diiodophenyl, 2,4,6-trichlorophenyl, etc.

Examples of 5- to 7-membered saturated heterocyclic groups containing on the heterocyclic ring one or two heteroatoms selected from the group consisting of nitrogen, oxygen and sulfur include pyrrolidinyl, piperazinyl, piperidinyl, morpholino, thiomorpholino, homopiperazinyl, homopiperidinyl, imidazolidinyl, thiazolidinyl, isothiazolidinyl, oxazolidinyl, isoxazolidinyl, isothiazolidinyl and pyrazolidinyl.

Examples of the above-mentioned heterocyclic groups substituted with one to three members selected from the group consisting of oxo group; lower alkyl groups; lower alkanoyl groups; phenyl lower alkyl groups; phenyl groups optionally substituted on the phenyl ring with one to three members selected from the group consisting of halogen atoms and lower alkoxy groups; and pyridyl groups:

include the above-mentioned heterocyclic groups substituted with one to three members selected from the group consisting of oxo groups; straight or branched $C_{1-6}$ alkyl groups; straight or branched $C_{1-6}$ alkanoyl groups; phenyl alkyl groups wherein the alkyl moiety is a straight or branched $C_{1-6}$ alkyl group; phenyl groups optionally substituted on the phenyl ring with one to three members selected from the group consisting of halogen atoms and straight or branched $C_{1-6}$ alkoxy groups; and pyridyl groups;

such as 2-oxo-(1-, 3-, 4-, or 5-)pyrrolidinyl, 2-oxo-(1-, 3-, 4-, 5-, or 6-)piperazinyl, 4-methyl-(1-, 2-, or 3-)piperazinyl, 4-acetyl-(1-, 2-, or 3-)piperazinyl, 4-ethyl-(1-, 2-, or 3-)piperazinyl, 2-methyl-(1-, 2-, 3-, 4-, or 5-)pyrrolidinyl, 2-methyl-(1-, 2-, 3-, 4-, 5-, or 6-)piperidinyl, 2,4-dimethyl-(1-, 2-, 3-, 5-, or 6-)piperidinyl, 3-methyl-(1-, 2-, 3-, 4-, or 5-)pyrrolidinyl, 2,3,4-trimethyl-(1-, 2-, 3-, 5-, or 6-)piperazinyl, 4-acetyl-3-methyl-(1-, 2-, 3-, 5-, or 6-)piperazinyl, 3-methyl-(2-, 3-, 4-, 5-, or 6-)morpholino, 2-acetyl-(2-, 3-, 4-, 5-, or 6-)morpholino, 4-(2-phenylethyl)-(1-, 2-, or 3-)piperazinyl, 4-(3,4-dichlorophenyl)-(1-, 2-, 3-, or 4-)piperazinyl, 4-(4-methoxyphenyl)-(1-, 2-, or 3-)piperazinyl, 4-(2-chlorophenyl)-(1-, 2-, or 3-)piperazinyl, 4-[(2-, 3-, or 4-) pyridyl]-(1-, 2-, or 3-)piperazinyl, 4-phenyl-(1-, 2-, or 3-)piperazinyl, 4-benzyl-(1-, 2-, or 3-)piperidinyl, 4-(3,4-dichlorophenyl)-(1-, 2-, or 3-)morpholino, 2-(4-methoxyphenyl)-(1-, 2-, 3-, 4-, or 5-)pyrrolidinyl, 4-(2-chlorophenyl)-(1-, 2-, or 3-)piperidinyl, 4-[(2-, 3-, or 4-) pyridyl]-(1-, 2-, or 3-)piperidinyl, 4-phenyl-(1-, 2-, or 3-) piperidinyl, 4-phenyl-3-methyl-(1-, 2-, 3-, 5-, or 6-) piperazinyl, 4-[(2-, 3-, or 4-)pyridyl]-2-acetyl-(1-, 2-, 3-, 5-, or 6-)piperazinyl, etc.

Examples of cycloalkyl lower alkyl groups include cycloalkyl alkyl groups wherein the cycloalkyl moiety is a $C_{3-8}$ cycloalkyl group and the alkyl moiety is a straight or branched $C_{1-6}$ alkyl group, such as cyclopropylmethyl, cyclohexylmethyl, 2-cyclopropylethyl, 1-cyclobutylethyl, cyclopentylmethyl, 3-cyclopentylpropyl, 4-cyclohexylbutyl, 5-cycloheptylpentyl, 6-cyclooctylhexyl, 1,1-dimethyl-2-cyclohexylethyl, 2-methyl-3-cyclopropylpropyl, etc.

Examples of lower alkylthio lower alkyl groups include alkylthioalkyl groups wherein the alkylthio moiety is a straight or branched $C_{1-6}$ alkylthio group and the alkyl moiety is a straight or branched $C_{1-6}$ alkyl group, such as methylthiomethyl, 2-methylthioethyl, 1-ethylthioethyl, 2-ethylthioethyl, 3-n-butylthiopropyl, 4-n-propylthiobutyl, 1,1-dimethyl-2-n-pentylthioethyl, 5-n-hexylthiopentyl, 6-methylthiohexyl, 1-ethylthioisopropyl, 2-methyl-3-methylthiopropyl, etc.

Examples of phenoxy lower alkyl groups include phenoxy alkyl groups wherein the alkyl moiety is a straight or branched $C_{1-6}$ alkyl group, such as phenoxymethyl, 1-phenoxyethyl, 2-phenoxyethyl, 3-phenoxypropyl, 2-phenoxypropyl, 4-phenoxybutyl, 5-phenoxypentyl, 4-phenoxypentyl, 6-phenoxyhexyl, 2-methyl-3-phenoxypropyl, 1,1-dimethyl-2-phenoxyethyl, etc.

Examples of pyridyloxy lower alkyl groups include pyridyloxyalkyl groups wherein the alkyl moiety is a straight or branched $C_{1-6}$ alkyl group, such as [2-, 3-, or 4-]pyridyloxy]methyl, 1-[2-, 3-, or 4-]pyridyloxy]ethyl, 2-[2-, 3-, or 4-]pyridyloxy]ethyl, 3-[2-, 3-, or 4-]pyridyloxy]propyl, 2-[2-, 3-, or 4-]pyridyloxy]propyl, 4-[2-, 3-, or 4-]pyridyloxy]butyl, 5-[2-, 3-, or 4-]pyridyloxy]pentyl, 4-[2-, 3-, or 4-]pyridyloxy]pentyl, 6-[2-, 3-, or 4-]pyridyloxy]hexyl, 2-methyl-3-[2-, 3-, or 4-]pyridyloxy]propyl, 1,1-dimethyl-2-[2-, 3-, or 4-]pyridyloxy]ethyl, etc.

Examples of lower alkynyl groups include $C_{2-6}$ straight or branched alkynyl groups, such as ethynyl, (1- or 2-) propynyl, 1-methyl-(1- or 2-)propynyl, 1-ethyl-(1- or 2-)propynyl, (1-, 2- or 3-)butynyl and (1-, 2-, 3- or 4-)pentynyl, (1-, 2-, 3-, 4- or 5-)hexynyl, etc.

Examples of phenyl lower alkenyl groups include phenylalkenyl groups containing one to three double bonds wherein the alkenyl moiety is a straight or branched $C_{2-6}$ alkenyl group, such as styryl, 3-phenyl-2-propenyl (trivial name: cinnamyl), 4-phenyl-2-butenyl, 4-phenyl-3-butenyl, 5-phenyl-4-pentenyl, 5-phenyl-3-pentenyl, 6-phenyl-5-hexenyl, 6-phenyl-4-hexenyl, 6-phenyl-3-hexenyl, 4-phenyl-1,3-butadienyl, 6-phenyl-1,3,5-hexatrienyl, etc.

Examples of cycloalkyl lower alkyl groups include cycloalkyl alkyl groups wherein the cycloalkyl moiety is a $C_{3-8}$ cycloalkyl group as defined above and the alkyl moiety is a straight or branched $C_{1-6}$ alkyl group as defined above.

Examples of lower alkylthio lower alkyl groups include alkylthio alkyl groups wherein the alkylthio moiety is a straight or branched $C_{1-6}$ alkylthio group as defined above and the alkyl moiety is a straight or branched $C_{1-6}$ alkyl group as defined above.

Examples of amino-substituted lower alkyl groups optionally substituted with one or two lower alkyl groups on the amino group include amino-substituted alkyl groups optionally substituted with one or two straight or branched $C_{1-6}$ alkyl groups on the amino group wherein the alkyl moiety is a straight or branched $C_{1-6}$ alkyl group as defined above.

Examples of phenoxy lower alkyl groups include phenoxy alkyl groups wherein the alkyl moiety is a straight or branched $C_{1-6}$ alkyl group as defined above.

Examples of pyridyloxy lower alkyl groups include pyridyloxy alkyl groups wherein the alkyl moiety is a straight or branched $C_{1-6}$ alkyl group as defined above.

Examples of 1,2,3,4-tetrahydronaphthyl lower alkyl groups include 1,2,3,4-tetrahydronaphthyl alkyl groups wherein the alkyl moiety is a straight or branched $C_{1-6}$ alkyl group as defined above.

Examples of imidazo[1,2-a]pyridyl lower alkyl groups include imidazo[1,2-a]pyridyl alkyl groups wherein the alkyl moiety is a straight or branched $C_{1-6}$ alkyl group as defined above.

Examples of thiazolyl lower alkyl groups include thiazolyl alkyl groups wherein the alkyl moiety is a straight or branched $C_{1-6}$ alkyl group as defined above.

Examples of tetrahydropyranyl lower alkyl groups include tetrahydropyranyl alkyl groups wherein the alkyl moiety is a straight or branched $C_{1-6}$ alkyl group as defined above.

Examples of piperidyl lower alkyl groups include piperidyl alkyl groups wherein the alkyl moiety is a straight or branched $C_{1-6}$ alkyl group as defined above.

Examples of diphenyl lower alkoxy-substituted lower alkyl groups include diphenyl alkoxy-substituted alkyl groups wherein the alkoxy moiety is a straight or branched $C_{1-6}$ alkoxy group as defined above and the alkyl moiety is a straight or branched $C_{1-6}$ alkyl group as defined above.

Examples of lower alkoxycarbonyl-substituted lower alkyl groups include alkoxycarbonyl-substituted alkyl groups wherein the alkoxy moiety is a straight or branched $C_{1-6}$ alkoxy group as defined above and the alkyl moiety is a straight or branched $C_{1-6}$ alkyl group as defined above.

Examples of phenyl lower alkoxycarbonyl-substituted lower alkyl groups include phenyl alkoxycarbonyl-substituted alkyl groups wherein the alkoxy moiety is a straight or branched $C_{1-6}$ alkoxy group as defined above and the alkyl moiety is a straight or branched $C_{1-6}$ alkyl group as defined above.

Examples of hydroxy-substituted lower alkyl groups include hydroxy-substituted alkyl groups wherein the alkyl moiety is a straight or branched $C_{1-6}$ alkyl group as defined above having 1 to 3 hydroxy groups, such as hydroxymethyl, 1-hydroxyethyl, 2-hydroxyethyl, 2,3-dihydroxypropyl, 3-hydroxypropyl, 2-hydroxypropyl, 4-hydroxybutyl, 3,4-dihydroxybutyl, 5-hydroxypentyl, 4-hydroxypentyl, 6-hydroxyhexyl, 2,2-dimethyl-3-hydroxypropyl, 1,1-dimethyl-2-hydroxyethyl, 2,3,4-trihydroxybutyl, etc.

Examples of lower alkoxy lower alkyl groups include alkoxy alkyl groups wherein the alkoxy moiety is a straight or branched $C_{1-6}$alkoxy group as defined above and the alkyl moiety is a straight or branched $C_{1-6}$ alkyl group as defined above, such as methoxymethyl, 1-methoxyethyl, 2-methoxyethyl, 2-ethoxypropyl, 3-methoxypropyl, 3-ethoxypropyl, 3-propoxypropyl, 4-methoxybutyl, 3-methoxybutyl, 5-methoxypentyl, 4-ethoxypentyl, 6-methoxyhexyl, 2,2-dimethyl-3-methoxypropyl, 1,1-dimethyl-2-methoxyethyl etc.

Examples of carboxy lower alkyl groups include carboxy alkyl groups wherein the alkyl moiety is a straight or branched $C_{1-6}$ alkyl group as defined above.

Examples of carbamoyl-substituted lower alkyl groups optionally substituted with one or two lower alkyl groups on the carbamoyl group include carbamoyl-substituted alkyl groups optionally substituted with one or two straight or branched $C_{1-6}$ alkyl groups on the carbamoyl group wherein the alkyl moiety is a straight or branched $C_{1-6}$ alkyl group as defined above.

Examples of morpholinylcarbonyl lower alkyl groups include morpholinylcarbonyl alkyl groups wherein the alkyl moiety is a straight or branched $C_{1-6}$ alkyl group as defined above.

Examples of benzoyl lower alkyl groups include benzoyl alkyl groups wherein the alkyl moiety is a straight or branched $C_{1-6}$ alkyl group as defined above.

Examples of phenylthio lower alkyl groups include phenylthio alkyl groups wherein the alkyl moiety is a straight or branched $C_{1-6}$ alkyl group as defined above.

Examples of naphthylthio lower alkyl groups include naphthylthio alkyl groups wherein the alkyl moiety is a straight or branched $C_{1-6}$ alkyl group as defined above.

Examples of cycloalkylthio lower alkyl groups include cycloalkylthio alkyl groups wherein the alkyl moiety is a straight or branched $C_{1-6}$ alkyl group as defined above.

Examples of pyridylthio lower alkyl groups include pyridylthio alkyl groups wherein the alkyl moiety is a straight or branched $C_{1-6}$ alkyl group as defined above.

Examples of pyrimidinylthio lower alkyl groups include pyrimidinylthio alkyl groups wherein the alkyl moiety is a straight or branched $C_{1-6}$ alkyl group as defined above.

Examples of furylthio lower alkyl groups include furylthio alkyl groups wherein the alkyl moiety is a straight or branched $C_{1-6}$ alkyl group as defined above.

Examples of thienylthio lower alkyl groups include thienylthio alkyl groups wherein the alkyl moiety is a straight or branched $C_{1-6}$ alkyl group as defined above.

Examples of 1,3,4-thiadiazolylthio lower alkyl groups include 1,3,4-thiadiazolylthio alkyl groups wherein the alkyl moiety is a straight or branched $C_{1-6}$ alkyl group as defined above.

Examples of benzimidazolylthio lower alkyl groups include benzimidazolylthio alkyl groups wherein the alkyl moiety is a straight or branched $C_{1-6}$ alkyl group as defined above.

Examples of benzthiazolylthio lower alkyl groups include benzthiazolylthio alkyl groups wherein the alkyl moiety is a straight or branched $C_{1-6}$ alkyl group as defined above.

Examples of tetrazolylthio lower alkyl groups include tetrazolylthio alkyl groups wherein the alkyl moiety is a straight or branched $C_{1-6}$ alkyl group as defined above.

Examples of benzoxazolylthio lower alkyl groups include benzoxazolylthio alkyl groups wherein the alkyl moiety is a straight or branched $C_{1-6}$ alkyl group as defined above.

Examples of thiazolylthio lower alkyl groups include thiazolylthio alkyl groups wherein the alkyl moiety is a straight or branched $C_{1-6}$ alkyl group as defined above.

Examples of imidazolylthio lower alkyl groups include imidazolylthio alkyl groups wherein the alkyl moiety is a straight or branched $C_{1-6}$ alkyl group as defined above.

Examples of amino-substituted lower alkylthio lower alkyl groups optionally substituted with one or two lower alkyl groups on the amino group include amino-substituted alkylthio alkyl groups optionally substituted with one or two straight or branched $C_{1-6}$ alkyl groups on the amino group wherein the alkylthio moiety is a straight or branched $C_{1-6}$ alkylthio group as defined above and the alkyl moiety is a straight or branched $C_{1-6}$ alkyl group as defined above.

Examples of phenyl-substituted lower alkylthio lower alkyl groups include phenyl-substituted alkylthio alkyl groups wherein the alkylthio moiety is a straight or branched $C_{1-6}$ alkylthio group as defined above and the alkyl moiety is a straight or branched $C_{1-6}$ alkyl group as defined above.

Examples of furyl-substituted lower alkylthio lower alkyl groups include furyl-substituted alkylthio alkyl groups wherein the alkylthio moiety is a straight or branched $C_{1-6}$ alkylthio group as defined above and the alkyl moiety is a straight or branched $C_{1-6}$ alkyl group as defined above.

Examples of pyridyl-substituted lower alkylthio lower alkyl groups include pyridyl-substituted alkylthio alkyl groups wherein the alkylthio moiety is a straight or branched $C_{1-6}$ alkylthio group as defined above and the alkyl moiety is a straight or branched $C_{1-6}$ alkyl group as defined above.

Examples of hydroxy-substituted lower alkylthio lower alkyl groups include hydroxy-substituted alkylthio alkyl groups wherein the alkylthio moiety is a straight or branched $C_{1-6}$ alkylthio group as defined above and the alkyl moiety is a straight or branched $C_{1-6}$ alkyl group as defined above.

Examples of phenoxy-substituted lower alkylthio lower alkyl groups include phenoxy-substituted alkylthio alkyl groups wherein the alkylthio moiety is a straight or branched $C_{1-6}$ alkylthio group as defined above and the alkyl moiety is a straight or branched $C_{1-6}$ alkyl group as defined above.

Examples of lower alkoxycarbonyl-substituted lower alkylthio lower alkyl groups include alkoxycarbonyl-substituted alkylthio alkyl groups wherein the alkoxy moiety is a straight or branched $C_{1-6}$ alkoxy group as defined above, the alkylthio moiety is a straight or branched $C_{1-6}$-alkylthio group as defined above and the alkyl moiety is a straight or branched $C_{1-6}$ alkyl group as defined above.

Examples of lower alkenyl groups include straight or branched $C_{2-6}$ alkenyl groups, such as vinyl, 1-propenyl, allyl, 1-methylallyl, (1-, 2- or 3-)butenyl, (1-, 2-, 3- or 4-) pentenyl and (1-, 2-, 3-, 4- or 5-)hexenyl.

Examples of dihydropyridyl groups include 1,2-dihydropyridyl, 3,4-dihydropyridyl and the like.

Examples of 5- to 7-membered saturated heterocyclic group-substituted sulfonyl groups, the heterocyclic group containing one or two heteroatoms selected from the group consisting of nitrogen, oxygen and sulfur, include pyrrolidinyl-sulfonyl, piperazinylsulfonyl, piperidinylsulfonyl, morpholino-sulfonyl, thiomorpholinosulfonyl, homopiperazinylsulfonyl, homopiperidinylsulfonyl, imidazolidinylsulfonyl, thiazolidinyl-sulfonyl, isothiazolidinylsulfonyl, oxazolidinylsulfonyl, isoxazolidinylsulfonyl, isothiazolidinylsulfonyl, pyrazolidinyl-sulfonyl, etc.

Examples of lower alkoxido groups include straight or branched $C_{1-6}$ alkoxido groups, such as methoxido, ethoxido, etc.

The pyrrolidine compounds represented by General Formula (1) can be produced by various methods, and for example, by a method according to the following Reaction Scheme 1.

[Reaction Scheme 1]

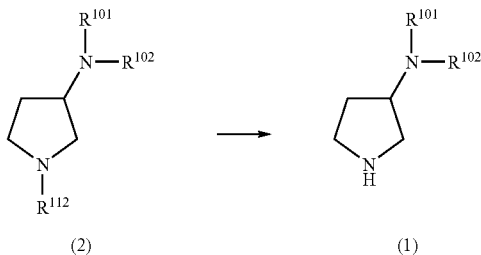

(2)          (1)

wherein $R^{101}$ and $R^{102}$ are as defined above, and $R^{112}$ is an amino-protecting group.

The pyrrolidine compound (1) can be prepared by subjecting a compound (2) to an elimination reaction to remove the amino-protecting group.

Examples of amino-protecting groups usable herein include lower alkoxycarbonyl groups, lower alkanoyl groups, aryloxy carbonyl groups, aryl-substituted lower alkyl groups, etc.

Examples of lower alkoxycarbonyl groups include straight or branched $C_{1-6}$ alkoxycarbonyl groups, such as methoxycarbonyl, ethoxycarbonyl, propoxycarbonyl, butoxycarbonyl, tert-butoxycarbonyl, pentyloxycarbonyl, hexyloxycarbonyl, etc.

Examples of lower alkanoyl groups include straight or branched $C_{1-6}$ alkanoyl groups, such as formyl, acetyl, propionyl, butyryl, isobutyryl, pentanoyl, tert-butylcarbonyl, hexanoyl, etc.

Examples of aryloxycarbonyl groups include phenoxy carbonyl groups optionally substituted with one to three substituents; naphthyloxy carbonyl groups optionally substituted with one to three substituents; etc. Examples of substituents for aryl groups include methyl, ethyl, propyl, n-butyl, sec-butyl, tert-butyl, n-pentyl, n-hexyl, hydroxymethyl, 2-hydroxyethyl, 1-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, 2-methyl-3-hydroxypropyl, trifluoromethyl, trichloromethyl, chloromethyl, bromomethyl, fluoromethyl, iodomethyl, difluoromethyl, dibromomethyl, 2-cloroethyl, 2,2,2-trifluoroethyl, 2,2,2-trichloroethyl, 3-chloropropyl, 2,3-dichloropropyl, 4,4,4-trichlorobutyl, 4-fluorobutyl, 5-chloropentyl, 3-chloro-2-methylpropyl, 5-bromohexyl, 5,6-dichlorohexyl, 3-hydroxy-2-chloropropyl, or like straight or branched $C_{1-6}$ alkyl groups optionally substituted with one to three members selected from the group consisting of halogen atoms and a hydroxyl group; methoxy, ethoxy, propoxy, n-butoxy, sec-butoxy, tert-butoxy, n-pentyloxy, n-hexyloxy, hydroxymethoxy, 2-hydroxyethoxy, 1-hydroxyethoxy, 3-hydroxypropoxy, 2,3-dihydroxypropoxy, 4-hydroxybutoxy, 1,1-dimethyl-2-hydroxyethoxy, 5,5,4-trihydroxypentyloxy, 5-hydroxypentyloxy, 6-hydroxyhexyloxy, 1-hydroxyisopropoxy, 2-methyl-3-hydroxypropoxy, trifluoromethoxy, trichloromethoxy, chloromethoxy, bromomethoxy, fluoromethoxy, iodomethoxy, difluoromethoxy, dibromomethoxy, 2-chloroethoxy, 2,2,2-trifluoroethoxy, 2,2,2-trichloroethoxy, 3-chloropropoxy, 2,3-dichloropropoxy, 4,4,4-trichlorobutoxy, 4-fluorobutoxy, 5-chloropentyloxy, 3-chloro-2-methylpropoxy, 5-bromohexyloxy, 5,6-dichlorohexyloxy, 3-hydroxy-2-chloropropoxy, or like straight or branched $C_{1-6}$ alkoxy groups optionally substituted with one to three members selected from the group consisting of halogen atoms and a hydroxyl group; halogen atoms such as fluorine, bromine, chlorine, and iodine; etc. When two or more substituents are present, the substituents may be the same or different.

Examples of aryl-substituted lower alkyl groups include benzyl, 2-phenylethyl, 1-phenylethyl, 3-phenylpropyl, 4-phenylbutyl, 5-phenylpentyl, 6-phenylhexyl, 1,1-dimethyl-2-phenylethyl, 2-methyl-3-phenylpropyl, α-naphthylmethyl, β-naphthylmethyl, 2-(α-naphthyl)ethyl, 1-(β-naphthyl)ethyl, 3-α-naphthyl)propyl, 4-(β-naphthyl)butyl, 5-(α-naphthyl)pentyl, 6-(β-naphthyl)hexyl, 1,1-dimethyl-2-(α-naphthyl)ethyl, 2-methyl-3-(β-naphthyl)propyl, like phenyl-substituted straight or branched $C_{1-6}$ alkyl groups optionally substituted with one to three substituents; or like naphthyl-substituted straight or branched $C_{1-6}$ alkyl groups optionally substituted with one to three substituents. Examples of substituents for aryl groups include methyl, ethyl, propyl, n-butyl, sec-butyl, tert-butyl, n-pentyl, n-hexyl, hydroxymethyl, 2-hydroxyethyl, 1-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, 2-methyl-3-hydroxypropyl, trifluoromethyl, trichloromethyl, chloromethyl, bromomethyl, fluoromethyl, iodomethyl, difluoromethyl, dibromomethyl, 2-chloroethyl, 2,2,2-trifluoroethyl, 2,2,2-trichloroethyl, 3-chloropropyl, 2,3-dichloropropyl, 4,4,4-trichlorobutyl, 4-fluorobutyl, 5-chloropentyl, 3-chloro-2-methylpropyl, 5-bromohexyl, 5,6-dichlorohexyl, 3-hydroxy-2-chloropropyl, or like straight or branched $C_{1-6}$ alkyl groups optionally substituted with one to three members selected from the group consisting of halogen atoms and a hydroxyl group; methoxy, ethoxy, propoxy, n-butoxy, sec-butoxy, tert-butoxy, n-pentyloxy, n-hexyloxy, hydroxymethoxy, 2-hydroxyethoxy, 1-hydroxyethoxy, 3-hydroxypropoxy, 2,3-dihydroxypropoxy, 4-hydroxybutoxy, 1,1-dimethyl-2-hydroxyethoxy, 5,5,4-trihydroxypentyloxy, 5-hydroxypentyloxy, 6-hydroxyhexyloxy, 1-hydroxyisopropoxy, 2-methyl-3-hydroxypropoxy, trifluoromethoxy, trichloromethoxy, chloromethoxy, bromomethoxy, fluoromethoxy, iodomethoxy, difluoromethoxy, dibromomethoxy, 2-chloroethoxy, 2,2,2-trifluoroethoxy, 2,2,2-trichloroethoxy, 3-chloropropoxy, 2,3-dichloropropoxy, 4,4,4-trichlorobutoxy, 4-fluorobutoxy, 5-chloropentyloxy, 3-chloro-2-methylpropoxy, 5-bromohexyloxy, 5,6-dichlorohexyloxy, 3-hydroxy-2-chloropropoxy, or like straight or branched $C_{1-6}$ alkoxy groups optionally substituted with one to three members selected from the group consisting of halogen atoms and a hydroxyl group; halogen atoms such as fluorine, bromine, chlorine, and iodine; etc. When two or more substituents are present, the substituents may be the same or different.

The reaction for producing compound (1) from compound (2) is carried out in a suitable solvent or without solvent in the presence of an acid or basic compound. This reaction is referred to as "Reaction A" hereinafter.

Examples of useful solvents include water; lower alcohols such as methanol, ethanol, isopropanol and tert-butanol; ketones such as acetone and methyl ethyl ketone; ethers such as diethyl ether, dioxane, tetrahydrofuran, monoglyme and diglyme; aliphatic acids such as acetic acid and formic acid; esters such as methyl acetate and ethyl acetate; halogenated hydrocarbons such as chloroform, dichloromethane, dichloroethane and carbon tetrachloride; amides such as N,N-dimethylformamide, N,N-dimethylacetamide and N-methylpyrrolidone; dimethyl sulfoxide; hexamethylphosphoric triamide; and mixtures of such solvents.

Examples of useful acids include mineral acids such as hydrochloric acid, sulfuric acid and hydrobromic acid; and organic acids such as formic acid, acetic acid, trifluoroacetic acid and p-toluenesulfonic acid.

Examples of useful basic compounds include carbonates such as sodium carbonate, potassium carbonate, sodium hydrogencarbonate and potassium hydrogencarbonate; and metal hydroxides such as sodium hydroxide, potassium hydroxide, calcium hydroxide and lithium hydroxide.

An acid or basic compound is usually used in an amount of at least about 1 mole, and preferably about 1 to about 10 moles, per mole of compound (2). However, an acid may also be used in a large excess relative to compound (2).

The reaction advantageously proceeds usually at about 0 to about 200° C., and preferably at about 0 to about 150° C., and usually finishes in about 10 minutes to about 30 hours.

When $R^{112}$ of compound (2) is an aryl-substituted lower alkyl group, it is also possible to produce compound (1) by the reduction of such compound (2).

The reduction reaction can be carried out, for example, by catalytic hydrogenation in a suitable solvent in the presence of a catalyst.

Examples of useful solvents include water; acetic acid; alcohols such as methanol, ethanol and isopropanol; hydrocarbons such as n-hexane and cyclohexane; ethers such as dioxane, tetrahydrofuran, diethyl ether and ethylene glycol dimethyl ether; esters such as ethyl acetate and methyl acetate; aprotic polar solvents such as dimethylformamide; and mixtures of such solvents.

Examples of useful catalysts include palladium, palladium black, palladium carbon, platinum, platinum oxide, copper chromite, Raney nickel and mixtures thereof. A catalyst is preferably used in an amount of about 0.02 to about 1 times by weight of compound (2).

The reaction temperature for the reduction reaction is usually about −20 to about 100° C., and preferably about 0 to about 80° C., and the hydrogen pressure is usually from 1 to 10 atm. The reaction usually finishes in about 0.5 to about 20 hours.

When $R^{112}$ of compound (2) is an aryl-substituted lower alkyl group, compound (2) can be reacted to form compound (1) by steps of (i) treating compound (2) with a dealkylating agent in a suitable solvent; and (ii) heating the resulting compound in a suitable solvent.

The solvent for use in the reaction of step (i) may be the same as any solvent used for reaction (A).

Examples of useful dealkylating agents include formic esters such as 1-chloroethyl chloroformate, ethyl chloroformate and tert-butyl chloroformate. A dealkylating agent is usually used in an amount of at least about 1 mole of compound (2), and preferably about 1 mole to about 10 moles, per mole of compound (2).

The reaction advantageously proceeds usually at about 0 to about 150° C., and preferably at room temperature to about 100° C., and usually completes in about 1 to about 25 hours.

Examples of solvents for use in step (ii) include alcohols such as methanol, ethanol and isopropanol. Heating is conducted usually at about 0 to about 150° C., and preferably at room temperature to about 100° C. for about 1 to about 10 hours.

The compound of General Formula (2) used as a starting material can be easily produced, for example, by the process shown by Reaction Scheme 2:

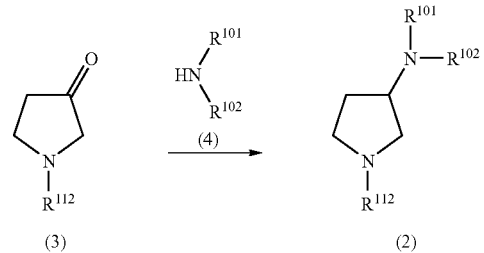

wherein $R^{101}$, $R^{102}$ and $R^{112}$ are the same as above.

The reaction of compound (3) with compound (4) is carried out, for example, without solvent or in a suitable solvent in the presence of a reducing agent.

For the reaction, compound (4) is usually used in an amount of at least about 1 mole per mole of compound (3), and preferably equivalent to a large excess relative to compound (3).

Examples of useful solvents include water; lower alcohols such as methanol, ethanol, isopropanol, butanol, tert-butanol and ethylene glycol; acetonitrile; aliphatic acids such as formic acid and acetic acid; ethers such as diethyl ether, tetrahydrofuran, dioxane, monoglyme and diglyme; aromatic hydrocarbons such as benzene, toluene and xylene; halogenated hydrocarbons such as dichloromethane, dichloroethane and carbon tetrachloride; and mixtures of such solvents.

Examples of reducing agents include aliphatic acids such as formic acid; aliphatic acid alkali metal salts such as sodium formate; hydride reducing agents such as sodium boronhydride, sodium cyanoborohydride, sodium triacetoxyborohydride, aluminium lithium hydride or mixtures of such hydride reducing agents; catalytic hydrogenation reducing agents such as palladium black, palladium carbon, platinum oxide, platinum black and Raney nickel.

When an aliphatic acid or aliphatic acid alkali metal salt is used as a reducing agent, a suitable temperature is usually from room temperature to about 200° C., and preferably from about 50 to about 150° C. The reaction usually completes in about 10 minutes to about 10 hours. The aliphatic acid or aliphatic acid alkali metal salt is preferably used in a large excess relative to compound (3).

When a hydride reducing agent is used as a reducing agent, a suitable reaction temperature is usually from about −80 to about 100° C., and preferably about −80 to about 70° C. The reaction usually finishes in about 30 minutes to about 60 hours. The hydride reducing agent is usually used in an amount of about 1 to about 20 moles per mole of compound (3), and preferably about 1 to about 6 moles per mole of compound (3). Especially when aluminium lithium hydride is used as a hydride reducing agent, it is preferable to use ethers, such as diethyl ether, tetrahydrofuran, dioxane, monoglyme and diglyme, and aromatic hydrocarbons, such as benzene, toluene and xylene, or mixtures of such solvents as solvents. To the reaction system of the reaction may be added amine(s) such as trimethylamine, triethylamine and N-ethyldiisopropyl amine or molecular sieves such as molecular sieves of the type 3A (MS-3A) and molecular sieves of the type 4A (MS-4A).

When a catalytic hydrogenation reducing agent is used as a reducing agent, the reaction is usually carried out at about −30 to about 100° C., and preferably about 0 to about 60° C., in a hydrogen atmosphere of about atmospheric pressure to about 20 atm, and preferably about atmospheric pressure to about 10 atm, or in the presence of a hydrogen donor such as formic acid, ammonium formate, cyclohexene and hydrazine hydrate. The reaction usually finishes in about 1 to about 12 hours. The catalytic hydrogenation reducing agent is usually used in an amount of about 0.1 to about 40 wt %, and preferably about 1 to about 20 wt %, of compound (3).

[Reaction Scheme 3]

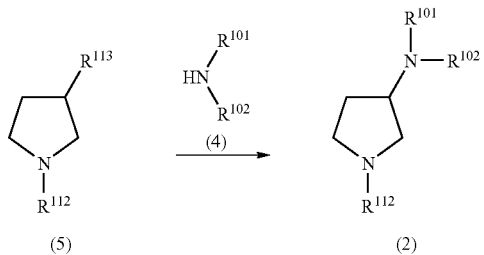

wherein $R^{101}$, $R^{102}$ and $R^{112}$ are the same as above; $R^{113}$ represents a lower alkylsulfonyloxy group, a phenylsulfonyloxy group optionally substituted on the phenyl ring with one or more lower alkyl groups, or a halogen atom.

The lower alkylsulfonyloxy group is a group consisting of a $C_{1-6}$ alkyl group and a sulfonyloxy group, examples of which include methanesulfonyloxy, ethanesulfonyloxy, propanesulfonyloxy, butanesulfonyloxy, pentanesulfonyloxy and hexanesulfonyloxy.

Examples of phenylsulfonyloxy groups optionally substituted on the phenyl ring with one or more lower alkyl groups are benzene sulfonyloxy groups which may be substituted with one to three straight or branched $C_{1-6}$ alkyl groups, such as benzenesulfonyloxy, o-toluenesulfonyloxy, m-toluenesulfonyloxy, p-toluenesulfonyloxy, 2-ethylbenzenesulfonyloxy, 3-ethylbenzenesulfonyloxy, 4-ethylbenzenesulfonyloxy, 2-propylbenzenesulfonyloxy, 3-propylbenzenesulfonyloxy, 4-propylbenzenesulfonyloxy, 2,3-dimethylbenzenesulfonyloxy, 2,4-dimethylbenzenesulfonyloxy and 2,4,6-trimethylbenzenesulfonyloxy.

Examples of halogen atoms include fluorine, bromine, chlorine and iodine atoms.

The reaction of compound (4) with compound (5) is carried out in a suitable solvent in the presence of a basic compound.

Examples of useful inert solvents include water; aromatic hydrocarbons such as benzene, toluene and xylene; ethers such as diethyl ether, tetrahydrofuran, dioxane, 2-methoxyethanol, monoglyme and diglyme; halogenated hydrocarbons such as dichloromethane, dichloroethane, chloroform and carbon tetrachloride; lower alcohols such as methanol, ethanol, isopropanol, butanol, tert-butanol and ethylene glycol; aliphatic acids such as acetic acid; esters such as ethyl acetate and methyl acetate; ketones such as acetone and methyl ethyl ketone; acetonitrile, pyridine, N-methylpyrrolidone, dimethylsulfoxide, N,N-dimethylformamide and hexamethyl phosphoramide; and mixtures of such solvents.

Examples of basic compounds include carbonates such as sodium carbonate, potassium carbonate, sodium hydrogencarbonate, potassium hydrogencarbonate and cesium carbonate; alkali metal hydroxides such as sodium hydroxide, potassium hydroxide and calcium hydroxide; phosphates such as potassium phosphate and sodium phosphate; alkali metal hydrides such as sodium hydride and potassium hydride; alkali metals such as potassium and sodium; sodium amide; metal alcoholates such as sodium methylate, sodium ethylate and sodium n-butoxide, sodium tert-butoxide and potassium tert-butoxide; organic bases such as pyridine, imidazole, N-ethyldiisopropylamine, dimethylaminopyridine, triethylamine, trimethylamine, dimethylaniline, N-methylmorpholine, 1,5-diazabicyclo[4.3.0]nonene-5 (DBN), 1,8-diazabicyclo[5.4.0]undecene-7 (DBU) and 1,4-diazabicyclo[2.2.2]octane (DABCO); and mixtures of such basic compounds.

Compound (5) is usually used in an amount of at least about 0.1 mole per mole of compound (4), and preferably about 0.1 to about 10 moles per mole of compound (4).

A basic compound is usually used in an amount of at least about 1 mole per mole of compound (4), and preferably about 1 to about 10 moles per mole of compound (4).

For the reaction, compound (4) may be used in a large excess instead of adding a basic compound.

Alkali metal halogen compound(s), such as sodium iodide and potassium iodide, may be added to the reaction system of the reaction.

The reaction is usually carried out at about 0 to about 200° C., and preferably about 0 to about 150° C., and usually completes in about 5 minutes to about 80 hours.

Reaction Scheme 4

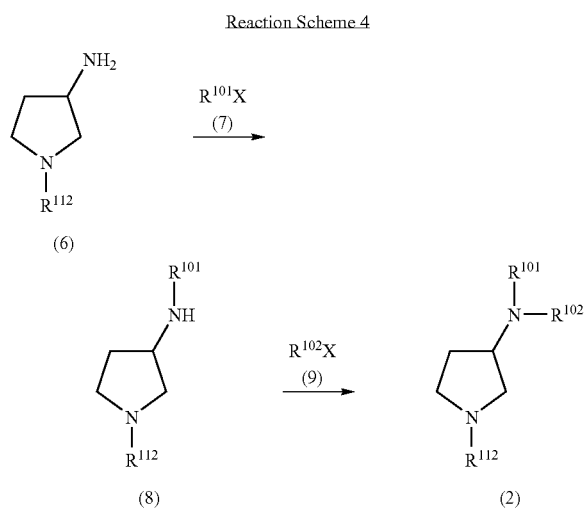

wherein $R^{101}$, $R^{102}$ and $R^{112}$ are the same as above, and X represents a halogen atom.

The reaction between compounds (6) and (7) and the reaction between compounds (8) and (9) are carried out under the same conditions as in the reaction between compounds (5) and (4) shown by Reaction Scheme 3.

When $R^{101}$ or $R^{102}$ of compound (6) represents any of the groups shown by (1) to (14), (17) to (32) and (40) to (50), the reaction between compound (6) and compound (7) is carried out in a suitable solvent in the presence of a basic compound and catalyst. Similarly, when $R^{101}$ or $R^{102}$ of compound (8) represents any of the groups shown by (1) to (14), (17) to (32) and (40) to (50), the reaction between compound (8) and compound (9) is carried out in a suitable solvent in the presence of a basic compound and catalyst.

The solvent and basic compound for use in the reaction may each be the same as those used for the reaction between compounds (5) and (4) shown by Reaction Scheme 3.

Examples of catalysts include palladium compounds such as palladium acetate, bis(tributyl tin)/bis(dibenzylideneacetone)palladium, copper iodide/2,2'-bipyridyl, bis(dibenzylideneacetone)palladium, tris (dibenzylideneacetone)dipalladium, [1,1-bis(diphenyl phosphino)ferrocene] dichloropalladium(II) and tetrakis(triphenyl phosphine) palladium; binaphthyl compounds such as R-2,2'-bis(diphenylphosphino)-1,1'-binaphthyl(R-BINAP), S-2,2'-bis(diphenylphosphino)-1,1'-binaphthyl(S-BINAP), and RAC-2,2'-bis(diphenylphosphino)-1,1'-binaphthyl(RAC-BINAP); xanthene compounds such as 4,5-bis(diphenylphosphino)-9,9-dimethylxanthene; borates such as tri-tert-butylphosphine tetrafluoroborate; 2,2-bis(diphenyl imidazolidinylidene); and mixtures thereof.

A basic compound is usually used in an amount of at least about 0.5 mole per mole of compound (6) or (8), and preferably about 0.5 to about 40 moles per mole of compound (6) or (8).

A catalyst may be used in a usual catalytic amount for compound (6) or (8).

Compounds (7) and (9) are usually used in amounts of at least about 0.5 mole per mole of compounds (6) and (8), respectively, and preferably about 0.5 to about 3 moles per mole of compounds (6) and (8).

These reactions advantageously proceed usually at room temperature to about 200° C., and preferably at room temperature to about 150° C., and usually complete in about 0.5 to about 20 hours.

When $R^{101}$ or $R^{102}$ of compound (6) represents any of the groups shown by (1) to (14), (17) to (32) and (40) to (50), the reaction between compound (6) and compound (7) is carried out in a suitable solvent in the presence of a basic compound, copper iodide and ethylene glycol. Similarly, when $R^{101}$ or $R^{102}$ of compound (8) represents any of the groups shown by (1) to (14), (17) to (32) and (40) to (50), the reaction between compound (8) and compound (9) is carried out in a suitable solvent in the presence of a basic compound, copper iodide and ethylene glycol.

The solvent and basic compound for use in the reaction may each be the same as those used for the reaction between compounds (5) and (4) shown by Reaction Scheme 3.

Copper iodide and ethylene glycol may each be used usually in an amount of about 0.01 to 3 moles, and preferably about 0.05 to about 1 mole, per mole of compound (6) or (7).

Compounds (7) and (9) are usually used in amounts of at least about 1 mole per mole of compounds (6) and (8), respectively, and preferably about 1 to about 2 moles per mole of compounds (6) and (8).

These reactions advantageously proceed usually at room temperature to about 200° C., and preferably at room temperature to about 150° C., and usually completes in about 0.5 to about 50 hours.

When $R^{101}$ or $R^{102}$ of compound (6) represents any of the groups shown by (1) to (14), (17) to (32) and (40) to (50), the reaction between compound (6) and compound (7) is carried out in a suitable solvent in the presence of a silane compound such as sodium bis(trimethylsilyl)amide. Similarly, when $R^{101}$ or $R^{102}$ of compound (8) represents any of the groups shown by (1) to (14), (17) to (32) and (40) to (50), the reaction between compound (8) and compound (9) is carried out in a suitable solvent in the presence of a silane compound such as sodium bis(trimethylsilyl)amide.

The solvent for use in the reaction may be the same as that used for the reaction between compounds (5) and (4) shown by Reaction Scheme 3.

A silane compound is usually used in an amount of about 0.1 to about 3 moles, and preferably about 0.1 to about 2 moles, per mole of compound (6) or (7).

Compounds (7) and (9) are usually used in amounts of at least about 1 mole per mole of compounds (6) and (8), respectively, and preferably about 1 to about 2 moles per mole of compounds (6) and (8).

These reactions advantageously proceed usually at about 0 to about 200° C., and preferably at about 0 to about 150° C., and usually finishes in about 0.5 to about 20 hours.

Depending on the kind of compound (7) used, the reaction of compound (6) and compound (7) produces, instead of compound (8), compound (10) shown below:

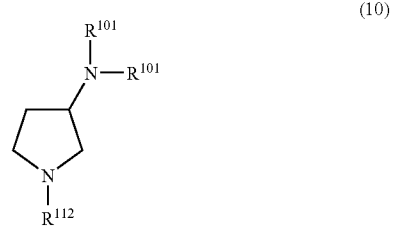

wherein $R^{101}$ and $R^{112}$ are the same as above.

[Reaction Scheme 5]

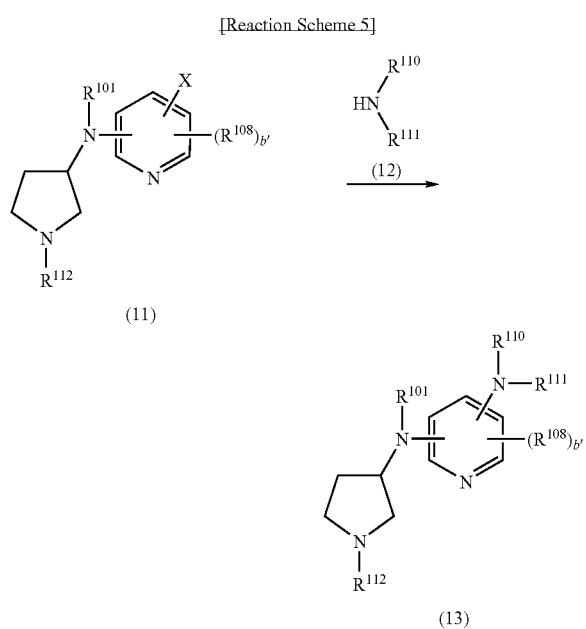

wherein $R^{101}$ and X are the same as above, $R^{108}$ represents any of the groups shown by (1-1) to (1-37) as defined in General Formula (1), $R^{110}$ and $R^{111}$ are linked together to form, together with the nitrogen atom to which they are bound, 5 to 7-membered one nitrogen atom-containing saturated heterocyclic groups which may have one heteroatom selected from the group consisting of nitrogen, oxygen and sulfur, the heterocyclic group optionally being substituted with one to three substituents selected from the group consisting of oxo group; lower alkyl groups; lower alkanoyl groups; phenyl lower alkyl groups; phenyl groups optionally substituted on the phenyl ring with one to three members selected from the group consisting of halogen atoms and lower alkoxy groups; and pyridyl groups, and b' represents an integer from 0 to 3.

Examples of 5- to 7-membered one nitrogen atom-containing saturated heterocyclic groups which may have one heteroatom selected from the group consisting of nitrogen, oxygen and sulfur include pyrrolidinyl, piperazinyl, piperidinyl, morpholino, thiomorpholino, homopiperazinyl, homopiperidinyl, imidazolidinyl, thiazolidinyl, isothiazolidinyl, oxazolidinyl, isoxazolidinyl, isothiazolidinyl and pyrazolidinyl.

Examples of the above-mentioned heterocyclic groups substituted with one to three members selected from the group consisting of oxo group; lower alkyl groups; lower alkanoyl groups; phenyl lower alkyl groups; phenyl groups optionally substituted on the phenyl ring with one to three members selected from the group consisting of halogen atoms and lower alkoxy groups; and pyridyl groups:

include the above-mentioned heterocyclic groups substituted with one to three members selected from the group consisting of oxo groups; straight or branched $C_{1-6}$ alkyl groups; straight or branched $C_{1-6}$ alkanoyl groups; phenyl alkyl groups wherein the alkyl moiety is a straight or branched $C_{1-6}$ alkyl group; phenyl groups optionally substituted on the phenyl ring with one to three members selected from the group consisting of halogen atoms and straight or branched $C_{1-6}$ alkoxy groups; and pyridyl groups;

such as 2-oxo-(1-, 3-, 4-, or 5-)pyrrolidinyl, 2-oxo-(1-, 3-, 4-, 5-, or 6-)piperidinyl, 4-methyl-(1-, 2-, or 3-)piperazinyl, 4-acetyl-(1-, 2-, or 3-)piperazinyl, 4-ethyl-(1-, 2-, or 3-)piperazinyl, 2-methyl-(1-, 2-, 3-, 4-, or 5-)pyrrolidinyl, 2-methyl-(1-, 2-, 3-, 4-, 5-, or 6-)piperidinyl, 2,4-dimethyl-(1-, 2-, 3-, 5-, or 6-)piperidinyl, 3-methyl-(1-, 2-, 3-, 4-, or 5-)pyrrolidinyl, 2,3,4-trimethyl-(1-, 2-, 3-, 5-, or 6-)piperazinyl, 4-acetyl-3-methyl-(1-, 2-, 3-, 5-, or 6-)piperazinyl, 3-methyl-(2-, 3-, 4-, 5-, or 6-)morpholino, 2-acetyl-(2-, 3-, 4-, 5-, or 6-)morpholino, 4-(2-phenylethyl)-(1-, 2-, or 3-)piperazinyl, 4-(3,4-dichlorophenyl)-(1-, 2-, 3-, or 4-)piperazinyl, 4-(4-methoxyphenyl)-(1-, 2-, or 3-)piperazinyl, 4-(2-chlorophenyl)-(1-, 2-, or 3-)piperazinyl, 4-[(2-, 3-, or 4-) pyridyl]-(1-, 2-, or 3-)piperazinyl, 4-phenyl-(1-, 2-, or 3-)piperazinyl, 4-benzyl-(1-, 2-, or 3-)piperidinyl, 4-(3,4-dichlorophenyl)-(1-, 2-, or 3-)morpholino, 2-(4-methoxyphenyl)-(1-, 2-, 3-, 4-, or 5-)pyrrolidinyl, 4-(2-chlorophenyl)-(1-, 2-, or 3-)piperidinyl, 4-[(2-, 3-, or 4-) pyridyl]-(1-, 2-, or 3-)piperidinyl, 4-phenyl-(1-, 2-, or 3-) piperidinyl, 4-phenyl-3-methyl-(1-, 2-, 3-, 5-, or 6-) piperidinyl, 4-[(2-, 3-, or 4-)pyridyl]-2-acetyl-(1-, 2-, 3-, 5-, or 6-)piperazinyl, etc.

The reaction between compound (11) and compound (12) is carried out under the same conditions as in the reaction between compounds (6) and (7) shown by Reaction Scheme 4.

[Reaction Scheme 6]

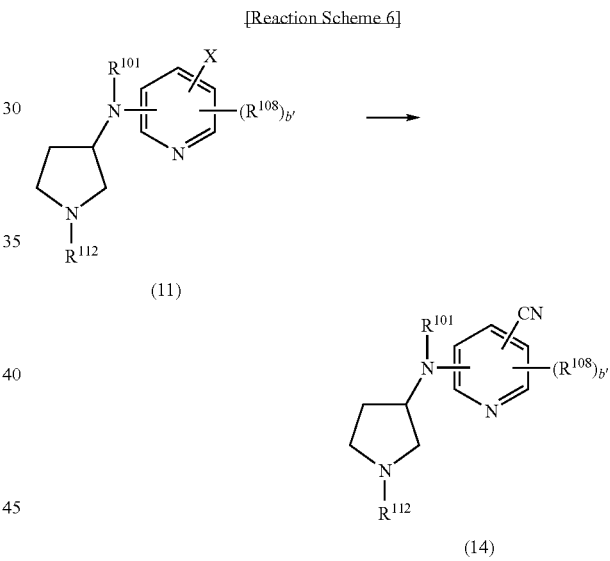

wherein $R^{101}$, $R^{108}$, b' and X are the same as above.

Compound (14) is produced by reacting compound (11) with a metal cyanide compound in a suitable solvent in the presence of a catalyst.

Examples of metal cyanide compounds include sodium cyanide, potassium cyanide, zinc cyanide, copper cyanide, etc.

The solvent and catalyst for use in the reaction may each be the same as those used for the reaction between compounds (6) and (7) shown by Reaction Scheme 4. The catalyst may be used in a usual catalytic amount for compound (11).

The metal cyanide compound is usually used in an amount of at least about 1 mole per mole of compound (11), and preferably about 1 to about 3 moles per mole of compound (11).

The reaction advantageously proceeds usually at room temperature to about 200° C., and preferably at room temperature to about 150° C., and usually completes in about 0.5 to about 20 hours.

[Reaction Scheme 7]

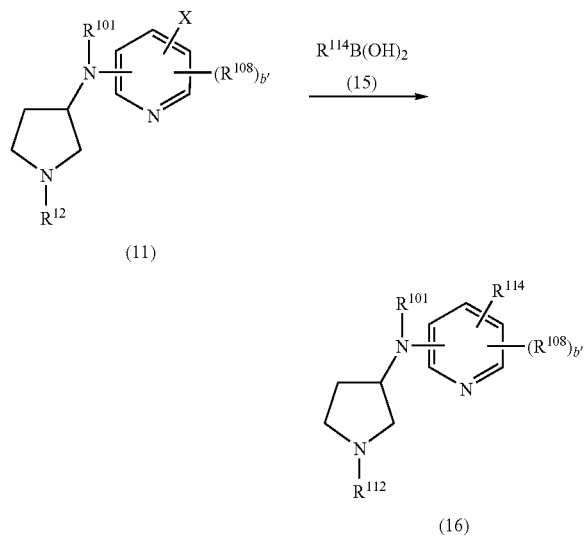

wherein $R^{101}$, $R^{108}$, b' and X are the same as above, and $R^{114}$ represents any of the groups shown by (1-3), (1-12), (1-14), (1-19), (1-23), (1-30), and (1-31) in General Formula (1).

The reaction between compound (11) and compound (15) is carried out under the same conditions as in the reaction between compounds (6) and (7) shown by Reaction Scheme 4.

[Reaction Scheme 8]

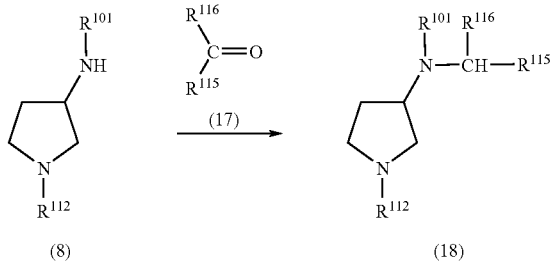

wherein $R^{101}$ and $R^{112}$ are the same as above; $R^{115}$ represents a phenyl group, phenyl lower alkyl group, cycloalkyl group, cycloalkyl lower alkyl group, lower alkylthio lower alkyl group, amino-substituted lower alkyl group optionally substituted on the amino group with one or two lower alkyl groups, phenoxy lower alkyl group, or pyridyl lower alkyl group; and $R^{116}$ represents a hydrogen atom or lower alkyl group. $R^{115}$ and $R^{116}$ may alternatively be linked together to form a cycloalkyl group, provided that the total number of carbon atoms of the portion $CH(R^{116})(R^{115})$ in the side chain —$(R^{101})CH(R^{116})(R^{115})$ of compound (18) does not exceed 6.

The reaction between compound (8) and compound (17) is carried out under the same conditions as in the reaction between compounds (3) and (4) shown by Reaction Scheme 2, except for using compound (17) usually in an amount of at least 1 mole per mole of compound (8), and preferably 1 to 5 moles per mole of compound (8).

[Reaction Scheme 9]

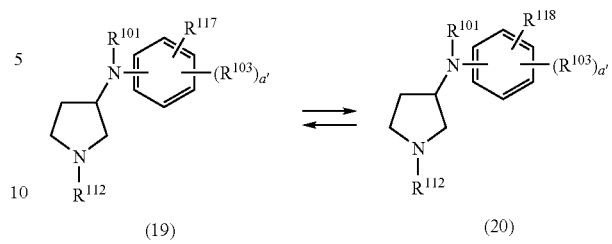

wherein $R^{101}$, and $R^{112}$ are the same as above; a' represents an integer from 0 to 4; $R^{103}$ represents any of the groups shown by (1-1) to (1-37) as defined in General Formula (1), $R^{117}$ represents a lower alkoxycarbonyl group; and $R^{118}$ represents a carboxy group.

Compound (20) is produced by the hydrolysis of compound (19).

The hydrolysis of compound (19) is carried out in a suitable solvent or without solvent in the presence of an acid or basic compound.

Examples of useful solvents include water; lower alcohols such as methanol, ethanol, isopropanol and tert-butanol; ketones such as acetone and methyl ethyl ketone; ethers such as diethyl ether, dioxane, tetrahydrofuran, monoglyme and diglyme; aliphatic acids such as acetic acid and formic acid; esters such as methyl acetate and ethyl acetate; halogenated hydrocarbons such as chloroform, dichloromethane, dichloroethane and carbon tetrachloride; dimethylsulfoxide, N,N-dimethylformamide, and hexamethylphosphortriamide; and mixtures of such solvents.

Examples of acids include mineral acids such as hydrochloric acid, sulfuric acid and hydrobromic acid; and organic acids such as formic acid, acetic acid and sulfonic acids such as trifluoroacetic acid and p-toluenesulfonic acid. Such acids may be used singly or in combination.

Examples of basic compounds include carbonates such as sodium carbonate, potassium carbonate, sodium hydrogencarbonate and potassium hydrogencarbonate; alkali metal hydroxides such as sodium hydroxide, potassium hydroxide and lithium hydroxide; alkaline earth metal hydroxides such as calcium hydroxide; and other like basic compounds. Such basic compounds may be used singly or in combination.

The hydrolysis reaction advantageously proceeds usually at about 0 to about 200° C., preferably about 0 to about 150° C., and usually finishes in about 10 minutes to about 30 hours.

Compound (19) is produced by reacting compound (20) with the compound shown by General Formula (21):

$$R^{119}OH \qquad (21)$$

wherein $R^{119}$ represents a lower alkyl group.

Conditions usually selected for esterification reactions are applicable to the reaction between compounds (20) and (21). For example, the reaction between compounds (20) and (21) can be carried out in the presence of a mineral acid such as hydrochloric acid and sulfuric acid; or a halogenating agent such as thionyl chloride, phosphorus oxychloride, phosphorus pentachloride and phosphorus trichloride. Compound (21) is used in a large excess relative to compound (20). The reaction advantageously proceeds usually at about 0 to about 150° C., and preferably about 50 to about 100° C., and usually completes in about 1 to about 10 hours.

[Reaction Scheme 10]

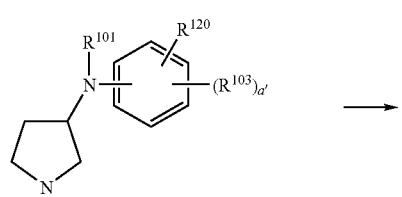

(22)

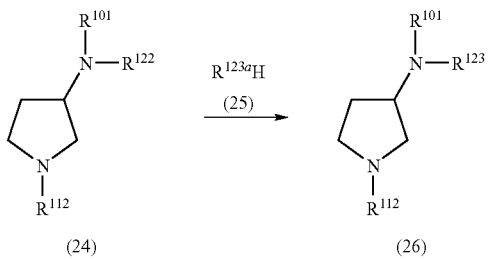

(23)

wherein $R^{101}$, $R^{103}$, a' and $R^{112}$ are the same as above; $R^{120}$ represents a lower alkylthio group; and $R^{121}$ represents a lower alkylsulfonyl group.

The reaction for producing compound (23) from compound (22) is carried out in a suitable solvent in the presence of an oxidizing agent.

Examples of useful solvents include water; aliphatic acids such as formic acid, acetic acid and trifluoroacetic acid; alcohols such as methanol and ethanol; halogenated hydrocarbons such as chloroform and dichloromethane; and mixtures of such solvents.

Examples of useful oxidizing agents include peracids such as performic acid, peracetic acid, pertrifluoroacetic acid, peroxybenzoic acids, m-chloroperoxybenzoic acid and o-carboxyperoxybenzoic acid; hydrogen peroxide; sodium metaperiodate; dichromates such as dichromic acid, sodium dichromate and potassium dichromate; permanganates such as permanganic acid, sodium permanganate and potassium permanganate; lead salts such as lead tetraacetate.

An oxidizing agent is usually used in an amount of at least about 2 moles per mole of compound (22), and preferably about 2 to 4 moles per mole of compound (22).

The reaction is usually carried out at about −10 to about 150° C., preferably at about −10 to about 100° C., and usually finishes in about 1 to about 10 hours.

[Reaction Scheme 11]

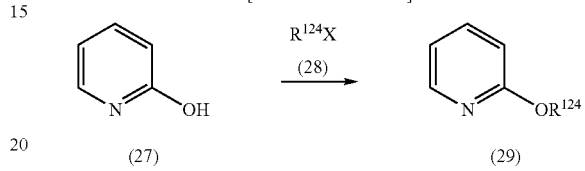

wherein $R^{101}$ and $R^{112}$ are the same as above; $R^{122}$ represents a lower alkyl group having one or more halogen atoms; $R^{123}$ represents an amino-substituted lower alkyl group optionally substituted on the amino group with one or two lower alkyl groups; and $R^{123a}$ represents an amino group optionally substituted on the amino group with one or two lower alkyl groups.

The reaction between compound (24) and compound (25) is carried out under the same conditions as in the reaction between compounds (5) and (4) shown by Reaction Scheme 3.

Compounds (7) and (9) used as starting materials can be easily produced, for example, by the process shown in Reaction Scheme below:

[Reaction Scheme 12]

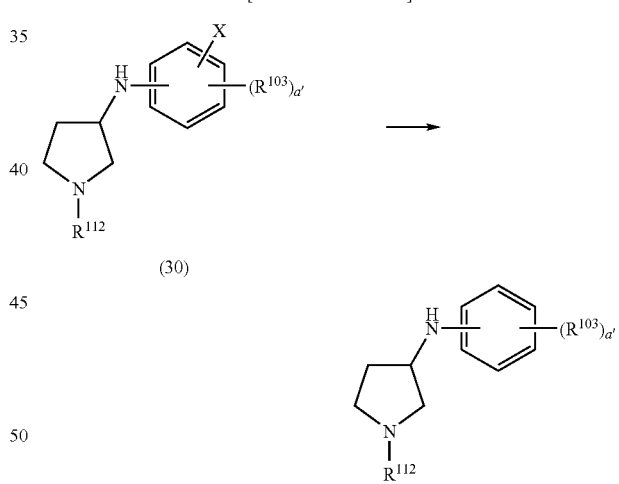

wherein X is the same as above, and $R^{124}$ represents a lower alkyl group having one or more halogen atoms.

The reaction between compound (27) and compound (28) is carried out under the same conditions as in the reaction between compounds (5) and (4) shown by Reaction Scheme 3.

Compound (8) as a starting material can be produced, for example, by the process shown by Reaction Scheme 13 below:

[Reaction Scheme 13]

wherein $R^{103}$, a', X and $R^{112}$ are the same as above.

The reaction for producing compound (31) from compound (30) is carried out, for example, without solvent or in a suitable solvent in the presence of a reducing agent.

Examples of useful solvents include water; lower alcohols such as methanol, ethanol, isopropanol, butanol, tert-butanol and ethylene glycol; acetonitrile; aliphatic acids such as formic acid and acetic acid; ethers such as diethyl ether, tetrahydrofuran, dioxane, monoglyme and diglyme; aromatic hydrocarbons such as benzene, toluene and xylene; halogenated hydrocarbons such as dichloromethane, dichloroethane, chloroform and carbon tetrachloride; and mixtures of such solvents.

Examples of a reducing agent include catalytic hydrogenation reducing agents such as palladium black, palladium carbon, platinum oxide, platinum black and Raney nickel, and the like.

A catalytic hydrogenation reducing agent is usually used in an amount of about 0.1 to 40 wt %, and preferably about 0.1 to about 20 wt %, of compound (30).

The reaction advantageously proceeds by adding basic compound(s) such as sodium hydroxide to the reaction system of the reaction.

The reaction is usually carried out at about −30 to about 100° C., and preferably at about 0 to about 60° C., in a hydrogen atmosphere of atmospheric pressure to about 20 atm, and preferably atmospheric pressure to about 10 atm. The reaction usually finishes in about 1 to about 12 hours.

Compounds (3), (5) and (6) used as starting materials can be easily produced by, for example, Reaction Scheme shown below:

[Reaction Scheme 14]

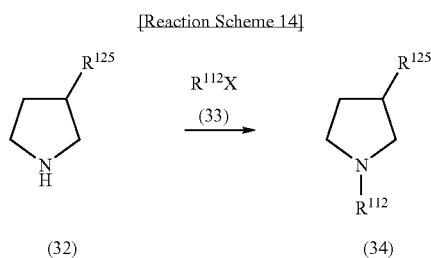

wherein $R^{112}$ and X are the same as above, and $R^{125}$ represents an oxo group, a group represented by $R^{113}$, or an amino group, $R^{113}$ being the same as above.

The reaction between compounds (32) and (33) is carried out under the same conditions as in the reaction between compounds (5) and (4) shown by Reaction Scheme 3 above.

Compound (4) used as a starting material is easily produced, for example, by the process shown by Reaction Scheme below:

[Reaction Scheme 15]

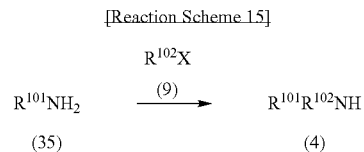

wherein $R^{101}$, $R^{102}$ and X are the same as the above.

The reaction of compound (35) with compound (9) is carried under the same conditions as described in connection with the reaction of compound (6) with compound (7) shown in Reaction Scheme 4.

Compounds (2), (8), (13), (14), (16), (18), (19), (20), (23) and (26) each of whose $R^{112}$ is a hydrogen atom, can be produced by replacing $R^{112}$ with a hydrogen atom in compounds (3), (5), (6), (8), (11), (19), (20), (22) and (24), which are used as starting materials in each reaction shown by Reaction Schemes 2-11, using the thus-obtained compound as a starting material, and reacting the starting material under the same conditions as in the reactions shown by Reaction Schemes 2-11.

If an optically active substance is used as a starting material (compounds (5), (6), (8), (11), (19), (20), (22) and (24)) in the reactions shown by Reaction Schemes 3-11, optically active compounds (2), (8), (13), (14), (16), (18), (19), (20), (23) and (26) can be produced by reacting the compound under the same conditions as in the reaction shown by Reaction Schemes 3-11.

It is also possible to produce compound (1) of the present invention by using compound (2), (8), (13), (14), (16), (18), (19), (20), (23) or (26) produced in the reactions of Reaction Schemes 2-11 as a starting material in the reaction of Reaction Scheme 1 without isolating it.

Each of the objective compounds obtained according to such an above reaction scheme can be isolated and purified from the reaction mixture by, for example, after cooling the reaction mixture, performing an isolation procedure such as filtration, concentration, extraction, etc., to separate a crude reaction product, and then subjecting the crude reaction product to a standard purification procedure such as column chromatography, recrystallization, etc.

The compound of General Formula (1) according to the present invention includes stereoisomers and optical isomers thereof.

Among the starting compounds and object pyrrolidine compound of the present invention, those having a basic group or groups may be suitable to form salts with common pharmaceutically acceptable acids. Examples of such acids include hydrochloric acid, hydrobromic acid, nitric acid, sulfuric acid, phosphoric acid and other inorganic acids; methansulfonic acid, p-toluenesulfonic acid, acetic acid, citric acid, tartaric acid, maleic acid, fumaric acid, malic acid, lactic acid and other organic acids, etc.

Among the starting compounds and object pyrrolidine compound of the present invention, those having an acidic group or groups may be suitable to form salts with common pharmaceutically acceptable basic compounds. Examples of such basic compounds include sodium hydroxide, potassium hydroxide, calcium hydroxide, sodium carbonate, potassium carbonate, sodium hydrogencarbonate, potassium hydrogencarbonate, etc.

In addition, compounds in the form in which solvate (for example, hydrate, ethanolate, etc.) was added to the starting compounds and object compound shown in each of the reaction formulae are included in each of the general formaulae.

Pharmaceutical preparations containing the compound of the present invention as an active ingredient are explained below.

Such pharmaceutical preparations are obtained by formulating the compound of the present invention into standard pharmaceutical preparations, using typically employed diluents and/or excipients such as fillers, extenders, binders, wetting agents, disintegrants, surfactants, lubricants, etc.

The form of such pharmaceutical preparations can be selected from various forms according to the purpose of therapy. Typical examples include tablets, pills, powders, solutions, suspensions, emulsions, granules, capsules, suppositories, injections (solutions, suspensions, etc.) and the like.

To form tablets, any of various known carriers can be used, including, for example, lactose, white sugar, sodium chloride, glucose, urea, starch, calcium carbonate, kaolin, crystalline cellulose and other excipients; water, ethanol, propanol, simple syrup, glucose solutions, starch solutions, gelatin solutions, carboxymethylcellulose, shellac, methylcellulose, potassium phosphate, polyvinylpyrrolidone and other binders; dry starch, sodium alginate, agar powder, laminaran powder, sodium hydrogencarbonate, calcium carbonate, fatty acid esters of polyoxyethylenesorbitan, sodium laurylsulfate, stearic acid monoglycerides, starch, lactose and other disintegrants; white sugar, stearin, cacao butter, hydrogenated oils and other disintegration inhibitors; quaternary ammonium bases, sodium lauryl sulfate and other absorption promoters; glycerol, starch and other wetting agents; starch, lactose, kaolin, bentonite, colloidal silicic acid and other adsorbents; purified talc, stearates, boric acid powder, polyethylene glycol and other lubricants; etc.

Such tablets may be coated with typical coating materials as required, to prepare, for example, sugar-coated tablets, gelatin-coated tablets, enteric-coated tablets, film-coated tablets, double- or multi-layered tablets, etc.

To form pills, any of various known carriers can be used, including, for example, glucose, lactose, starch, cacao butter, hydrogenated vegetable oils, kaolin, talc and other excipients; gum arabic powder, tragacanth powder, gelatin, ethanol and other binders; laminaran, agar and other disintegrants; etc.

To form suppositories, any of various known carriers can be used, including, for example, polyethylene glycol, cacao butter, higher alcohols, esters of higher alcohols, gelatin, semisynthetic glycerides, etc.

To form an injection, a solution, emulsion or suspension is sterilized and preferably made isotonic to blood. Any of various known widely used diluents can be employed to prepare the solution, emulsion or suspension. Examples of such diluents include water, ethanol, propylene glycol, ethoxylated isostearyl alcohol, polyoxylated isostearyl alcohol, fatty acid esters of polyoxyethylene sorbitan, etc. In this case, the pharmaceutical preparation may contain sodium chloride, glucose or glycerol in an amount sufficient to prepare an isotonic solution, and may contain typical solubilizers, buffers, analgesic agents, etc., and further, if necessary, coloring agents, preservatives, flavors, sweetening agents, etc., and/or other medicines.

The proportion of the compound of the present invention in the pharmaceutical preparation is not limited and can be suitably selected from a wide range. It is usually preferable that the pharmaceutical preparation contain the compound of the present invention in a proportion of 1 to 70 wt. %.

The route of administration of the pharmaceutical preparation of the present invention is not limited, and the preparation is administered by a route suitable to the form of the preparation, patient's age and sex, status of the disease, and other conditions. For example, tablets, pills, solutions, suspensions, emulsions, granules and capsules are administered orally. Injections are intravenously administered singly or as mixed with typical injection transfusions such as glucose solutions, amino acid solutions or the like, or singly administered intramuscularly, intracutaneously, subcutaneously or intraperitoneally, as required. Suppositories are administered intrarectally.

The dosage of the pharmaceutical preparation is suitably selected according to the method of use, patient's age and sex, severity of the disease, and other conditions, and is usually about 0.001 to about 100 mg/kg body weight/day, and preferably 0.001 to 50 mg/kg body weight/day, in single or divided doses.

Since the dosage varies depending on various conditions, a dosage smaller than the above range may be sufficient or a dosage larger than the above range may be required.

Effect of the Invention

The pyrrolidine compound of the present invention has an effect of inhibiting reuptake of one, two, or three kinds of monoamines (i.e., serotonin, norepinephrine, dopamine).

The pyrrolidine compound of the present invention exhibits significantly stronger uptake inhibitory activity to one of these three monoamines than known compounds having uptake inhibitory activity to monoamines in vitro or ex vivo experiments. In the microdialysis study, the pyrrolidine compound of the present invention also exhibits significantly stronger effects for increasing one of these three monoamines in the rat brain than known compounds having uptake inhibitory activity to monoamines.

The pyrrolidine compound of the present invention has wider spectrum for the medical treatment than known antidepressants.

The pyrrolidine compound of the present invention exhibits sufficient therapeutic effects even after short-term administration.

The pyrrolidine compound of the present invention has excellent bioavailability, little metabolic enzyme inhibitive activity in the liver, little side effects, and is very safe.

The pyrrolidine compound of the present invention exhibits strong activity in a mouse forced-swimming test/tail suspension test, which is used for screening for antidepressants. The pyrrolidine compound of the present invention also exhibits strong activity in the rat forced-swimming test, which is used for screening for antidepressants. The pyrrolidine compound of the present invention also exhibits strong activity in the reserpine-induced hypothermia model, which is used for screening for antidepressants The pyrrolidine compound of the present invention also exhibits strong activity in the mouse marble-burying behavior test, and a conditioned fear stress model, which are a anxiety- or stress-related disease models.

The pyrrolidine compound of the present invention has an effect of inhibiting reuptake of one, two, or three kinds of monoamines (i.e., serotonin, norepinephrine, dopamine), and therefore is effective for treating various disorders caused by reduced neurotransmission of serotonin, norepinephrine or dopamine.

Examples of such diseases include hypertension, depressions (e.g., major depression, bipolar 1 disorder, bipolar 2 disorder, mixed episode, dysthymic disorders, rapid cycler, atypical depression, seasonal affective disorders, postpartum depression, minor depression, recurrent brief depressive disorder, intractable depression/chronic depression, double depression, alcohol-induced mood disorders, mixed anxiety & depressive disorders; depressions induced by various physical disorders such as Cushing's disease, hypothyroidism, hyperparathyroidism syndrome, Addison's disease, amenorrhea and lactation syndrome, Parkinson's disease, Alzheimer's disease, intracerebral bleeding, diabetes, chronic fatigue syndrome and cancers; depression of the middle-aged, senile depression, depression of children and adolescents, depression induced by medicines such as interferons), depression induced by adjustment disorder, anxiety induced by adjustment disorder, anxiety induced by various physical disorders (e.g neuropathy (head trauma, brain infection, inner ear injury), cardiovascular disturbance (cardiac arrest, abnormal cardiac rhythm), endocrine disorder (adrenal hyperfunctio, cachexia exophthalmica), breathing problem (asthma, chronic obstructive pulmonary disease)), generalized anxiety disorders, fears (e.g., agoraphobia, social phobia, and simple phobias), posttraumatic stress syndrome, acute stress syndrome, avoidant personality disorders, body dysmorphic disorde, precocious ejaculation, eating disorders (e.g., anorexia nervosa and bulimia nervosa), obesity, chemical dependencies (e.g., to alcohol, cocaine, heroin, phenobarbital, nicotine, and benzodiazepines), cluster headache, migraine, pain disorder, Alzheimer's disease, obsessive-compulsive disorders, panic disorders, memory disorders (e.g., dementia, amnestic disorder, and age-related cognitive decline (ARCD)), Parkinson's disease (e.g., dementia caused by Parkinson's disease, neuroleptic agent induced Parkinson's syndrome, tardive dyskinesia), endocrine disorders (e.g., hyperprolactinaemia), vascular spasm (in particular, in the blood circulatory system in the cerebrum), cerebellar ataxia, gastrointestinal tract disorders (including change in movement and secretion), negative syndrome of schizophrenia, premenstrual syndrome, fibromyalgia syndrome, stress incontinence, Tourette's syndrome, trichotillomania, kleptomania, male impotence, attention deficit hyperactivity disorder (ADHD), chronic paroxysmal hemicrania, chronic fatigue, cataplexy, sleep apnea syndrome and headache (related to angiopathy).

BEST MODE FOR CARRYING OUT THE INVENTION

Preparation Example, Reference Examples, Examples, and Pharmacological Test Examples are explained below.

Preparation Example 1

The compound of the present invention (100 g), 40 g of Avicel (trade name, manufactured by Asahi Kasei Corporation), 30 g of cornstarch, and 2 g of magnesium stearate were mixed, ground, and then subjected to tableting using a punch of 10.0 mm in diameter for sugar-coating tablets. The thus-obtained tablets were coated using a film-coating agent comprising 10 g of TC-5 (trade name, Shin-Etsu Chemical Co., Ltd., hydroxypropyl methylcellulose), 3 g of polyethylene glucol 6000, 40 g of castor oil, and a suitable amount of ethanol, producing film-coated tables having the above-mentioned ingredients.

Reference Example 1

Synthesis of 3-[(3,4-dichlorophenyl)-(4-fluorophenyl)amino]pyrrolidine-1-carboxylic acid tert-butyl ester Sodium hydride (0.19 g, 60% in oil) was added to 10 ml of dimethyl sulfoxide (DMSO) and stirred at 60° C. for one hour. Subsequently, 1.0 g of (3,4-dichlorophenyl)-(4-fluorophenyl)amine was added to the mixture and stirred at 60° C. for one hour. A DMSO solution containing 2.0 g of 3-(toluene-4-sulfonyloxy)pyrrolidine-1-carboxylic acid tert-butyl ester was gradually added to the mixture and stirred at 60° C. for 15 hours. Ethyl acetate was added to the reaction solution. The solution was then washed with water, and dried over magnesium sulfate. The solvent was distilled off under reduced pressure, and the residue was purified by silica gel column chromatography (n-hexane:ethyl acetate=20:1). The eluent solvent was distilled off under reduced pressure to thereby obtain 0.29 g of oily brown 3-[(3,4-dichlorophenyl)-(4-fluorophenyl)amino]pyrrolidine-1-carboxylic acid tert-butyl ester.

$^1$H-NMR (CDCl$_3$) δ ppm:
1.43 (9H, s), 1.74-1.92 (1H, m), 2.04-2.22 (1H, m), 3.10-3.35 (3H, m), 3.61-3.85 (1H, m), 4.31-4.48 (1H, m), 6.42 (1H, dd=2.9 Hz, J=8.9 Hz), 6.67 (1H, d, J=2.8 Hz), 6.90-7.22 (5H, m).

Reference Example 2

Synthesis of 3(S)-[(3,4-dichlorophenyl)phenylamino]pyrrolidine-1-carboxylic acid tert-butyl ester Sodium hydride (0.36 g, 60% in oil) was added to 20 ml of dimethyl sulfoxide (DMSO) and stirred at 60° C. for one hour. Subsequently, 2.0 g of 3,4-dichlorophenyl-phenylamine was added to the mixture and stirred at 60° C. for one hour. A DMSO solution containing 1.5 g of 3(R)-methanesulfonyloxypyrrolidine-1-carboxylic acid tert-butyl ester was gradually added to the mixture and stirred at 60° C. for 15 hours. Ethyl acetate was added to the reaction solution, and the reaction solution was then washed with water and dried over magnesium sulfate. The solvent was distilled off under reduced pressure, and the residue was purified by silica gel column chromatography (n-hexane:ethyl acetate=20:1). The eluent solvent was distilled off under reduced pressure to thereby obtain 0.13 g of light brown amorphous solid 3(S)-[(3,4-dichlorophenyl)phenylamino]pyrrolidine 1-carboxylic acid tert-butyl ester.

$^1$H-NMR (CDCl$_3$) δ ppm:
1.42 (9H, s), 1.73-1.93 (1H, m), 2.05-2.23 (1H, m), 3.10-3.36 (3H, m), 3.61-3.83 (1H, m), 4.33-4.50 (1H, m), 6.48 (1H, dd, J=2.9 Hz, J=10.3 Hz), 6.74 (1H, d, J=2.8 Hz), 6.96-7.07 (2H, m), 7.16-7.34 (2H, m), 7.35-7.46 (2H, m).

Reference Example 3

Synthesis of ((S)-1-benzylpyrrolidin-3-yl)-(3-fluorophenyl)amine

A toluene solution containing 2.2 g of (S)-1-benzylpyrrolidin-3-ylamine (12.5 mmol), 2.2 g of 3-bromofluorobenzene (12.5 mmol), 0.31 g of 2,2'-bis(diphenylphosphino)-1,1'-binaphthyl (BINAP, 0.51 mmol), 0.14 g of bis(dibenzylideneacetone)palladium (Pd(dba)$_2$, 0.22 mmol), and 1.3 g of sodium tert-butoxide (13.2 mmol) was heated under reflux under a nitrogen atmosphere for 3 hours. The reaction solution was filtered to remove insoluble matter, and ethyl acetate and water were added to the filtrate to separate the solution into layers. The organic layer was washed with water, the solvent was distilled off under reduced pressure, and the residue was purified by silica gel column chromatography (n-hexane:ethyl acetate=20:1→1:1). The eluent solvent was distilled off under reduced pressure to thereby obtain 3.0 g of oily colorless ((S)-1-benzylpyrrolidin-3-yl)-(3-fluorophenyl)amine.

$^1$H-NMR (CDCl$_3$) δ ppm:
1.59-1.78 (2H, m), 2.21-2.38 (1H, m), 2.39-2.50 (1H, m), 2.55 (1H, dd, J=3.3 Hz, J=9.7 Hz), 2.71-2.85 (2H, m), 3.63 (2H, s), 3.90-4.10 (1H, m), 6.24 (1H, dt, J=2.3 Hz, J=11.6 Hz), 6.29-6.41 (2H, m), 7.02-7.11 (1H, m), 7.21-7.39 (5H, m).

Reference Example 4

Synthesis of ((S)-1-benzylpyrrolidin-3-yl)-phenylamine ((S)-1-benzylpyrrolidin-3-yl)-phenylamine was synthesized using (S)-1-benzylpyrrolidin-3-ylamine and bromobenzene in the same manner as in Reference Example 3. Oily Brown Substance $^1$H-NMR (CDCl$_3$) δ ppm:
1.56-1.78 (2H, m), 2.22-2.39 (1H, m), 2.41-2.58 (1H, m), 2.70-2.84 (2H, m), 3.63 (2H, s), 4.01 (1H, s), 6.57 (2H, d, J=8.5 Hz), 6.64-6.73 (1H, m), 7.11-7.19 (2H, m), 7.21-7.36 (5H, m).

Reference Example 5

Synthesis of ((S)-1-benzylpyrrolidin-3-yl)-(3-fluorophenyl)-(4-trifluoromethylphenyl)amine A toluene solution containing 0.7 g of ((S)-1-benzylpyrrolidin-3-yl)-(3-fluorophenyl)amine (2.6 mmol), 0.59 g of 4-bromobenzotrifluoride (2.6 mmol), 65 mg of BINAP (0.1 mmol), 23 mg of palladium acetate (0.1 mmol) and 0.28 g of sodium tert-butoxide (2.9 mmol) was heated under reflux under a nitrogen atmosphere for 3 hours. The reaction solution was filtered to remove insoluble matter, and ethyl acetate and water were added to the filtrate to separate the solution into layers. The organic layer was washed with water and dried over magnesium sulfate. The solvent was distilled off under reduced pressure, and the residue was purified by silica gel column chromatography (n-hexane:ethyl acetate=20: 1→10:1). The eluent solvent was distilled off under reduced pressure to thereby obtain 0.48 g of oily colorless ((S)-1-benzylpyrrolidin-3-yl)-(3-fluorophenyl)-(4-trifluoromethylphenyl)amine.

$^1$H-NMR (CDCl$_3$) δ ppm:
1.82-2.01 (1H, m), 2.17-2.31 (1H, m), 2.61-2.78 (3H, m), 3.45 (1H, d, J=12.9 Hz), 3.64 (1H, d, J=12.9 Hz), 4.55 (1H, m), 6.78-6.86 (3H, m), 6.88-6.96 (2H, m), 7.19-7.36 (6H, m).

Reference Example 6

Synthesis of 3(S)-(3-chloro-4-fluorophenylamino) pyrrolidine-1-carboxylic acid tert-butyl ester To a 50 ml of toluene solution containing 5.0 g of 3(S)-aminopyrrolidine-1-carboxylic acid tert-butyl ester (27 mmol) and 5.7 g of 4-bromo-2-chloro-1-fluorobenzene (27 mmol) were added 1.7 g of BINAP (2.7 mmol), 0.30 g of palladium acetate (1.3 mmol) and 3.5 g of sodium tert-butoxide (36 mmol). The mixture was heated under reflux under a nitrogen atmosphere for 8 hours, and then cooled to room temperature. Water was added to the reaction solution, and extraction with ethyl acetate was performed. After drying over sodium sulfate and concentration under reduced pressure, the residue was purified by silica gel column chromatography (n-hexane:ethyl acetate 4:1). The solvent was distilled off under reduced pressure, and the residue was recrystallized from diethyl ether to thereby obtain 4.76 g of white powdery 3(S)-(3-chloro-4-fluorophenylamino)pyrrolidine-1-carboxylic acid tert-butyl ester.

$^1$H-NMR (CDCl$_3$) δ ppm:
1.47 (9H, s), 1.78-1.96 (1H, m), 2.10-2.28 (1H, m), 2.10-2.28 (1H, m), 3.11-3.30 (1H, m), 3.30-3.56 (2H, m), 3.57-3.79 (2H, m), 3.85-4.03 (1H, m), 6.38-6.47 (1H, m), 6.60 (1H, dd, J=6.0 Hz, J=2.9 Hz), 6.90-7.00 (1H, m).

Reference Example 7

Synthesis of 3(S)-(3-chloro-4-fluorophenylamino) pyrrolidine-1-carboxylic acid tert-butyl ester To a 50 ml of isopropyl alcohol solution containing 15.0 g of 3(S)-aminopyrrolidine-1-carboxylic acid tert-butyl ester (80.5 mmol) and 24.8 g of 2-chloro-1-fluoro-4-iodobenzene (96.7 mmol) were added 1.54 g of copper (I) iodide (8.1 mmol), 9.0 ml of ethylene glycol (10.1 mmol) and 34.2 g of potassium phosphate (161 mmol), and heated under reflux under a nitrogen atmosphere for 46 hours. The reaction solution was cooled to room temperature and filtered using Celite. The substance remained in the filter was washed with ethyl acetate and the filtrate was concentrated under reduced pressure together with the washings, and the residue was purified by silica gel column chromatography (n-hexane:ethyl acetate=4:1). The solvent was distilled off under reduced pressure, and the residue was recrystallized from diethyl ether to thereby obtain 15.9 g of white powdery 3(S)-(3-chloro-4-fluorophenylamino)pyrrolidine-1-carboxylic acid tert-butyl ester.

$^1$H-NMR (CDCl$_3$) δ ppm:
1.47 (9H, s), 1.78-1.96 (1H, m), 2.10-2.28 (1H, m), 2.10-2.28 (1H, m), 3.11-3.30 (1H, m), 3.30-3.56 (2H, m), 3.57-3.79 (2H, m), 3.85-4.03 (1H, m), 6.38-6.47 (1H, m), 6.60 (1H, dd, J=6.0 Hz, J=2.9 Hz), 6.90-7.00 (1H, m).

Reference Example 8

Synthesis of 3(S)-(3-cyanophenylamino)pyrrolidine-1-carboxylic acid tert-butyl ester To a toluene solution (7 ml) containing 2.82 g of 3(S)-aminopyrrolidine-1-carboxylic acid tert-butyl ester (15 mmol) and 1.82 g of 3-bromobenzonitrile (10 mmol) were added 68.5 mg of BINAP (0.11 mmol), 22.5 mg of palladium acetate (0.1 mmol) and 3.91 g of cesium carbonate (12 mmol). The mixture was heated under reflux under a nitrogen atmosphere for 8 hours. After cooling to room temperature, water was added to the reaction solution, and extraction with dichloromethane was performed. After drying over sodium sulfate and concentration under reduced pressure, the residue was then purified by silica gel column chromatography (n-hexane:ethyl acetate=4:1). The purified product was concentrated to dryness under reduced pressure to thereby obtain 1.56 g of light yellow powdery 3(S)-(3-cyanophenylamino)pyrrolidine-1-carboxylic acid tert-butyl ester.

$^1$H-NMR (CDCl$_3$) δ ppm:
1.46 (9H, s), 1.8-2.0 (1H, m), 2.1-2.3 (1H, m), 3.1-3.6 (3H, m), 3.6-3.8 (1H, m), 3.9-4.1 (2H, m), 6.7-6.9 (2H, m), 6.99 (1H, d, J=7.6 Hz), 7.23 (1H, dd, J=7.6 Hz, J=8.4 Hz).

Reference Example 9

Synthesis of 3(S)-(3-chloro-4-methoxyphenylamino) pyrrolidine-1-carboxylic acid tert-butyl ester To a 5 ml of toluene solution containing 0.20 g of 3(S)-aminopyrrolidine-1-carboxylic acid tert-butyl ester (1.1 mmol) and 0.238 g of 2-chloro-3-bromoanisole (1.1 mmol) were added 67.0 mg of BINAP (0.11 mmol), 24 mg of tris (dibenzylideneacetone)dipalladium (0.027 mmol) and 144 mg of sodium tert-butoxide (1.5 mmol). The mixture was heated under reflux under a nitrogen atmosphere at 100° C. for one hour. After cooling to room temperature, the reaction solution was filtered using Celite. The filtrate was concentrated under reduced pressure, and the residue was purified by silica gel column chromatography (n-hexane:ethyl acetate=10:1→3:1). The purified product was concentrated to dryness under reduced pressure to thereby obtain 0.28 g of light yellow amorphous solid 3(S)-(3-chloro-4-methoxyphenylamino)pyrrolidine-1-carboxylic acid tert-butyl ester.

$^1$H-NMR (CDCl$_3$) δ ppm:
1.47 (9H, s), 1.80-1.90 (1H, m), 2.10-2.20 (1H, m), 3.10-3.25 (1H, m), 3.38-3.75 (3H, m), 3.83 (3H, s), 3.92-3.96 (1H, m), 6.47 (1H, dd, J=2.8 Hz, J=8.8 Hz), 6.67 (1H, d, J=2.8 Hz), 6.81 (1H, d, J=8.8 Hz).

Reference Example 10

Synthesis of 3(S)-(4-methoxyphenylamino)pyrrolidine-1-carboxylic acid tert-butyl ester To a 10 ml of ethanol solution containing 0.28 g of 3(S)-(3-chloro-4-methoxyphenylamino)pyrrolidine-1-carboxylic acid tert-butyl ester were added a 0.2 ml of a 5 N sodium hydroxide solution and 0.1 g of 10% palladium carbon. Catalytic reduction was conducted at room temperature and atmospheric pressure (ordinary pressure). The reaction solution was filtered using Celite and concentrated under reduced pressure. Water was added to the residue, and extraction with dichloromethane was performed. The extract was dried over magnesium sulfate and concentrated to dryness under reduced pressure to thereby obtain 0.25 g of yellow amorphous solid 3(S)-(4-methoxyphenylamino)pyrrolidine-1-carboxylic acid tert-butyl ester.

$^1$H-NMR (CDCl$_3$) δ ppm:
1.46 (9H, s), 1.79-1.88 (1H, m), 2.10-2.22 (1H, m), 3.12-3.25 (1H, m), 3.30-3.52 (3H, m), 3.60-3.75 (4H, m), 3.88-4.00 (1H, m), 6.50-6.58 (2H, m), 6.72-6.80 (2H, m).

Reference Example 11

Synthesis of 3(S)-[bis-(3-fluorophenyl)amino]pyrrolidine-1-carboxylic acid tert-butyl ester To a 10 ml of toluene solution containing 1.0 g of 3(S)-aminopyrrolidine-1-carboxylic acid tert-butyl ester (5.3 mmol) and 2.3 g of 3-bromo-1-fluorobenzene (13 mmol) were added 32 mg of tri-tert-butylphosphine•tetrafluoroborate (0.11 mmol), 24 mg of palladium acetate (0.11 mmol) and 1.5 g of sodium tert-butoxide (16 mmol). The mixture was heated under reflux under a nitrogen atmosphere for 8 hours. After cooling to room temperature, water was added to the reaction solution, and extraction with ethyl acetate was conducted. After drying over sodium sulfate and concentration under reduced pressure, the residue was then purified by silica gel column chromatography (n-hexane:ethyl acetate=4:1). The purified product was concentrated to dryness under reduced pressure to thereby obtain 1.56 g of oily yellow 3(S)-[bis-(3-fluorophenyl)amino]pyrrolidine-1-carboxylic acid tert-butyl ester.

$^1$H-NMR (CDCl$_3$) δ ppm:
1.43 (9H, s), 1.78-1.95 (1H, m), 2.02-2.26 (1H, m), 3.12-3.39 (3H, m), 3.65-3.83 (1H, m), 4.35-4.51 (1H, m), 6.61 (2H, dt, J=2.1 Hz, J=11.0 Hz), 6.61-6.68 (2H, m), 6.77 (2H, t, J=8.0 Hz), 7.18-7.31 (2H, m).

Reference Example 12

Synthesis of 3(S)-[(3,4-dichlorophenyl)-thiazole-2-ylamino]pyrrolidine-1-carboxylic acid tert-butyl ester To a 150 ml of toluene solution containing 20.0 g of 3(S)-(3,4-dichlorophenylamino)pyrrolidine-1-carboxylic acid tert-butyl ester (60.4 mmol) and 15.0 g of 2-bromothiazole (91.5 mmol) were added 1.86 g of tri-tert-butylphosphine•tetrafluoroborate (6.4 mmol), 2.88 g of tris(dibenzylideneacetone)dipalladium (3.15 mmol) and 11.6 g of sodium tert-butoxide (120 mmol). The mixture was heated under reflux under a nitrogen atmosphere for 9 hours. The reaction solution was cooled to room temperature and filtered using Celite. Water was added to the filtrate, and extraction with ethyl acetate was conducted. After drying over sodium sulfate and concentration under reduced pressure, the residue was then purified by silica gel column chromatography (n-hexane:ethyl acetate=4:1). The purified product was concentrated to dryness under reduced pressure to thereby obtain 7.94 g of yellow powdery 3(S)-[(3,4-dichlorophenyl)-thiazol-2-ylamino]pyrrolidine-1-carboxylic acid tert-butyl ester.

$^1$H-NMR (CDCl$_3$) δ ppm:
1.43 (9H, s), 1.83-2.03 (1H, m), 2.11-2.35 (1H, m), 3.18-3.42 (3H, m), 3.73-3.87 (1H, m), 4.97-5.09 (1H, m), 6.53 (1H, d, J=3.5 Hz), 7.14 (1H, dd, J=2.5 Hz, J=8.5 Hz), 7.22 (1H, brs), 7.39 (1H, d, J=2.5 Hz), 7.56 (1H, brd, J=8.5 Hz).

Reference Example 13

Synthesis of 3(S)-[(3-chloro-4-fluorophenyl)pyridin-3-ylamino]pyrrolidine-1-carboxylic acid tert-butyl ester To a 10 ml of toluene solution containing 1.0 g of 3(S)-(3-chloro-4-fluorophenylamino)pyrrolidine-1-carboxylic acid tert-butyl ester (3.2 mmol) and 0.75 g of 3-bromopyridine (4.75 mmol) were added 50 mg of 9,9-dimethyl-4,5-bis(diphenylphosphino)xanthene (XANTPHOS, 0.09 mmol), 21.4 mg of palladium acetate (0.10 mmol) and 11.6 g of sodium tert-butoxide (120 mmol). The mixture was heated under reflux under a nitrogen atmosphere for 9 hours. After cooling to room temperature, the reaction solution was filtered using Celite. Water was added to the filtrate, and extraction with ethyl acetate was conducted. After drying over sodium sulfate and concentration under reduced pressure, the residue was then purified by silica gel column chromatography (n-hexane:ethyl acetate=1:1). The purified product was concentrated under reduced pressure to thereby obtain 1.14 g of oily light yellow 3(S)-[(3-chloro-4-fluorophenyl)pyridin-3-ylamino]pyrrolidine-1-carboxylic acid tert-butyl ester.

$^1$H-NMR (CDCl$_3$) δ ppm:
1.43 (9H, s), 1.79-1.98 (1H, m), 2.08-2.29 (1H, m), 3.12-3.41 (3H, m), 3.65-3.85 (1H, m), 4.38-4.51 (1H, m), 6.83-6.91 (1H, m), 7.00-7.23 (4H, m[including 7.04 ppm (dd, J=2.7 Hz, J=6.4 Hz)]), 8.14 (1H, s), 8.22 (1H, d, J=4.4 Hz).

Reference Example 14

Synthesis of 3(S)-[(3-chloro-4-fluorophenyl)cyclohexyl amino]pyrrolidine-1-carboxylic acid tert-butyl ester A 3 ml of acetic acid solution containing 0.60 g of 3(S)-[(3-chloro-4-fluorophenyl)amino]pyrrolidine-1-carboxylic acid tert-butyl ester (1.9 mmol) and 0.56 g of cyclohexanone (5.7 mmol) was stirred at room temperature over night. To the mixture was added 1.21 g of sodium triacetoxyborohydride (5.7 mmol), followed by stirring at room temperature for 8 hours. Dichloromethane was added to the reaction solution, the reaction solution was washed with water and an aqueous saturated sodium hydrogencarbonate solution, and then dried over magnesium sulfate. The solvent was distilled off under reduced pressure, and the residue was purified by silica gel column chromatography (n-hexane:ethyl acetate=10:1). The solvent was distilled off from the purified product under reduced pressure to thereby obtain 0.24 g of oily colorless 3-[(S)-(3-chloro-4-fluorophenyl)cyclohexylamino]pyrrolidine-1-carboxylic acid tert-butyl ester.

$^1$H-NMR (CDCl$_3$) δ ppm:
0.81-1.32 (6H, m), 1.44 (9H, s), 1.60-2.00 (6H, m), 2.79-2.93 (1H, m), 2.98-3.10 (1H, m), 3.16-3.31 (1H, m), 3.35-3.70 (2H, m), 3.35-3.70 (2H, m), 3.85-4.07 (1H, m), 6.85-7.13 (3H, m).

Reference Example 15

Synthesis of 3(S)-[(4-carboxyphenyl)-(3-chloro-4-fluorophenyl)amino]pyrrolidine-1-carboxylic acid tert-butyl ester To an ethanol solution containing 1.7 g of 3(S)-[(3-chloro-4-fluorophenyl)-(4-ethoxycarbonylphenyl)amino]pyrrolidine-1-carboxylic acid tert-butyl ester (3.7 mmol) was added 6 ml of a 5 N sodium hydroxide solution, followed by stirring at room temperature for 15 hours. Dichloromethane and acetic acid were added to the reaction solution to make the reaction solution acidic. After washing with water three times and with an aqueous saturated sodium hydrogencarbonate solution once, the solvent was distilled off under reduced pressure to thereby obtain 1.50 g of white powdery 3(S)-[(4-carboxyphenyl)-(3-chloro-4-fluorophenyl)amino]pyrrolidine-1-carboxylic acid tert-butyl ester.
$^1$H-NMR (DMSO-d$_6$) δ ppm:
1.33 (9H, s), 1.72-1.88 (1H, m), 2.06-2.26 (1H, m), 2.99-3.23 (3H, m), 3.61 (1H, dd, J=6.4 Hz, J=11.3 Hz), 4.53-4.69 (1H, m), 6.57-6.65 (2H, m), 7.19-7.28 (1H, m), 7.46-7.58 (2H, m), 7.68-7.78 (2H, m), 12.3 (1H, brs).

Reference Example 16

Synthesis of 3(S)-[(3-chloro-4-fluorophenyl)-(4-methanesulfonylphenyl)amino]pyrrolidine-1-carboxylic acid tert-butyl ester To a dichloromethane solution containing 0.45 g of 3(S)-[(3-chloro-4-fluorophenyl)-(4-methanesulfanilphenyl)amino]pyrrolidine-1-carboxylic acid tert-butyl ester (1.0 mmol) was added 0.54 g of metachloroperoxybenzoic acid (3.1 mmol) at 0° C., followed by stirring at 0° C. for 2 hours. The reaction solution was washed with water and dried over magnesium sulfate, and the solvent was distilled off under reduced pressure. Subsequently, the residue was purified by silica gel column chromatography (n-hexane:ethyl acetate=5:1→1:1). The solvent was distilled off from the purified product under reduced pressure to thereby obtain 0.42 g of oily light yellow 3(S)-[(3-chloro-4-fluorophenyl)-(4-methanesulfonylphenyl)amino]pyrrolidine 1-carboxylic acid tert-butyl ester.
$^1$H-NMR (CDCl$_3$) δ ppm:
1.43 (9H, s), 1.80-1.91 (1H, m), 2.11-2.29 (1H, m), 3.01 (3H, s), 3.16-3.40 (3H, m), 3.70-3.86 (1H, m), 4.49-4.61 (1H, m), 6.62 (2H, d, J=9.0 Hz), 7.03 (1H, ddd, J=2.6 Hz, J=4.1 Hz, J=8.6 Hz), 7.01-7.06 (1H, m), 7.19-7.23 (1H, m), 7.24-7.31 (1H, m), 7.66-7.74 (2H, m).

Reference Example 17

Synthesis of 3(S)-[(3-chloro-4-fluorophenyl)-(6-cyanopyridin-2-yl)amino]pyrrolidine-1-carboxylic acid tert-butyl ester 3(S)-[(6-bromopyridin-2-yl)-(3-chloro-4-fluorophenyl)amino]pyrrolidine-1-carboxylic acid tert-butyl ester (500 mg, 1.06 mmol), zinc cyanide (250 mg, 2.12 mmol) and tetrakis(triphenylphosphine)palladium (122 mg, 0.106 mmol) were suspended in 8 ml of dimethylformamide (DMF), followed by stirring under a nitrogen atmosphere at 110° C. for 9 hours. After cooling to room temperature, ethyl acetate and water were added to the reaction solution to separate the solution into layers. The organic layer was washed with water and dried over magnesium sulfate. The solvent was distilled off under reduced pressure, and the residue was purified by silica gel column chromatography (n-hexane:ethyl acetate=6:1→3:1). The solvent was distilled off from the purified product under reduced pressure to thereby obtain 398 mg of oily colorless 3(S)-[(3-chloro-4-fluorophenyl)-(6-cyanopyridin-2-yl)amino]pyrrolidine-1-carboxylic acid tert-butyl ester.
$^1$H-NMR (CDCl$_3$) δ ppm:
1.44 (9H, s), 1.74-1.84 (1H, m), 2.03-2.24 (1H, m), 3.08-3.32 (3H, m), 3.76-3.86 (1H, m), 5.28-5.38 (1H, m), 6.21 (1H, d, J=8.7 Hz), 7.04-7.11 (2H, m), 7.23-7.42 (3H, m).

Reference Example 18

Synthesis of 3 (S)-{(3-chloro-4-fluorophenyl)-[5-(4-fluorophenyl)pyridin-2-yl]amino}pyrrolidine-1-carboxylic acid tert-butyl ester 3(S)-[(5-bromopyridin-2-yl)-(3-chloro-4-fluorophenyl)amino]pyrrolidine-1-carboxylic acid tert-butyl ester (300 mg, 0.64 mmol), 4-fluorophenylboric acid (98 mg, 0.7 mmol), tetrakis(triphenylphosphine)palladium (23 mg, 0.02 mmol) and a 2 M aqueous sodium carbonate solution (0.83 ml) were added to toluene (3 ml), followed by stirring under a nitrogen atmosphere at 100° C. for 10 hours. After cooling to room temperature, ethyl acetate and water were added to the reaction solution to separate the reaction solution into layers. The organic layer was washed with saturated saline, followed by drying over sodium sulfate. The solvent was distilled off under reduced pressure, and the residue was purified by silica gel column chromatography (n-hexane:ethyl acetate=5:1). The solvent was distilled off from the purified product under reduced pressure to thereby obtain 255 mg of white solid 3(S)-{(3-chloro-4-fluorophenyl)-[5-(4-fluorophenyl)pyridin-2-yl]amino}pyrrolidine-1-carboxylic acid tert-butyl ester.
$^1$H-NMR (CDC$_3$) δ ppm:
1.44 (9H, s), 1.78-1.89 (1H, m), 2.05-2.23 (1H, m), 3.07-3.31 (3H, m), 3.85 (1H, dd, J=7.1, 10.8 Hz), 5.31-5.42 (1H, m), 6.08 (1H, d, J=8.8 Hz), 7.06-7.14 (3H, m), 7.20-7.28 (2H, m), 7.41-7.50 (3H, m), 8.37-8.41 (1H, m).

Reference Example 19

Synthesis of 3(S)-[(3-chloro-4-fluorophenyl)-(4-thiophene-3-ylphenyl)amino]pyrrolidine-1-carboxylic acid tert-butyl ester Using 3(S)-[(4-bromophenyl)-(3-chloro-4-fluorophenyl)amino]pyrrolidine-1-carboxylic acid tert-butyl ester and 3-thiopheneboric acid, 3(S)-[(3-chloro-4-fluorophenyl)-(4-thiophene-3-ylphenyl)amino]pyrrolidine-1-carboxylic acid tert-butyl ester was synthesized in the same manner as in Reference Example 9.
Oily Colorless Substance
$^1$H-NMR (CDCl$_3$) δ ppm:
1.43 (9H, s), 1.83-1.88 (1H, m), 2.05-2.20 (1H, m), 3.18-3.31 (3H, m), 3.63-3.84 (1H, m), 4.40-4.51 (1H, m), 6.71-6.80 (1H, m), 6.85-6.88 (2H, m), 6.94 (1H, dd, J=2.8 Hz, J=6.4 Hz), 7.05-7.10 (1H, m), 7.30-7.45 (3H, m), 7.50-7.55 (2H, m).

Reference Example 20

Synthesis of (S)-{(3-chloro-4-fluorophenyl)-[6-(4-methylpiperazin-1-yl)pyridin-2-yl]amino}pyrrolidine-1-carboxylic acid tert-butyl ester 3(S)-[(6-bromopyridin-2-yl)-(3-chloro-4-fluorophenyl)amino]pyrrolidine-1-carboxylic acid tert-butyl ester (200 mg, 0.43 mmol), 1-methylpiperazine (0.61 ml, 0.55 mmol), 9,9-dimethyl-4,5-bis(diphenylphosphino)xanthene (XANT-PHOS, 12 mg, 0.02 mmol), tris(dibenzylideneacetone)dipalladium (9 mg, 0.01 mmol) and sodium t-butoxide (61 mg, 0.63 mmol) were added to toluene (5 ml), followed by stirring under a nitrogen atmosphere at 100° C. for 8 hours. Insoluble matter was removed by filtration, and the resultant filtrate was concentrated under reduced pressure. The residue was purified by silica gel column chromatography (n-hexane:ethyl acetate=4:1). The solvent was distilled off from the purified product under reduced pressure to thereby obtain 102 mg of oily colorless (S)-{(3-chloro-4-fluorophenyl)-[6-(4-methylpiperazin-1-yl)pyridin-2-yl]amino}pyrrolidine-1-carboxylic acid tert-butyl ester.

$^1$H-NMR (CDCl$_3$) δ ppm:
1.44 (9H, s), 1.74-1.89 (1H, m), 2.03-2.21 (1H, m), 2.36 (3H, s), 2.51-2.55 (4H, m), 3.08-3.31 (3H, m), 3.54 (4H, brs), 3.64-3.90 (1H, m), 5.10-5.23 (1H, m), 5.32 (1H, d, J=8.1 Hz), 6.01 (1H, d, J=8.1 Hz), 7.03-7.08 (1H, m), 7.19-7.25 (3H, m).

Reference Example 21

Synthesis of 3(S)-[(3-chloro-4-fluorophenyl)-(4-piperidin-1-ylphenyl)amino]pyrrolidine-1-carboxylic acid tert-butyl ester Using 3(S)-[(4-bromophenyl)-(3-chloro-4-fluorophenyl) amino]pyrrolidine-1-carboxylic acid tert-butyl ester and piperidine, 3(S)-[(3-chloro-4-fluorophenyl)-(4-piperidin-1-ylphenyl)amino]pyrrolidine-1-carboxylic acid tert-butyl ester was synthesized in the same manner as in Reference Example 11.
Oily Colorless Substance $^1$H-NMR (CDCl$_3$) δ ppm:
1.43 (9H, s), 1.55-1.62 (2H, m), 1.68-1.73 (4H, m), 1.74-1.90 (1H, m), 2.02-2.18 (1H, m), 3.16-3.29 (7H, m), 3.61-3.81 (1H, m), 4.23-4.38 (1H, m), 6.40-6.46 (1H, m), 6.59-6.62 (1H, m), 6.86-6.92 (5H, m).

Reference Example 22

Synthesis of 3(S)-[(3-chloro-4-cyanophenyl)-(3-chloro-4-fluorophenyl)amino]pyrrolidine-1-carboxylic acid tert-butyl ester To an anhydrous toluene solution containing 3(S)-[(3-chloro-4-fluorophenyl)amino]pyrrolidine-1-carboxylic acid tert-butyl ester (0.50 g, 1.6 mmol) and 2-chloro-4-fluorobenzonitrile (0.30 g, 1.9 mmol) was added a 1.45 ml tetrahydrofuran solution containing sodium bis(trimethylsilyl)amide (1.1 M) using a syringe. The mixture was heated under reflux under a nitrogen atmosphere for 8 hours and cooled to room temperature. Water was added to the reaction solution, and extraction with diethyl ether was conducted. After drying over sodium sulfate and concentration under reduced pressure, the residue was purified by silica gel column chromatography (n-hexane:ethyl acetate=4:1). The purified product was concentrated to dryness under reduced pressure to thereby obtain 0.56 g of white amorphous solid 3(S)-[(3-chloro-4-cyanophenyl)-(3-chloro-4-fluorophenyl)amino] pyrrolidine-1-carboxylic acid tert-butyl ester.

$^1$H-NMR (CDCl$_3$) δ ppm:
1.43 (9H, s), 1.76-1.93 (1H, m), 2.11-2.27 (1H, m), 3.15-3.39 (3H, m), 3.66-3.87 (1H, m), 4.39-4.55 (1H, m), 6.42 (1H, dd, J=2.5 Hz, J=9.0 Hz), 6.57 (1H, d, J=2.5 Hz), 6.98-7.04 (1H, m), 7.20 (1H, dd, J=2.5 Hz, J=6.5 Hz), 7.23-7.32 (1H, m), 7.40 (1H, d, J=8.5 Hz).

Reference Example 23

Synthesis of 2-(4-chlorobutoxy)pyridine

To a DMF solution (110 ml) containing 2-pyridinol (10 g, 105 mmol) and 1-bromo-4-chlorobutane (36 ml, 315 mmol) was added potassium carbonate (16 g, 116 mmol), followed by stirring at room temperature for 8 hours. Water (300 ml) was added to the reaction solution, and extraction with ethyl acetate (300 ml) was then conducted. The organic layer was washed with water (300 ml) twice and dried over magnesium sulfate. The solvent was distilled off under reduced pressure, and the residue was then purified by silica gel column chromatography (n-hexane:ethyl acetate=5:1). The purified product was concentrated under reduced pressure to thereby obtain 3.32 g of oily colorless 2-(4-chlorobutoxy)pyridine.

Reference Example 24

Synthesis of 3(S)-[4-(pyridin-2-yloxy)butylamino] pyrrolidine-1-carboxylic acid tert-butyl ester 3(S)-aminopyrrolidine-1-carboxylic acid tert-butyl ester (0.93 g, 5.0 mmol), 2-(4-chlorobutoxy)pyridine (0.93 g, 5.0 mmol), potassium carbonate (0.83 g, 6.0 mmol) and sodium iodide (0.83 g, 5.5 mmol) were suspended in acetonitrile (20 ml) and heated under reflux for 24 hours. After cooling to room temperature, water (50 ml) was added to the reaction solution and extraction with ethyl acetate (50 ml) was conducted. The organic layer was washed with water twice and dried over magnesium sulfate. The solvent was distilled off under reduced pressure, and the residue was then purified by silica gel column chromatography (n-hexane:ethyl acetate=3:1). The purified product was concentrated under reduced pressure to thereby obtain 372 mg of oily colorless 3(S)-[4-(pyridin-2-yloxy)butylamino]pyrrolidine-1-carboxylic acid tert-butyl ester.

$^1$H-NMR (CDCl$_3$) δ ppm:
1.46 (9H, s), 1.5-1.9 (6H, m), 1.95-2.15 (1H, m), 2.68 (2H, t, J=7 Hz), 2.95-3.15 (1H, m), 3.25-3.65 (4H, m), 4.30 (2H, t, J=6.5 Hz), 6.71 (1H, d, J=8.5 Hz), 6.85 (1H, dd, J=5.5 Hz, J=6.5 Hz), 7.5-7.65 (1H, m), 8.14 (1H, dd, J=2 Hz, J=5 Hz).

Reference Example 25

Synthesis of 3(S)-[(3-chloro-4-fluorophenyl)-(3-chloropropyl)amino]pyrrolidine-1-carboxylic acid tert-butyl ester 3(S)-[(3-chloro-4-fluorophenyl)amino]pyrrolidine-1-carboxylic acid tert-butyl ester (3 g, 9.5 mmol), 1-bromo-3-chloropropane (4.7 ml, 48 mmol) and potassium carbonate (1.97 g, 14.3 mmol) were suspended in N-methylpyrrolidone (NMP, 15 ml), followed by stirring at 100° C. for 8 hours. After cooling to room temperature, water was added to the reaction solution, and extraction with ethyl acetate was conducted. After drying the organic layer over sodium sulfate, the solvent was distilled off under reduced pressure. The residue was purified by silica gel column chromatography (n-hexane: ethyl acetate=3:1), and the purified product was concentrated under reduced pressure to thereby obtain 1.0 g of oily colorless 3(S)-[(3-chloro-4-fluorophenyl)-(3-chloropropyl) amino]pyrrolidine-1-carboxylic acid tert-butyl ester.

$^1$H-NMR (CDCl$_3$) δ ppm:
1.46 (9H, s), 1.7-2.1 (4H, m), 3.1-3.35 (4H, m), 3.35-3.7 (4H, m), 3.8-4.1 (1H, m), 6.7-6.9 (1H, m), 6.9-7.1 (2H, m).

Reference Example 26

Synthesis of 3(S)-[(3-chloro-4-fluorophenyl)-(3-dimethylamino propyl)amino]pyrrolidine-1-carboxylic acid tert-butyl ester 3(S)-[(3-chloro-4-fluorophenyl)-(3-chloropropyl)amino]pyrrolidine-1-carboxylic acid tert-butyl ester (0.5 g, 1.24 mmol), 50% dimethylamine solution (1 ml) and sodium iodide (0.37 g, 2.5 mmol) were suspended in DMF (3 ml), followed by stirring at 60° C. for 4 hours. After cooling to room temperature, water was added to the reaction solution, and extraction with ethyl acetate was conducted. The organic layer was dried over sodium sulfate, and the solvent was then distilled off under reduced pressure. The residue was purified with basic silica gel column chromatography (ethyl acetate), and the purified product was then concentrated under reduced pressure to thereby obtain 0.36 g of oily colorless 3(S)-[(3-chloro-4-fluorophenyl)-(3-dimethylamino propyl)amino]pyrrolidine-1-carboxylic acid tert-butyl ester.

$^1$H-NMR (CDCl$_3$) δ ppm:
1.46 (9H, s), 1.5-1.75 (4H, m), 1.75-2.1 (2H, m), 2.19 (6H, s), 3.0-3.3 (4H, m), 3.3-3.75 (2H, m), 3.8-4.2 (1H, m), 6.6-6.8 (1H, m), 6.8-7.1 (2H, m).

The compounds shown below were produced in the same manners as in the above Reference Examples.

TABLE 1

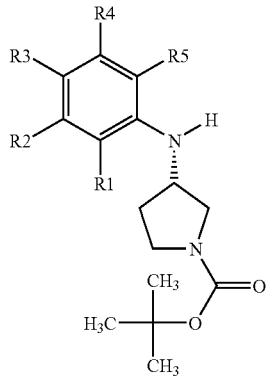

| Ref. Ex. No. | R1 | R2 | R3 | R4 | R5 | NMR |
|---|---|---|---|---|---|---|
| 27 | —H | —H | —H | —H | —H | $^1$H-NMR (CDCl$_3$) δppm 1.46(9 H, s), 1.85-1.95(1 H, m), 2.15-2.23(1 H, m), 3.18-3.26(1 H,m), 3.39-3.51(2 H, m), 3.62-3.75(2 H, m), 4.00-4.05(1 H, m), 6.60(2 H, d, J = 7.8 Hz), 6.69-6.73(1 H, m), 7.15-7.20(2 H, m). |
| 28 | —H | —H | —OCH$_3$ | —H | —H | $^1$H-NMR (CDCl$_3$) δppm 1.46(9 H, s), 1.79-1.88(1 H, m), 2.10-2.22(1 H, m), 3.12-3.25(1 H, m), 3.30-3.52(3 H, m), 3.60-3.75(4 H, m), 3.88-4.00(1 H, m), 6.50-6.58 (2 H, m), 6.72-6.80(2 H, m). |
| 29 | —H | —H | —CH$_3$ | —H | —H | $^1$H-NMR (CDCl$_3$) δppm 1.46(9H, s), 1.80-1.92(1 H, m), 2.10-2.22(1 H, m), 2.24(3 H, s), 3.15-3.23(1 H, m), 3.35-3.75(4 H, m), 3.95-4.05(1 H, m), 6.51-6.55(2 H, m), 6.95-7.04(2 H, m). |
| 30 | —H | —H | —OCH$_3$ | —Cl | —H | $^1$H-NMR (CDCl$_3$) δppm 1.47(9 H, s), 1.80-1.90(1 H, m), 2.10-2.20(1 H, m), 3.10-3.25(1 H, m), 3.38-3.75(3 H, m), 3.83(3 H, s), 3.92-3.96(1 H, m), 6.47(1 H, dd, J = 2.8, 8.8 Hz), 6.67(1 H, d, J = 2.8 Hz), 6.81(1 H, d, J = 8.8 Hz). |
| 31 | —H | —H | —F | —H | —H | $^1$H-NMR (CDCl$_3$) δppm 1.46(9 H, s), 1.75-1.82(1 H, m), 2.00-2.24(1 H, m), 3.03-3.79(5 H, m), 3.80-4.05(1 H, m), 6.51-6.57(2 H, m), 6.90(2 H, dd, J = 8.5 Hz, 8.5 Hz). |
| 32 | —H | —H | —H | —F | —H | 1.47(9 H, s), 1.80-1.99(1 H, m), 2.10-2.26(1 H, m), 3.11-3.35(1 H, m), 3.38-3.57(2 H, m), 3.61-3.77(1 H, m), 3.79-3.91(1 H, m), 3.94-4.08(1 H, m), 6.29(1 H, dt, J = 2.3 Hz and 11.4Hz), 6.33-6.39(1 H, m), 6.40-6.47(1 H, m), 7.04-7.16(1 H, m) |
| 33 | —H | —H | —F | —Cl | —H | $^1$H-NMR (CDCl$_3$) δppm 1.47(9 H, s), 1.78-1.96(1 H, m), 2.10-2.28(1 H, m), 2.10-2.28(1 H, m), 3.11-3.30(1 H, m), 3.30-3.56(2 H, m), 3.57-3.79(2 H, m), 3.85-4.03(1 H, m), 6.38-6.47(1 H, m), 6.60(1 H, dd, J = 6.0 Hz and 2.9 Hz), 6.90-7.00(1 H, m) |
| 34 | —H | —H | —F | —CH$_3$ | —H | $^1$H-NMR (CDCl$_3$) δppm 1.46(9 H, s), 1.7-1.9(1 H, m), 2.1-2.2(1 H, m), 2.21(3 H, s), 3.1-3.3(1 H, m), 3.3-3.8(4 H, m), 3.8-4.1(1 H, m), 6.3-6.5(2 H, m), 6.83(1 H, dd, J = 8.9 Hz, J = 8.9 Hz) |
| 35 | —H | —H | —H | —CN | —H | $^1$H-NMR (CDCl$_3$) δppm 1.46(9 H, s), 1.8-2.0(1 H, m), 2.1-2.3(1 H, m), 3.1-3.6(3 H, m), 3.6-3.8 (1 H, m), 3.9-4.1(2 H, m), 6.7-6.9(2 H, m), 6.99(1 H, d, J = 7.6 Hz), 7.23 (1 H, dd, J = 7.6 Hz, J = 8.4 Hz) |
| 36 | —H | —H | —F | —CF$_3$ | —H | $^1$H-NMR (CDCl$_3$) δppm 1.47(9 H, s), 1.76-1.96(1 H, m), 2.11-2.27(1 H, m), 3.13-3.32(1 H, m), 3.37-3.53(2 H, m), 3.61-3.84(2 H, m), 3.92-4.06(1 H, m), 6.66-6.76 (2 H, m), 7.02(1 H, dd, J = 9.5 Hz, 9.5 Hz). |

TABLE 1-continued

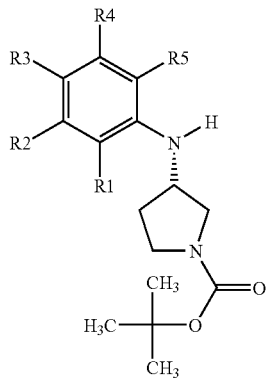

| Ref. Ex. No. | R1 | R2 | R3 | R4 | R5 | NMR |
|---|---|---|---|---|---|---|
| 37 | —H | —H | —Cl | —Cl | —H | $^1$H-NMR (CDCl$_3$) δppm 1.47(9 H, s), 1.80-1.92(1 H, brs), 2.11-2.26(1 H, m), 3.15-3.30(1 H, m), 3.40-3.55(2 H, m), 3.60-3.75(1 H, m), 3.79-3.89(1 H, m), 3.91-4.04 (1 H, m), 6.42(1 H, dd, J = 2.7 Hz and 8.7 Hz), 6.66(1 H, d, J = 2.7 Hz), 7.19(1 H, d, J = 8.6 Hz) |

TABLE 2

| Ref. Ex. No. | R1 | NMR |
|---|---|---|
| 38 | cyclopentyl | $^1$H-NMR (CDCl$_3$) δppm 1.20-1.30(2 H, m), 1.46(9 H, s), 1.50-1.70(5 H, m), 1.80-1.92(2 H, m), 2.05-2.12 (1 H, m), 2.92-3.05(1 H, m), 3.06-3.15(1 H, m), 3.25-3.65(4 H, m). |
| 39 | cyclohexyl | $^1$H-NMR (CDCl$_3$) δppm 1.00-1.30(5 H, m), 1.46(9 H, s), 1.47-1.96(6 H, m), 2.00-2.10(1 H, m), 2.40-2.50 (1 H, m), 2.91-3.02(1 H, m), 3.25-3.35( 1 H, m), 3.38-3.65(3 H, m). |
| 40 | pyridin-3-yl | $^1$H-NMR (CDCl$_3$) δppm 1.47(9 H, s), 1.8-2.0(1 H, m), 2.1-2.3(1 H, m), 3.1-3.3(1 H, m), 3.4-3.6(2 H, m), 3.6-3.8(2 H, m), 3.9-4.1(1 H, m), 6.88(1 H, d, J = 8.3 Hz), 7.0-7.2(1 H, m), 6.8-7.1 (2 H, m), 7.9-8.0(1 H, m), 8.03(1 H, s) |
| 41 | pyrazin-2-yl | $^1$H-NMR (CDCl$_3$) δppm 1.47(9 H, s), 1.82-2.00(1 H, m), 2.18-2.32(1 H, m), 3.14-3.37(1 H, m), 3.39-3.56 (2 H, m), 3.73(1 H, dd, J = 6.0 Hz, 11.5 Hz), 4.37-4.52(1 H, m), 4.59-4.71(1 H, m), 7.84(1 H, d, J = 2.5 Hz), 7.90(1 H, d, J = 1.0 Hz), 8.00(1 H, brs). |
| 42 | 5-methylindan-yl | $^1$H-NMR (CDCl$_3$) δppm 1.46(9 H, s), 1.79-1.95(1 H, m), 1.97-2.24(3 H, m), 2.82(4 H, dd, J = 7.5 Hz, 14.5 Hz), 3.13-3.29(1 H, m), 3.36-3.81(4 H, m), 3.95-4.08(1 H, m), 6.42(1 H, dd, J = 2.0 Hz, 8.0 Hz), 6.52(1 H, brs), 7.04( 1 H, d, J = 8.0 Hz). |

TABLE 2-continued

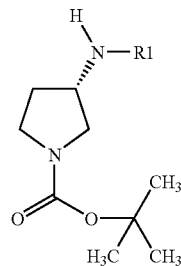

| Ref. Ex. No. | R1 | NMR |
|---|---|---|
| 43 | 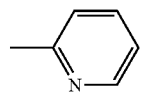 | ¹H-NMR (CDCl₃) δppm<br>1.46(9 H, s), 1.73-2.01(1 H, m), 2.15-2.31(1 H, m), 3.12-3.35( 1 H, m), 3.38-3.59 (2 H, m), 3.65-3.79(1 H, m), 4.27-4.42(1 H, m), 4.48-4.65(1 H, m), 6.35-6.42(1 H, m), 6.56-6.64(1 H, m), 7.38-7.46(1 H, m), 8.04-8.15(2 H, m) |
| 44 | 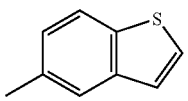 | ¹H-NMR (CDCl₃) δppm<br>1.46(9 H, s), 1.55-1.71(1 H, m), 1.74-2.01(1 H, m), 2.16-2.29(1 H, m), 3.19-3.36 (1 H, m), 3.40-3.59(1 H, m), 3.63-3.85(2 H, m), 4.01-4.19(1 H, m), 6.71(1 H, dd, J = 2.2 Hz and 8.6 Hz), 6.99(1 H, d, J = 2.2 Hz), 7.13-7.21(1 H, m), 7.35-7.43(1 H, m), 7.59-7.68(1 H, m) |
| 45 | 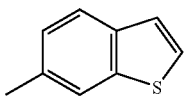 | ¹H-NMR (CDCl₃) δppm<br>1.46(9 H, s), 1.88-2.01(1 H, m), 2.19-2.29(1 H, m), 3.20-3.36(1 H, m), 3.41-3.59 (2 H, m), 3.68-3.90(2 H, m), 4.03-4.18(1 H, m), 6.69(1 H, dd, J = 2.1 Hz and 8.6 Hz), 7.03(1 H, d, J = 2.0 Hz), 7.11(1 H, d, J = 5.2 Hz), 7.17(1 H, d, J = 5.3 Hz), 7.59(1 H, d, J = 8.4 Hz) |

TABLE 3

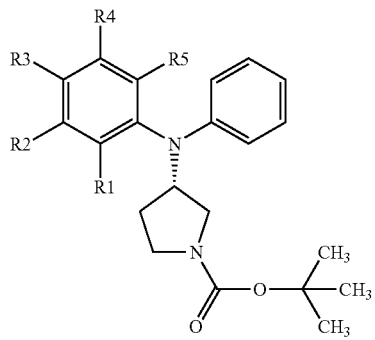

| Ref. Ex. No. | R1 | R2 | R3 | R4 | R5 | NMR |
|---|---|---|---|---|---|---|
| 46 | —H | —H | —Cl | —Cl | —H | ¹H-NMR (CDCl₃) δppm<br>1.42(9 H, s), 1.73-1.93(1 H, m), 2.05-2.23(1 H, m), 3.10-3.36(3 H, m), 3.61-3.83(1 H, m), 4.33-4.50(1 H, m), 6.48(1 H, dd, J = 2.9 Hz and J = 10.3 Hz), 6.74(1 H, d, J = 2.8 Hz), 6.96-7.07(2 H, m), 7.16-7.34(2 H, m), 7.35-7.46(2 H, m). |
| 47 | —H | —H | —SCH₃ | —H | —H | ¹H-NMR (CDCl₃) δppm<br>1.42(9 H, s), 1.75-1.92(1 H, m), 2.00-2.20(1 H, m), 2.46(3 H, s), 3.09-3.33(3 H, m), 3.62-3.83(1 H, m), 4.38-4.55(1 H, m), 6.77-6.88(4 H, m), 6.97-7.08(1 H, m), 7.18-7.33(4 H, m) |
| 48 | —H | —H | —Cl | —H | —H | ¹H-NMR (CDCl₃) δppm<br>1.42(9 H, s), 1.78-1.87(1 H, m), 2.05-2.16(1 H, m), 3.13-3.27(3 H, m), 3.68-3.79(1 H, m), 4.39-4.45(1 H, m), 6.68-6.75(2 H, m), 6.90(2 H, d, J = 7.7 Hz), 7.05-7.15(1 H, m), 7.16-7.25(2 H, m), 7.30-7.40(2 H, m). |
| 49 | —H | —H | —H | —Cl | —Cl | ¹H-NMR (CDCl₃) δppm<br>1.36-1.49(9 H, m), 1.80-1.98(1 H, m), 2.03-2.29(1 H, m), 3.19-3.41 (3 H, m), 3.64-3.89(1 H, m), 4.44-4.59(1 H, m), 6.52(2 H, d, J = 8.2 Hz), 6.74-6.85(2 H, m), 7.12-7.33(4 H, m), 7.46-7.52(1 H, m) |
| 50 | —H | —H | —OCF₃ | —H | —H | ¹H-NMR (CDCl₃) δppm<br>1.42(9 H, s), 1.76-1.91(1 H, m), 2.02-2.21(1 H, m), 3.08-3.86(4 H, m), 4.38-4.53(1 H, m), 6.76(2 H, d, J = 9.0 Hz), 6.90-6.96(2 H, m), 7.03-7.22 (3 H, m), 7.29-7.40(2 H, m) |

TABLE 3-continued

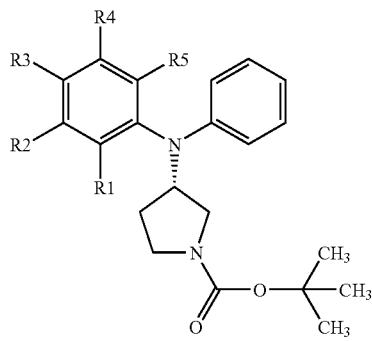

| Ref. Ex. No. | R1 | R2 | R3 | R4 | R5 | NMR |
|---|---|---|---|---|---|---|
| 51 | —H | —H | —CO$_2$CH$_3$ | —H | —H | $^1$H-NMR (CDCl$_3$) δppm<br>1.42(9 H, s), 1.73-1.92(1 H, m), 2.08-2.28(1 H, m), 3.12-3.34(3 H, m), 3.69-3.88(4 H, m with s at φ3.84), 4.49-4.65(1 H, m), 6.50-6.59(2 H, m,), 7.08-7.16(2 H, m), 7.31-7.51(3 H, m), 7.82(2 H, d, J = 6.1 Hz) |
| 52 | —H | —Cl | —H | —Cl | —H | $^1$H-NMR (CDCl$_3$) δppm<br>1.42(9 H, s), 1.73-1.89(1 H, m), 2.02-2.21(1 H, m), 3.09-3.33(3 H, m), 3.62-3.85(1 H, m), 4.35-4.45(1 H, m), 6.42(2 H, d, J = 1.6 Hz), 6.74(1 H, s), 7.02-7.11(2 H, m), 7.30-7.50(3 H, m) |
| 53 | —H | —H | —NO$_2$ | —H | —H | $^1$H-NMR (CDCl$_3$) δppm<br>1.42(9 H, s), 1.78-1.95(1 H, m), 2.09-2.28(1 H, m), 3.10-3.38(3 H, m), 3.71-3.92(1 H, m), 4.52-4.69(1 H, m), 6.48-6.55(2 H, m), 7.08-7.18 (2 H, m), 7.39-7.58(3 H, m), 8.04(2 H, d, J = 8.1 Hz) |
| 54 | —H | —H | —CH$_3$ | —H | —H | $^1$H-NMR (CDCl$_3$) δppm<br>1.42(9 H, s), 1.80-1.85(1 H, m), 2.00-2.15(1 H, m), 2.34(3 H, s), 3.18-3.25(3 H, m), 3.65-3.80(1 H, m), 4.40-4.50(1 H, m), 6.73(2 H, d, J = 8.1 Hz), 6.85-6.90(3 H, m), 7.10-7.26(4 H, m). |
| 55 | —H | —H | —CHO | —H | —H | $^1$H-NMR (CDCl$_3$) δppm<br>1.42(9 H, s), 1.80-1.88(1 H, m), 2.10-2.20(1 H, m), 3.15-3.30(3 H, m), 3.70-3.85(1 H, m), 4.55-4.65(1 H, m), 6.59(2 H, d, J = 8.4 Hz), 7.10-7.15 (2 H, m), 7.40-7.60(3 H, m), 7.60-7.70(2 H, m), 9.75(1 H, s). |
| 56 | —H | —H | —Br | —H | —H | $^1$H-NMR (CDCl$_3$) δppm<br>1.41(9 H, s), 1.80-1.88(1 H, m), 2.05-2.20(1 H, m), 3.15-3.30(3 H, m), 3.65-3.75(1 H, m), 4.38-4.46(1 H, m), 6.65(2 H, d, J = 8.9 Hz), 6.94(2 H, d, J = 8.5 Hz), 7.10-7.40(5 H, m). |
| 57 | —H | —H | —OCH$_3$ | —Cl | —H | $^1$H-NMR (CDCl$_3$) δppm<br>1.43(9 H, s), 1.80-1.88(1 H, m), 2.05-2.15(1 H, m), 3.15-3.30(3 H, m), 3.65-3.80(1 H, m), 3.90(3 H, s), 4.38-4.44(1 H, m), 6.65-6.70(2 H, m), 6.82-6.90(3 H, m), 7.07(1 H, s), 7.15-7.25(2 H, m). |

TABLE 4

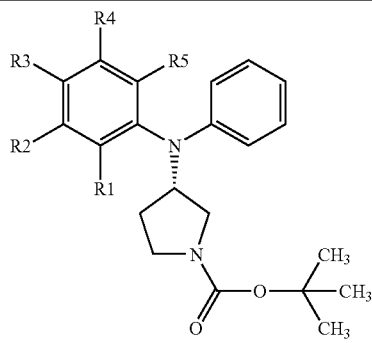

| Ref. Ex. No. | R1 | R2 | R3 | R4 | R5 | NMR |
|---|---|---|---|---|---|---|
| 58 | —H | —H | —OCH$_3$ | —H | —H | $^1$H-NMR (CDCl$_3$) δppm<br>1.42(9 H, s), 1.80-1.86(1 H, m), 2.00-2.12(1 H, m), 3.15-3.26(3 H, m), 3.65-3.78(1 H, m), 3.82(3 H, s), 4.40-4.50(1 H, m), 6.63(2 H, d, J = 7.6 Hz), 6.75-6.80(1 H, m), 6.86-6.95(2 H, m), 7.00(2 H, d, J = 7.6 Hz), 7.10-7.20(2 H, m). |

TABLE 4-continued

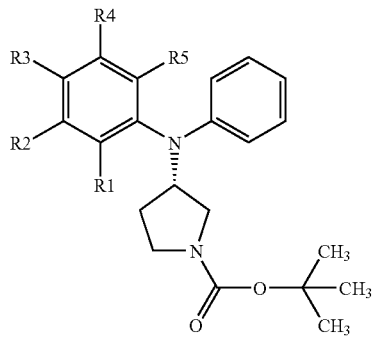

| Ref. Ex. No. | R1 | R2 | R3 | R4 | R5 | NMR |
|---|---|---|---|---|---|---|
| 59 | —H | —H | —OC$_2$H$_5$ | —Cl | —H | $^1$H-NMR (CDCl$_3$) δppm<br>1.43(9 H, s), 1.47(3 H, t, J = 7.0 Hz), 1.75-1.92(1 H, m), 2.01-2.21 (1 H, m), 3.11-3.36(3 H, m), 3.64-3.83(1 H, m), 4.10(2 H, q, J = 7.0 Hz), 4.36-4.51(1 H, m), 6.67-6.74(2 H, m), 6.83-6.93(3 H, m), 7.04-7.08(2 H, m), 7.14-7.27(2 H, m . . . |
| 60 | —H | —H | —OC$_3$H$_7$ | —Cl | —H | $^1$H-NMR (CDCl$_3$) δppm<br>1.08(3 H, t, J = 7.4 Hz), 1.43(9 H, s), 1.79-1.95(1 H, m), 1.96-2.20 (1 H, m), 3.15-3.38(3 H, m), 3.60-3.85(1 H, m), 3.98(2 H, t, J = 6.5 Hz), 4.37-4.51(1 H, m), 6.66-6.73(2 H, m), 6.81-6.93(3 H, m), 7.03-7.09(1 H, m), 7.14-7.28(2 H, m) |
| 61 | —H | —H | —F | —CH$_3$ | —H | $^1$H-NMR (CDCl$_3$) δppm<br>1.43(9 H, s), 1.7-1.9(1 H, m), 2.0-2.2(1 H, m), 2.24(3 H, s), 3.1-3.4 (3 H, m), 3.6-3.8(1 H, m), 4.4-4.6(1 H, m), 6.69(2 H, d, J = 7.9 Hz), 6.7-7.1(4 H, m), 7.1-7.3(2 H, m) |
| 62 | —H | —OCH$_3$ | —F | —F | —H | $^1$H-NMR (CDCl$_3$) δppm<br>1.43(9 H, s), 1.7-1.9(1 H, m), 2.0-2.2(1 H, m), 3.1-3.4(3 H, m), 3.6-3.8(1 H, m), 3.76(3 H, s), 4.3-4.5(1 H, m), 6.0-6.3(2 H, m), 6.92 (2 H, d, = 7.5 Hz), 7.0-7.2(1 H, m), 7.2-7.4(2 H, m) |
| 63 | —H | —H | —F | —H | —H | $^1$H-NMR (CDCl$_3$) δppm<br>1.42(9 H, s), 1.75-1.92(1 H, m), 2.00-2.24(1 H, m), 3.10-3.32(3 H, m), 3.61-3.83(1 H, m), 4.41-4.53(1 H, m), 6.72(2 H, d, J = 8.2 Hz), 6.85-7.10(5 H, m), 7.16-7.28(2 H, m) |
| 64 | —H | —H | —H | —H | —Cl | $^1$H-NMR (CDCl$_3$) δppm<br>1.30-1.50(total 9 H, m with two ss at δ1.41 and 1.44), 1.79-1.96 (1 H, m), 2.06-2.32(1 H, m), 3.12-3.41(3 H, m), 3.64-3.91(1 H, m), 4.41-4.60(1 H, m), 6.52(2 H, d, J = 8.2 Hz), 6.70-6.81(1 H, m), 7.21-7.41(5 H, m), 7.47-7.58(1 H, m) |
| 65 | —H | —H | —H | —Cl | —H | $^1$H-NMR (CDCl$_3$) δppm<br>1.43(9 H, s), 1.78-1.88(1 H, m), 2.07-2.20(1 H, m), 3.15-3.31(3 H, m), 3.65-3.74(1 H, m), 4.40-4.51(1 H, m), 6.55(2 H, dd, J = 1.2 Hz and 4.8 Hz), 6.67(1 H, t, J = 1.2 Hz), 6.80-6.85(1 H, m), 6.98-7.03 (1 H, m), 7.07-7.14(1 H, m), 7.21-7.28(1 H, m), 7.34-7.43(1 H, m) |

TABLE 5

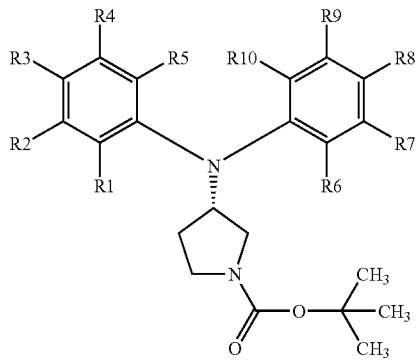

| Ref. Ex. No. | R1 | R2 | R3 | R4 | R5 | R6 | R7 | R8 | R9 | R10 | NMR |
|---|---|---|---|---|---|---|---|---|---|---|---|
| 66 | —H | —H | —Cl | —Cl | —H | —H | —H | —F | —H | —H | $^1$H-NMR (CDCl$_3$) δppm 1.43(9 H, s), 1.73-1.91(1 H, m), 2.01-2.21(1 H, m), 3.09-3.38 (3 H, m), 3.60-3.82(1 H, m), 4.29-4.48(1 H, m), 6.41(1 H, dd, J = 2.9 Hz and J = 8.9 Hz), 6.67(1 H, d, J = 2.8 Hz), 6.90-7.22(5 H, m) |
| 67 | —H | —H | —Cl | —Cl | —H | —F | —H | —H | —H | —H | $^1$H-NMR (CDCl$_3$) δppm 1.42(9 H, s), 1.73-1.92(1 H, m), 2.05-2.28(1 H, m), 3.12-3.35 (3 H, m), 3.63-3.86(1 H, m), 4.35-4.51(1 H, m), 6.39(1 H, dd, J = 2.9 Hz and 9.0 Hz), 6.66(1 H, d, J = 2.7 Hz), 7.08-7.28(4 H, m), 7.31-7.45(1 H, m) |
| 68 | —H | —H | —H | —F | —H | —H | —Cl | —H | —H | —H | $^1$H-NMR (CDCl$_3$) δppm 1.43(9 H, s), 1.74-1.91(1 H, m), 2.02-2.21(1 H, m), 3.10-3.35 (3 H, m), 3.62-3.82(1 H, m), 4.39-4.51(1 H, m), 6.39(1 H, dt, J = 1.4 Hz and J = 11.7 Hz), 6.47(1 H, d, J = 8.3 Hz), 6.55-6.65(1 H, m), 6.89-6.98(2 H, m), 7.09-7.21(1 H, m), 7.29-7.38(2 H, m) |
| 69 | —H | —H | —H | —F | —H | —H | —H | —F | —H | —H | $^1$H-NMR (CDCl$_3$) δppm 1.43(9 H, s), 1.74-1.92(1 H, m), 2.06-2.29(1 H, m), 3.08-3.89 (4 H, m), 4.35-4.51(1 H, m), 6.27(1 H, dt, J = 2.3 Hz and J = 12.3 Hz), 6.35(1 H, d, J = 7.0 Hz), 6.41-6.53(1 H, m), 7.01-7.21 (5 H, m) |
| 70 | —H | —H | —H | —F | —H | —H | —H | —SCH$_3$ | —H | —H | $^1$H-NMR (CDCl$_3$) δppm 1.43(9 H, s), 1.75-1.91(1 H, m), 2.01-2.21(1 H, m), 2.50 (1 H, s), 3.11-3.32(3 H, m), 3.63-3.83(1 H, m), 4.38-4.51(1 H, m), 6.34(1 H, dt, J = 2.3 Hz and J = 12.1 Hz), 6.42(1 H, d, J = 8.4 Hz), 6.48-6.58(1 H, m), 6.92-7.01(2 H, m), 7.05-7.18(1 H, m), 7.22-7.31 (2 H, m) |
| 71 | —H | —H | —F | —H | —H | —H | —Cl | —H | —H | —H | $^1$H-NMR (CDCl$_3$) δppm 1.42(9 H, s), 1.75-1.92(1 H, m), 2.01-2.20(1 H, m), 3.10-3.33 (3 H, m), 3.61-3.81(1 H, m), 4.32-4.99(1 H, m), 6.61(2 H, d, J = 8.8 Hz), 6.94-7.19 (6 H, m) |
| 72 | —H | —H | —F | —H | —H | —H | —F | —H | —H | —H | $^1$H-NMR (CDCl$_3$) δppm 1.42(9 H, s), 1.80-1.88(1 H,m), 2.00-2.15(1 H, m), 3.10-3.30 (3 H, m), 3.60-3.75(1 H, m), 4.30-4.38(1 H, m), 6.75-6.85(4 H, m), 6.90-7.00(4 H, m). |
| 73 | —H | —H | —H | —F | —H | —F | —H | —H | —H | —H | $^1$H-NMR (CDCl$_3$) δppm 1.43(9 H, s), 1.78-1.95(1 H, m), 2.02-2.26(1 H, m), 3.12-3.39 (3 H, m), 3.65-3.83(1 H, m), 4.35-4.51(1 H, m), 6.61 (2 H, dt, J = 2.1 Hz and J = 11.0 Hz), 6.61-6.68(2 H, m), 6.77(2 H, t, J = 8.0 Hz), 7.18-7.31(2 H, m) |
| 74 | —H | —H | —F | —Cl | —H | —H | —F | —H | —H | —H | $^1$H-NMR (CDCl$_3$) δppm 1.43(9 H, s), 1.75-1.92(1 H, m), 2.02-2.35(1 H, m), 3.12-3.38 (3 H, m), 3.63-3.85(1 H, m), 4.35-4.50(1 H, m), 6.38(1 H, dt, J = 2.3 Hz and 11.7 Hz), 6.90(1 H, ddd, J = 4.2 Hz, J = 4.2 Hz and J = 8.8 Hz), 7.08(1 H, dd, J = 2.6 Hz and J = 6.5 Hz), 7.11-7.22(1 H, m) |
| 75 | —H | —H | —F | —CH$_3$ | —H | —H | —CH$_3$ | —F | —H | —H | $^1$H-NMR (CDCl$_3$) δppm 1.43(9 H, s), 1.8-2.0(1 H, m), 2.0-2.2(1 H, m), 2.21(6 H, s), 3.1-3.4(3 H, m), 3.6-3.8(1 H, m), 4.3-4.5(1 H, m), 6.6-6.7(4 H, m), 6.8-7.0(2 H, m) |
| 76 | —H | —H | —F | —CH$_3$ | —H | —H | —F | —H | —H | —H | $^1$H-NMR (CDCl$_3$) δppm 1.43(9 H, s), 1.7-1.9(1 H, m), 2.0-2.2(1 H, m), 2.27(3 H, s), 3.1-3.4(3 H, m), 3.6-3.8(1 H, m), 4.3-4.5(1 H, m), 6.26(1 H, d, J = 12.4 Hz), 6.3-6.5(2 H, m), 6.8-7.2(4 H, m) |

TABLE 6

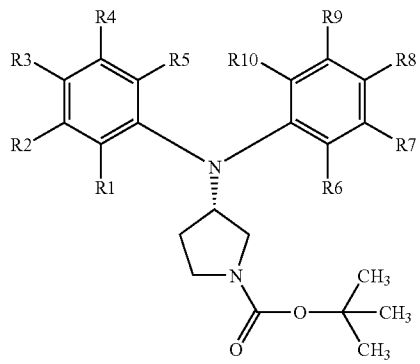

| Ref. Ex. No. | R1 | R2 | R3 | R4 | R5 | R6 | R7 | R8 | R9 | R10 | NMR |
|---|---|---|---|---|---|---|---|---|---|---|---|
| 77 | —H | —H | —F | —Cl | —H | —H | —CH$_3$ | —H | —H | —H | $^1$H-NMR (CDCl$_3$) δppm 1.43(9 H, s), 1.7-1.9(1 H, m), 2.0-2.2(1 H, m), 2.40 (3 H, s), 3.1-3.4(3 H, m), 3.6-3.8( 1 H, m), 4.3-4.5(1 H, m), 6.6-6.8(3 H, m), 6.85(1 H, d, J = 6.4 Hz), 6.92(1 H, d, J = 7.3 Hz), 6.9-7.1(1 H, m), 7.1-7.3(1 H, m) |
| 78 | —H | —H | —H | —F | —H | —H | —CH$_3$ | —H | —H | —H | $^1$H-NMR (CDCl$_3$) δppm 1.43(9 H, s), 1.7-1.9(1 H, m), 2.0-2.2(1 H, m), 2.34 (3 H, s), 3.1-3.4(3 H, m), 3.6-3.8(1 H, m), 4.3-4.5(1 H, m), 6.33(1 H, d, J = 12.2 Hz), 6.42(1 H, d, J = 8.3 Hz), 6.4-6.6(1 H, m), 6.8-6.9(2 H, m), 7.0-7.2(2 H, m), 7.2-7.3(1 H, m) |
| 79 | —H | —H | —F | —CH$_3$ | —H | —H | —H | —F | —H | —H | $^1$H-NMR (CDCl$_3$) δppm 1.43(9 H, s), 1.7-1.9(1 H, m), 2.0-2.2(1 H, m), 2.22 (3 H, s), 3.1-3.4(3 H, m), 3.6-3.8(1 H, m), 4.3-4.5(1 H, m), 6.6-6.8(4 H, m), 6.8-7.1(3 H, m) |
| 80 | —H | —H | —H | —CH$_3$ | —H | —H | —H | —F | —H | —H | $^1$H-NMR (CDCl$_3$) δppm 1.43(9 H, s), 1.7-1.9(1 H, m), 2.0-2.2(1 H, m), 2.27 (3 H, s), 3.1-3.4(3 H, m), 3.6-3.8(1 H, m), 4.4-4.6(1 H, m), 6.54(2 H, d, J = 6.5 Hz), 6.74(1 H, d, J = 7.1 Hz), 6.8-7.2(5 H, m) |
| 81 | —H | —H | —H | —F | —H | —H | —H | —CH$_3$ | —H | —H | $^1$H-NMR (CDCl$_3$) δppm 1.42(9 H, s), 1.7-1.9(1 H, m), 2.0-2.2(1 H, m), 2.38 (3 H, s), 3.1-3.4(3 H, m), 3.6-3.8(1 H, m), 4.3-4.5(1 H, m), 6.28(1 H, d, J = 12.5 Hz), 6.3-6.5(2 H, m), 6.96 (2 H, d, J = 8.2 Hz), 7.0-7.3(3 H, m) |
| 82 | —H | —H | —CH$_3$ | —Cl | —H | —H | —F | —H | —H | —H | $^1$H-NMR (CDCl$_3$) δppm 1.43(9 H, s), 1.7-1.9(1 H, m), 2.0-2.2(1 H, m), 2.37 (3 H, s), 3.1-3.4(3 H, m), 3.6-3.8(1 H, m), 4.3-4.5(1 H, m), 6.38(1 H, d, J = 11.9 Hz), 6.46(1 H, d, J = 8.3 Hz), 6.57(1 H, dd ,J = 8.1 Hz, 7.8 Hz), 6.82(1 H, d, J = 8.1 Hz), 7.02(1 H, s), 7.1-7.3(2 H, m) |
| 83 | —H | —H | —Cl | —CH$_3$ | —H | —H | —F | —H | —H | —H | $^1$H-NMR (CDCl$_3$) δppm 1.43(9 H, s), 1.7-1.9(1 H, m), 2.0-2.2(1 H, m), 2.35 (3 H, s), 3.1-3.4(3 H, m), 3.6-3.8(1 H, m), 4.3-4.5(1 H, m), 6.36(1 H, d, J = 11.9 Hz), 6.43(1 H, d, J = 8.3 Hz), 6.55(1 H, dd, J = 8.0 Hz, 8.1 Hz), 6.80(1 H, d, J = 8.3 Hz), 6.89(1 H, s), 7.1-7.2(1 H, m), 7.3-7.4(1 H, m) |
| 84 | —H | —H | —F | —Cl | —H | —H | —Cl | —F | —H | —H | $^1$H-NMR (CDCl$_3$) δppm 1.75-1.92(1 H, m), 2.03-2.22(1 H, m), 3.11-3.39(3 H, m), 3.61-3.79(1 H, m), 4.26-4.42(1 H, m), 6.42-6.75 (2 H, m), 6.87-6.91(2 H, m), 7.06(1 H, dd, J = 8.5 Hz, 8.5 Hz). |
| 85 | —H | —H | —H | —F | —H | —H | —CN | —H | —H | —H | $^1$H-NMR (CDCl$_3$) δppm 1.43(9 H, s), 1.8-1.9(1 H, m), 2.1-2.3(1 H, m), 3.1-3.4 (3 H, m), 3.6-3.8(1 H, m), 4.4-4.5(1 H, m), 6.68(1 H, d, J = 10.2 Hz), 6.75(1 H, d, J = 8.0 Hz), 6.9-7.0(3 H, m), 7.1-7.4(3 H, m) |

TABLE 7

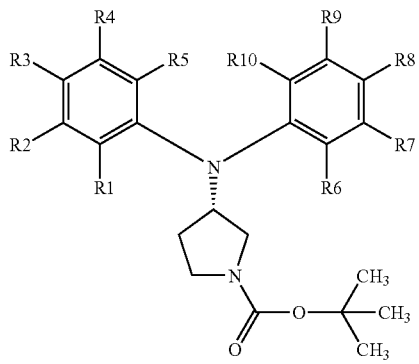

| Ref. Ex. No. | R1 | R2 | R3 | R4 | R5 | R6 | R7 | R8 | R9 | R10 | NMR |
|---|---|---|---|---|---|---|---|---|---|---|---|
| 86 | —H | —H | —F | —Cl | —H | —H | —CN | —H | —H | —H | $^1$H-NMR (CDCl$_3$) δppm 1.44(9 H, s), 1.7-1.9(1 H, m), 2.0-2.2(1 H, m), 3.1-3.4 (3 H, m), 3.6-3.8(1 H, m), 4.3-4.5(1 H, m), 6.7-6.9 (2 H, m), 6.9-7.0(1 H, m), 7.0-7.4(4 H, m), |
| 87 | —H | —H | —F | —Cl | —H | —H | —H | —OCH$_3$ | —H | —H | $^1$H-NMR (CDCl$_3$) δppm 1.43(9 H, s), 1.75-1.91(1 H, m), 2.02-2.18(1 H, m), 3.11-3.35(3 H, m), 3.60-3.79(1 H, m), 3.83(3 H, s), 4.29-.42(1 H, m), 6.44(1 H, dt, J = 3.5 Hz and J = 8.9 Hz), 6.61(1 H, dd, J = 2.8 Hz and J = 6.1 Hz), 6.86-7.01(5 H, m) |
| 88 | —H | —H | —F | —Cl | —H | —H | —H | —CH$_3$ | —H | —H | $^1$H-NMR (CDCl$_3$) δppm 1.43(9 H, s), 1.75-1.91(1 H, m), 2.02-2.20(1 H, m), 2.37(1 H, s), 3.11-3.38(3 H, m), 3.60-3.83(1 H, m), 4.29-4.49(1 H, m), 6.56(1 H, dt, J = 3.6 Hz and J = 9.0 Hz), 6.74(1 H, dd, J = 2.9 Hz and J = 6.3 Hz), 6.86 (2 H, d, J = 8.3 Hz), 6.91-7.02(1 H, m), 7.11-7.21(2 H, m) |
| 89 | —H | —H | —F | —Cl | —H | —H | —H | —OC$_2$H$_5$ | —H | —H | $^1$H-NMR (CDCl$_3$) δppm 1.32-1.50(12 H, m, with s at δ1.42 and t at δ 1.43, J = 7.0 Hz), 1.74-1.91(1 H, m), 2.01-2.18(1 H, m), 3.10-3.32(3 H, m), 3.58-3.81(1 H, m), 4.06(2 H, q, J = 7.0 Hz), 4.28-4.42(1 H, m), 6.44(1 H, dt, J = 3.2 Hz and J = 9.0 Hz), 6.61(1 H, dd, J = 2.9 Hz and J = 6.1 Hz), 6.84-7.01(5 H, m) with at δ6.96, J = 2.5 Hz) |
| 90 | —H | —H | —F | —Cl | —H | —H | —H | —C$_2$H$_5$ | —H | —H | $^1$H-NMR (CDCl$_3$) δppm 1.25(3 H, t, J = 7.5 Hz), 1.43(9 H, s), 1.72-1.91(1 H, m), 2.00-2.20(1 H, m), 2.64(2 H, q, J = 7.5 Hz), 3.10-3.46(3 H, m), 3.60-3.81(1 H, m), 4.30-4.49(1 H, m), 6.53-6.61(1 H, m), 6.76(1 H, dd, J = 2.9 Hz and J = 6.3 Hz), 6.87(1 H, d, J = 8.2 Hz), 6.91-7.03(1 H, m), 7.12-7.22(2 H, m) |
| 91 | —H | —H | —F | —Cl | —H | —H | —H | —CO$_2$C$_2$H$_5$ | —H | —H | $^1$H-NMR (CDCl$_3$) δppm 1.35(3 H, t, J = 7.1 Hz), 1.43(9 H, s), 1.78-1.95(1 H, m), 2.09-2.27(1 H, m), 3.11-3.39(3 H, m), 3.69-3.85(1 H, m), 4.32(2 H, q, J = 7.1 Hz), 4.93-4.61(1 H, m), 6.57(2 H, d, J = 8.9 Hz), 6.96-7.04(1 H, m), 7.14-7.29(2 H, m), 7.81-7.94(2 H, m) |
| 92 | —H | —H | —F | —Cl | —H | —H | —H | —CO$_2$H | —H | —H | 1H-NMR (DMSO-d6) δppm 1.33(9 H, s), 1.72-1.88(1 H, m), 2.06-2.26(1 H, m), 2.99-3.23(3 H, m), 3.61(1 H, dd, J = 6.4 Hz and J = 11.3 Hz), 4.53-4.69(1 H, m), 6.57-6.65(2 H, m), 7.19-7.28(1 H, m), 7.46-7.58(2 H, m), 7.68-7.78(2 H, m), 12.3 (1 H, brs) |
| 93 | —H | —H | —CH$_3$ | —H | —H | —H | —H | —F | —H | —H | $^1$H-NMR (CDCl$_3$) δppm 1.42(9 H, s), 1.74-1.92(1 H, m), 2.00-2.20(1 H, m), 2.30(3 H, s), 3.13-3.32(3 H, m), 3.62-3.80(1 H, m), 4.33-4.48(1 H, m), 6.74(2 H, d, J = 8.5 Hz), 6.80-6.88 (2 H, m), 6.90-7.02(2 H, m), 7.03-7.13(2 H, m). |

TABLE 8

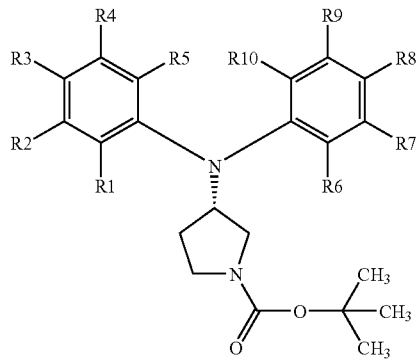

| Ref. Ex. No. | R1 | R2 | R3 | R4 | R5 | R6 | R7 | R8 | R9 | R10 | NMR |
|---|---|---|---|---|---|---|---|---|---|---|---|
| 94 | —H | —H | —F | —Cl | —H | —H | —H | —N(CH$_3$)$_2$ | —H | —H | $^1$H-NMR (CDCl$_3$) δppm 1.43(9 H, s), 1.70-1.87(1 H, m), 2.00-2.13(1 H, m), 2.97(6 H, s), 3.10-3.29(3 H, m), 3.59-3.77(1 H, m), 4.28-4.38(1 H, m), 6.41(1 H, dt, J = 3.4, 9.1 Hz), 6.57-6.61(1 H, m), 6.68-6.72(2 H, m), 6.84-6.94(3 H, m). |
| 95 | —H | —H | —F | —Cl | —H | —H | —H | —CN | —H | —H | $^1$H-NMR (CDCl$_3$) δppm 1.43(9 H, s), 1.79-1.92(1 H, m), 2.09-2.17(1 H, m), 3.11-3.32(3 H, m), 3.70-3.89(1 H, m), 4.45-4.53(1 H, m), 6.56(2 H, d, J = 9.0 Hz), 7.02(1 H, ddd, J = 2.6, 4.2, 8.7 Hz)), 7.18-7.28(2 H, m), 7.43(2 H, d, J = 7.9 Hz). |
| 96 | —H | —H | —F | —Cl | —H | —H | —H | —CF$_3$ | —H | —H | $^1$H-NMR (CDCl$_3$) δppm 1.43(9 H, s), 1.78-1.90(1 H, m), 2.09-2.23(1 H, m), 3.12-3.34(3 H, m), 3.65-3.80(1 H, m), 4.40-4.52(1 H, m), 6.64(2 H, d, J = 8.8 Hz), 7.02(1 H, ddd, J = 2.7, 4.1, 8.6 Hz), 7.15-7.25(2 H, m), 7.42(2 H, d, J = 7.7 Hz). |
| 97 | —H | —H | —F | —Cl | —H | —H | —OCH$_3$ | —H | —H | —H | $^1$H-NMR (CDCl$_3$) δppm 1.43(9 H, s), 1.82-1.90(1 H, m), 2.04-2.18(1 H, m), 3.15-3.32(3 H, m), 3.65-3.80(1 H, m), 3.76(3 H, s), 4.33-4.43(1 H, m), 6.35(1 H, t, J = 2.3 Hz), 6.59(1 H, dd, J = 1.8, 8.2 Hz), 6.74-6.79(1 H, m), 6.95(1 H, dd, J = 2.7, 6.4 Hz), 7.02-7.10(1 H, m), 7.15-7.22(1 H, m). |
| 98 | —H | —H | —F | —Cl | —H | —H | —OC$_2$H$_5$ | —H | —H | —H | $^1$H-NMR (CDCl$_3$) δppm 1.38(3 H, t, J = 7.0 Hz), 1.43(9 H, s), 1.80-1.90(1 H, m), 2.03-2.18(1 H, m), 3.16-3.32(3 H, m), 3.60-3.69 (1 H, m), 3.96(2 H, q, J = 7.0), 4.31-4.41(1 H, m), 6.37 (1 H, t, J = 2.2 Hz), 6.41(1 H, dd, J = 1.58, 8.0 Hz), 6.59 (1 H, d, J = 8.1 Hz), 6.75(1 H, ddd, J = 2.9, 3.9, 8.8 Hz), 6.93(1 H, dd, J = 2.8, 6.4 Hz), 7.00-7.08(1 H, m), 7.14-7.25(1 H, m). |
| 99 | —H | —H | —F | —Cl | —H | —H | —SCH$_3$ | —H | —H | —H | $^1$H-NMR (CDCl$_3$) δppm 1.43(9 H, s), 1.78-1.92(1 H, m), 2.04-2.20(1 H, m), 2.44(3 H, s), 3.11-3.33(3 H, m), 3.60-3.80(1 H, m), 4.31-4.45(1 H, m), 6.57(1 H, ddd, J = 0.8, 2.3, 8.1 Hz), 6.70(1 H, t, 1.9 Hz), 6.76(1 H, ddd, J = 2.8, 4.0, 8.9 Hz), 6.90-6.96(2 H, m), 7.03-7.11(1 H, m), 7.16-7.23(1 H, m). |
| 100 | —H | —H | —F | —CH$_3$ | —H | —H | —H | —NO$_2$ | —H | —H | $^1$H-NMR (CDCl$_3$) δppm 1.43(9 H, s), 1.80-1.90(1 H, m), 2.01-2.20(1 H, m), 2.31(3 H, s), 3.18-3.38(3 H, m), 3.70-3.88(1 H, m), 4.50-4.59(1 H, m), 6.50(2 H, d, J = 9.5 Hz), 6.85-6.97 (2 H, m), 7.07-7.15(1 H, m), 8.03(2 H, d, J = 7.9 Hz). |
| 101 | —H | —H | —F | —CH$_3$ | —H | —H | —H | —CN | —H | —H | $^1$H-NMR (CDCl$_3$) δppm 1.43(9 H, s), 1.81-1.93(1 H, m), 2.08-2.20(1 H, m), 2.35(3 H, s), 3.18-3.30(3 H, m), 3.65-3.78(1 H, m), 4.45-4.55(1 H, m), 6.50(2 H, d, J = 9.5 Hz), 6.83-6.99 (2 H, m), 7.03-7.15(1 H, m), 7.32-7.43(2 H, m). |

TABLE 9

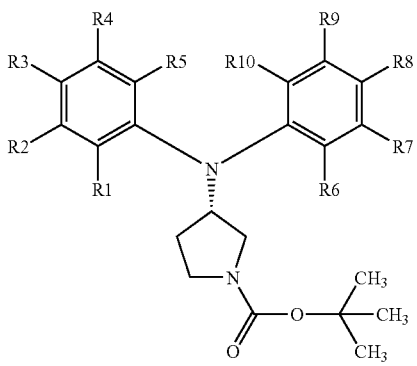

| Ref. Ex. No. | R1 | R2 | R3 | R4 | R5 | R6 | R7 | R8 | R9 | R10 | NMR |
|---|---|---|---|---|---|---|---|---|---|---|---|
| 102 | —H | —H | —F | —CH$_3$ | —H | —H | —CH$_3$ | —H | —H | —H | $^1$H-NMR (CDCl$_3$) δppm 1.43(9 H, s), 1.79-1.90(1 H, m), 2.00-2.18(1 H, m), 2.24(3 H, s), 2.27(3 H, s), 3.12-3.30(3 H, m), 3.62-3.71(1 H, m), 4.39-4.50(1 H, m), 6.50-6.52(2 H, m), 6.68-6.72(1 H, m), 6.77-6.84(2 H, m), 6.93-7.01(1 H, m), 7.06-7.11(1 H, m). |
| 103 | —H | —H | —F | —Cl | —H | —H | —H | —C$_3$H$_7$ | —H | —H | $^1$H-NMR (CDCl$_3$) δppm 0.96(3 H, t, J = 7.3 Hz), 1.43(9 H, s), 1.61-1.70(2 H, m), 1.76-1.89(1 H, m), 2.01-2.18(1 H, m), 2.51-2.65 (2 H, m), 3.11-3.35(3 H, m), 3.62-3.82(1 H, m), 4.31-4.43(1 H, m), 6.55-6.59(1 H, m), 6.76(1 H, dd, J = 2.9 Hz and 6.3 Hz), 6.86(2 H, d, J = 8.2 Hz), 6.97 (1 H, q, J = 9.1 Hz), 7.11-7.19(2 H, m) |
| 104 | —H | —H | —F | —Cl | —H | —H | —H | —C(CH$_3$)$_3$ | —H | —H | $^1$H-NMR (CDCl$_3$) δppm 1.31(9 H, s), 1.43(9 H, s), 1.78-1.89(1 H, m), 2.02-2.19(1 H, m), 3.11-3.34(3 H, m), 3.62-3.80(1 H, m), 4.32-4.45(1 H, m), 6.59-6.65(1 H, m), 6.79-6.88(2 H, m with dd at δ6.81, J = 2.8 Hz and 6.3 Hz), 6.99(1 H, q, J = 8.9 Hz), 7.29-7.38(2 H, m) |
| 105 | —H | —H | —F | —Cl | —H | —H | —H | —SCH$_3$ | —H | —H | $^1$H-NMR (CDCl$_3$) δppm 1.43(9 H, s), 1.79-1.89(1 H, m), 2.03-2.09(1 H, m), 2.51(3 H, s), 3.13-3.34(3 H, m), 3.63-3.80(1 H, m), 6.65-6.69(1 H, m), 6.80-6.86(3 H, m), 7.02(1 H, q, J = 8.8 Hz), 7.21-7.27(2 H, m) |
| 106 | —H | —H | —F | —Cl | —H | —H | —H | —SO$_2$CH$_3$ | —H | —H | $^1$H-NMR (CDCl$_3$) δppm 1.43(9 H, s), 1.80-1.91(1 H, m), 2.11-2.29(1 H, m), 3.01(3 H, s), 3.16-3.40(3 H, m), 3.70-3.86(1 H, m), 4.49-4.61(1 H, m), 6.62(2 H, d, J = 9.0 Hz), 7.03(1 H, ddd, J = 2.6 Hz, 4.1 Hz and 8.6 Hz), 7.01-7.06(1 H, m), 7.19-7.23(1 H, m), 7.24-7.31(1 H, m), 7.66-7.74(2 H, m) |
| 107 | —H | —H | —H | —SCH$_3$ | —H | —H | —H | —F | —H | —H | $^1$H-NMR (CDCl$_3$) δppm 1.43(9 H, s), 1.78-1.91(1 H, m), 2.02-2.18(1 H, m), 2.40(3 H, s), 3.11-3.30(3 H, m), 3.71-3.80(1 H, m), 4.35-4.50(1 H, m), 6.45(1 H, dd, J = 2.0, 8.1 Hz), 6.56(1 H, brs), 6.75(1 H, d, J = 7.9 Hz), 6.97-7.15(5 H, m). |
| 108 | —H | —H | —H | —NO$_2$ | —H | —H | —CH$_3$ | —F | —H | —H | $^1$H-NMR (CDCl$_3$) δppm 1.43(9 H, s), 1.78-1.91(1 H, m), 2.08-2.23(1 H, m), 2.29(3 H, s), 3.14-3.33(3 H, m), 3.71-3.82(1 H, m), 4.45-4.55(1 H, m), 6.75-6.84(1 H, m), 6.89-6.99(2 H, m), 7.03-7.28(2 H, m), 7.41-7.55(1 H, m), 7.55-7.58 (1 H, m). |
| 109 | —H | —H | —F | —CH$_3$ | —H | —H | —OCH$_3$ | —H | —H | —H | $^1$H-NMR (CDCl$_3$) δppm 1.43(9 H, s), 1.78-1.90(1 H, m), 2.02-2.19(1 H, m), 2.24(3 H, s), 3.13-3.30(3 H, m), 3.63-3.82(1 H, m), 3.73(3 H, s), 4.39-4.52(1 H, m), 6.19(1 H, s), 6.25-6.28(1 H, m), 6.38-6.41(1 H, m), 6.80-6.91(2 H, m), 6.92-7.06(1 H, m), 7.07-7.13(1 H, m). |

TABLE 10

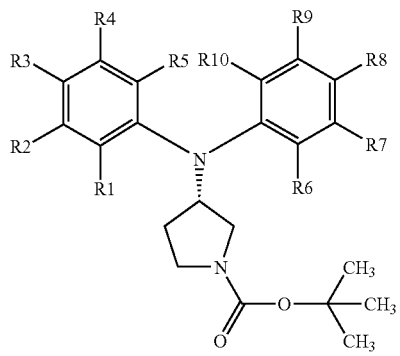

| Ref. Ex. No. | R1 | R2 | R3 | R4 | R5 | R6 | R7 | R8 | R9 | R10 | NMR |
|---|---|---|---|---|---|---|---|---|---|---|---|
| 110 | —H | —H | —Cl | —Cl | —H | —H | —F | —H | —H | —H | $^1$H-NMR (CDCl$_3$) δppm 1.43 (9H, s), 1.78-1.92 (1H, m), 2.03-2.23 (1H, m), 3.12-3.36 (3H, m), 3.61-3.82 (1H, m), 4.31-4.50 (1H, m), 6.57 (1H, dt, J = 2.2 Hz and 10.7 Hz), 6.61-6.66 (1H, m), 6.69 (1H, dd, J = 2.7 Hz and 8.7 Hz), 6.75-6.85 (1H, m), 6.95 (1H, d, J = 2.7 Hz), 7.19-7.39 (2H, m) |
| 111 | —H | —H | —F | —Cl | —H | —H | —H | 2-methoxytetrahydropyran | —H | —H | $^1$H-NMR (CDCl$_3$) δppm 1.43 (9H, s), 1.59-1.75 (3H, m), 1.79-1.92 (3H, m), 1.95-2.15 (2H, m), 3.11-3.32 (3H, m), 3.58-3.79 (2H, m), 3.89-3.99 (1H, m), 4.30-4.43 (1H, m), 5.30 (1H, s), 6.43-6.44 (1H, m), 6.62-6.67 (1H, m)1 6.85-6.97 (3H, m), 7.02-7.10 (2H, m) |
| 112 | —H | —H | —F | —CF$_3$ | —H | —H | —Cl | —F | —H | —H | $^1$H-NMR (CDCl$_3$) δppm 1.43 (9H, s), 1.76-1.91 (1H, m), 2.03-2.09 (1H, m), 3.11-3.37 (3H, m), 3.61-3.79 (1H, m), 4.32-4.45 (1H, m), 6.73-6.79 (1H, m), 6.93-6.98 (2H, m), 7.01-7.04 (1H, m), 7.05-7.16 (2H, m) |

TABLE 11

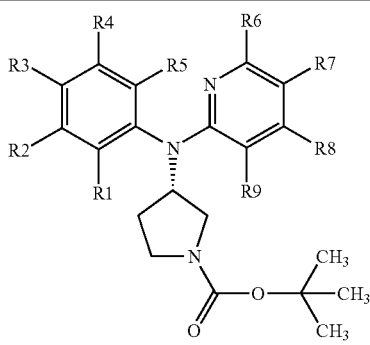

| Ref Ex. No. | R1 | R2 | R3 | R4 | R5 | R6 | R7 | R8 | R9 | NMR |
|---|---|---|---|---|---|---|---|---|---|---|
| 113 | —H | —H | —H | —H | —H | —H | —H | —H | —H | $^1$H-NMR (CDCl$_3$) δppm 1.42 (9H, s), 1.68-1.72 (1H, m), 1.99-2.21 (1H, m), 3.06-3.31 (3H, m), 3.83 (1H, dd, J = 7.2 Hz and 10.7 Hz), 5.32-5.49 (1H, m), 5.96 (1H, d, J = 6.0 Hz), 6.52-6.65 (1H, m), 7.10-7.29 (3H, m), 7.31-7.52 (3H, m), 8.15-8.23 (1H, m) |
| 114 | —H | —F | —H | —H | —H | —H | —H | —H | —H | $^1$H-NMR (CDCl$_3$) δppm 1.43 (9H, s), 1.75-1.94 (1H, m), 2.09-2.38 (1H, m), 3.12-3.49 (3H, m), 3.70-3.85 (1H, m), 4.40-4.60 (1H, m), 6.49-6.61 (2H, m), 6.68-6.79 (1H, m), 7.16-7.31 (3H ,m), 8.27 (1H, s), 8.36-8.44 (1H, m) |

TABLE 11-continued

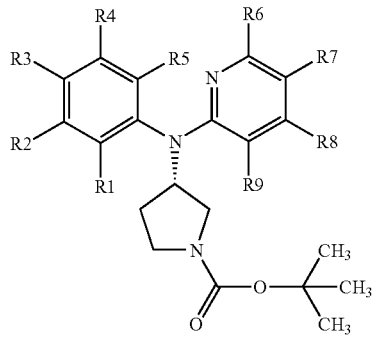

| Ref Ex. No. | R1 | R2 | R3 | R4 | R5 | R6 | R7 | R8 | R9 | NMR |
|---|---|---|---|---|---|---|---|---|---|---|
| 115 | —H | —Cl | —F | —H | —H | —H | —H | —H | —H | $^1$H-NMR (CDCl$_3$) δppm 1.45 (9H, s), 1.70-1.89 (1H, m), 2.02-2.25 (1H, m), 3.04-3.49 (3H, m), 3.84 (1H, dd, J = 7.1 Hz and 10.8 Hz), 5.30-5.49 (1H, m), 6.02 (1H, d, J = 8.6 Hz), 6.58-6.72 (1H, m), 7.02-7.39 (4H, m), 8.16-8.28 (1H, m) |
| 116 | —H | —H | —H | —H | —H | —CH$_3$ | —H | —H | —H | $^1$H-NMR (CDCl$_3$) δppm 1.43 (9H, s), 1.68-1.89 (1H, m), 2.00-2.20 (1H, m), 2.43 (3H, d, J = 4.6 Hz), 3.09-3.30 (3H, m), 3.72-3.95 (1H, m), 5.39-5.58 (1H, m), 5.74 (1H, d, J = 8.5 Hz), 6.33-6.53 (1H, m), 7.05-7.20 (3H, m), 7.29-7.50 31H, m) |
| 117 | —H | —H | —H | —H | —H | —H | —CH$_3$ | —H | —H | $^1$H-NMR (CDCl$_3$) δppm 1.42 (9H, s), 1.68-1.85 (1H, m), 1.95-2.20 (4H, m with s at δ2.17), 3.03-3.31 (3H, m), 3.75-3.88 (1H, m), 5.24-5.47 (1H, m), 5.92 (1H, d, J = 8.6 Hz), 7.07 (1H, d, J = 8.6 Hz), 7.11-7.19 (2H, m), 7.29-7.31 (3H, m), 8.00 (1H, d, J = 5.2 Hz) |
| 118 | —H | —H | —H | —H | —H | —H | —H | —CH$_3$ | —H | $^1$H-NMR (CDCl$_3$) δppm 1.42 (9H, s), 1.65-1.87 (1H, m), 1.95-2.12 (1H, m), 2.17 (3H, s), 3.05-3.31 (3H, m), 3.78-3.88 (1H, m), 5.21-5.45 (1H, m), 5.92 (1H, d, J = 8.6 Hz), 7.07 (1H, d, J = 8.6 Hz), 7.10-7.20 (2H, m), 7.28-7.31 (3H, m), 7.96-8.05 (1H, m) |
| 119 | —H | —Cl | —F | —H | —H | —H | —CH$_3$ | —H | —H | $^1$H-NMR (CDCl$_3$) δppm 1.43 (9H, s), 1.69-1.71 (1H, m), 1.90-2.10 (1H, m), 2.19 (3H, s), 3.01-3.36 (3H, m), 3.76-3.86 (1H, m), 5.19-5.36 (1H, m), 5.96 (1H, d, J = 8.6 Hz), 7.01-7.06 (1H, m), 7.07-7.17 (2H, m), 7.18-7.26 (2H, m), 8.01 (1H, d, J = 12.5 Hz) |
| 120 | —H | —Cl | —F | —H | —H | —H | —H | —CH$_3$ | —H | $^1$H-NMR(CDCl$_3$) δppm 1.43 (9H, s), 1.68-1.81 (1H, m), 2.02-2.20 (4H, m with s at δ2.12), 3.04-3.32 (3H, m), 3.78-3.84 (1H, m), 5.29-5.42 (1H, m), 5.80 (1H, s), 6.40-6.53 (1H, m), 7.02-7.10 (1H, m), 7.11-7.25 (2H, m), 8.05 (1H, dd, J = 5.0 Hz and 12.2 Hz) |

TABLE 12

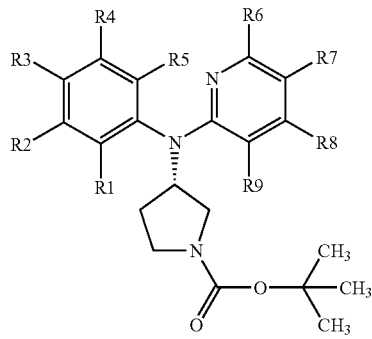

| Ref. Ex. No. | R1 | R2 | R3 | R4 | R5 | R6 | R7 | R8 | R9 | NMR |
|---|---|---|---|---|---|---|---|---|---|---|
| 121 | —H | —Cl | —F | —H | —H | —CH$_3$ | —H | —H | —H | $^1$H-NMR (CDCl$_3$) δppm 1.44 (9H, s), 1.68-1.82 (1H, m), 2.00-2.19 (1H, m), 2.39-2.49 (3H, m), 3.02-3.37 (3H, m), 3.74-3.84 (1H, m), 5.32-5.51 (1H, m), 5.70-5.81 (1H, m), 6.41-6.57 (1H, m), 7.04 (1H, ddd, J = 2.6 Hz, 4.3 Hz and 8.7 Hz), 7.10-7.30 (3H, m) |
| 122 | —H | —Cl | —F | —H | —H | —H | —Cl | —H | —H | $^1$H-NMR (CDCl$_3$) δppm 1.43 (9H, s), 1.62-1.82 (1H, m), 2.01-2.22 (1H, m), 3.03-3.31 (3H, m), 3.79 (1H, dd, J = 7.0, 10.8 Hz), 5.21-5.27 (1H, m), 5.96 (1H, d, J = 9.0 Hz), 7.04 (1H, ddd, J = 2.6, 4.2, 8.6), 7.20-7.26 (4H, m), 8.12-8.14 (1H, m). |
| 123 | —H | —CF$_3$ | —F | —H | —H | —H | —H | —H | —H | $^1$H-NMR (CDCl$_3$) δppm 1.43 (9H, s), 1.63-1.79 (1H, m), 2.02-2.26 (1H, m), 3.03-3.35 (3H, m), 3.84 (1H, dd, J = 7.0 Hz, 11.0 Hz), 5.30-5.41 (1H, m), 5.97 (1H, d, J = 8.5 Hz), 6.62-6.73 (1H, m), 7.26-7.47 (4H, m), 8.18-8.26 (1H, m). |
| 124 | —H | —CH$_3$ | —F | —H | —H | —H | —Cl | —H | —H | $^1$H-NMR (CDCl$_3$) δppm 1.43 (9H, s), 1.68-1.82 (1H, m), 2.00-2.19 (1H, m), 2.29 (3H, s), 3.10-3.29 (3H, m), 3.79 (1H, dd, J = 7.1, 10.8 Hz), 5.15-5.32 (1H, m), 5.93 (1H, d, J = 9.1 Hz), 6.90-6.99 (2H, m), 7.01-7.21 (2H, m), 8.11-8.12 (1H, m). |
| 125 | —H | —H | —F | —H | —H | —H | —Cl | —H | —H | $^1$H-NMR (CDCl$_3$) δppm 1.42 (9H, s), 1.73-1.82 (1H, m), 2.00-2.17 (1H, m), 3.06-3.29 (3H, m), 3.79 (1H, dd, J = 7.1, 10.8 Hz), 5.15-5.32 (1H, m), 5.92 (1H, d, J = 9.0 Hz), 7.07-7.27 (5H, m), 8.12 (1H, d, J = 4.7). |
| 126 | —H | —Cl | —F | —H | —H | —H | —H | —CF$_3$ | —H | $^1$H-NMR (CDCl$_3$) δppm 1.43 (9H, s), 1.7-1.9 (1H, m), 2.0-2.2 (1H, m), 3.0-3.4 (3H, m), 3.7-3.9 (1H, m), 5.2-5.4 (1H, m), 6.15 (1H, s), 6.82 (1H, d, J = 5.0 Hz), 7.0-7.1 (1H, m), 7.2-7.4 (2H, m), 8.3-8.4 (1H, m) |
| 127 | —H | —Cl | —F | —H | —H | —OCH$_3$ | —H | —H | —H | $^1$H-NMR (CDCl$_3$) δppm 1.43 (9H, s), 1.7-1.9 (1H, m), 2.0-2.2 (1H, m), 3.1-3.4 (3H, m), 3.7-3.9 (1H, m), 3.90 (3H, s), 5.1-5.3 (1H, m), 5.51 (1H, d, J = 8.1 Hz), 6.09 (1H, d, J = 8.3 Hz), 7.0-7.1 (1H, m), 7.2-7.4 (3H, m) |

TABLE 13

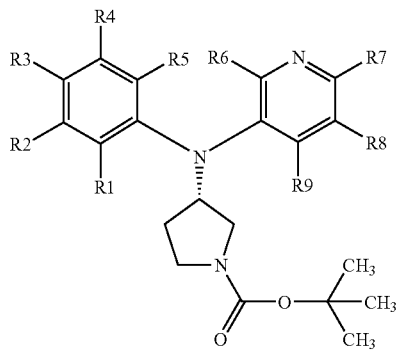

| Ref. Ex. No. | R1 | R2 | R3 | R4 | R5 | R6 | R7 | R8 | R9 | NMR |
|---|---|---|---|---|---|---|---|---|---|---|
| 128 | —H | —Cl | —F | —H | —H | —H | —H | —H | —H | $^1$H-NMR (CDCl$_3$) δppm 1.43 (9H, s), 1.79-1.98 (1H, m), 2.08-2.29 (1H, m), 3.12-3.41 (3H, m), 3.65-3.85 (1H, m), 4.38-4.51 (1H, m), 6.83-6.91 (1H, m), 7.00-7.23 (4H, m with dd at δ7.04, J = 2.7 Hz and J = 6.4 Hz), 8.14 (1H, s), 8.22 (1H, d, J = 4.4 Hz) |
| 129 | —H | —CH$_3$ | —F | —H | —H | —H | —H | —H | —H | $^1$H-NMR (CDCl$_3$) δppm 1.43 (9H, s), 1.7-1.9 (1H, m), 2.0-2.2 (1H, m), 2.26 (3H, s), 3.1-3.4 (3H, m), 3.6-3.8 (1H, m), 4.3-4.5 (1H, m), 6.8-7.1 (5H, m), 7.9-8.1 (2H, m) |
| 130 | —H | —H | —H | —H | —H | —H | —F | —H | —H | $^1$H-NMR (CDCl$_3$) δppm 1.43 (9H, s), 1.73-1.96 (1H, m), 2.01-2.29 (1H, m), 3.11-3.40 (3H, m), 3.64-3.86 (1H, m), 4.37-4.56 (1H, m), 6.79-6.94 (3H, m), 7.02-7.15 (1H, m), 7.19-7.40 (3H, m), 7.80 (1H, brs) |
| 131 | —H | —Cl | —F | —H | —H | —H | —OCH$_3$ | —H | —H | $^1$H-NMR (CDCl$_3$) δppm 1.43 (9H, s), 1.7-1.9 (1H, m), 2.0-2.2 (1H, m), 3.1-3.4 (3H, m), 3.6-3.8 (1H, m), 3.96 (3H, s), 4.3-4.5 (1H, m), 6.50 (1H, d, J = 9.0 Hz), 6.67 (1H, d, J = 6.0 Hz), 6.78 (1H, d, J = 8.8 Hz), 6.9-7.0 (1H, m), 7.26 (1H, d, J = 8.8 Hz), 7.92 (1H, s) |
| 132 | —H | —Cl | —H | —H | —H | —H | —H | —H | —H | $^1$H-NMR (CDCl$_3$) δppm 1.41 (9H, s), 1.7-1.9 (1H, m), 2.1-2.3 (1H, m), 3.1-3.4 (3H, m), 3.7-3.9 (1H, m), 4.4-4.6 (1H, m), 6.71 (1H, d, J = 6.9 Hz), 6.83 (1H, s), 7.03 (1H, dd, J = 6.9 Hz, J = 7.8 Hz), 7.1-7.3 (2H, m), 8.24 (1H, s), 8.36 (1H, s) |

TABLE 14

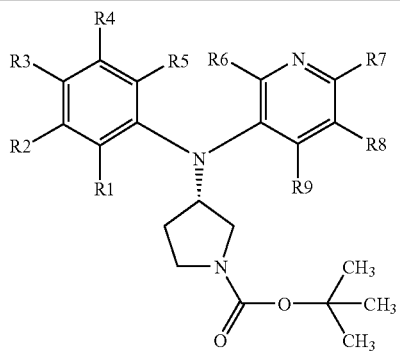

| Ref. Ex. No. | R1 | R2 | R3 | R4 | R5 | R6 | R7 | R8 | R9 | NMR |
|---|---|---|---|---|---|---|---|---|---|---|
| 133 | —H | —F | —F | —H | —H | —H | —H | —H | —H | $^1$H-NMR (CDCl$_3$) δppm 1.43 (9H, s), 1.8-2.0 (1H, m), 2.1-2.3 (1H, m), 3.1-3.4 (3H, m), 3.6-3.8 (1H, m), 4.4-4.5 (1H, m), 6.6-6.7 (1H, m), 6.7-6.9 (1H, m), 7.0-7.3 (3H, m), 8.16 (1H, d, J = 6.6 Hz), 8.25 (1H, s) |

TABLE 14-continued

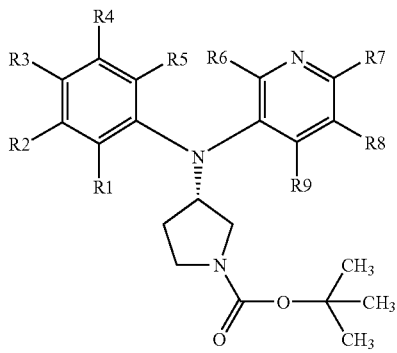

| Ref. Ex. No. | R1 | R2 | R3 | R4 | R5 | R6 | R7 | R8 | R9 | NMR |
|---|---|---|---|---|---|---|---|---|---|---|
| 134 | —H | —F | —Cl | —H | —H | —H | —H | —H | —H | $^1$H-NMR (CDCl$_3$) δppm 1.42 (9H, s), 1.8-1.9 (1H, m), 2.1-2.3 (1H, m), 3.1-3.4 (3H, m), 3.7-3.9 (1H, m), 4.4-4.5 (1H, m), 6.47 (1H, d, J = 8.1 Hz), 6.54 (1H, d, J = 11.2 Hz), 7.2-7.4 (3H, m), 8.30 (1H, s), 8.45 (1H, s) |
| 135 | —H | —Cl | —Cl | —H | —H | —H | —H | —H | —H | $^1$H-NMR (CDCl$_3$) δppm 1.43 (9H, s), 1.5-1.9 (1H, m), 2.1-2.3 (1H, m), 3.1-3.4 (3H, m), 3.7-3.9 (1H, m), 4.4-45 (1H, m), 6.63 (1H, d, J = 8.7 Hz), 6.90 (1H, s), 7.2-7.4 (3H, m), 8.27 (1H, s), 8.41 (1H, s) |
| 136 | —H | —CF$_3$ | —F | —H | —H | —H | —H | —H | —H | $^1$H-NMR (CDCl$_3$) δppm 1.43 (9H, s), 1.74-1.94 (1H, m), 2.06-2.28 (1H, m), 3.12-3.38 (3H, m), 3.65-3.82 (1H, m), 4.38-4.56 (1H, m), 7.01-7.25 (5H, m), 8.16 (1H, s), 8.28 (1H, d, J = 4.5 Hz). |
| 137 | —H | —H | —F | —H | —H | —H | —H | —H | —H | $^1$H-NMR (CDCl$_3$) δppm 1.43 (9H, s), 1.79-1.97 (1H, m), 2.03-2.23 (1H, m), 3.11-3.29 (3H, m), 3.63-3.79 (1H, m), 4.38-4.50 (1H, m), 6.83-6.92 (1H, m), 7.01-7.12 (5H, m), 8.01-8.10 (2H, m). |

TABLE 15

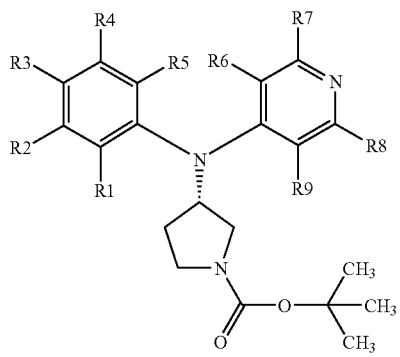

| Ref. Ex. No. | R1 | R2 | R3 | R4 | R5 | R6 | R7 | R8 | R9 | NMR |
|---|---|---|---|---|---|---|---|---|---|---|
| 138 | —H | —H | —H | —H | —H | —H | —H | —H | —H | $^1$H-NMR (CDCl$_3$) δppm 1.42 (9H, s), 1.77-1.92 (1H, m), 1.95-2.27 (1H, m), 3.10-3.38 (3H, m), 3.68-3.89 (1H, m), 4.41-4.61 (1H, m), 6.32-6.40 (2H, m), 7.08-7.15 (2H, m), 7.38-7.54 (3H, m), 8.12-8.22 (1H, m) |
| 139 | —H | —Cl | —F | —H | —H | —H | —H | —H | —H | $^1$H-NMR (CDCl$_3$) δppm 1.43 (9H, s), 1.73-1.95 (1H, m), 2.07-2.27 (1H, m), 3.12-3.38 (3H, m), 3.65-3.84 (1H, m), 4.41-4.61 (1H, m), 6.32-6.41 (2H, m), 6.99-7.08 (1H, m), 7.18-7.32 (2H, m with dd at δ7.21, J = 2.5 Hz and J = 6.6 Hz), 8.12-8.31 (2H, m) |

TABLE 15-continued

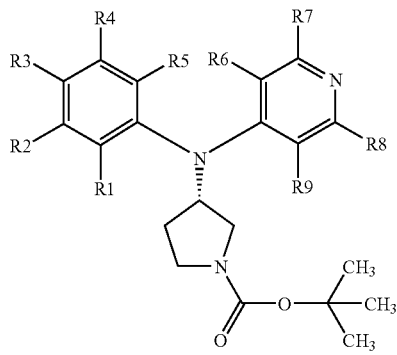

| Ref. Ex. No. | R1 | R2 | R3 | R4 | R5 | R6 | R7 | R8 | R9 | NMR |
|---|---|---|---|---|---|---|---|---|---|---|
| 140 | —H | —Cl | —F | —H | —H | —H | —H | —CH₃ | —H | ¹H-NMR (CDCl₃) δppm<br>1.43 (9H, s), 1.8-2.0 (1H, m), 2.1-2.3 (1H, m), 2.40 (3H, s), 3.1-3.4 (3H, m), 3.7-3.9 (1H, m), 4.4-4.6 (1H, m), 6.1-6.3 (2H, m), 6.9-7.1 (1H, m), 7.1-7.3 (2H, m), 8.12 (1H, d, J = 5.0 Hz) |

TABLE 16

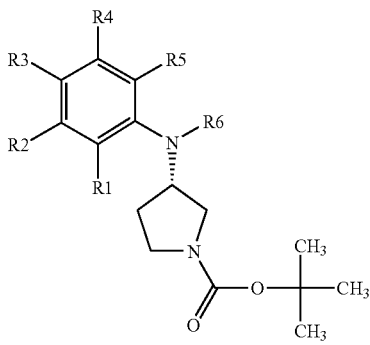

| Ref. Ex. No. | R1 | R2 | R3 | R4 | R5 | R6 | NMR |
|---|---|---|---|---|---|---|---|
| 141 | —H | —H | —F | —H | —H | cyclohexyl | ¹H-NMR (CDCl₃) δppm<br>0.80-1.36 (6H, m), 1.44 (9H, s), 1.61-1.99 (6H, m), 2.75-2.93 (1H, m), 2.95-3.09 (1H, m), 3.15-3.31 (1H, m), 3.33-3.68 (2H, m), 3.87-4.07 (1H, m), 6.86-6.98 (2H, m), 6.98-7.07 (2H, m) |
| 142 | —H | —H | —F | —H | —H | tetrahydropyran-4-yl | ¹H-NMR (CDCl₃) δppm<br>1.44 (9H, s), 1.61-1.81 (3H, m), 1.89-2.01 (1H, m), 2.95-3.70 (7H, m), 3.88-4.01 (1H, m), 6.88-7.10 (4H, m) |
| 143 | —H | —H | —F | —Cl | —H | cyclopentyl | ¹H-NMR (CDCl₃) δppm<br>1.19-1.74 (18H, m with s at δ1.46), 1.89-2.02 (1H, m), 2.97-3.63 (5H, m), 3.71-3.91 (1H, m), 6.89-7.07 (2H, m), 7.10 (1H, d, J = 6.4 Hz) |
| 144 | —H | —H | —F | —H | —H | benzo[1,3]dioxol-5-yl | ¹H-NMR (CDCl₃) δppm<br>1.43 (9H, s), 1.8-2.0 (1H, m), 2.0-2.2 (1H, m), 3.1-3.4 (3H, m), 3.6-3.8 (1H, m), 4.2-4.4 (1H, m), 5.95 (2H, s), 6.4-6.5 (2H, m), 6.6-6.8 (3H, m), 6.8-7.0 (2H, m) |
| 145 | —H | —H | —F | —Cl | —H | benzo[1,3]dioxol-5-yl | ¹H-NMR (CDCl₃) δppm<br>1.44 (9H, s), 1.7-1.9 (1H, m), 2.0-2.2 (1H, m), 3.1-3.4 (3H, m), 3.6-3.8 (1H, m), 4.2-4.4 (1H, m), 6.00 (2H, s), 6.4-6.5 (3H, m), 6.66 (1H, d, J = 6.2 Hz), 6.7-7.0 (2H, m) |

TABLE 16-continued

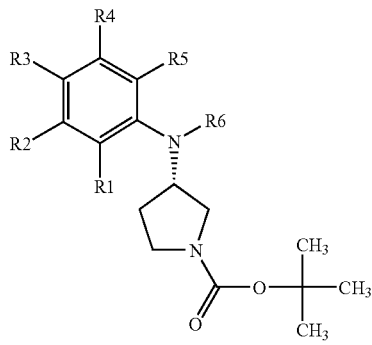

| Ref. Ex. No. | R1 | R2 | R3 | R4 | R5 | R6 | NMR |
|---|---|---|---|---|---|---|---|
| 146 | —H | —H | —H | —F | —H | (5-methyl-benzo[1,3]dioxole) | $^1$H-NMR (CDCl$_3$) δppm 1.43 (9H, s), 1.8-1.9 (1H, m), 2.0-2.2 (1H, m), 3.1-3.4 (3H, m), 3.6-3.8 (1H, m), 4.3-4.5 (1H, m), 6.02 (2H, s), 6.27 (1H, d, J = 12.6 Hz), 6.37 (1H, d, J = 8.5 Hz), 6.4-6.5 (1H, m), 6.5-6.7 (2H, m), 6.8-6.9 (1H, m), 7.0-7.2 (1H, m) |
| 147 | —H | —H | —F | —Cl | —H | (5-methyl-indane) | $^1$H-NMR (CDCl$_3$) δppm 1.43 (9H, s), 1.78-1.90 (1H, m), 2.04-2.16 (3H, m), 2.79-2.95 (4H, m), 3.13-3.32 (3H, m), 3.61-3.80 (1H, m), 4.27-4.45 (1H, m), 6.50-6.57 (1H, m), 6.61-6.79 (2H, m), 6.83 (1H, s), 6.88-7.02 (1H, m), 7.13-7.22 (1H, m). |
| 148 | —H | —H | —F | —Cl | —H | (7-methyl-2,3-dihydro-benzo[1,4]dioxine) | $^1$H-NMR (CDCl$_3$) δppm 1.45 (9H, s), 1.7-1.9 (1H, m), 2.0-2.2 (1H, m), 3.1-3.4 (3H, m), 3.6-3.8 (1H, m), 4.27 (4H, s), 4.3-4.5 (1H, m), 6.4-6.6 (3H, m), 6.68 (1H, d, J = 6.2 Hz), 6.84 (1H, dd, J = 9.1 Hz, J = 9.1 Hz), 6.9-7.0 (1H, m) |
| 149 | —H | —H | —H | —H | —H | (6-methyl-naphthalene) | $^1$H-NMR (CDCl$_3$) δppm: 1.41 (9H, s), 1.8-2.0 (1H, m), 2.05-2.3 (1H, m), 3.1-3.4 (3H, m), 3.7-3.95 (1H, m), 4.5-4.7 (1H, m), 6.85-7.0 (3H, m), 7.08 (1H, dd, J = 7,7 Hz), 7.2-7.5 (5H, m), 7.6-7.8 (3H, m). |
| 150 | —H | —H | —H | —H | —H | (1-methyl-naphthalene) | $^1$H-NMR (CDCl$_3$) δppm: 1.40 (9H, d, J = 4.5 Hz), 1.65-1.9 (1H, m), 2.0-2.25 (1H, m), 3.05-3.4 (3H, m), 3.7-4.0 (1H, m), 4.6-4.8 (1H, m), 6.54 (2H, d, J = 8 Hz), 6.65-6.8 (1H, m), 7.0-7.25 (2H, m), 7.31 (1H, d, J = 7 Hz), 7.35-7.6 (3H, m), 7.75-8.0 (3H, m). |

TABLE 17

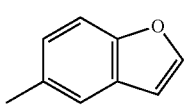

| Ref. Ex. No. | R1 | R2 | R3 | R4 | R5 | R6 | NMR |
|---|---|---|---|---|---|---|---|
| 151 | —H | —H | —H | —H | —H | 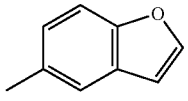 | $^1$H-NMR (CDCl$_3$) δppm: 1.40 (9H, s), 1.75-2.0 (1H, m), 2.0-2.25 (1H, m), 3.1-3.4 (3H, m), 3.65-3.9 (1H, m), 4.45-4.65 (1H, m), 6.65 (2H, d, J = 8 Hz), 6.7-6.85 (2H, m), 7.00 (1H, dd, J = 2, 8,5 Hz), 7.1-7.25 (2H, m), 7.34 (1H, d, J = 2 Hz), 7.50 (1H, dd, J = 3.5, 8.5 Hz), 7.65 (1H, bs). |
| 152 | —H | —H | —F | —Cl | —H | 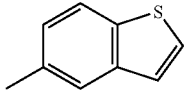 | $^1$H-NMR (CDCl$_3$) δppm 1.40 (9H, s), 1.7-1.9 (1H, m), 2.1-2.3 (1H, m), 3.1-3.4 (3H, m), 3.6-3.9 (1H, m), 4.3-4.5 (1H, m), 6.4-6.6 (1H, m), 6.64 (1H, s), 6.76 (1H, d, J = 7.4 Hz), 6.8-7.1 (2H, m), 7.31 (1H, s), 7.52 (1H, dd, J = 8.9 Hz, J = 9.0 Hz), 7.67 (1H, s) |
| 153 | —H | —H | —F | —Cl | —H | 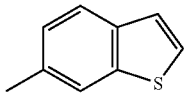 | $^1$H-NMR (CDCl$_3$) δppm 1.41 (9H, s), 1.7-1.9 (1H, m), 2.1-2.3 (1H, m), 3.1-3.4 (3H, m), 3.6-3.8 (1H, m), 4.3-4.5 (1H, m), 6.5-6.7 (1H, m), 6,76 (1H, d, J = 6.2 Hz), 6.9-7.1 2H, m), 7.2-7.3 (1H, m), 7.4-7.6 (2H, m), 7.8-7.9 (1H, m) |
| 154 | —H | —H | —H | —H | —H | 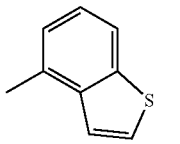 | $^1$H-NMR (CDCl$_3$) δppm: 1.41 (9H, s), 1.8-2.0 (1H, m), 2.0-2.25 (1H, m), 3.1-3.4 (3H, m), 3.65-3.95 (1H, m), 4.4-4.65 (1H, m), 6.82 (2H, dd, J = 1, 8.5 Hz), 6.95 (2H, dd, J = 2, 8.5 Hz), 7.15-7.3 (3H, m), 7.36 (1H, d, J = 5.5 Hz), 7.47 (1H, d, J = 2 Hz), 7.73 (1H, dd, J = 2.5, 8.5 Hz). |
| 155 | —H | —H | —H | —H | —H | 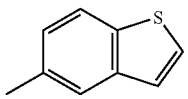 | $^1$H-NMR (CDCl$_3$) δppm: 1.41 (9H, s), 1.75-1.95 (1H, m), 2.0-2.25 (1H, m), 3.1-3.4 (3H, m), 3.7-3.95 (1H, m), 4.5-4.75 (1H, m), 6.59 (2H, d, J = 8 Hz), 6.7-6.8 (1H, m), 7.05-7.25 (4H, m), 7.3-7.5 (2H, m), 7.86 (1H, d, J = 8 Hz). |
| 156 | —H | —H | —H | —H | —H | 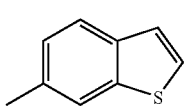 | $^1$H-NMR (CDCl$_3$) δppm: 1.40 (9H, s), 1.75-2.0 (1H, m), 2.0-2.25 (1H, m), 3.1-3.4 (3H, m), 3.7-3.9 (1H, m), 4.45-4.65 (1H, m), 6.76 (2H, d, J = 8 Hz), 6.89 (1H, dd, J = 7.5, 7.5 Hz), 6.99 (1H, dd, J = 2.5, 8,5 Hz), 7.15-7.3 (3H, m), 7.4-7.5 2H, m), 7.82 (1H, dd, J = 3.5, 8.5 Hz). |
| 157 | —H | —H | —F | —Cl | —H | | $^1$H-NMR (CDCl$_3$) δppm: 1.41 (9H, s), 1.75-2.0 (1H, m), 2.0-2.25 (1H, m), 3.15-3.4 (3H, m), 3.65-3.9 (1H, m), 4.35-4.55 (1H, m), 6.55-6.7 (1H, m), 6.82 (1H, dd, J = 3, 6.5 Hz), 6.85-7.1 (2H, m), 7.30 (1H, d, J = 5.5 Hz), 7.41 (1H, d, J = 5.5 Hz), 7.48 (1H, d, J = 2 Hz), 7.76 (1H. d, J = 9 Hz). |

TABLE 18

| Ref. Ex. No. | R1 | R2 | R3 | R4 | R5 | R6 | NMR |
|---|---|---|---|---|---|---|---|
| 158 | —H | —H | —F | —Cl | —H | 4-methyl-1-(tBuO-C(O))-indol-7-yl | ¹H-NMR (CDCl₃) δppm: 1.41 (9H, s), 1.68 (9H, s), 1.7-1.95 (1H, m), 2.0-2.2 (1H, m), 3.1-3.3 (3H, m), 3.65-3.9 (1H, m), 4.4-4.6 (1H, m), 6.26 (1H, d, J = 4 Hz), 6.35-6.45 (1H, m), 6.60 (1H, dd, J = 3, 6 Hz), 6.8-6.95 (1H, m), 6.99 (1H, d, J = 7.5 Hz), 7.25-7.4 (1H, m), 7.53 (1H, br), 8.15 (1H, d, J = 8.5 Hz). |
| 159 | —H | —H | —F | —Cl | —H | 6-methyl-1-(tBuO-C(O))-indol-7-yl | ¹H-NMR (CDCl₃) δppm: 1.41 (9H, s), 1.63 (9H, s), 1.8-2.0 (1H, m), 2.0-2.25 (1H, m), 3.15-3.4 (3H, m), 3.65-3.85 (1H, m), 4.35-4.45 (1H, m), 6.5-6.65 (2H, m), 6.6-6.8 (1H, m), 6.86 (1H, dd, J = 2, 8.5 Hz), 6.9-7.0 (1H, m), 7.45-7.55 (1H, m), 7.55-7.65 (1H, m), 7.86 (1H, br). |
| 160 | —H | —H | —F | —Cl | —H | 3-methyl-1-(triisopropylsilyl)-indol-7-yl | ¹H-NMR (CDCl₃) δppm: 1.17 (18H. d, J = 7.5 Hz), 1.40 (9H, s), 1.71 (3H, qq, J = 7.5, 7.5 Hz), 1.75-1.95 (1H, m), 2.0-2.25 (1H, m), 3.05-3.35 (3H, m), 3.65-3.95 (1H, m), 4.4-4.6 (1H, m), 6.35-6.5 (1H, m), 6.6-6.75 (1H, m), 6.8-6.95 (1H, m), 7.0-7.3 (4H, m), 7.52 (1H, d, J = 8 Hz). |
| 161 | —H | —H | —F | —Cl | —H | quinolin-3-yl | ¹H-NMR (CDCl₃) δppm 1.42 (9H, s), 1.8-2.0 (1H, m), 2.1-2.3 (1H, m), 3.2-3.5 (3H, m), 3.7-3.9 (1H, m), 4.4-4.6 (1H, m), 6.8-7.0 (1H, m), 7.0-7.2 (2H, m), 7.4-7.8 (4H, m), 8.02 (1H, d, J = 8.2 Hz), 8.41 (1H, s) |
| 162 | —H | —H | —F | —Cl | —H | 2,3-dimethylquinolin-5-yl | ¹H-NMR (CDCl₃) δppm 1.45 (9H, s), 1.90 (3H, s), 2.1-2.2 (1H, m), 2.2-2.3 (1H, m), 3.2-3.5 (3H, m), 3.8-4.0 (1H, m), 4.8-5.0 (1H, m), 6.8-7.0 (1H, m), 7.0-7.1 (2H, m), 7.3-7.5 (1H, m), 7.5-7.7 (2H, m), 7.76 (1H, d, J = 5.9 Hz), 7.9-8.0 (1H, m) |
| 163 | —H | —H | —F | —Cl | —H | 5-methylquinolin-8-yl | ¹H-NMR (CDCl₃) δppm: 1.39 (9H, d, J = 7.5 Hz), 1.65-1.85 (1H, m), 1.95-2.2 (1H, m), 3.05-3.35 (3H, m), 3.6-3.95 (1H, m), 4.5-4.75 (1H, m), 6.25-6.4 (1H, m), 6.57 (1H, dd, J = 3, 6 Hz), 6.75-7.0 (1H, m), 7.3-7.45 (2H, m), 7.78 (1H, dd, J = 7.5, 7.5 Hz), 8.05-8.25 (2H, m), 8.95 (1H, d, J = 3.5 Hz). |
| 164 | —H | —H | —H | —H | —H | 6-methylquinolin-8-yl | ¹H-NMR (CDCl₃) δppm: 1.39 (9H, d, J = 6 Hz), 1.65-1.85 (1H, m), 1.95-2.25 (1H, m), 3.05-3.35 (3H, m), 3.7-3.95 (1H, m), 4.6-4.8 (1H, m), 6.54 (2H, d, J = 8 Hz), 6.65-6.8 (1H, m), 7.05-7.2 (2H, m), 7.3-7.45 (2H, m), 7.77 (1H, dd, J = 7.5, 7.5 Hz), 8.1-8.25 (2H, m), 8.93 (1H, d, J = 3.5 Hz). |

TABLE 18-continued
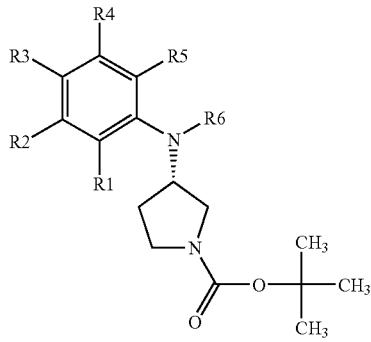
| Ref. Ex. No. | R1 | R2 | R3 | R4 | R5 | R6 | NMR |
|---|---|---|---|---|---|---|---|
| 165 | —H | —H | —F | —Cl | —H | 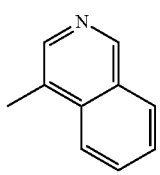 | $^1$H-NMR (CDCl$_3$) δppm<br>1.40 (9H, s), 1.7-1.9 (1H, m), 2.0-2.3 (1H, m), 3.1-3.4 (3H, m), 3.7-3.9 (1H, m), 4.5-4.8 (1H, m), 6.3-6.5 (1H, m), 6.5-6.7 (1H, m), 6.8-7.0 (1H, m), 7.5-7.8 (3H, m), 8.08 (1H, d, J = 6.7 Hz), 8.37 (1H, s), 9.28 (1H, s) |
TABLE 19
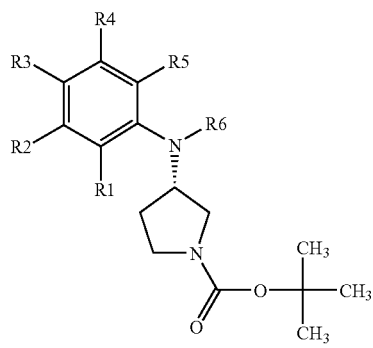
| Ref. Ex. No. | R1 | R2 | R3 | R4 | R5 | R6 | NMR |
|---|---|---|---|---|---|---|---|
| 166 | —H | —H | —H | —H | —H | 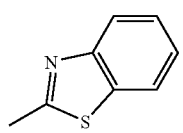 | $^1$H-NMR (CDCl$_3$) δppm 1.43 (9H, s), 1.8-2.0 (1H, m), 2.1-2.4 (1H, m), 3.1-3.4 (3H, m), 3.7-3.9 (1H, m), 5.3-5.5 (1H, m), 7.0-7.1 (1H, m), 7.2-7.4 (3H, m), 7.45 (1H, d, J = 7.7 Hz), 7.4-7.6 (3H, m), 7.61 (1H, dd, J = 8.2 Hz, J = 8.5 Hz) |
| 167 | —H | —H | —F | —Cl | —H | 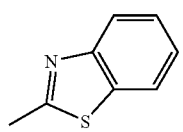 | $^1$H-NMR (CDCl$_3$) δppm 1.44 (9H, s), 1.8-2.0 (1H, m), 2.2-2.4 (1H, m), 3.2-3.5 (3H, m), 3.8-4.0 (1H, m), 5.2-5.4 (1H, m), 7.0-7.4 (4H, m), 7.40 (1H, d, J = 8.0 Hz), 7.50 (1H, d, J = 7.7 Hz), 7.62 (1H, dd, J = 8.2 Hz, J = 8.6 Hz) |
| 168 | —H | —H | —F | —Cl | —H | 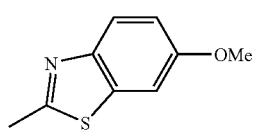 | $^1$H-NMR (CDCl$_3$) δppm<br>1.43 (9H, s), 1.8-2.0 (1H, m), 2.2-2.4 (1H, m), 3.2-3.5 (3H, m), 3.80 (3H, s), 3.8-4.0 (1H, m), 5.2-5.4 (1H, m), 6.92 (1H, d, J = 8.6 Hz), 7.03 (1H, s), 7.1-7.3 (2H, m), 7.39 (1H, d, J = 8.6 Hz), 7.52 (1H, dd, J = 9.0 Hz, J = 9.0 Hz) |

TABLE 19-continued

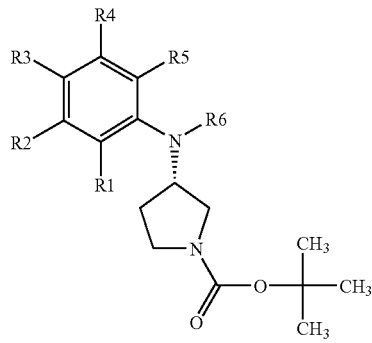

| Ref. Ex. No. | R1 | R2 | R3 | R4 | R5 | R6 | NMR |
|---|---|---|---|---|---|---|---|
| 169 | —H | —H | —F | —Cl | —H | (thieno[3,2-b]pyridin-7-yl) | $^1$H-NMR (CDCl$_3$) δppm 1.44 (9H, s), 1.9-2.1 (1H, m), 2.1-2.3 (1H, m), 3.2-3.4 (3H, m), 3.7-3.9 (1H, m), 4.6-4.8 (1H, m), 6.77 (1H, d, J = 5.6 Hz), 7.1-7.2 (2H, m), 7.29 (1H, d, J = 6.4 Hz), 7.37 (1H, d, J = 5.6 Hz), 7.45 (1H, d, J = 5.6 Hz), 8.49 (1H, d, J = 5.6 Hz) |
| 170 | —H | —H | —H | —F | —H | (3-thienyl) | $^1$H-NMR (CDCl$_3$) δppm 1.43 (9H, s), 1.82-2.00 (1H, m), 2.03-2.25 (1H, m), 3.10-3.39 (3H, m), 4.32-4.50 (1H, m), 6.37 (1H, dt, J = 2.3 Hz and 12.2 Hz), 6.41-6.57 (2H, m), 6.76 (1H, dd, J = 1.4 Hz and J = 5.1 Hz), 6.96 (1H ,dd, J = 1.4 Hz and J = 3.1 Hz), 7.06-7.18 (1H, m . . . |
| 171 | —H | —H | —F | —Cl | —H | (1-triisopropylsilyl-3-pyrrolyl) | $^1$H-NMR (CDCl$_3$) δppm 1.11 (18H, d, J = 7.4 Hz), 1.43 (9H, s), 1.77-2.21 (2H, m), 3.07-3.35 (3H, m), 3.59-3.82 (1H, m), 4.26-4.42 (1H, m), 5.97-6.02 (1H, m), 6.43-6.58 (2H, m), 6.62-6.70 (1H, m), 6.76 (1H, s), 6.83-6.95 (1H, m) |

TABLE 20

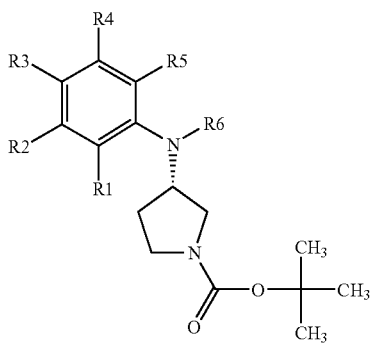

| Ref. Ex. No. | R1 | R2 | R3 | R4 | R5 | R6 | NMR |
|---|---|---|---|---|---|---|---|
| 172 | —H | —H | —Cl | —Cl | —H | (2-methyl-5-thiazolyl) | $^1$H-NMR (CDCl$_3$) δppm 1.42 (9H, s), 1.81-2.011 (1H, m), 2.03-2.31 (1H, m), 2.23 (3H, d, J = 1.0 Hz), 3.12-3.38 (3H, m), 3.69-3.85 (1H, m), 4.89-5.01 (1H, m), 6.85 (1H, brs), 7.11 (1H, dd, J = 2.5 Hz, 8.5 Hz), 7.37 (1H, d, J = 2.5 Hz), 7.51-7.54 (1H, m) |
| 173 | —H | —H | —F | —Cl | —H | (2-methyl-thiazol-4-yl) | $^1$H-NMR (CDCl$_3$) δppm 1.43 (9H, s), 1.81-2.00 (1H, m), 2.10-2.40 (1H, m), 3.11-3.41 (3H, m), 3.68-3.88 (1H, m), 4.99-5.13 (1H, m), 6.51 (1H, d, J = 3.5 Hz), 7.12-7.31 (3H, m), 7.35 (1H, dd, J = 6.5 Hz and J = 2.5 Hz) |

TABLE 20-continued

| Ref. Ex. No. | R1 | R2 | R3 | R4 | R5 | R6 | NMR |
|---|---|---|---|---|---|---|---|
| 174 | —H | —H | —Cl | —Cl | —H | 2-thiazolyl | $^1$H-NMR (CDCl$_3$) δppm 1.43 (9H, s), 1.83-2.03 (1H, m), 2.11-2.35 (1H, m), 3.18-3.42 (3H, m), 3.73-3.87 (1H, m), 4.97-5.09 (1H, m), 6.53 (1H, d, J = 3.5 Hz), 7.14 (1H, dd, J = 2.5 Hz, 8.5 Hz), 7.22 (1H, brs), 7.39(1H, d, J = 2.5 Hz), 7.56 (1H, brd, J = 8.5 Hz) |
| 175 | —H | —H | —F | —Cl | —H | 5-methyl-2-thiazolyl | $^1$H-NMR (CDCl$_3$) δppm 1.42 (9H, s), 1.80-2.03 (1H, m), 2.08-2.22 (1H, m), 2.22 (3H, s), 3.13-3.38 (3H, m), 3.68-3.85 (1H, m), 4.98 (1H, tt, J = 6.5 Hz, 6.5 Hz), 6.84 (1H, brs), 7.11-7.23 (2H, m), 7.33 (1H, dd, J = 2.5 Hz, 6.5 Hz) |
| 176 | —H | —H | —F | —H | —H | 2-thiazolyl | $^1$H-NMR (CDCl$_3$) δppm 1.42 (9H, s), 1.76-2.03 (1H, m), 2.08-2.33 (1H, m), 3.08-3.42 (3H, m), 3.71-3.87 (1H, m), 5.03-5.20 (1H, m), 6.47 (1H, d, J = 3.5 Hz), 7.11-7.32 (5H, m) |
| 177 | —H | —H | —F | —Cl | —H | 5-pyrimidinyl | $^1$H-NMR (CDCl$_3$) δppm 1.43 (9H, s), 1.80-2.00 (1H, m), 2.10-2.31 (1H, m), 3.18-3.42 (3H, m), 3.63-3.80 (1H, m), 4.38-4.50 (1H, m), 6.95-7.05 (1H, m), 7.14-7.30 (2H, m with dd at δ7.17, J = 2.6 Hz and 6.4 Hz), 8.12 (2H, s), 8.72 (1H, s) |
| 178 | —H | —H | —F | —Cl | —H | 2-pyrimidinyl | $^1$H-NMR (CDCl$_3$) δppm 1.44 (9H, s), 1.70-1.90 (1H, m), 2.02-2.21 (1H, m), 3.09-3.41 (3H, m), 3.75-3.90 (1H, m), 5.21-5.38 (1H, m), 6.62 (1H, s), 6.99-7.09 (1H, m), 7.15-7.29 (2H, m), 8.21-8.41 (2H, m) |
| 179 | —H | —H | —F | —Cl | —H | 2-(methylthio)-4-methylpyrimidinyl | $^1$H-NMR (CDCl$_3$) δppm 1.43 (9H, s), 1.7-1.9 (1H, m), 2.1-2.3 (1H, m), 2.53 (3H, s), 3.1-3.4 (3H, m), 3.7-3.9 (1H, m), 5.3-5.5 (1H, m), 5.56 (1H, d, J = 5.7 Hz), 7.0-7.1 (1H, m), 7.2-7.3 (2H, m), 7.91 (1H, d, J = 5.7 Hz) |

TABLE 21

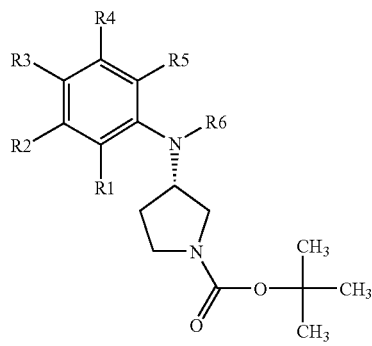

| Ref. Ex. No. | R1 | R2 | R3 | R4 | R5 | R6 | NMR |
|---|---|---|---|---|---|---|---|
| 180 | —H | —H | —F | —Cl | —H | 3-methylpyrazinyl | $^1$H-NMR (CDCl$_3$) δppm 1.43 (9H, s), 1.71-1.90 (1H, m), 2.01-2.25 (1H, m), 3.08-3.40 (3H, m), 3.71-3.89 (1H, m), 5.12-5.39 (1H, m), 7.05-7.13 (1H, m), 7.23-7.33 (2H, m), 7.49 (1H, s), 7.90 (1H, s), 8.09 (1H, s) |
| 181 | —H | —H | —F | —H | —H | 3-methylpyrazinyl | $^1$H-NMR (CDCl$_3$) δppm 1.43 (9H, s), 1.69-1.87 (1H, m), 2.00-2.21 (1H, m), 3.05-3.34 (3H, m), 3.71-3.87 (1H, m), 5.13-5.27 (1H, m), 7.17 (4H, d, J = 5.5 Hz), 7.44 (1H, s), 7.85 (1H, s), 8.08 (1H, s). |
| 182 | —H | —H | —F | —Cl | —H | 5-methyl-2-oxo-1H-pyridinyl | $^1$H-NMR (CDCl$_3$) δppm 1.40 (9H, s), 1.8-1.9 (1H, m), 2.0-2.2 (1H, m), 3.1-3.4 (3H, m), 3.6-3.8 (1H, m), 4.2-4.4 (1H, m), 6.5-6.6 (1H, m), 6.62 (1H, dd, J = 10.0 Hz, J = 9.8 Hz), 6.72 (1H, d, J = 6.0 Hz), 6.9-7.1 (1H, m), 7.2-7.3 (2H, m), 13.17 (1H, brs) |
| 183 | —H | —H | —F | —Cl | —H | 5-methyl-1-benzyl-2-oxopyridinyl | $^1$H-NMR (CDCl$_3$) δppm 1.44 (9H, s), 1.7-1.9 (1H, m), 2.0-2.2 (1H, m), 3.0-3.4 (3H, m), 3.6-3.8 (1H, m), 4.2-4.4 (1H, m), 4.9-5.3 (2H, m), 6.4-6.5 (1H, m), 6.6-6.7 (2H, m), 6.7-7.1 (3H, m), 7.2-7.4 (5H, m) |

TABLE 22

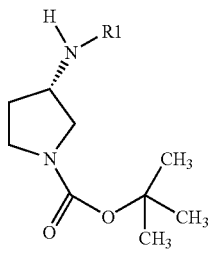

| Ref. Ex. No. | R1 | NMR |
|---|---|---|
| 184 | naphthalen-2-yl | $^1$H-NMR (CDCl$_3$) δppm: 1.47 (9H, s), 2.04 (1H, br), 2.15-2.35 (1H, m), 3.2-3.4 (1H, m), 3.4-3.6 (2H, m), 3.65-3.95 (2H, m), 4.17 (1H, br), 6.81 (1H, d, J = 2.3 Hz), 6.86 (1H, dd, J = 2.4, 8.7 Hz), 7.15-7.3 (1H, m), 7.37 (1H, dd, J = 7.8, 7.8 Hz), 7.55-7.7 (3H, m). |
| 185 | benzofuran-5-yl | $^1$H-NMR (CDCl$_3$) δppm: 1.47 (9H, s), 1.91 (1H, br), 2.1-2.3 (1H, m), 3.1-3.35 (1H, m), 3.35-3.85 (4H, m), 4.05 (1H, br), 6.55-6.7 (2H, m), 6.77 (1H, d, J = 2.3 Hz), 7.31 (1H, d, J = 8.8 Hz), 7.54 (1H, d, J = 2.0 Hz). |

TABLE 22-continued

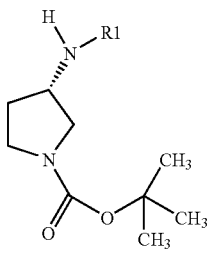

| Ref. Ex. No. | R1 | NMR |
|---|---|---|
| 186 | 3-chloro-6-methylbenzothiophene | ¹H-NMR (CDCl₃) δppm: 1.47 (9H, s), 1.93 (1H, br), 2.15-2.3 (1H, m), 3.15-3.4 (1H, m), 3.4-3.6 (2H, m), 3.65-3.85 (1H, m), 3.85-4.0 (1H, m), 4.0-4.2 (1H, m), 6.75 (1H, dd, J = 2.1, 8.7 Hz), 6.9-7.0 (2H, m), 7.60 (1H, d, J = 8.6 Hz). |
| 187 | 3-chloro-5-methylbenzothiophene | ¹H-NMR (CDCl₃) δppm: 1.47 (9H, s), 1.85-2.05 (1H, m), 2.15-2.35 (1H, m), 3.2-3.4 (1H, m), 3.4-3.6 (2H, m), 3.65-3.9 (2H, m), 4.16 (1H, br), 6.76 (1H, dd, J = 2.2, 8.6 Hz), 6.96 (1H, d, J = 2.3 Hz), 7.26 (1H, s), 7.59 (1H, d, J = 8.6 Hz). |
| 188 | 3,6-dimethylbenzothiophene | ¹H-NMR (CDCl₃) δppm: 1.47 (9H, s), 1.85-2.0 (1H, m), 2.1-2.3 (1H, m), 2.36 (3H, d, J = 1.1 Hz), 3.1-3.35 (1H, m), 3.4-3.6 (2H, m), 3.65-3.85 (2H, m), 4.0-4.2 (1H, m), 6.71 (1H, dd, J = 2.2, 8.6 Hz), 6.76 (1H, d, J = 0.8 Hz), 7.01 (1H, d, J = 2.1 Hz), 7.49 (1H, d, J = 8.6 Hz). |
| 189 | 3,5-dimethylbenzothiophene | ¹H-NMR (CDCl₃) δppm: 1.47 (9H, s), 1.85-2.0 (1H, m), 2.15-2.3 (1H, m), 2.37 (3H, s), 3.15-3.35 (1H, m), 3.4-3.6 (2H, m), 3.65-3.85 (2H, m), 4.05-4.25 (1H, m), 6.72 (1H, dd, J = 2.2, 8.6 Hz), 6.85 (1H, d, J = 2.1 Hz), 7.03 (1H, s), 7.61 (1H, d, J = 8.5 Hz). |
| 190 | 4-chloro-6-methylbenzothiophene | ¹H-NMR (CDCl₃) δppm: 1.65 (9H, s), 2.04 (1H, br), 2.1-2.3 (1H, m), 3.15-3.35 (1H, m), 3.35-3.6 (2H, m), 3.6-3.8 (1H, m), 3.8-3.95 (1H, m), 3.95-4.1 (1H, m), 6.71 (1H, d, J = 1.9 Hz), 6.90 (1H, d, J = 1.5 Hz), 7.15 (1H, d, J = 5.5 Hz), 7.30 (1H, d, J = 5.7 Hz). |
| 191 | 4-methylbenzothiophene | ¹H-NMR (CDCl₃) δppm: 1.47 (9H, s), 1.9-2.1 (1H, m), 2.05-2.35 (1H, m), 3.2-3.65 (3H, m), 3.65-3.9 (1H, m), 4.0-4.3 (2H, m), 6.53 (1H, d, J = 7.4 Hz), 7.15-7.4 (4H, m). |
| 192 | 2-methyl-6-methylbenzothiophene | ¹H-NMR (CDCl₃) δppm: 1.47 (9H, s), 1.91 (1H, br), 2.0-2.3 (1H, m), 2.51 (3H, d, J = 0.9 Hz), 3.15-3.35 (1H, m), 3.35-3.6 (2H, m), 3.6-3.85 (2H, m), 4.07 (1H, br), 6.62 (1H, dd, J = 2.2, 8.5 Hz), 6.80 (1H, s), 6.93 (1H, d, J = 2.1 Hz), 7.42 (1H, d, J = 8.5 Hz). |

TABLE 23

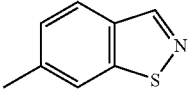

| Ref. Ex. No. | R1 | NMR |
|---|---|---|
| 193 | 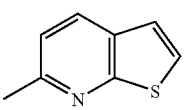 | ¹H-NMR (CDCl₃) δppm: 1.47 (9H, s), 1.97 (1H, br), 2.15-2.3 (1H, m), 3.15-3.4 (1H, m), 3.4-3.6 (2H, m), 3.65-3.85 (1H, m), 4.0-4.25 (2H, m), 6.70 (1H, dd, J = 2.0, 8.7 Hz), 6.96 (1H, d, J = 1.5 Hz), 7.79 (1H, d, J = 8.7 Hz), 8.65 (1H, s). |
| 194 | | ¹H-NMR (CDCl₃) δppm: 1.47 (9H, s), 1.8-2.0 (1H, m), 2.15-2.35 (1H, m), 3.15-3.6 (3H, m), 3.7-3.85 (1H, m), 4.4-4.65 (2H, m), 6.43 (1H, d, J = 8.6 Hz), 7.07 (2H, s), 7.76 (1H, d, J = 8.6 Hz). |
| 195 | | ¹H-NMR (CDCl₃) δppm: 1.47 (9H, s), 1.93 (1H, br), 2.17-2.29 (1H, m), 3.27 (1H, br), 3.49 (2H, br), 3.69 (3H, s), 3.92 (2H, br), 4.08 (1H, br), 6.69 (1H, d, J = 9.6 Hz), 6.71 (1H, d, J = 2.9 Hz), 6.91 (1H, dd, J = 9.0 Hz), 7.23 (1H, d, J = 2.9, 9.0 Hz), 7.55 (1H, d, J = 9.6 Hz). |

TABLE 24

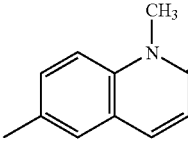

| Ref. Ex. No. | R1 | R2 | R3 | R4 | R5 | NMR |
|---|---|---|---|---|---|---|
| 196 | —H | —H | —F | —F | —H | ¹H-NMR (CDCl₃) δppm: 1.47 (9H, s), 1.76-1.95 (1H, m), 2.09-2.25 (1H, m), 3.11-3.32 (1H, m), 3.36-3.56 (2H, m), 3.58-3.78 (2H, m), 3.85-4.03 (1H, m), 6.19-6.30 (1H, m), 6.34-6.43 (1H, m), 6.96 (1H, dd, J = 9.0, 19.0 Hz) |
| 197 | —H | —Cl | —H | —Cl | —H | ¹H-NMR (CDCl₃) δppm: 1.47 (9H, s), 1.77-1.95 (1H, m), 2.02-2.27 (1H, m), 3.15-3.75 (3H, m), 3.87-4.02 (2H, m), 6.45-6.46 (2H, m), 6.68-6.70 (1H, m). |
| 198 | —H | —H | —Cl | —CH₃ | —H | ¹H-NMR (DMSO-d₆) δppm: 1.39 (9H, s), 1.64-1.85 (1H, m), 2.00-2.18 (1H, m), 2.21 (3H, s), 2.97-3.10 (1H, m), 3.22-3.39 (2H, m), 3.42-3.60 (1H, m), 3.78-3.96 (1H, m), 5.89 (1H, d, J = 6.8 Hz), 6.43 (1H, dd, J = 8.6, 2.5 Hz), 6.55 (1H, d, J = 2.5 Hz), 7.06 (1H, d, J = 8.6 Hz). |
| 199 | —H | —OCH₃ | —F | —F | —H | ¹H-NMR (DMSO-d₆) δppm: 1.39 (9H, s), 1.60-1.82 (1H, m), 1.93-2.17 (1H, m), 2.92-3.10 (1H, m), 3.20-3.44 (1H, m), 3.48-3.57 (1H, m), 3.75 (3H, s), 3.80-4.00 (1H, m), 6.01-8.19 (2H, m). |

TABLE 24-continued

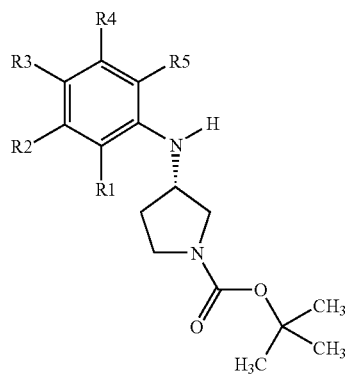

| Ref. Ex. No. | R1 | R2 | R3 | R4 | R5 | NMR |
|---|---|---|---|---|---|---|
| 200 | —H | —F | —F | —F | —H | $^1$H-NMR (CDCl$_3$) δppm: 1.47 (9H, s), 1.74-1.92 (1H, m), 2.08-2.21 (1H, m), 3.08-3.28 (1H, m), 3.33-3.51 (2H, m), 3.61-3.95 (2H, m), 6.08-6.21 (2H, m). |
| 201 | —H | —F | —Cl | —F | —H | $^1$H-NMR (CDCl$_3$) δppm: 1.45 (9H, s), 1.78-1.93 (1H, m), 2.03-2.24 (1H, m), 3.09-3.31 (1H, m), 3.36-3.52 (2H, m), 3.60-3.75 (1H, m), 3.85-4.08 (1H, m), 6.15-6.24 (2H, m). |
| 202 | —H | —H | —CH$_3$ | —F | —H | $^1$H-NMR (CDCl$_3$) δppm: 1.46 (9H, s), 1.87 (1H, br), 2.14-2.23 (1H, m), 2.15 (3H, d, J = 1.4 Hz), 3.21 (1H, br), 3.45 (2H, br), 3.68 (2H, br), 3.97 (1H, br), 6.26-6.31 (2H, m), 6.95 (1H, dd, J = 8.5, 10.7 Hz). |
| 203 | —H | —H | —Cl | —H | —H | $^1$H-NMR (CDCl$_3$) δppm 1.46 (9H, s), 1.78-1.96 (1H, m), 2.10-2.20 (1H, m), 3.11-3.30 (1H, m), 3.40-3.56 (2H, m), 3.60-3.80 (2H, m), 3.85-4.03 (1H, m), 6.52 (2H, d, J = 8.7 Hz), 7.12 (1H, d, 8.7 Hz) |

TABLE 25

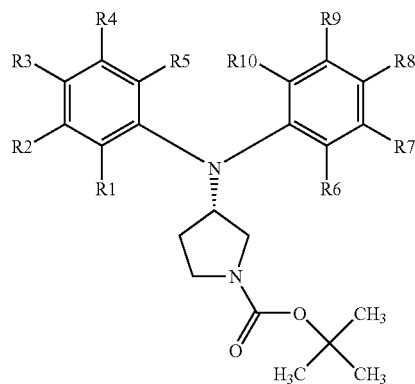

| Ref. Ex. No. | R1 | R2 | R3 | R4 | R5 | R6 | R7 | R8 | R9 | R10 | NMR |
|---|---|---|---|---|---|---|---|---|---|---|---|
| 204 | —H | —H | —F | —Cl | —H | —CH$_3$ | —H | —F | —H | —H | $^1$H-NMR (CDCl$_3$) δppm: {1.42 (s), 1.44 (s) total 9 H, 1:1}, 1.71-1.89 (1 H, m), 2.03-2.19 (1 H, m), 2.08 (3 H, s), 3.12-3.36 (3 H, m), 3.61-3.82 (1 H, m), 4.32-4.45 (1 H, m), 6.23-6.29 (1 H, m), 6.46 (1 H, dd, J = 3.0, 6.0 Hz), 6.86-7.07 (4 H, m) |
| 205 | —H | —H | —F | —F | —H | —H | —F | —F | —H | —H | $^1$H-NMR (CDCl$_3$) δppm: 1.43 (9 H, s), 1.73-1.92 (1 H, m), 2.00-2.22 (1 H, m), 3.11-3.36 (3 H, m), 3.59-3.78 (1 H, m), 4.25-4.41 (1 H, m), 6.51-6.72 (4 H, m), 7.09 (2 H, dd, J = 8.5, 18.0 Hz) |

TABLE 26

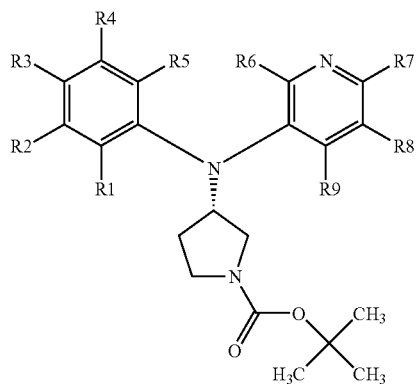

| Ref. Ex. No. | R1 | R2 | R3 | R4 | R5 | R6 | R7 | R8 | R9 | NMR |
|---|---|---|---|---|---|---|---|---|---|---|
| 206 | —H | —Cl | —Cl | —H | —H | —H | —H | —H | —H | $^1$H-NMR (CDCl$_3$) δppm; 1.43 (9 H, s), 1.79-1.90 (1 H, m), 2.10-2.20 (1 H, m), 3.15-3.33 (3 H, m), 3.67-3.84 (1 H, m), 4.39-4.52 (1 H, m), 6.63 (1 H, dd, J = 2.7, 8.8 Hz), 6.89 (1 H, d, J = 2.7 Hz), 7.24-7.32 (3 H, m), 8.28 (1 H, brs), 8.42 (1 H, brs). |
| 207 | —H | —Cl | —F | —H | —H | —H | —H | —H | —CH$_3$ | $^1$H-NMR (CDCl$_3$) δppm; 1.44 (9 H, s), 1.74-1.89 (1 H, m), 2.04-2.20 (1 H, m), 2.12 (3 H, s), 3.13-3.21 (1H, m), 3.24-3.38 (2 H, m), 3.69-3.85 (1 H, m), 4.39-4.55 (1 H, m), 6.25-6.36 (1 H, m), 6.52 (1 H, dd, J = 3.1, 6.0 Hz), 6.90-6.98 (1 H, m), 7.25-7.28 (1 H, m), 8.30 (1 H, s), 8.48 (1 H, d, J = 4.8 Hz). |
| 208 | —H | —Cl | —Cl | —H | —H | —H | —H | —H | —CH$_3$ | $^1$H-NMR (CDCl$_3$) δppm; 1.43 (9 H, s), 1.70-1.86 (1 H, m), 2.04-2.28 (1 H, m), 2.12 (3 H, s), 3.14-3.21 (1 H, m), 3.23-3.35 (2 H, m), 3.68-3.84 (1 H, m), 4.43-4.51-5.35 (1 H, m), 6.29 (1 H, d, 8.7 Hz), 6.56 (1 H, d, J = 2.9 Hz), 7.16-7.20 (1 H, m), 7.27-7.30 (1 H, m), 8.29 (1 H, s), 8.50 (1 H, d, J = 4.7 Hz). |

TABLE 27

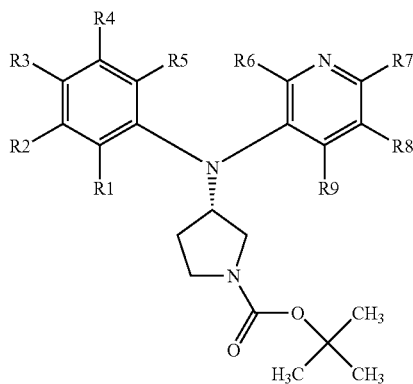

| Ref. Ex. No. | R1 | R2 | R3 | R4 | R5 | R6 | R7 | R8 | R9 | NMR |
|---|---|---|---|---|---|---|---|---|---|---|
| 209 | —H | —Cl | —H | —Cl | —H | —H | —H | —H | —H | $^1$H-NMR (CDCl$_3$) δppm: 1.43 (9 H, s), 1.72-1.89 (1 H, m), 2.08-2.24 (1 H, m), 3.09-3.32 (3 H, m), 3.67-3.84 (1 H, m), 4.38-4.52 (1 H, m), 6.52-6.53 (2 H, m), 6.87-6.89 (1 H, m), 7.35-7.40 (2 H, m), 8.34-8.35 (1 H, m), 8.54-8.56 (1 H, m). |
| 210 | —H | —CH$_3$ | —Cl | —H | —H | —H | —H | —H | —H | $^1$H-NMR (CDCl$_3$) δppm: 1.43 (9 H, s), 1.79-1.92 (1 H, m), 2.04-2.22 (1 H, m), 2.34 (3 H, s), 3.15-3.38 (3 H, m), 6.76 (1 H, dd, J = 8.4, 2.5 Hz), 6.85 (1 H, d, J = 2.5 Hz), 6.97-7.05 (1 H, m), 6.87-6.89 (1 H, dd, J = 8.4, 4.6 Hz), 7.27-7.35 (1 H, m), 8.09-8.145 (1 H, m), 8.18 (1 H, d, J = 3.8 Hz). |

TABLE 27-continued

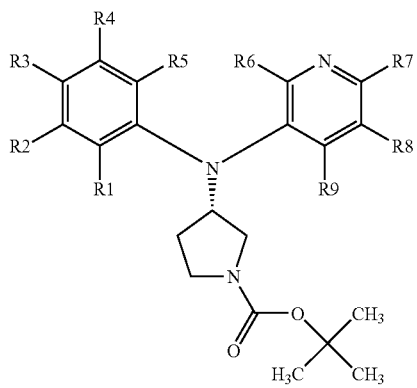

| Ref. Ex. No. | R1 | R2 | R3 | R4 | R5 | R6 | R7 | R8 | R9 | NMR |
|---|---|---|---|---|---|---|---|---|---|---|
| 211 | —H | —Cl | —F | —H | —H | —H | —H | —F | —H | $^1$H-NMR (CDCl$_3$) δppm: 1.43 (9 H, s), 1.8-1.95 (1 H, m), 2.05-2.3 (1 H, m), 3.15-3.4 (3 H, m), 3.65-3.8 (1 H, m), 4.35-4.5 (1 H, m), 6.59 (1 H, d, J = 10.2 Hz), 6.95-7.05 (1 H, m), 7.1-7.3 (2 H, m), 7.84 (1 H, br), 7.96 (1 H, d, J = 2.1 Hz). |
| 212 | —H | —CH$_3$ | —F | —H | —H | —H | —H | —F | —H | $^1$H-NMR (CDCl$_3$) δppm: 1.43 (9 H, s), 1.8-1.95 (1 H, m), 2.05-2.25 (1 H, m), 2.29 (3 H, s), 3.15-3.35 (3 H, m), 3.65-3.8 (1 H, m), 4.35-4.5 (1 H, m), 6.45-6.55 (1 H, m), 6.85-6.95 (2 H, m), 7.0-7.15 (1 H, m), 7.79 (1 H, br), 7.87 (1 H, d, J = 1.9 Hz). |
| 213 | —H | —H | —F | —H | —H | —H | —H | —F | —H | $^1$H-NMR (CDCl$_3$) δppm: 1.43 (9 H, s), 1.8-1.95 (1 H, m), 2.05-2.25 (1 H, m), 3.1-3.35 (3 H, m), 3.65-3.8 (1 H, m), 4.35-4.5 (1 H, m), 6.45-6.55 (1 H, m), 7.05-7.2 (4 H, m), 7.80 (1 H, br), 7.88 (1 H, d, J = 2.1 Hz). |

TABLE 28

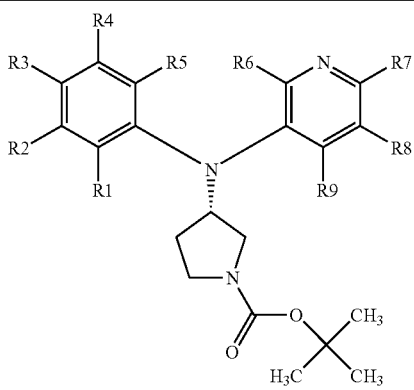

| Ref. Ex. No. | R1 | R2 | R3 | R4 | R5 | R6 | R7 | R8 | R9 | NMR |
|---|---|---|---|---|---|---|---|---|---|---|
| 214 | —H | —Cl | —F | —H | —H | —H | —H | —F | —H | $^1$H-NMR (CDCl$_3$) δppm: 1.43 (9 H, s), 1.8-1.95 (1 H, m), 2.05-2.3 (1 H, m), 3.15-3.4 (3 H, m), 3.65-3.8 (1 H, m), 4.35-4.5 (1 H, m), 6.59 (1 H, d, J = 10.2 Hz), 6.95-7.05 (1 H, m), 7.1-7.3 (2 H, m), 7.84 (1 H, br), 7.96 (1 H, d, J = 2.1 Hz). |
| 215 | —H | —CH$_3$ | —F | —H | —H | —H | —H | —F | —H | $^1$H-NMR (CDCl$_3$) δppm: 1.43 (9 H, s), 1.8-1.95 (1 H, m), 2.05-2.25 (1 H, m), 2.29 (3 H, s), 3.15-3.35 (3 H, m), 3.65-3.8 (1 H, m), 4.35-4.5 (1 H, m), 6.45-6.55 (1 H, m), 6.85-6.95 (2 H, m), 7.0-7.15 (1 H, m), 7.79 (1 H, br), 7.87 (1 H, d, J = 1.9 Hz). |

TABLE 28-continued

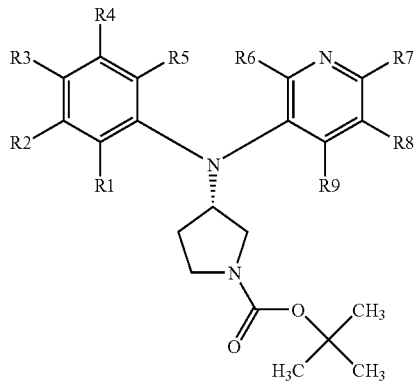

| Ref. Ex. No. | R1 | R2 | R3 | R4 | R5 | R6 | R7 | R8 | R9 | NMR |
|---|---|---|---|---|---|---|---|---|---|---|
| 216 | —H | —H | —F | —H | —H | —H | —H | —F | —H | $^1$H-NMR (CDCl$_3$) δppm: 1.43 (9 H, s), 1.8-1.95 (1 H, m), 2.05-2.25 (1 H, m), 3.1-3.35 (3 H, m), 3.65-3.8 (1 H, m), 4.35-4.5 (1 H, m), 6.45-6.55 (1 H, m), 7.05-7.2 (4 H, m), 7.80 (1 H, br), 7.88 (1 H, d, J = 2.1 Hz). |

TABLE 29

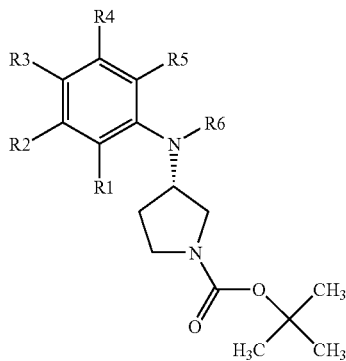

| Ref. Ex. No. | R1 | R2 | R3 | R4 | R5 | R6 | NMR |
|---|---|---|---|---|---|---|---|
| 217 | —H | —H | —Cl | —Cl | —H | 5-chloro-2-methylpyridin-3-yl | $^1$H-NMR (CDCl$_3$) δppm: 1.43 (9 H, s), 1.75-1.89 (1 H, m), 2.03-2.20 (1 H, m), 3.08-3.33 (3 H, m), 3.80 (1 H, dd, J = 7.1, 10.9 Hz), 5.17-5.29 (1 H, m), 6.00 (1 H, d, J = 9.0 Hz), 7.03 (1 H, dd, J = 2.4, 8.4 Hz), 7.25 (1 H, dd, J = 2.2, 9.0 Hz), 7.29 (1 H, d, J = 2.2 Hz), 7.52-7.57 (1 H, dd, J = 4.7, 8.3 Hz), 8.13 (1 H, d, J = 4.7 Hz). |
| 218 | —H | —H | —F | —Cl | —H | 3-chloro-2-methylpyridin-? | $^1$H-NMR (CDCl$_3$) δppm: 1.44 (9 H, s), 1.80-2.21 (2 H, m), 3.20-3.47 (3 H, m), 3.57-3.78 (1 H, m), 4.68-4.74 (1 H, m), 6.85-7.03 (4 H, m), 7.55-7.59 (1 H, m), 8.29-8.32 (1 H, m). |
| 219 | —H | —H | —F | —Cl | —H | 6-methyl-5-(3-chlorophenyl)pyridin-3-yl | $^1$H-NMR (CDCl$_3$) δppm: 1.44 (9 H, s), 1.71-1.89 (1 H, m), 2.04-2.28 (1 H, m), 3.10-3.34 (3 H, m), 3.85 (1 H, dd, J = 7.5, 10.3 Hz), 5.35-5.43 (1 H, m), 6.08 (1 H, d, J = 8.8 Hz), 7.07-7.12 (1 H, m), 7.26-7.36 (5 H, m), 7.46-7.51 (2 H, m), 8.42 (1 H, d, J = 5.9 Hz). |

TABLE 29-continued

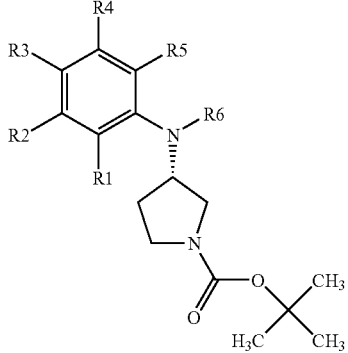

| Ref. Ex. No. | R1 | R2 | R3 | R4 | R5 | R6 | NMR |
|---|---|---|---|---|---|---|---|
| 220 | —H | —H | —F | —Cl | —H | 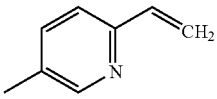 | $^1$H-NMR (CDCl$_3$) δppm: 1.43 (9 H, s), 1.80-1.93 (1 H, m), 2.05-2.21 (1 H, m), 3.14-3.35 (3 H, m), 3.67-3.82 (1 H, m), 4.35-4.46 (1 H, m), 5.36 (1 H, d, J = 10.8 Hz), 6.05 (1 H, d, J = 17.4 Hz), 6.75 (1 H, dd, J = 10.8, 17.4 Hz), 6.83-6.89 (1 H, m), 7.02-7.19 (3 H, m), 7.24 (1 H, d, J = 8.6 Hz), 8.09 (1 H, s). |
| 221 | —H | —H | —Cl | —Cl | —H | 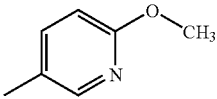 | $^1$H-NMR (CDCl$_3$) δppm: 1.32 (9 H, s), 1.75-1.89 (1 H, m), 2.08-2.20 (1 H, m), 3.07-3.32 (3 H, m), 3.67-3.81 (1 H, m), 3.97 (3 H, s), 4.38-4.46 (1 H, m), 6.42 (1 H, dd, J = 2.9, 9.0 Hz), 6.66 (1 H, d, J = 2.9 Hz), 6.81 (1 H, dd, J = 3.1, 8.4 Hz), 7.17 (1 H, d, J = 6.8 Hz), 7.30 (1 H, dd, J = 2.7, 8.8 Hz), 7.94 (1 H, d, 2.3 Hz). |
| 222 | —H | —H | —F | —Cl | —H | 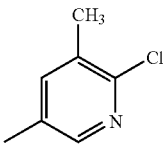 | $^1$H-NMR (CDCl$_3$) δppm: 1.43 (9 H, s), 1.80-1.93 (1 H, m), 2.15-2.20 (1 H, m), 2.29 (3 H, s), 3.18-3.39 (3 H, m), 3.63-3.77 (1 H, m), 4.41 (1 H, brs), 6.85-6.91 (2 H, m), 7.03-7.07 (1 H, m), 7.11-7.18 (1 H, m), 7.73 (1 H, brs). |
| 223 | —H | —H | —F | —Cl | —H | 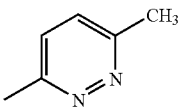 | $^1$H-NMR (CDCl$_3$) δppm: 1.43 (9 H, s), 1.78-1.92 (1 H, m), 2.09-2.36 (1 H, m), 2.55 (3 H, s), 3.15-3.32 (3 H, m), 3.68-3.99 (1 H, m), 5.31-5.52 (1 H, m), 6.24 (1 H, d, J = 9.2 Hz), 6.96 (1 H, d, J = 9.2 Hz), 7.06 (1 H, ddd, J = 2.6, 4.2, 8.6 Hz), 7.15-7.27 (1 H, m), 7.55-7.59 (1 H, m). |
| 224 | —H | —H | —F | —Cl | —H | 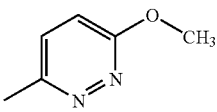 | $^1$H-NMR (CDCl$_3$) δppm: 1.43 (9 H, s), 1.78-1.97 (1 H, m), 2.08-2.36 (1 H, m), 3.12-3.32 (3 H, m), 3.67-3.96 (1 H, m), 4.05 (3 H, s), 5.14-5.33 (1 H, m), 6.39 (1 H, d, J = 9.6 Hz), 6.72 (1 H, d, J = 9.6 Hz), 7.07 (1 H, ddd, J = 2.6, 4.2, 8.6 Hz), 7.11-7.32 (2 H, m). |

TABLE 30

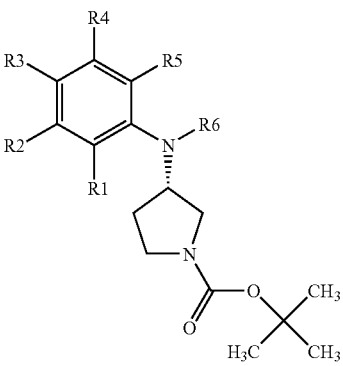

| Ref. Ex. No. | R1 | R2 | R3 | R4 | R5 | R6 | NMR |
|---|---|---|---|---|---|---|---|
| 225 | —H | —H | —F | —Cl | —H | 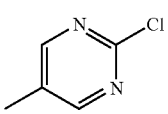 | ¹H-NMR (CDCl₃) δppm: 1.43 (9 H, s), 1.81-1.95 (1 H, m), 2.10-2.35 (1 H, m), 3.12-3.30 (3 H, m), 3.74-3.95 (1 H, m), 5.34-5.45 (1 H, m), 6.31 (1 H, d, J = 9.4 Hz), 7.06-7.10 (2 H, m), 7.21-7.33 (2 H, m). |
| 226 | —H | —H | —F | —Cl | —H | 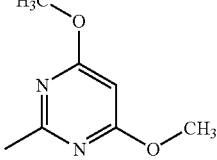 | ¹H-NMR (CDCl₃) δppm: 1.43 (9 H, s), 1.84-1.99 (1 H, m), 2.10-2.99 (1 H, m), 3.12-3.38 (3 H, m), 3.70-3.76 (1 H, m), 4.36-4.45 (1 H, m), 7.02 (1 H, ddd, J = 2.7, 4.1, 8.6 Hz), 7.20 (1 H, dd, J = 2.5, 6.4 Hz), 7.21-7.28 (1 H, m), 7.97 (2 H, m). |
| 227 | —H | —H | —F | —Cl | —H | 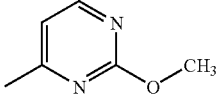 | ¹H-NMR (CDCl₃) δppm: 1.44 (9 H, s), 1.80-1.95 (1 H, m), 2.04-2.20 (1 H, m), 3.20-3.40 (3 H, m), 3.70 (6 H, s), 3.77-3.88 (1 H, m), 5.21-5.30 (1 H, m), 5.46 (1 H, s), 7.02 (1 H, ddd, J = 2.5, 4.3, 8.7 Hz), 7.13-7.19 (1 H, m), 7.24 (1 H, dd, J = 2.4, 6.6 Hz). |
| 228 | —H | —H | —F | —Cl | —H | 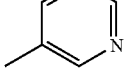 | ¹H-NMR (CDCl₃) δppm: 1.43 (9 H, s), 1.70-1.88 (1 H, m), 1.97-2.20 (1 H, m), 3.07-3.30 (3 H, m), 3.72-3.82 (1 H, m), 3.83 (3 H, s), 3.96 (3 H, s), 4.86 (1 H, s), 5.37-5.41 (1 H, m), 7.05 (1 H, ddd, J = 2.6, 4.2, 8.7 Hz), 7.21-7.31 (2 H, m). |
| 229 | —H | —H | —F | —H | —H | 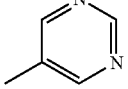 | ¹H-NMR (CDCl₃) δppm: 1.43 (9 H, s), 1.86-1.96 (1 H, m), 2.16-2.28 (1 H, m), 3.10-3.35 (3 H, m), 3.72-3.77 (1 H, m), 4.41-4.51 (1 H, m), 7.09-7.71 (4 H, m), 8.07 (2 H, s), 8.64 (1 H, s). |
| 230 | —H | —H | —F | —CH₃ | —H | 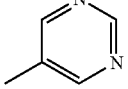 | ¹H-NMR (CDCl₃) δppm: 1.43 (9 H, s), 1.85-1.97 (1 H, m), 2.05-2.28 (1 H, m), 2.29 (3 H, s), 3.20-3.35 (3 H, m), 3.70-3.78 (1 H, m), 4.43-4.47 (1 H, m), 6.89-7.97 (2 H, m), 7.06-7.13 (1 H, m), 8.06 (2 H, s), 8.63 (1 H, s). |
| 231 | —H | —H | —Cl | —Cl | —H | 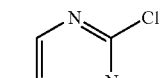 | ¹H-NMR (CDCl₃) δppm: 1.43 (9 H, s), 1.81-1.96 (1 H, m), 2.10-2.31 (1 H, m), 3.15-3.39 (3 H, m), 3.63-3.78 (1 H, m), 4.37-4.45 (1 H, m), 6.90 (1 H, dd, J = 2.5, 8.6 Hz), 7.16 (1 H, d, J = 2.4 Hz), 7.51 (1 H, d, J = 8.3 Hz), 8.05 (2 H, s). |
| 232 | —H | —H | —F | —H | —H | 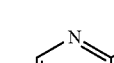 | ¹H-NMR (CDCl₃) δppm: 1.42 (9 H, s), 1.78-1.93 (1 H, m), 2.10-2.96 (1 H, m), 3.09-3.37 (3 H, m), 3.63-3.70 (1 H, m), 4.37-4.45 (1 H, m), 7.07-7.29 (4 H, m), 7.92 (2 H, s). |
| 233 | —H | —H | —F | —CH₃ | —H | 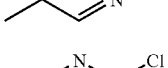 | ¹H-NMR (CDCl₃) δppm: 1.43 (9 H, s), 1.81-1.95 (1 H, m), 2.05-2.27 (1 H, m), 2.29 (3 H, s), 3.19-3.43 (3 H, m), 3.65-3.80 (1 H, m), 4.35-4.43 (1 H, m), 6.90-6.97 (2 H, m), 7.07-7.13 (1 H, m), 7.91 (2 H, s). |

TABLE 31

| Ref. Ex. No. | R1 | R2 | R3 | R4 | R5 | R6 | NMR |
|---|---|---|---|---|---|---|---|
| 234 | —H | —H | —F | —Cl | —H | 2-methyl-4-(trifluoromethyl)pyrimidin-5-yl | $^1$H-NMR (CDCl$_3$) δppm: 1.44 (9 H, s), 1.74-1.90 (1 H, m), 2.08-2.26 (1 H, m), 3.09-3.35 (3 H, m), 3.78-3.88 (1 H, m), 5.20-5.35 (1 H, m), 6.92 (1 H, d, J = 4.8 Hz), 7.04 (1 H, ddd, J = 2.5, 4.2, 8.7 Hz), 7.20-7.25 (2 H, m), 8.47 (1 H, d, J = 4.6 Hz). |
| 235 | —H | —H | —Cl | —Cl | —H | 4-methyl-2-(methylthio)pyrimidin-5-yl | $^1$H-NMR (CDCl$_3$) δppm: 1.43 (9 H, s), 1.77-1.88 (1 H, m), 2.05-2.28 (1 H, m), 2.52 (3 H, s), 3.15-3.33 (3 H, m), 3.70-3.90 (1 H, m), 5.28-5.43 (1 H, m), 5.60 (1 H, d, J = 6.0 Hz), 7.03 (1 H, dd, J = 2.4, 8.5 Hz), 7.29 (1 H, d, J = 2.4 Hz), 7.58 (1 H, d, J = 8.3 Hz), 7.90 (1 H, d, J = 6.0 Hz). |
| 236 | —H | —H | —Cl | —Cl | —H | 2-methylpyrimidin-5-yl | $^1$H-NMR (CDCl$_3$) δppm: 1.44 (9 H, s), 1.75-1.88 (1 H, m), 2.05-2.20 (1 H, m), 3.12-3.36 (3 H, m), 3.77-3.87 (1 H, m), 5.24-5.34 (1 H, m), 6.62 (1 H, brs), 7.02 (1 H, dd, J = 2.4, 8.5 Hz), 7.27 (1 H, d, J = 2.4 Hz), 7.51 (1 H, dd, J = 4.1, 8.4 Hz), 8.32 (2 H, brs). |
| 237 | —H | —H | —F | —Cl | —H | 3-methoxy-2-methylpyrazin-5-yl | $^1$H-NMR (CDCl$_3$) δppm: 1.44 (9 H, s), 1.87-1.96 (1 H, m), 2.04-2.20 (1 H, m), 3.15-3.39 (3 H, m), 3.61 (3 H, s), 3.72-3.84 (1 H, m), 4.77-4.86 (1 H, m), 6.96 (1 H, ddd, J = 2.6, 4.3, 8.7 Hz), 7.06 (1 H, dd, J = 2.6, 8.5 Hz), 7.11 (1 H, dd, J = 2.6, 6.6 Hz), 7.65 (1 H, brs), 7.79 (1 H, d, J = 4.4 Hz). |
| 238 | —H | —H | —F | —Cl | —H | 3,5,6-trimethylpyrazin-2-yl | $^1$H-NMR (CDCl$_3$) δppm: 1.42 (9 H, s), 1.90-2.20 (2 H, m), 2.00 (3 H, s), 2.48 (3 H, s), 3.22-3.45 (3 H, m), 3.61-3.82 (1 H, m), 4.67-4.76 (1 H, m), 6.80-6.84 (1 H, m), 6.95-7.02 (1 H, m), 7.08 (1 H, t, J = 8.6 Hz), 8.04 (1 H, d, J = 5.2 Hz). |
| 239 | —H | —H | —F | —Cl | —H | 6-chloro-3-methylpyrazin-2-yl | $^1$H-NMR (CDCl$_3$) δppm: 1.44 (9 H, s), 1.78-1.86 (1 H, m), 2.05-2.24 (1 H, m), 3.08-3.31 (3 H, m), 3.80 (1 H, dd, J = 7.0, 9.0 Hz), 5.17-5.23 (1 H, m), 7.10 (1 H, ddd, J = 2.6, 3.9, 8.7 Hz), 7.26-7.32 (3 H, m), 7.88 (1 H, s). |
| 240 | —H | —H | —Cl | —Cl | —H | 6-methylpyrazin-2-yl | $^1$H-NMR (CDCl$_3$) δppm: 1.44 (9 H, s), 1.77-1.87 (1 H, m), 2.04-2.21 (1 H, m), 3.11-3.35 (3 H, m), 3.75-3.86 (1 H, m), 5.14-5.23 (1 H, m), 7.07 (1 H, dd, J = 2.4, 8.5 Hz), 7.33 (1 H, d, J = 2.4 Hz), 7.51 (1 H, d, J = 1.1 Hz), 7.58 (1 H, dd, J = 3.9, 8.2 Hz), 7.90 (1 H, s), 8.09 (1 H, s). |
| 241 | —H | —H | —Cl | —Cl | —H | 5-fluoro-2-methylpyridin-3-yl | $^1$H-NMR (CDCl$_3$) δppm: 1.44 (9 H, s), 1.73-1.80 (1 H, m), 2.01-2.18 (1 H, m), 3.03-3.33 (3 H, m), 3.81 (1 H, dd, J = 6.1, 10.7 Hz), 5.13-5.22 (1 H, m), 6.06 (1 H, dd, J = 3.4, 9.2 Hz), 7.02 (1 H, dd, J = 2.4, 8.4 Hz), 7.06-7.12 (1 H, m), 7.28 (1 H, d, J = 2.4 Hz), 7.50-7.55 (1 H, m), 8.06 (1 H, brs). |

TABLE 32

| Ref. Ex. No. | R1 | R2 | R3 | R4 | R5 | R6 | NMR |
|---|---|---|---|---|---|---|---|
| 242 | —H | —H | —Cl | —Cl | —H | 6-methyl-3-fluoropyridin-2-yl | $^1$H-NMR (CDCl$_3$) δppm: 1.43 (9 H, s), 1.75-1.84 (1 H, m), 2.04-2.18 (1 H, m), 3.03-3.33 (3 H, m), 3.77-3.85 (1 H, m), 5.29-5.38 (1 H, m), 5.68 (1 H, dd, J = 2.1, 12.0 Hz), 6.38-6.46 (1 H, m), 7.03 (1 H, dd, J = 2.4, 8.5 Hz), 7.29 (1 H, d, J = 2.3 Hz), 7.54-7.59 (1 H, m), 8.10-8.18 (1 H, m). |
| 243 | —H | —H | —Cl | —Cl | —H | 6-methylpyridin-2-yl | $^1$H-NMR (CDCl$_3$) δppm: 1.43 (9 H, s), 1.72-1.86 (1 H, m), 2.04-2.22 (1 H, m), 3.08-3.33 (3 H, m), 3.83 (1 H, dd, J = 7.1, 10.8 Hz), 5.28-5.37 (1 H, m), 6.04 (1 H, d, J = 8.6 Hz), 6.63-6.68 (1 H, m), 7.03 (1 H, dd, J = 2.4, 8.5 Hz), 7.27-7.35 (2 H, m), 7.51-7.56 (1 H, m), 8.17-8.22 (1 H, m). |
| 244 | —H | —H | —F | —Cl | —H | 5-methylpyrazin-2-yl | $^1$H-NMR (CDCl$_3$) δppm: 1.44 (9 H, s), 1.73-1.90 (1 H, m), 2.05-2.22 (1 H, m), 3.08-3.34 (3 H, m), 3.82 (1 H, dd, J = 7.2, 10.7 Hz), 5.16-5.25 (1 H, m), 7.08-7.14 (1 H, m), 7.27-7.33 (2 H, m), 7.49 (1 H, s), 7.89 (1 H, brs), 8.09 (1 H, brs). |
| 245 | —H | —H | —Cl | —Cl | —H | 5-methylpyrazin-2-yl | $^1$H-NMR (CDCl$_3$) δppm: 1.44 (9 H, s), 1.76-1.89 (1 H, m), 2.05-2.28 (1 H, m), 3.10-3.35 (3 H, m), 3.77-3.87 (1 H, m), 5.14-5.25 (1 H, m), 7.08 (1 H, dd, J = 2.4, 8.5 Hz), 7.34 (1 H, d, J = 2.3 Hz), 7.52 (1 H, s), 7.59 (1 H, dd, J = 4.0, 8.2 Hz), 8.10 (1 H, brs), 8.66 (1 H, brs). |
| 246 | —H | —H | —Cl | —Cl | —H | 3-chloro-6-methylpyrazin-2-yl | $^1$H-NMR (CDCl$_3$) δppm: 1.44 (9 H, s), 1.75-1.86 (1 H, m), 2.09-2.28 (1 H, m), 3.12-3.34 (3 H, m), 3.80 (1 H, dd, 7.1, 10.0 Hz), 5.13-5.24 (1 H, m), 7.07 (1 H, dd, J = 2.4, 8.5 Hz), 7.32-7.34 (2 H, m), 7.59 (1 H, d, J = 8.0 Hz), 8.49 (1 H, s). |
| 247 | —H | —H | —Cl | —Cl | —H | 5-methylpyrimidin-2-yl | $^1$H-NMR (CDCl$_3$) δppm: 1.43 (9 H, s), 1.82-1.95 (1 H, m), 2.09-2.25 (1 H, m), 3.13-3.37 (3 H, m), 3.70-3.80 (1 H, m), 4.41-4.50 (1 H, m), 6.86 (1 H, dd, J = 2.5, 8.6 Hz), 7.13 (1 H, d, J = 2.5 Hz), 7.48 (1 H, d, J = 8.8 Hz), 8.22 (2 H, s), 8.82 (1 H, s). |
| 248 | —H | —H | —Cl | —Cl | —H | 2-methylpyrimidin-4-yl | $^1$H-NMR (CDCl$_3$) δppm: 1.44 (9 H, s), 1.74-1.88 (1 H, m), 2.05-2.20 (1 H, m), 3.10-3.38 (3 H, m), 3.77-3.87 (1 H, m), 5.22-5.34 (1 H, m), 6.63 (1 H, brs), 7.02 (1 H, dd, J = 2.4, 8.5 Hz), 7.28 (1 H, d, J = 2.4 Hz), 7.51 (1 H, dd, J = 4.3, 8.4 Hz), 8.32 (2 H, brs). |
| 249 | —H | —H | —Cl | —Cl | —H | 2-chloro-5-methylpyrimidin-4-yl | $^1$H-NMR (CDCl$_3$) δppm: 1.43 (9 H, s), 1.79-1.90 (1 H, m), 2.04-2.27 (1 H, m), 3.14-3.36 (3 H, m), 3.67-3.80 (1 H, m), 4.36-4.45 (1 H, m), 6.89 (1 H, dd, J = 2.5, 8.5 Hz), 7.16 (1 H, d, J = 2.3 Hz), 7.51 (1 H, d, J = 8.4 Hz), 8.05 (1 H, brs). |
| 250 | —H | —H | —F | —Cl | —H | 2-chloro-5-methylpyrimidin-4-yl | $^1$H-NMR (CDCl$_3$) δppm: 1.43 (9 H, s), 1.80-1.98 (1 H, m), 2.11-2.28 (1 H, m), 3.15-3.39 (3 H, m), 3.68-3.78 (1 H, m), 4.36-4.45 (1 H, m), 6.99-7.05 (1 H, m), 7.18-7.27 (2 H, m), 7.97 (2 H, s). |

TABLE 33

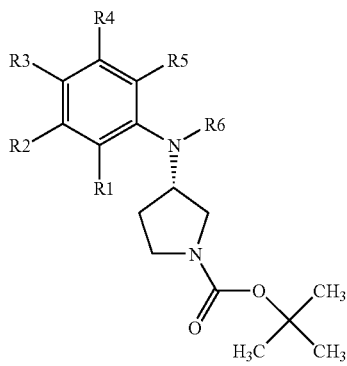

| Ref. Ex. No. | R1 | R2 | R3 | R4 | R5 | R6 | NMR |
|---|---|---|---|---|---|---|---|
| 251 | —H | —H | —F | —F | —H | 3-methylthiophene | $^1$H-NMR (CDCl$_3$) δppm: 1.43 (9 H, s), 1.79-1.97 (1 H, m), 2.01-2.22 (1 H, m), 3.08-3.38 (3 H, m), 3.60-3.78 (1 H, m), 4.25-4.41 (1 H, m), 6.42-6.62 (2 H, m), 6.66 (1 H, dd, J = 1.5, 5.0 Hz), 6.78 (1 H, dd, J = 1.5, 3.0 Hz), 6.91-7.07 (1 H, m), 7.30 (1 H, d, J = 3.0 Hz) |
| 252 | —H | —H | —Cl | —CH$_3$ | —H | 3-methylthiophene | $^1$H-NMR (CDCl$_3$) δppm: 1.43 (9 H, s), 1.78-1.97 (1 H, m), 2.03-2.20 (1 H, m), 2.29 (3 H, s), 3.18-3.38 (3 H, m), 3.61-3.82 (1 H, m), 4.34-4.43 (1 H, m), 6.54-6.73 (4 H, m), 7.11-7.30 (2 H, m). |
| 253 | —H | —Cl | —H | —Cl | —H | 3-methylthiophene | $^1$H-NMR (CDCl$_3$) δppm: 1.44 (9 H, s), 1.78-1.94 (1 H, m), 2.04-2.20 (1 H, m), 3.13-3.34 (3 H, m), 3.67-3.80 (1 H, m), 4.29-4.45 (1 H, m), 6.48 (2 H, d, J = 1.7 Hz), 6.72-6.83 (2 H, m), 7.04 (1 H, dd, J = 3.1, 1.7 Hz), 7.37-7.42 (1 H, m). |
| 254 | —H | —H | —F | —H | —H | 3-methylthiophene | $^1$H-NMR (CDCl$_3$) δppm: 1.43 (9 H, s), 1.82-2.00 (1 H, m), 2.01-2.23 (1 H, m), 3.10-3.40 (3 H, m), 3.61-3.79 (1 H, m), 4.26-4.42 (1 H, m), 6.41-6.44 (1 H, m), 6.50 (1 H, dd, J = 1.5, 5.0 Hz), 6.89-7.02 (4 H, m), 7.18 (1 H, brs) |
| 255 | —H | —H | —Cl | —Cl | —H | 3-methylthiophene | $^1$H-NMR (CDCl$_3$) δppm: 1.43 (9 H, s), 1.81-1.98 (1 H, m), 2.05-2.24 (1 H, m), 3.12-3.38 (3 H, m), 3.63-3.82 (1 H, m), 4.30-4.46 (1 H, m), 6.50 (1 H, dd, J = 3.0, 9.0 Hz), 6.72-6.76 (2 H, m), 6.96 (1 H, dd, J = 1.5, 3.0 Hz), 7.20 (1 H, brd, J = 9.5 Hz), 7.36 (1 H, brs) |
| 256 | —H | —H | —F | —Cl | —H | 4-methyltetrahydropyran | $^1$H-NMR (CDCl$_3$) δppm: 1.27-1.52 (11 H, m), 1.62-1.82 (3 H, m), 1.90-2.05 (1 H, m), 2.95-3.69 (7 H, m), 3.85-4.05 (3 H, m), 6.95-7.00 (1 H, m), 7.00-7.16 (2 H, m). |
| 257 | —H | —H | —F | —Cl | —H | 4-ethyltetrahydropyran | $^1$H-NMR (CDCl$_3$) δppm: 1.15-1.35 (2 H, m), 1.46 (9 H, s), 1.5-1.73 (3 H, m), 1.76-2.05 (2 H, m), 2.91 (2 H, d, J = 6.7 Hz), 3.08-3.35 (4 H, m), 3.35-3.65 (2 H, m), 3.80-4.00 (3 H, m), 6.76-6.88 (1 H, m), 6.95-7.10 (2 H, m). |
| 258 | —H | —H | —F | —Cl | —H | 3-chloro-6-methylbenzothiophene | $^1$H-NMR (CDCl$_3$) δppm: 1.42 (9 H, s), 1.8-1.95 (1 H, m), 2.1-2.25 (1 H, m), 3.15-3.35 (3 H, m), 3.65-3.85 (1 H, m), 4.45-4.6 (1 H, m), 6.7-6.8 (1 H, m), 6.9-7.0 (2 H, m), 7.0-7.1 (1 H, m), 7.21 (1 H, s), 7.31 (1 H, d, J = 1.7 Hz), 7.65-7.8 (1 H, m). |
| 259 | —H | —H | —H | —H | —H | 3-chloro-6-methylbenzothiophene | $^1$H-NMR (CDCl$_3$) δppm: 1.42 (9 H, s), 1.8-1.95 (1 H, m), 2.1-2.25 (1 H, m), 3.15-3.35 (3 H, m), 3.65-3.9 (1 H, m), 4.45-4.6 (1 H, m), 6.85-7.0 (3 H, m), 7.05-7.2 (2 H, m), 7.25-7.4 (3 H, m), 7.6-7.75 (1 H, m). |
| 260 | —H | —H | —F | —Cl | —H | 3-chloro-5-methylbenzothiophene | $^1$H-NMR (CDCl$_3$) δppm: 1.42 (9 H, s), 1.8-2.0 (1 H, m), 2.1-2.3 (1 H, m), 3.15-3.4 (3 H, m), 3.65-3.85 (1 H, m), 4.4-4.6 (1 H, m), 6.65-6.75 (1 H, m), 6.86 (1 H, dd, J = 2.9, 6.3 Hz), 6.95 (1 H, dd, J = 2.2, 8.6 Hz), 6.95-7.1 (1 H, m), 7.35 (1 H, s), 7.42 (1 H, d, J = 2.1 Hz), 7.74 (1 H, d, J = 8.6 Hz). |

TABLE 34

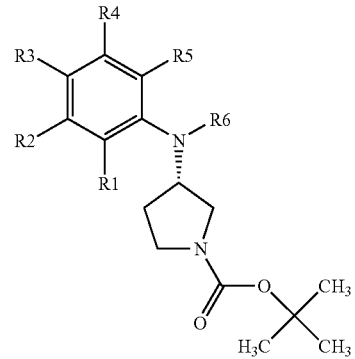

| Ref. Ex. No. | R1 | R2 | R3 | R4 | R5 | R6 | NMR |
|---|---|---|---|---|---|---|---|
| 261 | —H | —H | —H | —H | —H | 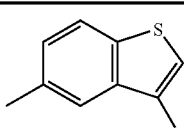 | $^1$H-NMR (CDCl$_3$) δppm: 1.41 (9 H, s), 1.8-2.0 (1 H, m), 2.05-2.3 (1 H, m), 3.15-3.4 (3 H, m), 3.7-3.9 (1 H, m), 4.5-4.7 (1 H, m), 6.8-6.9 (2 H, m), 6.9-7.1 (2 H, m), 7.2-7.35 (3 H, m), 7.42 (1 H, d, J = 2.1 Hz), 7.65-7.75 (1 H, m). |
| 262 | —H | —H | —F | —H | —H | 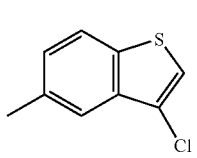 | $^1$H-NMR (CDCl$_3$) δppm: 1.42 (9 H, s), 1.8-2.0 (1 H, m), 2.05-2.3 (1 H, m), 3.15-3.4 (3 H, m), 3.7-3.85 (1 H, m), 4.45-4.6 (1 H, m), 6.80 (1 H, dd, J = 2.3, 8.8 Hz), 6.9-7.1 (4 H, m), 7.2-7.35 (2 H, m), 7.62 (1 H, d, J = 8.6 Hz). |
| 263 | —H | —H | —F | —H | —H | 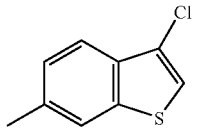 | $^1$H-NMR (CDCl$_3$) δppm: 1.43 (9 H, s), 1.8-1.95 (1 H, m), 2.05-2.25 (1 H, m), 3.1-3.4 (3 H, m), 3.65-3.9 (1 H, m), 4.4-4.6 (1 H, m), 6.82 (1 H, dd, J = 2.0, 8.8 Hz), 6.95-7.2 (6 H, m), 7.55-7.7 (1 H, m). |
| 264 | —H | —H | —H | —H | —H |  | $^1$H-NMR (CDCl$_3$) δppm: 1.41 (9 H, s), 1.8-1.95 (1 H, m), 2.05-2.25 (1 H, m), 2.42 (3 H, d, J = 0.6 Hz), 3.15-3.35 (3 H, m), 3.7-3.9 (1 H, m), 4.45-4.65 (1 H, m), 6.75-6.85 (2 H, m), 6.9-7.05 (3 H, m), 7.15-7.3 (2 H, m), 7.45 (1 H, d, J = 1.9 Hz), 7.63 (1 H, dd, J = 3.9, 8.5 Hz). |
| 265 | —H | —H | —H | —H | —H | 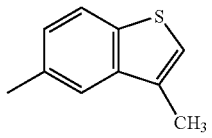 | $^1$H-NMR (CDCl$_3$) δppm: 1.40 (9 H, d, J = 2.9 Hz), 1.8-1.95 (1 H, m), 2.05-2.25 (1 H, m), 2.39 (3 H, d, J = 0.8 Hz), 3.15-3.35 (3 H, m), 3.7-3.9 (1 H, m), 4.45-4.65 (1 H, m), 6.65-6.75 (2 H, m), 6.8-6.9 (1 H, m), 7.01 (1 H, dd, J = 1.8, 8.5 Hz), 7.11 (1 H, bs), 7.15-7.3 (2 H, m), 7.39 (1 H, d, J = 1.9 Hz), 7.81 (1 H, dd, J = 3.6, 8.4 Hz). |
| 266 | —H | —H | —H | —H | —H |  | $^1$H-NMR (CDCl$_3$) δppm: 1.42 (9 H, s), 1.8-1.95 (1 H, m), 2.05-2.25 (1 H, m), 3.15-3.35 (3 H, m), 3.7-3.9 (1 H, m), 4.45-4.6 (1 H, m), 6.87 (1 H, d, J = 1.9 Hz), 6.93 (2 H, dd, J = 1.0, 8.5 Hz), 7.05-7.15 (1 H, m), 7.23 (1 H, s), 7.25-7.4 (4 H, m). |
| 267 | —H | —H | —H | —H | —H | 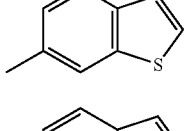 | $^1$H-NMR (CDCl$_3$) δppm: 1.41 (9 H, s), 1.75-1.95 (1 H, m), 2.0-2.2 (1 H, m), 2.57 (3 H, s), 3.15-3.35 (3 H, m), 3.7-3.9 (1 H, m), 4.45-4.6 (1 H, m), 6.75 (2 H, d, J = 7.8 Hz), 6.8-7.0 (3 H, m), 7.15-7.3 (2 H, m), 7.39 (1 H, d, J = 1.7 Hz), 7.58 (1 H, dd, J = 3.8, 8.2 Hz). |
| 268 | —H | —H | —F | —H | —H | 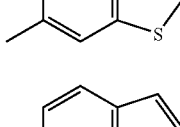 | $^1$H-NMR (CDCl$_3$) δppm: 1.42 (9 H, s), 1.75-1.95 (1 H, m), 2.0-2.2 (1 H, m), 2.55 (3 H, d, J = 1.0 Hz), 3.15-3.35 (3 H, m), 3.657-3.85 (1 H, m), 4.35-4.55 (1 H, m), 6.75-6.9 (4 H, m), 6.9-7.05 (2 H, m), 7.26 (1 H, s), 7.51 (1 H, d, J = 8.6 Hz). |

TABLE 35

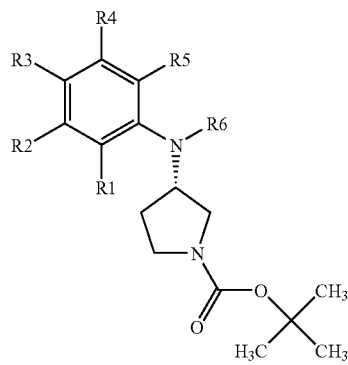

| Ref. Ex. No. | R1 | R2 | R3 | R4 | R5 | R6 | NMR |
|---|---|---|---|---|---|---|---|
| 269 | —H | —H | —F | —Cl | —H | 6-methylbenzo[d]isothiazol-3-yl | $^1$H-NMR (CDCl$_3$) δppm: 1.42 (9 H, s), 1.8-1.95 (1 H, m), 2.1-2.3 (1 H, m), 3.15-3.4 (3 H, m), 3.7-3.9 (1 H, m), 4.45-4.6 (1 H, m), 6.71 (1 H, dd, J = 2.1, 8.9 Hz), 6.9-7.05 (1 H, m), 7.1-7.3 (3 H, m), 7.81 (1 H, d, J = 8.8 Hz), 8.72 (1 H, s). |
| 270 | —H | —H | —H | —H | —H | 6-methylbenzo[d]isothiazol-3-yl | $^1$H-NMR (CDCl$_3$) δppm: 1.43 (9 H, s), 1.8-2.0 (1 H, m), 2.1-2.25 (1 H, m), 3.15-3.35 (3 H, m), 3.75-3.95 (1 H, m), 4.5-4.65 (1 H, m), 6.69 (1 H, dd, J = 2.2, 8.9 Hz), 7.05-7.15 (3 H, m), 7.3-7.4 (1 H, m), 7.4-7.5 (2 H, m), 7.76 (1 H, d, J = 7.7 Hz), 8.68 (1 H, bs). |
| 271 | —H | —H | —F | —H | —H | 6-methylbenzo[d]isothiazol-3-yl | $^1$H-NMR (CDCl$_3$) δppm: 1.43 (9 H, s), 1.8-1.95 (1 H, m), 2.1-2.3 (1 H, m), 3.1-3.35 (3 H, m), 3.7-3.9 (1 H, m), 4.5-4.65 (1 H, m), 6.65 (1 H, dd, J = 2.2, 9.0 Hz), 7.05-7.2 (5 H, m), 7.75 (1 H, d, J = 8.3 Hz), 8.67 (1 H, s). |
| 272 | —H | —H | —H | —H | —H | 6-methylthieno[2,3-b]pyridin-2-yl | $^1$H-NMR (CDCl$_3$) δppm: 1.43 (9 H, s), 1.7-1.9 (1 H, m), 2.05-2.25 (1 H, m), 3.1-3.35 (3 H, m), 3.8-3.95 (1 H, m), 5.4-5.55 (1 H, m), 6.03 (1 H, d, J = 8.9 Hz), 7.0-7.05 (1 H, m), 7.05-7.1 (1 H, m), 7.1-7.2 (2 H, m), 7.35-7.55 (3 H, m), 7.58 (1 H, d, J = 8.9 Hz). |
| 273 | —H | —H | —F | —H | —H | 6-methylthieno[2,3-b]pyridin-2-yl | $^1$H-NMR (CDCl$_3$) δppm: 1.43 (9 H, s), 1.7-1.9 (1 H, m), 2.05-2.25 (1 H, m), 3.05-3.35 (3 H, m), 3.8-3.95 (1 H, m), 5.4-5.55 (1 H, m), 6.02 (1 H, d, J = 8.9 Hz), 7.0-7.2 (6 H, m), 7.60 (1 H, d, J = 8.8 Hz). |
| 274 | —H | —H | —H | —H | —H | 5-methylthieno[3,2-b]pyridin-2-yl | $^1$H-NMR (CDCl$_3$) δppm: 1.43 (9 H, s), 1.7-1.9 (1 H, m), 2.05-2.25 (1 H, m), 3.1-3.35 (3 H, m), 3.8-3.95 (1 H, m), 5.4-5.55 (1 H, m), 6.06 (1 H, d, J = 9.0 Hz), 7.15-7.2 (2 H, m), 7.3-7.55 (4 H, m), 7.55-7.65 (1 H, m), 7.67 (1 H, d, J = 10.0 Hz). □ |
| 275 | —H | —H | —F | —Cl | —H | 6-methylquinolin-2-yl | $^1$H-NMR (CDCl$_3$) δppm: 1.43 (9 H, s), 1.85-2.00 (1 H, m), 2.08-2.26 (1 H, m), 3.16-3.40 (3 H, m), 3.68-3.90 (1 H, m), 4.50-4.61 (1 H, m), 6.88-6.96 (1 H, m), 7.05-7.20 (4 H, m), 7.35 (1 H, dd, J = 4.2, 8.3 Hz), 7.88-8.05 (2 H, m), 8.76 (1 H, d, J = 2.9 Hz) |
| 276 | —H | —H | —F | —CH$_3$ | —H | 2,6-dimethyl-1-oxo-1,2,3,4-tetrahydroisoquinolin-7-yl | $^1$H-NMR (CDCl$_3$) δppm: 1.43 (9 H, s), 1.75-1.88 (1 H, m), 2.12 (1 H, br), 2.28 (3 H, s), 2.85 (2 H, t, J = 6.6 Hz), 3.10 (3 H, s), 3.19-3.28 (3 H, m), 3.48 (2 H, t, J = 6.6 Hz), 3.69-3.83 (1 H, m), 4.49-4.55 (1 H, m), 6.22 (1 H, d, J = 12.3 Hz), 6.49 (1 H, dd, J = 8.1, 8.6 Hz), 6.87-6.95 (2 H, m), 7.03-7.09 (1 H, m), 7.87 (1 H, d, J = 8.7, 8.7 Hz). |
| 277 | —H | —H | —F | —Cl | —H | 2-methoxy-6-methylquinolin-7-yl | $^1$H-NMR (CDCl$_3$) δppm: 1.41 (9 H, s), 1.83-1.95 (1 H, m), 2.15 (1 H, m, br), 3.22-3.34 (3 H, m), 3.69-3.85 (1 H, m), 4.06 (3 H, s), 4.47 (1 H, br), 6.65-6.70 (1 H, m), 6.85 (1 H, dd, J = 2.8, 6.3 Hz), 6.90 (1 H, d, J = 8.8 Hz), 6.99-7.05 (1 H, m), 7.17 (1 H, dd, J = 8.8 Hz), 7.26-7.27 (1 H, m), 7.77-7.90 (2 H, m). |

TABLE 36

[Structure: phenyl ring with substituents R1-R5, connected via N(R6) to a (3-position) pyrrolidine ring bearing N-Boc (tert-butoxycarbonyl) group]

| Ref. Ex. No. | R1 | R2 | R3 | R4 | R5 | R6 | NMR |
|---|---|---|---|---|---|---|---|
| 278 | —H | —H | —F | —Cl | —H | 1-methyl-6-yl-3,4-dihydroquinolin-2(1H)-one | ¹H-NMR (CDCl₃) δppm: 1.43 (9 H, s), 1.78-1.90 (1 H, m), 2.04-2.17 (1 H, m), 2.66 (2 H, dd, J = 6.7, 7.7 Hz), 2.86 (2 H, dd, J = 6.7, 7.7 Hz), 3.19-3.29 (3 H, m), 3.36 (3 H, s), 3.66-3.78 (1 H, m), 4.35-4.41 (1 H, m), 6.60 (1 H, ddd, J = 3.0, 3.8, 9.0 Hz), 6.75-6.78 (2 H, m), 6.86 (1 H, dd, J = 1.9, 8.6 Hz), 6.93-7.02 (2 H, m). |
| 279 | —H | —H | —F | —H | —H | 1-methyl-6-yl-3,4-dihydroquinolin-2(1H)-one | ¹H-NMR (CDCl₃) δppm: 1.43 (9 H, s), 1.78-1.91 (1 H, m), 2.05-2.17 (1 H, m), 2.62 (2 H, dd, J = 6.1 8.3 Hz), 2.82 (2 H, dd, J = 6.1, 8.3 Hz), 3.26 (3 H, br), 3.33 (3 H, s), 3.69-3.79 (1 H, m), 4.41 (1 H, br), 6.62 (1 H, br), 6.72 (1 H, dd, J = 2.5, 8.7 Hz), 6.84-6.91 (3 H, m), 6.93-7.03 (2 H, m). |
| 280 | —H | —H | —F | —Cl | —H | 1-methyl-6-ylquinolin-2(1H)-one | ¹H-NMR (CDCl₃) δppm: 1.41 (9 H, s), 1.81-1.93 (1 H, m), 2.13-2.18 (1 H, m), 3.24-3.31 (3 H, m), 3.67-3.81 (1 H, m), 3.72 (3 H, s), 4.41-4.45 (1 H, m), 6.62-6.67 (1 H, m), 6.73 (1 H, d, J = 9.4 Hz), 6.81 (1 H, dd, J = 2.7, 6.2 Hz), 6.82-7.05 (1 H, m), 7.14-7.18 (2 H, m), 7.27-7.32 (1 H, m), 7.59 (1 H, d, J = 9.4 Hz). |
| 281 | —H | —H | —CH₃ | —F | —H | 1-methyl-6-yl-3,4-dihydroquinolin-2(1H)-one | ¹H-NMR (CDCl₃) δppm: 1.43 (9 H, s), 1.78-1.91 (1 H, m), 2.08-2.18 (1 H, m), 2.18 (3 H, s), 2.66 (2 H, dd, J = 6.6, 7.6 Hz), 2.86 (2 H, dd, J = 6.6, 7.6 Hz), 3.18-3.27 (3 H, m), 3.36 (3 H, s), 3.68-3.78 (1 H, m), 4.38-4.44 (1 H, m), 6.36-6.43 (2 H, m), 6.79 (1 H, d, J = 2.2 Hz), 6.87-7.02 (3 H, m). |
| 282 | —H | —H | —CH₃ | —F | —H | 1-methyl-6-ylquinolin-2(1H)-one | ¹H-NMR (CDCl₃) δppm: 1.41 (9 H, s), 1.60-1.72 (1 H, m), 2.15 (1 H, br), 2.20 (3 H, s), 3.24-3.32 (3 H, m), 3.72 (3 H, s), 3.75-3.81 (1 H, m), 4.46 (1 H, br), 6.40-6.45 (2 H, m), 6.72 (1 H, d, J = 9.5 Hz), 7.02 (1 H, br), 7.18-7.21 (2 H, m), 7.31-7.34 (1 H, m), 7.58 (1 H, dd, J = 2.9, 9.4 Hz). |
| 283 | —H | —H | —F | —CH₃ | —H | 1-methyl-6-yl-3,4-dihydroquinolin-2(1H)-one | ¹H-NMR (CDCl₃) δppm: 1.43 (9 H, s), 1.78-1.90 (1 H, m), 2.02-2.13 (1 H, m), 2.24 (3 H, s), 2.62 (2 H, dd, J = 5.4, 8.0 Hz), 2.79-2.84 (2 H, m), 3.19-3.29 (3 H, m), 3.32 (3 H, s), 3.98-3.79 (1 H, m), 4.35-4.46 (1 H, m), 6.58 (1 H, br), 6.70-6.76 (3 H, m), 6.84-6.99 (2 H, m). |
| 284 | —H | —H | —F | —CH₃ | —H | 1-methyl-6-ylquinolin-2(1H)-one | ¹H-NMR (CDCl₃) δppm: 1.42 (9 H, s), 1.80-1.92 (1 H, m), 2.08-2.18 (1 H, m), 2.24 (3 H, s), 3.24-3.31 (3 H, m), 3.69 (3 H, s), 3.75-3.81 (1 H, m), 4.44 (1 H, br), 6.69 (1 H, d, J = 9.4 Hz), 6.74-6.79 (2 H, m), 6.96-7.01 (3 H, m), 7.21-6.79 (1 H, m), 7.55 (1 H, d, J = 9.4 Hz). |

TABLE 37

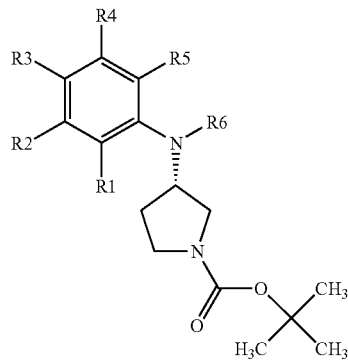

| Ref. Ex. No. | R1 | R2 | R3 | R4 | R5 | R6 | NMR |
|---|---|---|---|---|---|---|---|
| 285 | —H | —H | —F | —Cl | —H | ![structure] | $^1$H-NMR (CDCl$_3$) δppm: 1.42 (9 H, s), 1.77-1.82 (1 H, m), 2.06-2.10 (1 H, m), 2.72-2.80 (2 H, m), 2.86-2.91 (2 H, m), 3.15-3.27 (3 H, m), 3.64-3.73 (1 H, m), 3.78 (3 H, s), 4.34 (1 H, br), 5.09 (2 H, br), 6.53-6.89 (7 H, m), 6.97-7.00 (1 H, m), 7.14-7.17 (2 H, m). |
| 286 | —H | —H | —F | —F | —H | ![structure] | $^1$H-NMR (CDCl$_3$) δppm: 1.42 (9 H, s), 1.61-1.73 (1 H, m), 1.90-2.00 (1 H, m), 2.74 (2 H, dd, J = 5.8, 7.9 Hz), 2.87 (2 H, dd, J = 5.8, 7.9 Hz), 3.10-3.23 (3 H, m), 3.56-3.68 (1 H, m), 3.77 (3 H, s), 4.23-4.28 (1 H, m), 4.81 (1 H, d, J = 15.5 Hz), 5.02 (1 H, d, J = 15.5 Hz), 6.12 (1 H, d, J = 2.3 Hz), 6.37 (1 H, d, J = 8.4 Hz), 6.72-6.99 (9 H, m). |
| 287 | —H | —H | —CH$_3$ | —F | —H | ![structure] | $^1$H-NMR (CDCl$_3$) δppm: 1.42 (9 H, s), 1.76-1.86 (1 H, m), 2.04-2.11 (1 H, m), 2.18 (3 H, s), 2.75-2.79 (2 H, m), 2.88-2.93 (2 H, m), 3.13-3.25 (3 H, m), 3.66-3.76 (1 H, m), 3.78 (3 H, s), 4.34-4.38 (1 H, m), 5.09 (2 H, s), 6.36 (2 H, m), 6.70-6.74 (2 H, m), 6.83-6.91 (3 H, m), 6.99 (1 H, br), 7.17 (1 H, d, J = 8.6 Hz). |
| 288 | —H | —H | —F | —CH$_3$ | —H | ![structure] | $^1$H-NMR (CDCl$_3$) δppm: 1.42 (9 H, s), 1.76-1.85 (1 H, m), 2.01-2.09 (1 H, m), 2.22 (3 H, s), 2.71-2.75 (2 H, m), 2.84-2.88 (2 H, m), 3.13-3.28 (3 H, m), 3.63-3.75 (1 H, m), 3.77 (3 H, s), 4.33-4.37 (1 H, m), 5.06 (2 H, s), 6.47-6.53 (2 H, m), 6.69-6.85 (5 H, m), 6.91-6.95 (1 H, m), 7.14 (2 H, d, J = 8.5 Hz). |

TABLE 38

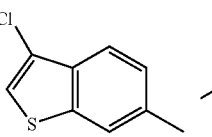

| Ref. Ex. No. | R1 | R6 | NMR |
|---|---|---|---|
| 289 | 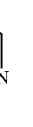 |  | $^1$H-NMR (CDCl$_3$) δppm: 1.41 (9 H, s), 1.8-2.0 (1 H, m), 2.1-2.3 (1 H, m), 3.15-3.4 (3 H, m), 3.7-3.9 (1 H, m), 4.45-4.6 (1 H, m), 7.0-7.1 (2 H, m), 7.1-7.2 (1 H, m), 7.28 (1 H, s), 7.45 (1 H, d, J = 1.6 Hz), 7.75-7.8 (1 H, m), 8.1-8.3 (2 H, m). |
| 290 | 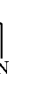 | 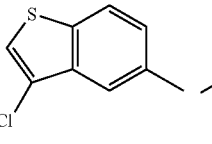 | $^1$H-NMR (CDCl$_3$) δppm: 1.42 (9 H, s), 1.8-2.0 (1 H, m), 2.1-2.3 (1 H, m), 3.15-3.4 (3 H, m), 3.7-3.9 (1 H, m), 4.5-4.7 (1 H, m), 6.78 (1 H, dd, J = 2.0, 8.9 Hz), 7.28 (1 H, s), 7.3-7.4 (2 H, m), 7.86 (1 H, d, J = 9.4 Hz), 8.37 (1 H, s), 8.45-8.55 (1 H, m), 8.75 (1 H, s). |
| 291 |  | 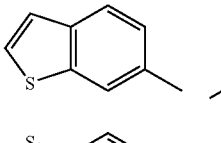 | $^1$H-NMR (CDCl$_3$) δppm: 1.40 (9 H, s), 1.8-2.0 (1 H, m), 2.1-2.3 (1 H, m), 3.15-3.4 (3 H, m), 3.7-3.9 (1 H, m), 4.5-4.65 (1 H, m), 6.95-7.2 (3 H, m), 7.38 (1 H, s), 7.53 (1 H, d, J = 2.0 Hz), 7.75-7.9 (1 H, m), 8.05-8.2 (2 H, m). |
| 292 | 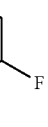 | 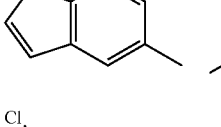 | $^1$H-NMR (CDCl$_3$) δppm: 1.40 (9 H, s), 1.8-2.0 (1 H, m), 2.1-2.3 (1 H, m), 3.15-3.4 (3 H, m), 3.7-3.9 (1 H, m), 4.45-4.6 (1 H, m), 6.45-6.6 (1 H, m), 7.09 (1 H, dd, J = 1.9, 8.4 Hz), 7.38 (1 H, d, J = 5.4 Hz), 7.54 (1 H, d, J = 5.4 Hz), 7.65 (1 H, d, J = 1.7 Hz), 7.8-7.95 (3 H, m). |
| 293 | 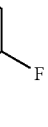 | 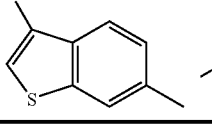 | $^1$H-NMR (CDCl$_3$) δppm: 1.42 (9 H, s), 1.8-2.0 (1 H, m), 2.1-2.3 (1 H, m), 3.1-3.4 (3 H, m), 3.7-3.9 (1 H, m), 4.45-4.6 (1 H, m), 6.45-6.6 (1 H, m), 7.07 (1 H, dd, J = 2.0, 8.4 Hz), 7.3-7.4 (1 H, m), 7.55 (1 H, d, J = 5.4 Hz), 7.59 (1 H, d, J = 2.0 Hz), 7.8-7.9 (2 H, m), 7.96 (1 H, d, J = 5.4 Hz). |
| 294 |  | | $^1$H-NMR (CDCl$_3$) δppm: 1.40 (9 H, s), 1.8-2.0 (1 H, m), 2.1-2.3 (1 H, m), 3.1-3.4 (3 H, m), 3.7-3.9 (1 H, m), 4.45-4.6 (1 H, m), 6.5-6.65 (1 H, m), 7.18 (1 H, dd, J = 1.9, 8.5 Hz), 7.40 (1 H, s), 7.59 (1 H, d, J = 1.7 Hz), 7.8-8.0 (3 H, m). |

Example 1

Synthesis of (3,4-dichlorophenyl)phenylpyrrolidin-3-ylamine dihydrochloride

An acetic acid solution (15 ml) containing 3-oxopyrrolidine-1-carboxylic acid tert-butyl ester (0.67 g) and (3,4-dichlorophenyl)phenylamine (0.94 g) was stirred at room temperature over night. To the mixture was added 1.5 g of sodium triacetoxyborohydride, followed by stirring at room temperature for 8 hours. Dichloromethane was added to the reaction solution and washed with water, followed by drying over magnesium sulfate. The solvent was distilled off under reduced pressure, and the residue was then purified by silica gel column chromatography (n-hexane:ethyl acetate=20:1). The solvent was distilled off from the purified product under reduced pressure, and the residue was dissolved in 1 N hydrochloric acid-ethanol and heated under reflux for one hour. The reaction solution was concentrated to dryness to thereby obtain 50 mg of brown amorphous solid (3,4-dichlorophenyl)phenylpyrrolidin-3-ylamine dihydrochloride.

$^1$H-NMR (DMSO-d$_6$) δ ppm:
1.50-1.68 (1H, m), 2.10-2.29 (1H, m), 2.74-2.90 (1H, m), 3.02-3.22 (2H, m), 3.51-3.66 (1H, m), 4.61-4.79 (1H, m), 6.58 (1H, dd, J=2.9 Hz, J=9.0 Hz), 6.87 (1H, d, J=2.9 Hz), 7.13-7.19 (2H, m), 7.29-7.44 (2H, m), 7.45-7.54 (2H, m), 9.03 (2H, brs).

Example 2

Synthesis of (S)-(3,4-dichlorophenyl)phenylpyrrolidin-3-ylamine dihydrochloride

3(S)-[(3,4-dichlorophenyl)phenylamino]pyrrolidine-1-carboxylic acid tert-butyl ester (0.13 g) was dissolved in 1 N hydrochloric acid-ethanol and heated under reflux for one hour. The reaction solution was concentrated to dryness to thereby obtain 0.11 g of brown amorphous solid 3(S)-(3,4-dichlorophenyl)phenylpyrrolidin-3-ylamine hydrochloride.

¹H-NMR (DMSO-d₆) δ ppm:

1.50-1.68 (1H, m), 2.10-2.29 (1H, m), 2.75-2.90 (1H, m), 3.02-3.23 (2H, m), 3.51-3.65 (1H, m), 4.60-4.80 (1H, m), 6.58 (1H, dd, J=2.9 Hz, J=9.0 Hz), 6.87 (1H, d, J=2.9 Hz), 7.12-7.19 (2H, m), 7.29-7.44 (2H, m), 7.45-7.54 (2H, m), 9.05 (2H, brs).

Example 3

Synthesis of (3-fluorophenyl)-(S)-pyrrolidin-3-yl-(4-trifluoromethylphenyl)amine difumarate To a 1,2-dichloromethane solution (1 ml) containing ((S)-1-benzylpyrrolidin-3-yl)-(3-fluorophenyl)-(4-trifluoromethylphenyl)amine (0.48 g, 1.1 mmol) was added 1-chloroethyl chloroformate (0.82 g, 5.8 mmol). The mixture was stirred at room temperature for 15 hours and heated under reflux for 3 hours. The solvent was distilled off under reduced pressure, and 5 ml methanol was then added to the residue and heated under reflux for 3 hours. After distilling the solvent off under reduced pressure, the residue was then dissolved in dichloromethane and washed with an aqueous saturated sodium hydrogencarbonate solution. After drying over magnesium sulfate, the solvent was distilled off under reduced pressure. The residue was dissolved in ethanol, fumaric acid (128 mg, 1.1 mmol) was then added thereto, giving a uniform solution. The solvent was distilled off under reduced pressure, and the crystals produced by adding dichloromethane to the residue were separated by filtration and dried, giving 0.24 g of light brown powdery (3-fluorophenyl)-(S)-pyrrolidin-3-yl-(4-trifluoromethylphenyl)amine difumarate.

Melting point 144.0-146.2° C.

Example 4

Synthesis of (3-chloro-4-fluorophenyl)-(4-methanesulfonylphenyl)-(S)-pyrrolidin-3-ylamine hydrochloride 3(S)-[(3-chloro-4-fluorophenyl)-(4-methanesulfonylphenyl)amino]pyrrolidine-1-carboxylic acid tert-butyl ester (0.42 g, 0.9 mmol) was added to 4 N hydrochloric acid/ethyl acetate, followed by stirring at room temperature for one hour. The reaction solution was concentrated to dryness under reduced pressure to thereby obtain 0.35 g of white powdery (3-chloro-4-fluorophenyl)-(4-methanesulfonylphenyl)-(S)-pyrrolidin-3-ylamine hydrochloride.

¹H-NMR (DMSO-d₆) δ ppm:

1.56-1.68 (1H, m), 2.19-2.29 (1H, m), 2.82-2.94 (1H, m), 3.08 (3H, s), 3.10-3.20 (2H, m), 3.57-3.68 (1H, m), 4.70-4.85 (1H, m), 6.69-6.75 (2H, m), 7.32-7.37 (1H, m), 7.58-7.64 (1H, m), 7.65-7.69 (3H, m), 9.10-9.45 (2H, m).

Example 5

Synthesis of (3-chloro-4-fluorophenyl)-[4-(pyridin-2-yloxy)butyl]-(S)-pyrrolidin-3-ylamine difumarate To a toluene solution (4 ml) containing 3(S)-[4-(pyridin-2-yloxy)butylamino]pyrrolidine-1-carboxylic acid tert-butyl ester (0.2 g, 0.6 mmol) and 4-bromo-2-chloro-1-fluorobenzene (0.8 ml, 0.65 mmol) were added tri-tert-butylphosphine tetrafluoroborate (14 mg, 0.05 mmol), tris(dibenzylideneacetone)dipalladium (11 mg, 0.012 mmol) and sodium tert-butoxide (110 mg, 1.2 mmol) and heated under reflux under a nitrogen atmosphere for 12 hours. After cooling to room temperature, water was added to the reaction solution, and extraction with ethyl acetate was conducted. The extract was dried over magnesium sulfate and concentrated under reduced pressure, and the residue was then purified by silica gel column chromatography (n-hexane:ethyl acetate=3:1). The solvent was distilled off from the purified product under reduced pressure. The residue was dissolved in 0.4 ml dichloromethane, and trifluoroacetic acid (0.06 ml, 0.8 mmol) was added thereto, followed by stirring at room temperature for 3 hours. After concentrating under reduced pressure, the residue was purified by HPLC. After collecting objective fractions, the solvent was distilled off under reduced pressure, and 10% aqueous potassium carbonate solution was added to the residue, followed by extraction with dichloromethane. The extract was dried over magnesium sulfate and concentrated under reduced pressure, and an ethanol solution containing fumaric acid (8.1 mg) was added to the residue (ethanol solution) to thereby obtain a uniform solution. After concentration under reduced pressure, water (3 ml) was added to the residue, followed by freeze-drying to thereby obtain 19 mg of white solid (3-chloro-4-fluorophenyl)-[4-(pyridin-2-yloxy)butyl]-(S)-pyrrolidin-3-ylamine difumarate.

¹H-NMR (DMSO-d₆) δ ppm:

1.45-1.55 (2H, m), 1.65-1.8 (2H, m), 1.8-1.95 (1H, m), 2.05-2.15 (1H, m), 2.6-4.05 (11H, m), 4.25 (2H, t, J=6.5 Hz), 4.3-4.4 (1H, m), 6.55 (4H, s), 6.77 (1H, d, J=8.5 Hz), 6.8-6.9 (1H, m), 6.9-7.0 (1H, m), 7.03 (1H, dd, J=3 Hz, J=6.5 Hz), 7.22 (1H, dd, J=9 Hz, J=9 Hz), 7.65-7.7 (1H, m), 8.1-8.15 (1H, m).

Example 6

Synthesis of (3-chloro-4-fluorophenyl)-(3-methylsulfanylpropyl)-(S)-pyrrolidin-3-ylamine hydrochloride An acetic acid solution (3 ml) containing 3(S)-[(3-chloro-4-fluorophenyl)amino]pyrrolidine-1-carboxylic acid tert-butyl ester (0.60 g, 1.9 mmol) and 3-methylthiopropionic aldehyde (0.6 g, 5.7 mmol) was stirred at room temperature over night. Sodium triacetoxy borohydride (0.81 g, 3.8 mmol) was added to the mixture, followed by stirring at room temperature for 15 hours. Dichloromethane was added to the reaction solution, and the reaction solution was washed with water and an aqueous saturated sodium hydrogencarbonate solution, and dried over magnesium sulfate. The solvent was distilled off under reduced pressure, and the residue was then dissolved in 1 N hydrochloric acid-ethanol (10 ml) and heated under reflux for one hour. The reaction solution was concentrated to dryness to thereby obtain 0.16 g of yellow amorphous solid (3-chloro-4-fluorophenyl)-(3-methylsulfanylpropyl)-(S)-pyrrolidin-3-ylamine hydrochloride.

¹H-NMR (DMSO-d₆) δ ppm:

1.52-1.70 (2H, m), 1.80-2.18 (including 5H, m[2.07 ppm(s)]), 2.40-2.51 (2H, m), 2.84-3.49 (6H, m), 4.29-4.49 (1H, m), 6.85-6.95 (1H, m), 7.05-7.35 (2H, m), 9.30-9.79 (2H, m).

Example 7

Synthesis of (3-chloro-4-fluorophenyl)pyridin-3-yl-(S)-pyrrolidin-3-ylamine dimethanesulfonate To a dichloromethane solution (100 ml) containing 3(S)-[(3-chloro-4-fluorophenyl)pyridin-3-ylamino]pyrrolidine-1-carboxylic acid tert-butyl ester (16.0 g, 41 mmol) was added trifluoroacetic acid (20 ml), followed by stirring at room temperature for 3 hours. The solvent was distilled off under reduced pressure, and an aqueous saturated sodium hydrogencarbonate solution was added to the residue to make the residue alkaline, followed by extraction with dichloromethane. The extract was dried over magnesium sulfate, the solvent was distilled off under reduced pressure, and the residue was purified by basic silica gel column chromatography (dichloromethane:methanol=10:1). The solvent was distilled off from the purified product under reduced pressure. To an ethanol solution containing the residue was added methanesulfonic acid (9.2 g), and the solvent was then distilled off under reduced pressure. The residue was recrystallized from ethanol to thereby obtain 16.9 g of white powdery (3-chloro-4-fluorophenyl)pyridin-3-yl-(S)-pyrrolidin-3-ylamine dimethanesulfonate.

Melting point 194.0-195.0° C.

The compounds of Example 8 to 1180 shown in the below Tables can be prepared in the same manners as in the above Examples, using corresponding starting compounds. In the following Tables, compounds with the physical properties, such as crystalline form, m.p. (melting point), salt, $^1$H-NMR and MS (mass spectrum), were produced actually.

TABLE 39

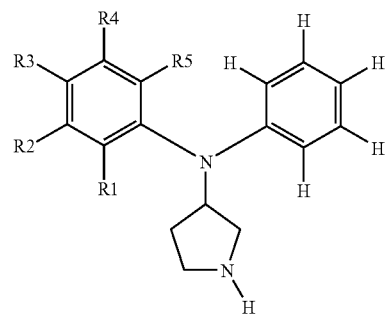

| Ex. No. | R1 | R2 | R3 | R4 | R5 | M.p. (° C.) | Salt |
|---|---|---|---|---|---|---|---|
| 8 | —H | —H | —Cl | —H | —H | 173.7-175.0 | Fumarate |
| 9 | —Cl | —Cl | —H | —H | —H | 160.3-162.6 | Fumarate |
| 10 | —H | —Cl | —H | —H | —H | 144.2-146.7 | Fumarate |

TABLE 40

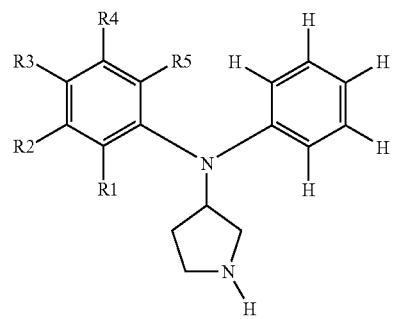

| Ex. No. | R1 | R2 | R3 | R4 | R5 | NMR | Salt |
|---|---|---|---|---|---|---|---|
| 11 | —H | —H | —Cl | —Cl | —H | 1H-NMR (DMSO-d6) δppm 1.50-1.68(1 H, m), 2.10-2.29(1 H, m), 2.74-2.90(1 H, m), 3.02-3.22(2 H, m), 3.51-3.66(1 H, m), 4.61-4.79(1 H, m), 6.58(1 H, dd, J = 2.9 Hz and 9.0 Hz), 6.87(1 H, d, = 2.9 Hz), 7.13-7.19(2 H, m), 7.29-7.44(2 H, m), 7.45-7.54(2 H, m) | 2 Hydrochloride |
| 12 | —H | —H | —Cl | —Cl | —H | 1H-NMR (DMSO-d6) δppm 1.49-1.68(1 H, m), 2.05-2.25(1 H, m), 2.69-2.82(1 H,m), 2.92-3.15(2 H, m), 3.44-3.60(1 H, m), 4.55-4.74(1 H, m), 6.44(2 H, s), 6.57(1 H, dd, J = 2.9 Hz and 9.0 Hz), 6.85(1 H, d, J = 2.8 Hz), 7.11-7.21(2 H, m), 7.29-7.41(2 H, m), 7.43-7.54 (2 H, m) | Fumarate |

TABLE 41

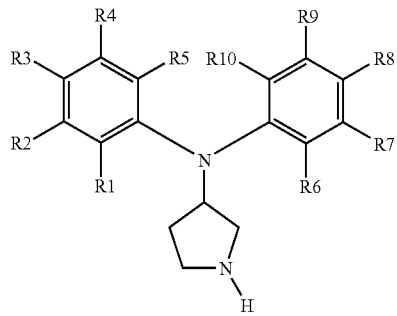

| Ex. No. | R1 | R2 | R3 | R4 | R5 | R6 | R7 | R8 | R9 | R10 | M.p. (° C.) | Salt |
|---|---|---|---|---|---|---|---|---|---|---|---|---|
| 13 | —H | —H | —F | —H | —H | —H | —H | —F | —H | —H | 155.4-156.4 | Fumarate |
| 14 | —H | —H | —F | —H | —H | —H | —H | —Cl | —Cl | —H | 178.7-180.1 | Fumarate |
| 15 | —H | —H | —H | —H | —F | —H | —H | —Cl | —Cl | —H | 156.6-158.7 | Fumarate |
| 16 | —H | —F | —H | —H | —H | —H | —Cl | —Cl | —H | —H | 156.4-158.5 | Fumarate |

TABLE 42

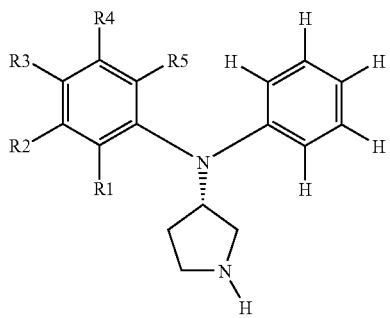

| Ex. No. | R1 | R2 | R3 | R4 | R5 | M.p. (° C.) | Salt |
|---|---|---|---|---|---|---|---|
| 17 | —H | —H | —Cl | —H | —H | 152.0-153.0 | Fumarate |
| 18 | —H | —Cl | —Cl | —H | —H | 144.0-147.9 | Fumarate |
| 19 | —H | —H | —SCH₃ | —H | —H | 152.9-155.5 | Fumarate |
| 20 | —H | —H | —F | —H | —H | 143.0-145.0 | Fumarate |
| 21 | —Cl | —H | —H | —H | —H | 138.1-141.8 | Fumarate |
| 22 | —H | —H | —CH₃ | —H | —H | 141.7-143-8 | Fumarate |
| 23 | —Cl | —Cl | —H | —H | —H | 130.2-132.2 | Fumarate |
| 24 | —H | —H | —OCF₃ | —H | —H | 131.2-133.6 | Fumarate |
| 25 | —H | —Cl | —H | —H | —H | 146.6-149.1 | Fumarate |
| 26 | —H | —H | —CF₃ | —H | —H | 120.3-124.6 | Fumarate |
| 27 | —H | —H | —OCH₃ | —H | —H | 137.5-139.2 | Fumarate |
| 28 | —H | —H | —NO₂ | —H | —H | 153.0-135.5 | Fumarate |
| 29 | —H | —OCH₃ | —H | —H | —H | 135.3-140.7 | Fumarate |
| 30 | —H | —H | —CO₂CH₃ | —H | —H | 147.5-149.0 | Fumarate |
| 31 | —H | —Cl | —H | —Cl | —H | 164.8-166.8 | Fumarate |
| 32 | —H | —H | —Br | —H | —H | 156-158 | Fumarate |
| 33 | —H | —H | —SO₂CH₃ | —H | —H | 184.5-185.8 (dec.) | Fumarate |
| 34 | —H | —F | —F | —H | —H | 137.5-138.5 | Fumarate |
| 35 | —H | —H | —CN | —H | —H | 146.7-149.6 | Fumarate |
| 36 | —H | —Cl | —OCH₃ | —H | —H | 142-144 | Fumarate |
| 37 | —H | —H | —H | —F | —H | 144.2-145.2 | Fumarate |
| 38 | —H | —F | —Cl | —H | —H | 155.4-158.4 | Fumarate |
| 39 | —H | —Cl | —OC₂H₅ | —H | —H | 135.0-137.2 | Fumarate |
| 40 | —H | —Cl | —OC₃H₇ | —H | —H | 129.6-132.4 | Fumarate |

TABLE 43

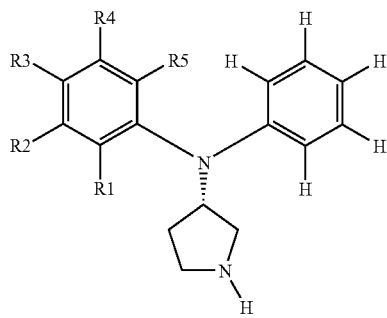

| Ex. No. | R1 | R2 | R3 | R4 | R5 | NMR | Salt |
|---|---|---|---|---|---|---|---|
| 41 | —H | —Cl | —Cl | —H | —H | 1H-NMR (DMSO-d6) δppm 1.50-1.68(1 H, m), 2.10-2.29(1 H, m), 2.75-2.90 (1 H, m), 3.02-3.23(2 H, m), 3.51-3.65(1 H, m), 4.60-4.80(1 H, m), 6.58(1 H, dd, J = 2.9 Hz and 9.0 Hz), 6.87(1 H, d, J = 2.9 Hz), 7.12-7.19(2 H, m), 7.29-7.44(2 H, m), 7.45-7.54(2 H, m), 9.05(2 H, brs) | Hydrochloride |
| 42 | —H | —H | —NH2 | —H | —H | 1H-NMR (DMSO-d6) δppm 1.52-1.69(1 H, m), 2.09-2.24(1 H, m), 2.71-2.86 (1 H, m), 3.00-3.21(2 H, m), 3.48-3.62(1 H, m), 4.52-4.75(1 H, m), 6.82-6.90(2 H, m), 6.98-7.08 (2 H, m), 7.14-7.23(1 H, m), 7.24-7.32(2 H, m), 7.35-7.44(2 H, m), 9.30-10.9(5 H, m) | 2 Hydro chloride |
| 43 | —H | —H | —N(CH3)2 | —H | —H | 1H-NMR (DMSO-d6) δppm 1.50-1.70(1 H,m), 2.09-2.27(1 H, m), 2.69-2.87 (1 H, m), 2.92-3.24(8 H, m with s at δ3.01), 4.60-4.77(1 H, m), 6.83(2 H, d, J = 8.6Hz), 6.90-7.20 (3 H, m), 7.22-7.70(4 H, m), 9.12-9.60(2 H, m) | 2 Hydro chloride |
| 44 | —H | —Cl | —F | —H | —H | 1H-NMR (DMSO-d6) δppm 1.50-1.68(1 H, m), 2.05-2.20(1 H, m), 2.72-2.86 (1 H, m), 2.96-3.13(2 H, m), 3.43-3.57(1 H, m), 4.52-4.69(1 H, m), 6.45(2 H, s), 6.77-6.86(1 H, m), 6.97(2 H, d, J = 8.2 Hz), 7.05(1 H, dd, J = 2.8 Hz and 6.4 Hz), 7.09-7.17(1 H, m), 7.26-7.41(3 H, m) | Fumarate |
| 45 | —H | —H | —CO2H | —H | —H | 1H-NMR (DMSO-d6) δppm 1.50-1.70(1 H, m), 2.14-2.30(1 H, m), 2.70-2.90 (1 H, m), 2.99-3.22(2 H, m), 3.51-3.70(1 H, m), 4.69-4.89(1 H, m), 6.54-6.64(2 H, m), 7.19-7.29 (2 H, m), 7.38-7.48(1 H, m), 7.49-7.59(2 H, m), 7.68-7.79(2 H, m), 9.34(2 H, brs), 12.32(1 H, brs) | Hydrochloride |
| 46 | —H | —CH3 | —F | —H | —H | 1H-NMR (DMSO-d6) δppm 1.5-1.7(1 H, m), 2.0-2.2(1 H, m), 2.20(3 H, s), 2.7-2.9(1 H, m), 3.0-3.2(2 H, m), 3.5-3.6(1 H, m), 4.5-4.7(1 H, m), 6.44(2 H, s), 6.6-6.8(2 H, m), 6.8-6.9(2 H, m), 6.9-7.0(1 H, m), 7.0-7.3(3 H, m) | Fumarate |
| 47 | —H | —F | —F | —OCH3 | —H | 1H-NMR (DMSO-d6) δppm 1.5-1.7(1 H, m), 2.0-2.2(1 H, m), 2.7-2.9(1 H, m), 3.0-3.2(2 H, m), 3.5-3.7(1 H, m), 3.77(3 H, s), 4.6-4.8(1 H, m), 6.2-6.4(2 H, m), 6.47(2 H, s), 7.00(2 H, d, J = 7.6 Hz), 7.15(1 H, dd, J = 7.3 Hz, J = 7.3 Hz), 7.3-7.5(2 H, m) | Fumarate |

TABLE 44

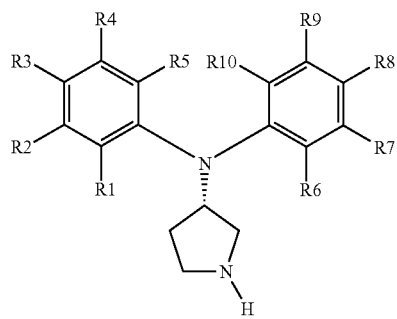

| Ex. No. | R1 | R2 | R3 | R4 | R5 | R6 | R7 | R8 | R9 | R10 | M.p. (° C.) | Salt |
|---|---|---|---|---|---|---|---|---|---|---|---|---|
| 48 | —H | —H | —F | —H | —H | —H | —H | —F | —H | —H | 156.0-157.0 | Fumarate |
| 49 | —H | —H | —F | —H | —H | —H | —H | —Cl | —Cl | —H | 170.5-171.8 | Fumarate |
| 50 | —H | —H | —H | —H | —F | —H | —H | —Cl | —Cl | —H | 133.1-135.8 | Fumarate |
| 51 | —H | —H | —Cl | —H | —H | —H | —F | —H | —H | —H | 154.3-155.6 | Fumarate |
| 52 | —H | —H | —F | —H | —H | —H | —F | —H | —H | —H | 143.2-144.4 | Fumarate |
| 53 | —H | —H | —CF₃ | —H | —H | —H | —F | —H | —H | —H | 144.0-146.2 | 2 Fumarate |
| 54 | —H | —H | —SCH₃ | —H | —H | —H | —F | —H | —H | —H | 161.1-163.2 | Fumarate |
| 55 | —H | —H | —F | —H | —H | —H | —H | —Cl | —H | —H | 174.1-176.2 | Fumarate |
| 56 | —H | —H | —F | —H | —H | —H | —F | —F | —H | —H | 148.6-151.3 | Fumarate |
| 57 | —H | —H | —F | —H | —H | —H | —Cl | —F | —H | —H | 176.7-178.4 | Fumarate |
| 58 | —H | —H | —F | —H | —H | —H | —F | —Cl | —H | —H | 163.1-164.1 | Fumarate |
| 59 | —H | —H | —H | —F | —H | —H | —Cl | —H | —H | —H | 149.0-152.0 | Fumarate |
| 60 | —H | —CH₃ | —H | —H | —H | —H | —H | —F | —H | —H | 142-143 | Fumarate |
| 61 | —H | —Cl | —F | —H | —H | —H | —H | —OCH₃ | —H | —H | 133.1-135.1 | Fumarate |
| 62 | —H | —H | —CH₃ | —H | —H | —H | —Cl | —F | —H | —H | 144.0-146.0 | Fumarate |
| 63 | —H | —Cl | —F | —H | —H | —H | —H | —OC₂H₅ | —H | —H | 138.0-141.0 | Fumarate |
| 64 | —H | —H | —SCH₃ | —H | —H | —H | —H | —F | —Cl | —H | 136.7-139.0 | Fumarate |
| 65 | —H | —H | —C₃H₇ | —H | —H | —H | —H | —F | —Cl | —H | 136.6-138.0 | Fumarate |
| 66 | —H | —H | —C(CH₃)₃ | —H | —H | —H | —H | —F | —Cl | —H | 132.0-134.8 | Fumarate |
| 67 | —H | —Cl | —F | —H | —H | —H | —Cl | —F | —H | —H | 165-167 | Fumarate |
| 68 | —H | —H | —F | —Cl | —H | —H | —H | —OH | —H | —H | 191.5-194.5 | Fumarate |
| 69 | —H | —H | —F | —H | —H | —H | —H | —CH₃ | —H | —H | 145-148 | Fumarate |

TABLE 45

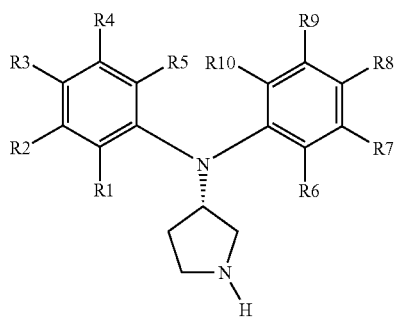

| Ex. No. | R1 | R2 | R3 | R4 | R5 | R6 | R7 | R8 | R9 | R10 | M.p. (° C.) | Salt |
|---|---|---|---|---|---|---|---|---|---|---|---|---|
| 70 | —H | —H | —Br | —H | —H | —H | —H | —F | —Cl | —H | 141-143 | Fumarate |
| 71 | —H | —H | -3-THIENYL | —H | —H | —H | —Cl | —F | —H | —H | 158-160 | Fumarate |
| 72 | —H | —CF₃ | —F | —H | —H | —H | —H | —F | —Cl | —H | 105-108 | 2 Fumarate |
| 73 | —H | —H | —CN | —H | —H | —H | —Cl | —F | —H | —H | 174-175 | Fumarate |
| 74 | —H | —H | —CF₃ | —H | —H | —H | —Cl | —F | —H | —H | 169-170 | Fumarate |
| 75 | —H | —H | —N(CH₃)₂ | —H | —H | —H | —Cl | —F | —H | —H | 153-154 | Fumarate |
| 76 | —H | —OCH₃ | —H | —H | —H | —H | —Cl | —F | —H | —H | 135-137 | Fumarate |
| 77 | —H | —OC₂H₅ | —H | —H | —H | —H | —Cl | —F | —H | —H | 155-156 | Fumarate |
| 78 | —H | —H | —NO₂ | —H | —H | —H | —CH₃ | —F | —H | —H | 162-164 | Fumarate |
| 79 | —H | —H | —CN | —H | —H | —H | —CH₃ | —F | —H | —H | 169-170 | Fumarate |
| 80 | —H | —CH₃ | —H | —H | —H | —H | —CH₃ | —F | —H | —H | 129-130 | Fumarate |
| 81 | —H | —H | —F | —H | —H | —H | —SCH₃ | —H | —H | —H | 156-158 | Fumarate |
| 82 | —H | —NO₂ | —H | —H | —H | —H | —CH₃ | —F | —H | —H | 108-110 | Fumarate |
| 83 | —H | —OCH₃ | —H | —H | —H | —H | —H | —F | —CH₃ | —H | 140-142 | Fumarate |
| 84 | —H | —H | —OC₂H₅ | —H | —H | —H | —H | —F | —CH₃ | —H | 112-113 | Fumarate |

TABLE 45-continued
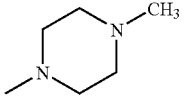
| Ex. No. | R1 | R2 | R3 | R4 | R5 | R6 | R7 | R8 | R9 | R10 | M.p. (° C.) | Salt |
|---|---|---|---|---|---|---|---|---|---|---|---|---|
| 85 | —H | —F | —H | —H | —H | —H | —F | —H | —H | —H | 149.0-153.0 (dec.) | Fumarate |
| 86 | —H | —SCH$_3$ | —H | —H | —H | —H | —Cl | —F | —H | —H | 143-144 | Fumarate |
TABLE 46
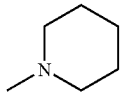
| Ex. No. | R1 | R2 | R3 | R4 | R5 | R6 | R7 | R8 | R9 | R10 | M.p. (° C.) | Salt |
|---|---|---|---|---|---|---|---|---|---|---|---|---|
| 87 | —H | —H | 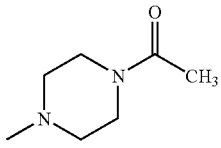 | —H | —H | —H | —H | —F | —Cl | —H | 199-203 | 3 Hydro chloride |
| 88 | —H | —H | (N-methylpiperidinyl) | —H | —H | —H | —Cl | —F | —H | —H | 108-110 | Fumarate |
| 89 | —H | —H | (4-acetyl-1-methylpiperazinyl) | —H | —H | —H | —H | —F | —Cl | —H | 198-201 | 3 Hydro chloride |
| 90 | —H | —H | 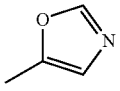 | —H | —H | —H | —H | —F | —Cl | —H | 115-117 | |

TABLE 47

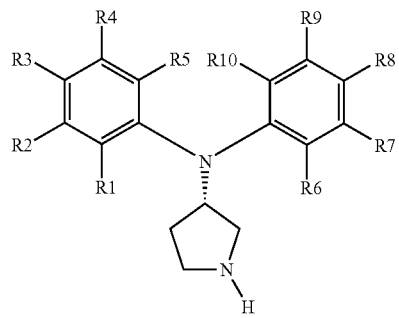

| Ex. No. | R1 | R2 | R3 | R4 | R5 | R6 | R7 | R8 | R9 | R10 | NMR | Salt |
|---|---|---|---|---|---|---|---|---|---|---|---|---|
| 91 | —H | —F | —H | —H | —H | —H | —Cl | —Cl | —H | —H | 1H-NMR (DMSO-d6) δppm 1.49-1.69(1 H, m), 2.03-2.22(1 H, m), 2.73-2.86(1 H, m), 2.92-3.10(2 H, m), 3.42-3.58(1 H, m), 4.54-4.72(1 H, m), 6.73-6.91(3 H, m with dd at δ6.82, J = 2.7 Hz and 8.8 Hz, and dt at δ6.88, J = 2.4 Hz and 11.1 Hz), 6.93-7.01(1 H, m), 7.14(1 H, d, J = 2.7 Hz), 7.32-7.43(1 H, m), 7.51(1 H, d, J = 8.8 Hz) | Fumarate |
| 92 | —H | —CH₃ | —F | —H | —H | —H | —CH₃ | —F | —H | —H | 1H-NMR (DMSO-d6) δppm 1.5-1.7(1 H, m), 2.0-2.2(1 H, m), 2.17(6 H, s), 2.7-2.9 (1 H, m), 3.0-3.2 (2 H, m), 3.5-3.6(1 H, m), 4.5-4.7(1 H, m), 6.44(2 H, s), 6.7-6.9(4 H, m), 7.05(2 H, dd, J = 9.1 Hz, J = 9.1 Hz) | Fumarate |
| 93 | —H | —F | —H | —H | —H | —H | —CH₃ | —F | —H | —H | 1H-NMR (DMSO-d6) δppm 1.5-1.7(1 H, m), 2.0-2.2(1 H, m), 2.23(3 H, s), 2.7-2.9 (1 H, m), 3.0-3.2 (2 H, m), 3.5-3.6(1 H, m), 4.5-4.7(1 H, m), 6.3-6.6(3 H, m), 6.44(2 H, s), 7.0-7.2(3 H, m), 7.22 (1 H, dd, J = 9.2 Hz, J = 8.9 Hz) | Fumarate |
| 94 | —H | —CH₃ | —H | —H | —H | —H | —Cl | —F | —H | —H | 1H-NMR (DMSO-d6) δppm 1.5-1.7(1 H, m), 2.0-2.2(1 H, m), 2.27(3 H, s), 2.7-2.9(1 H, m), 3.0-3.2(2 H, m), 3.5-3.6(1 H, m), 4.5-4.7(1 H, m), 6.45(2 H, s), 6.7-7.1(5 H, m), 7.2-7.4(2 H, m) | Fumarate |
| 95 | —H | —CH₃ | —H | —H | —H | —H | —F | —H | —H | —H | 1H-NMR (DMSO-d6) δppm 1.5-1.7(1 H, m), 2.0-2.2(1 H, m), 2.30(3 H, s), 2.7-2.9 (1 H, m), 3.0-3.2 (2 H, m), 3.5-3.6(1 H, m), 4.5-4.7 (1 H, m), 6.3-6.6(3 H, m), 6.43(2 H, s), 6.8-7.0(2 H, m), 7.1-7.3(2 H, m), 7.33(1 H, dd, J = 7.7 Hz, J = 7.7 Hz) | Fumarate |
| 96 | —H | —H | —F | —H | —H | —H | —CH₃ | —F | —H | —H | 1H-NMR (DMSO-d6) δppm 1.5-1.7(1 H, m), 2.0-2.2(1 H, m), 2.48(3 H, s), 2.7-2.9(1 H, m), 3.0-3.2 (2 H, m), 3.5-3.6(1 H, m), 4.5-4.7(1 H, m), 6.43(2 H, s), 6.7-6.9(4 H, m), 7.0-7.2(3 H, m) | Fumarate |

TABLE 48

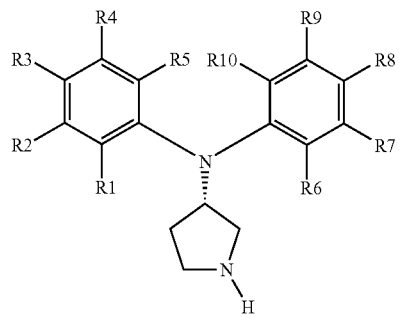

| Ex. No. | R1 | R2 | R3 | R4 | R5 | R6 | R7 | R8 | R9 | R10 | NMR | Salt |
|---|---|---|---|---|---|---|---|---|---|---|---|---|
| 97 | —H | —H | —CH₃ | —H | —H | —H | —F | —H | —H | —H | 1H-NMR (DMSO-d6) δppm 1.5-1.7(1 H, m), 2.0-2.2(1 H, m), 2.33(3 H, s), 2.7-2.9(1 H, m), 3.0-3.2(2 H, m), 3.5-3.6(1 H, m), 4.5-4.7(1 H, m), 6.3-6.6(3 H, m), 6.43(2 H, s), 7.05(2 H, d, J = 8.1 Hz), 7.1-7.2(1 H, m), 7.28(2 H, d, J = 8.1 Hz) | Fumarate |

TABLE 48-continued

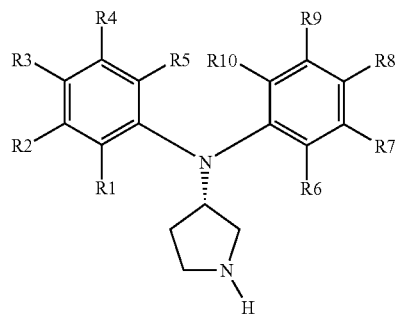

| Ex. No. | R1 | R2 | R3 | R4 | R5 | R6 | R7 | R8 | R9 | R10 | NMR | Salt |
|---|---|---|---|---|---|---|---|---|---|---|---|---|
| 98 | —H | —Cl | —CH₃ | —H | —H | —H | —F | —H | —H | —H | 1H-NMR (DMSO-d6) δppm 1.5-1.7(1 H, m), 2.0-2.2(1 H, m), 2.32(3 H, s), 2.7-2.9 (1 H, m), 3.0-3.2(2 H, m), 3.5-3.6(1 H, m), 4.5-4.7(1 H, m), 6.4-6.7(3 H, m), 6.43(2 H, s), 6.98(1 H, d, J = 8.1 Hz), 7.16(1 H, s), 7.2-7.3(1 H, m), 7.38(1 H, d, J = 8.1 Hz) | Fumarate |
| 99 | —H | —Cl | —F | —H | —H | —H | —H | —C₂H₅ | —H | —H | 1H-NMR (DMSO-d6) δppm 1.18(3 H, t, J = 7.6 Hz), 1.49-1.68(1 H, m), 2.01-2.19(1 H, m), 2.60(2 H, q, J = 7.6 Hz), 2.69-2.81(1 H, m), 2.92-3.14(2 H, m), 3.40-3.55 (1 H, m), 4.50-4.69(1 H, m), 6.44(2 H, s), 6.63-6.71 (1 H, m), 6.89(1 H, dd, J = 2.8 Hz and 6.3 Hz), 7.00(2 H, d, J = 8.3 Hz), 7.19-7.29(2 H, m) | Fumarate |
| 100 | —H | —F | —H | —H | —H | —H | —CH₃ | —Cl | —H | —H | 1H-NMR (DMSO-d6) δppm 1.5-1.7(1 H, m), 2.0-2.2(1 H, m), 2.30(3 H, s), 2.7-2.9(1 H, m), 3.0-3.2(2 H, m), 3.5-3.6(1 H, m), 4.5-4.7(1 H, m), 6.4-6.7(3 H, m), 6.46(2 H, s), 6.93(1 H, d, J = 8.5 Hz), 7.12(1 H, s), 7.2-7.3(1 H, m), 7.43(1 H, d, J = 8.5 Hz) | Fumarate |
| 101 | —H | —F | —H | —H | —H | —H | —CN | —H | —H | —H | 1H-NMR (DMSO-d6) δppm 1.5-1.7(1 H, m), 2.1-2.3( 1H, m), 2.8-3.0(1 H, m), 3.0-3.2(2 H, m), 3.5-3.7(1 H, m), 4.6-4.8(1 H, m), 6.48(2 H, s), 6.7-7.0(3 H, m), 7.1-7.2(1 H,m), 7.3-7.5(4 H, m) | Fumarate |
| 102 | —H | —H | —F | —Cl | —H | —H | —CN | —H | —H | —H | 1H-NMR (DMSO-d6) δppm 1.5-1.7(1 H, m), 2.0-2.2(1 H, m), 2.7-2.9(1 H, m), 3.0-3.2(2 H, m), 3.6-3.8(1 H, m), 4.6-4.8(1 H, m), 6.44(2 H, s), 6.93(1 H, d, J = 8.4 Hz), 7.1-7.2(1 H, m), 7.19(1 H, s), 7.27(1 H, d, J = 7.6 Hz), 7.37(1 H, dd, J = 7.6 Hz, J = 8.2 Hz), 7.4-7.6(2 H, m) | Fumarate |

TABLE 49

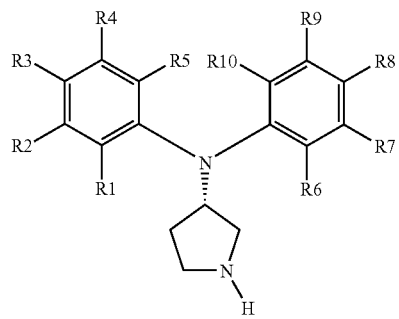

| Ex. No. | R1 | R2 | R3 | R4 | R5 | R6 | R7 | R8 | R9 | R10 | NMR | Salt |
|---|---|---|---|---|---|---|---|---|---|---|---|---|
| 103 | —H | —H | —CO₂C₂H₅ | —H | —H | —H | —Cl | —F | —H | —H | 1H-NMR (DMSO-d6) δppm 1.26(3 H, t, J = 7.1 Hz), 1.55-1.68(1 H, m), 2.18-2.29(1 H, m), 2.83-2.92(1 H, m), 3.07-3.19 (2 H, m), 3.58-3.68(1 H, m), 4.23 (2 H, q, J = 7.1 Hz), 4.71-4.82(1 H, m), 6.65(2 H, d, J = 9.0 Hz), 7.28-7.34(1 H, m), 7.55-7.64(2 H, m), 7.76(2 H, d, J = 9.0 Hz), 8.90-9.51(2 H, br) | Hydrochloride |

TABLE 49-continued

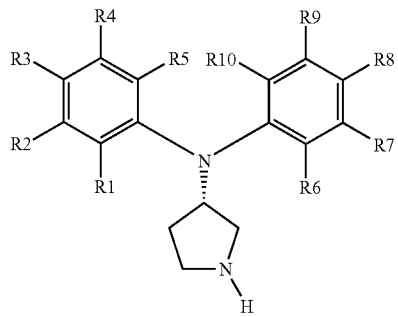

| Ex. No. | R1 | R2 | R3 | R4 | R5 | R6 | R7 | R8 | R9 | R10 | NMR | Salt |
|---|---|---|---|---|---|---|---|---|---|---|---|---|
| 104 | —H | —H | —CO$_2$H | —H | —H | —H | —Cl | —F | —H | —H | 1H-NMR (DMSO-d6) δppm 1.52-1.70(1 H, m), 2.15-2.21(1 H, m), 2.81-2.92 (1 H, m), 3.06-3.18(2 H, m), 3.53-3.67(1 H, m), 4.65-4.80(1 H, m), 6.64(1 H, d, J = 9.0 Hz), 7.25-7.33(1 H, m), 7.52-7.62(2 H, m), 7.75(2 H, d, J = 9.0 Hz), 8.50-10.50(1 H, br), 11.00-13.00(2 H, br) | Hydro-chloride |
| 105 | —H | —H | —SO$_2$CH$_3$ | —H | —H | —H | —Cl | —F | —H | —H | 1H-NMR (DMSO-d6) δppm 1.56-1.68(1 H, m), 2.19-2.29(1 H, m), 2.82-2.94(1 H, m), 3.08 (3 H, s), 3.10-3.20(2 H, m), 3.57-3.68 (1 H, m), 4.70-4.85(1 H, m), 6.69-6.75(2 H, m), 7.32-7.37(1 H, m), 7.58-7.64 (1 H, m), 7.65-7.69(3 H, m), 9.10-9.45(2 H, m) | Hydro-chloride |
| 106 | —H | —H | —N(CH$_3$)$_2$ | —H | —H | —H | —CH$_3$ | —F | —H | —H | 1H-NMR (DMSO-d6) δppm 1.52-1.70(1 H, m), 2.08-2.25(1 H, m), 2.24(3 H, s), 2.73-2.87(1 H, m), 3.03(6 H, s), 3.02-3.19(2 H, m), 3.50-3.67(1 H, m), 4.65-4.76(1 H, m), 6.73(2 H, d, J = 9.1 Hz), 7.00-7.20(2 H, m), 7.25(1 H, t, J = 9.1 Hz), 7.56(2 H, d, J = 7.2 Hz), 9.47(1 H, brs), 9.58(1 H, brs). | 2-Hydro chloride |

TABLE 50

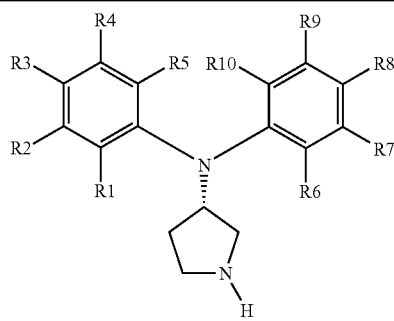

| Ex. No. | R1 | R2 | R3 | R4 | R5 | R6 | R7 | R8 | R9 | R10 | NMR |
|---|---|---|---|---|---|---|---|---|---|---|---|
| 107 | —H | —Cl | —F | —H | —H | —H | —H | ![S(=O)(=O)N-pyrrolidine] | —H | —H | 1H-NMR (CDCl3) δppm 1.56-1.86(5 H, m), 2.17-2.30(1 H, m), 2.96(1 H, dd, J = 7.4, 11.5 Hz), 3.08-3.21(6 H, m), 3.52(1 H, dd, J = 6.8, 11.4 Hz), 4.58-4.72(1 H, m), 6.62(2 H, d, J = 9.0 Hz), 7.02-7.09(1 H, m), 7.21-7.30(2 H, m), 7.59(2 H, d, J = 9.0 Hz). |

TABLE 51
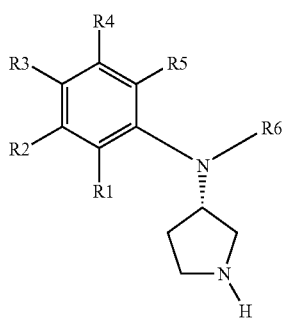
| Ex. No. | R1 | R2 | R3 | R4 | R5 | R6 | M.p. (° C.) | Salt |
|---|---|---|---|---|---|---|---|---|
| 108 | —H | —Cl | —F | —H | —H | 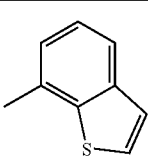 | 126-129 | |
| 109 | —H | —H | —H | —H | —H | 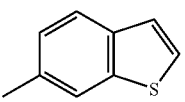 | 141-142 | Fumarate |
| 110 | —H | —H | —H | —H | —H | 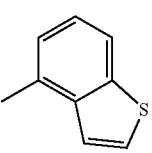 | 148-150 | Fumarate |
| 111 | —H | —Cl | —F | —H | —H | 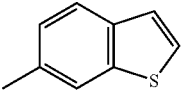 | 144-146 (dec.) | Fumarate |
| 112 | —H | —H | —F | —Cl | —H | 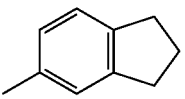 | 168-170 | Fumarate |
| 113 | —H | —H | —H | —H | —H | 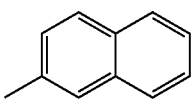 | 133-135 | Fumarate |
| 114 | —H | —H | —F | —H | —H | 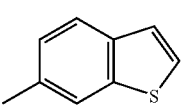 | 131.6-133.3 | Fumarate |
| 115 | —H | —H | —F | —H | —H | 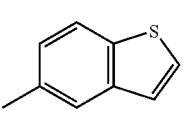 | 133.2-135.6 | Fumarate |
| 116 | —H | —H | —H | —H | —H | 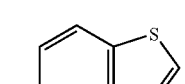 | 158-160 | Hydrochloride |

TABLE 52

[Structure: N-substituted aniline with pyrrolidin-3-yl group; R1-R5 on phenyl, R6 on N]

| Ex. No. | R1 | R2 | R3 | R4 | R5 | R6 | NMR | Salt |
|---|---|---|---|---|---|---|---|---|
| 117 | —H | —H | —F | —H | —H | (benzo[1,3]dioxole) | 1H-NMR (DMSO-d6) δ ppm 1.5-1.7 (1 H, m), 2.0-2.2 (1 H, m), 2.7-2.9 (1 H, m), 3.0-3.2 (2 H, m), 3.4-3.5 (1 H, m), 4.4-4.6 (1 H, m), 6.02 (2 H, s), 6.43 (2 H, s), 6.54 (1 H, d, J = 8.2 Hz), 6.69 (1 H, s), 6.7-6.8 (2 H, m), 6.90 (1 H, d, J = 8.2 Hz), 7.0-7.1 (2 H, m) | Fumarate |
| 118 | —H | —H | —F | —Cl | —H | (benzo[1,3]dioxole) | 1H-NMR (DMSO-d6) δ ppm 1.5-1.7 (1 H, m), 2.0-2.2 (1 H, m), 2.7-2.9 (1 H, m), 3.0-3.2 (2 H, m), 3.5-3.6 (1 H, m), 4.5-4.7 (1 H, m), 6.06 (2 H, s), 6.44 (2 H, s), 6.5-6.7 (1 H, m), 6.7-6.8 (2 H, m), 6.96 (1 H, d, J = 8.2 Hz), 7.12 (1 H, s), 7.1-7.3 (1 H, m) | Fumarate |
| 119 | —H | —H | —H | —F | —H | (benzo[1,3]dioxole) | 1H-NMR (DMSO-d6) δ ppm 1.5-1.7 (1 H, m), 2.0-2.2 (1 H, m), 2.7-2.9 (1 H, m), 2.9-3.1 (2 H, m), 3.4-3.6 (1 H, m), 4.5-4.7 (1 H, m), 6.08 (2 H, s), 6.3-6.5 (3 H, m), 6.44 (2 H, s), 6.67 (1 H, d, J = 8.1 Hz), 6.82 (1 H, s), 6.99 (1 H, d, J = 8.1 Hz), 7.0-7.2 (1 H, m) | Fumarate |
| 120 | —H | —H | —F | —Cl | —H | (2,3-dihydrobenzo[1,4]dioxine) | 1H-NMR (DMSO-d6) δ ppm 1.5-1.7 (1 H, m), 2.0-2.2 (1 H, m), 2.7-2.9 (1 H, m), 3.0-3.2 (2 H, m), 3.4-3.6 (1 H, m), 4.24 (4 H, s), 4.5-4.7 (1 H, m), 6.45 (2 H, s), 6.5-6.7 (2 H, m), 6.70 (1 H, s), 6.7-6.8 (1 H, m), 6.91 (1 H, d, J = 8.5 Hz), 7.20 (1 H, dd, J = 9.1 Hz, J = 9.1 Hz) | Fumarate |
| 121 | —H | —H | —F | —Cl | —H | (benzothiophene) | 1H-NMR (DMSO-d6) δ ppm 1.5-1.7 (1 H, m), 2.1-2.3 (1 H, m), 2.7-2.9 (1 H, m), 3.0-3.2 (2 H, m), 3.5-3.7 (1 H, m), 4.6-4.8 (1 H, m), 6.45 (2 H, s), 6.9-7.0 (1 H, m), 7.08 (1 H, d, J = 8.5 Hz), 7.23 (1 H, dd, J = 9.1 Hz), J = 9.1 Hz), 7.42 (1 H, d, J = 5.4 Hz), 7.66 (1 H, s), 7.80 (1 H, d, J = 5.4 Hz), 8.02 (1 H, d, J = 8.5 Hz) | Fumarate |
| 122 | —H | —H | —F | —Cl | —H | (benzofuran) | 1H-NMR (DMSO-d6) δ ppm 1.5-1.7 (1 H, m), 2.1-2.3 (1 H, m), 2.7-2.9 (1 H, m), 3.0-3.2 (2 H, m), 3.5-3.7 (1 H, m), 4.6-4.8 (1 H, m), 6.46 (2 H, s), 6.5-6.6 (1 H, m), 6.7-6.8 (1 H, m), 6.96 (1 H, d, J = 2.2 Hz), 7.09 (1 H, d, J = 8.7 Hz), 7.18 (1 H, dd, J = 9.1 Hz, J = 9.1 Hz), 7.50 (1 H, d, J = 2.2 Hz), 7.67 (1 H, d, J = 8.7 Hz), 8.05 (1 H, d, J = 2.2 Hz) | Fumarate |

TABLE 53

| Ex. No. | R1 | R2 | R3 | R4 | R5 | R6 | NMR |
|---|---|---|---|---|---|---|---|
| 123 | —H | —Cl | —F | —H | —H | 4-methyl-1H-indol-3-yl | 1H-NMR (CDCl3) δppm<br>1.7-1.9(2 H, m), 2.0-2.25(1 H, m),<br>2.8-3.0(3 H, m), 3.05-3.25(1 H, m), 4.35-4.6( 1 H, m), 6.24(1 H, d, J = 1 Hz),<br>6.4-6.5(1 H, m), 6.65-6.75(1 H, m), 6.8-7.0(2 H, m), 7.1-7.2(1 H, m), 7.22(1 H, d, J = 7.5 Hz), 7.36(1 H, d, J = 8. Hz), 8.43(1 H, br). |
| 124 | —H | —H | —H | —H | —H | 4-methyl-1H-indol-3-yl | 1H-NMR (CDCl3) δppm<br>1.68(1 H, br), 1.8-1.95(1 H, m),<br>2.0-2.2( 1H, m), 2.86(2 H, t, J = 7.5 Hz), 2.99(1 H, dd, J = 5.5, 12 Hz), 3.13( 1 H, dd, J = 6.5, 11.5 Hz), 4.5-4.6(1 H, m), 6.2-6.3(1 H, m), 6.6-6.75(3 H, m), 6.92(1 H, d, J = 7.5 Hz), 7.05-7.25(4 H, m), 7.35(1 H, d, J = 8 Hz), 8.34(1 H, br). |
| 125 | —H | —Cl | —F | —H | —H | 6-methyl-1H-indol-3-yl | 1H-NMR (CDCl3) δppm<br>1.65-1.9(2 H, m), 2.0-2.2(1 H, m),<br>2.8-3.0(3 H, m), 3.05-3.2( 1H, m), 4.25-4.4(1 H, m), 6.4-6.5(1 H, m), 6.57(1 H, d, J = 3 H), 6.67(1 H, dd, J = 3, 6 Hz), 6.75-6.85(1 H, m), 6.90(1 H, dd, J = 9, 9 Hz),<br>7.13(1 H, s), 7.2-7.3(1 H, m), 7.64(1 H, d, J = 8.5 Hz), 8.38(1 H, br). |
| 126 | —H | —Cl | —F | —H | —H | 5-methyl-1H-indol-3-yl | 1H-NMR(CDCl3) δppm<br>1.74-1.91(1 H, m), 2.03-2.18(1 H, m),<br>2.82-3.00(3 H, m), 3.14(1 H, dd, J = 6.5 Hz, 11.5 Hz), 4.30-4.40(1 H, m), 6.39-6.46(1 H, m),<br>6.55(1 H, d, J = 3.0 Hz), 6.63(1 H, dd, J = 3.0 Hz, 3.0 Hz), 6.83-6.91(1 H, m), 7.18-7.41(3 H, m), 8.50(1 H, br) |

TABLE 54

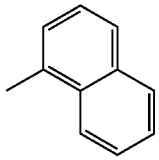

| Ex. No. | R1 | R2 | R3 | R4 | R5 | R6 | NMR | Salt |
|---|---|---|---|---|---|---|---|---|
| 127 | —H | —H | —H | —H | —H | 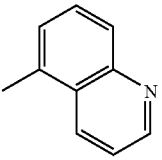 | 1H-NMR (DMSO-d6) δppm 1.4-1.6(1 H, m), 2.05-2.25(1 H, m), 2.8-2.95(1 H, m), 3.0-3.2(2 H, m), 3.55-3.7(1 H, m), 4.8-5.0(1 H, m), 6.47(2 H, s), 6.53(2 H, d, J = 8 Hz), 6.68(1 H, dd, J = 7.5, 7.5 Hz), 7.0-7.2(2 H, m), 7.4-7.7(4 H, m), 7.7-7.85(1 H, m), 8.02(2 H, d, J = 7.5, 7.5 Hz). | Fumarate |
| 128 | —H | —H | —F | —Cl | —H | 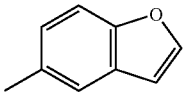 | 1H-NMR (DMSO-d6) δppm 1.35-1.55(1 H, m), 2.0-2.2(1 H, m), 2.25-5.45(8 H, m), 6.3-6.45(1 H, m), 6.48(2 H, s), 6.77(1 H, dd, J = 3, 6 Hz), 7.14(1 H, dd, J = 9, 9 Hz), 7.55(1 H, dd, J = 4, 8.5 Hz), 7.62(1 H, dd, J = 1, 7.5 Hz), 7.88(1 H, dd, J = 7.5, 7.5 Hz), 8.12(1 H, d, J = 8.5 Hz), 8.22(1 H, d, J = 8 Hz), 8.96(1 H, dd, J = 1.5, 4 Hz). | Fumarate |
| 129 | —H | —H | —H | —H | —H | 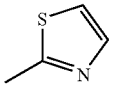 | 1H-NMR (DMSO-d6) δppm 1.45-1.8(1 H, m), 1.95-2.25(1 H, m), 2.6-4.8(8 H, m), 6.44(2 H, s), 6.67(2 H, d, J = 8 Hz), 6.77(1 H, dd, J = 7.5, 7.5 Hz), 6.96(1 H, dd, J = 1, 2 Hz), 7.06(1 H, dd, J = 2, 8.5 Hz), 7.16(2 H, dd, J = 7.5, 8.5 Hz), 7.47(1 H, d, J = 2 Hz), 7.65(1 H, d, J = 8.5 Hz), 8.04(1 H, d, J = 2 Hz). | Fumarate |

TABLE 55

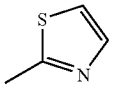

| Ex. No. | R1 | R2 | R3 | R4 | R5 | R6 | M.p. (° C.) | Salt |
|---|---|---|---|---|---|---|---|---|
| 130 | —H | —Cl | —F | —H | —H | 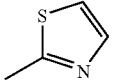 | 183-186 | Hydrochloride |
| 131 | —H | —Cl | —F | —H | —H | 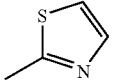 | 128.0-129.9 | Fumarate |
| 132 | —H | —H | —F | —H | —H | 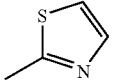 | 172-176 | 2 Hydrochloride |

TABLE 55-continued
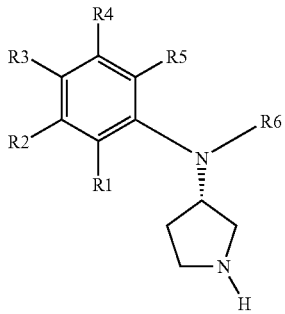
| Ex. No. | R1 | R2 | R3 | R4 | R5 | R6 | M.p. (° C.) | Salt |
|---|---|---|---|---|---|---|---|---|
| 133 | —H | —Cl | —F | —H | —H | 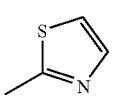 | 183-186 | 2 Hydrochloride |
| 134 | —H | —Cl | —Cl | —H | —H | 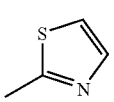 | 209-211 | 2Methanesulfonate |
| 135 | —H | —Cl | —Cl | —H | —H | 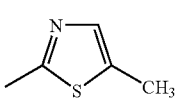 | 193-195 | 2Methanesulfonate |
| 136 | —H | —Cl | —Cl | —H | —H | 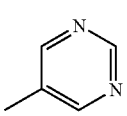 | 122-126 | 2 Hydrochloride |
| 137 | —H | —Cl | —F | —H | —H | 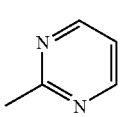 | 137.0-140.0 | Fumarate |
| 138 | —H | —H | —F | —H | —H | 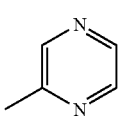 | 115-119 (dec.) | Fumarate |
| 139 | —H | —Cl | —F | —H | —H | 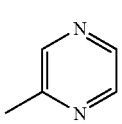 | 162.0-164.0 | Fumarate |

TABLE 56

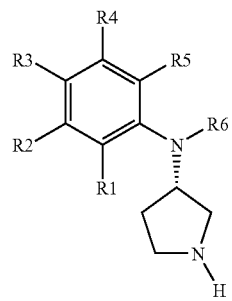

| Ex. No. | R1 | R2 | R3 | R4 | R5 | R6 | NMR | Salt |
|---|---|---|---|---|---|---|---|---|
| 140 | —H | —CH₃ | —F | —H | —H | 2-methylthiazol-4-yl | H-NMR (DMSO-d6) δppm1.8-2.0 (1 H, m), 2.2-2.4 (1 H, m), 2.27 (3 H, s), 3.1-3.3 (3 H, m), 3.5-3.7 (1 H, m), 4.8-5.0 (1 H, m), 6.79 (1 H, d. J = 3.7 Hz), 7.23 (1 H, d, J = 3.7 Hz), 7.3-7.4 (1 H, m), 7.43 (1 H, d, J = 7.5 Hz), 9.25 (1 H, brs), 9.44 (1 H, brs) | 2 Hydro chloride |
| 141 | —H | —Cl | —F | —H | —H | 2,5-dimethylthiazol-4-yl | 1H-NMR (DMSO-d6) δppm 1.79-1.98 (1 H, m), 2.14-2.33 (1 H, m), 2.19 (3 H, d, J = 1.0 HZ), 2.98-3.39 (2 H, m), 3.46-3.63 (1 H, m), 4.71-4.90 (1 H, m), 6.93 (1 H, d, J = 1.0 Hz), 7.50-7.65 (2 H, m), 7.84 (1 H, dd, J = 2.5 Hz, 6.5 Hz), 9.05 (1 H, br), 9.24 (1 H, br). | 2 Hydro chloride |
| 142 | —H | —Cl | —F | —H | —H | 5-methylpyrimidin-2-yl | 1H-NMR (DMSO-d6) δppm 1.55-1.72 (1 H, m), 2.05-2.29 (1 H, m), 2.82-2.95 (1 H, m), 3.02-3.14 (2 H, m), 3.51-3.65 (1 H, m), 4.65-4.83 (1 H, s), 6.51 (4 H, s), 7.20-7.29 (1 H, m), 7.46-7.60 (2 H, m with dd, J = 2.6 Hz and 6.7 Hz), 8.24 (2 H, s), 8.68 (1 H, s), | 2 Fumarate |
| 143 | —H | —Cl | —F | —H | —H | 4-methyl-2-(methylthio)pyrimidin-5-yl | 1H-NMR (DMSO-d6) δppm 1.6-1.7 (1 H, m), 2.1-2.2 (1 H, m), 2.57 (3 H, s), 2.9-3.1 (1 H, m), 3.1-3.2 (2 H, m), 3.6-3.8 (1 H, m), 5.2-5.4 (1 H, m), 5.87 (1 H, d, J = 6.1 Hz), 7.4-7.5 (1 H, m), 7.65 (1 H, dd, J = 8.9 Hz, J = 8.9 Hz), 7.8-7.9 (1 H, m), 8.01 (1 H, d, J = 6.1 Hz), 9.39 (1 H, brs), 9.59 (1 H, brs) | 2 Hydro chloride |
| 144 | —H | —Cl | —F | —H | —H | 3-methylpyrazin-2-yl | 1H-NMR (DMSO-d6) δppm 1.66-1.88 (1 H, m), 2.10-2.29 (1 H, m), 2.96-3.30 (3 H, m), 3.48-3.64 (1 H, m), 4.95-5.09 (1 H, m), 7.38-7.49 (1 H, m), 7.53 (1 H, d, J = 1.5 Hz), 7.55-7.66 (1 H, m), 7.7 (1 H, dd, J = 2.5 Hz and 6.8 Hz), 7.94 (1 H, d, J = 2.7 Hz), 8.19-8.26 (1 H, m), 9.30 (1 H, brs), 9.62 (1 H, brs) | 2 Hydro chloride |

TABLE 57

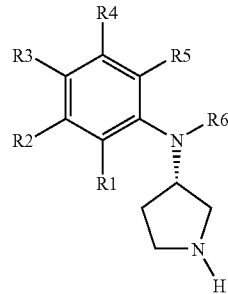

| Ex. No. | R1 | R2 | R3 | R4 | R5 | R6 | NMR | Salt |
|---|---|---|---|---|---|---|---|---|
| 145 | —H | —Cl | —F | —H | —H | benzothiazol-2-yl | 1H-NMR (DMSO-d6) δppm 1.8-2.0 (1 H, m), 2.2-2.4 (1 H, m), 3.1-3.4 (3 H, m), 3.5-3.7 (1 H, m), 5.0-5.2 (1 H, m), 7.11 (1 H, dd, J = 7.3 Hz, J = 7.7 Hz), 7.32 (1 H, dd, J = 7.3 Hz, J = 8.2 Hz), 7.6-7.8 (4 H, m), 7.9-8.1 (1 H, m), 9.22 (1 H, brs), 9.46 (1 H, brs) | 2 Hydro chloride |

TABLE 57-continued

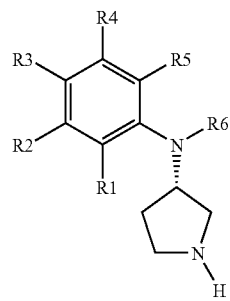

| Ex. No. | R1 | R2 | R3 | R4 | R5 | R6 | NMR | Salt |
|---|---|---|---|---|---|---|---|---|
| 146 | —H | —Cl | —F | —H | —H | 2-methyl-6-methoxybenzothiazol-5-yl | 1H-NMR (DMSO-d6) δppm 1.8-2.0 (1 H, m), 2.2-2.4 (1 H, m), 2.57 (3 H, s), 3.1-3.4 (3 H, m), 3.5-3.7 (1 H, m), 3.72 (3 H, s), 4.9-5.1 (1 H, m), 6.92 (1 H, d, J = 8.8 Hz), 7.31 (1 H, s), 7.52 (1 H, d, J = 8.8 Hz), 7.6-7.7 (2 H, m), 7.9-8.1 (1 H, m), 9.17 (1 H, brs), 9.42 (1 H, brs) | 2 Hydro chloride |
| 147 | —H | —H | —H | —H | —H | 2-methylbenzothiazol-5-yl | 1H-NMR (DMSO-d6) δppm 1.8-2.0 (1 H, m), 2.2-2.4 (1 H, m), 3.1-3.4 (3 H, m), 3.6-3.7 (1 H, m), 5.0-5.2 (1 H, m), 7.08 (1 H, dd, J = 7.2 Hz, J = 7.9 Hz), 7.31 (1 H, dd, J = 7.2 Hz, J = 8.2 Hz), 7.5-7.8 (7 H, m), 9.28 (1 H, brs), 9.50 (1 H, brs) | 2 Hydro chloride |
| 148 | —H | —Cl | —F | —H | —H | thieno[3,2-b]pyridin-7-yl | 1H-NMR (DMSO-d6) δppm 1.6-1.8 (1 H, m), 2.3-2.4 (1 H, m), 2.9-3.1 (1 H, m), 3.1-3.2 (2 H, m), 3.7-3.8 (1 H, m), 5.1-5.2 (1 H, m), 7.39 (1 H, d, J = 5.7 Hz), 7.55 (1 H, d, J = 5.7 Hz), 7.7-7.8 (2 H, m), 8.08 (1 H, d, J = 7.2 Hz), 8.22 (1 H, d, J = 5.7 Hz), 8.69 (1 H, d, J = 7.0 Hz), 9.43 (1 H, brs), 9.59 (1 H, brs) | 2 Hydro chloride |

TABLE 58

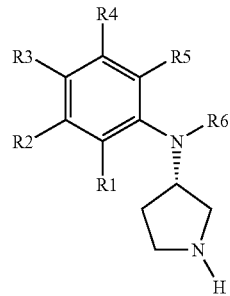

| Ex. No. | R1 | R2 | R3 | R4 | R5 | R6 | NMR | Salt |
|---|---|---|---|---|---|---|---|---|
| 149 | —H | —Cl | —F | —H | —H | quinolin-3-yl | 1H-NMR (DMSO-d6) δppm 1.6-1.8 (1 H, m), 2.2-2.4 (1 H, m), 2.9-3.1 (1 H, m), 3.1-3.3 (2 H, m), 3.6-3.8 (1 H, m), 4.8-5.0 (1 H, m), 7.3-7.4 (1 H, m), 7.56 (1 H, dd, J = 9.0 Hz, J = 9.0 Hz), 7.6-7.7 (1 H, m), 7.7-7.9 (2 H, m), 8.08 (1 H, d, J = 7.8 Hz), 8.22 (1 H, d, J = 8.4 Hz), 8.27 (1 H, s), 8.67 (1 H, s), 9.57 (1 H, brs), 9.64 (1 H, brs) | 2 Hydro chloride |
| 150 | —H | —Cl | —F | —H | —H | 2,3-dimethylquinolin-? | H-NMR (DMSO-d6) δppm 1.82 (3 H, s), 1.9-2.1 (1 H, m), 2.2-2.3 (1 H, m), 3.1-3.2 (1 H, m), 3.2-3.3 (1 H, m), 3.4-3.5 (1 H, m), 3.6-3.8 (1 H, m), 4.9-5.0 (1 H, m), 7.0-7.1 (1 H, m), 7.3-7.4 (2 H, m), 7.4-7.5 (1 H, m), 7.68 (1 H, dd, J = 8.0 Hz, J = 8.3 Hz), 7.81 (1 H, d, J = 7.2 Hz), 7.92 (1 H, d, J = 8.3 Hz), 8.04 (1 H, s), 8.94 (1 H, brs), 9.11 (1 H, brs) | 2 Hydro chloride |
| 151 | —H | —CH3 | —F | —H | —H | 3-methylquinolin-? | H-NMR (CDCl3) δppm 1.8-2.0 (1 H, m), 2.32 (3 H, s), 2.4-2.5 (1 H, m), 3.1-3.3 (1 H, m), 3.4-3.5 (1 H, m), 3.5-3.7 (1 H, m), 4.1-4.3 (1 H, m), 5.2-5.4 (1 H, m), 7.0-7.3 (3 H, m), 7.5-7.7 (2 H, m), 7.89 (1 H, d, J = 7.9 Hz), 8.04 (1 H, s), 8.47 (1 H, d, J = 8.3 Hz), 8.87 (1 H, s), 9.72 (1 H, brs), 10.28 (1 H, brs) | 2 Hydro chloride |

TABLE 58-continued

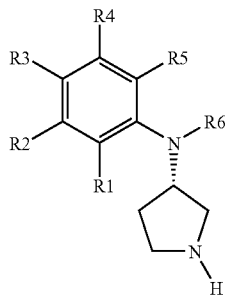

| Ex. No. | R1 | R2 | R3 | R4 | R5 | R6 | NMR | Salt |
|---|---|---|---|---|---|---|---|---|
| 152 | —H | —Cl | —F | —H | —H | 4-methylisoquinolinyl | 1H-NMR (DMSO-d6) δppm 1.6-1.8 (1 H, m), 2.2-2.4 (1 H, m), 2.9-3.1 (1 H, m), 3.1-3.3 (2 H, m), 3.6-3.8 (1 H, m), 4.8-5.0 (1 H, m), 6.3-6.4 (1 H, m), 6.48 (2 H, s), 6.7-6.8 (1 H, m), 7.15 (1 H, dd, J = 9.0 Hz, J = 9.0 Hz), 7.6-7.8 (3 H, m), 8.1-8.3 (1 H, m), 8.51 (1 H, s), 9.41 (1 H, s) | Fumarate |

TABLE 59

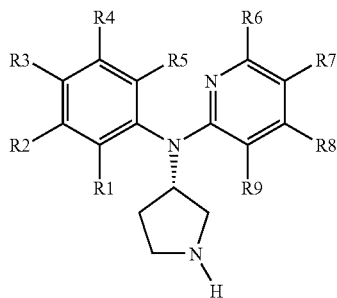

| Ex. No. | R1 | R2 | R3 | R4 | R5 | R6 | R7 | R8 | R9 | M.p. (° C.) | Salt |
|---|---|---|---|---|---|---|---|---|---|---|---|
| 153 | —H | —H | —H | —H | —H | —H | —H | —H | —H | 208.0-211.0 (dec.) | 2 Hydrochloride |
| 154 | —H | —Cl | —F | —H | —H | —H | —H | —H | —H | 152.4-154.4 | Fumarate |
| 155 | —H | —Cl | —F | —H | —H | —H | —CH₃ | —H | —H | 141.8-143.1 | Fumarate |
| 156 | —H | —Cl | —F | —H | —H | —H | —H | —CH₃ | —H | 138.6-140.2 | Fumarate |
| 157 | —H | —Cl | —F | —H | —H | —H | —H | —H | —H | 207.0-208.0 | 2Methane-sulfonamide |
| 158 | —H | —Cl | —F | —H | —H | —H | -3-THIENYL | —H | —H | 148-151 | 2 Hydrochloride |
| 159 | —H | —Cl | —F | —H | —H | —H | -4-PYRIDYL | —H | —H | 157-158 | 3 Hydrochloride |
| 160 | —H | —Cl | —F | —H | —H | —H | —C₆H₅ | —H | —H | 150-153 | 2 Hydrochloride |
| 161 | —H | —Cl | —F | —H | —H | —H | —H | —H | —F | 83-85 | 2 Hydrochloride |
| 162 | —H | —Cl | —F | —H | —H | —H | —H | —F | —H | 150-153 | 2 Hydrochloride |
| 163 | —H | —Cl | —F | —H | —H | —H | —CF₃ | —H | —H | 87-89 | Hydrochloride |
| 164 | —H | —Cl | —F | —H | —H | —H | —H | —OCH₃ | —H | 153-156 | 2 Hydrochloride |
| 165 | —H | —Cl | —F | —H | —H | —Br | —H | —H | —H | 220-223 | Hydrochloride |
| 166 | —H | —Cl | —F | —H | —H | —Cl | —H | —H | —H | 219-220 | Hydrochloride |
| 167 | —H | —Cl | —F | —H | —H | —H | —C₂H₅ | —H | —H | 112-115 | Fumarate |
| 168 | —H | —Cl | —F | —H | —H | -2-THIENYL | —H | —H | —H | 98-103 | Hydrochloride |
| 169 | —H | —Cl | —F | —H | —H | -3-THIENYL | —H | —H | —H | 95-98 | Hydrochloride |
| 170 | —H | —Cl | —F | —H | —H | —H | —H | —Cl | —H | 125-128 | 2 Hydrochloride |
| 171 | —H | —Cl | —Cl | —H | —H | —H | —F | —H | —H | 111-115 | 2 Hydrochloride |
| 172 | —H | —Cl | —Cl | —H | —H | —H | —Br | —H | —H | 115-118 | 2 Hydrochloride |
| 173 | —H | —Cl | —Cl | —H | —H | —H | —H | —H | —F | 75-80 | 2 Hydrochloride |
| 174 | —H | —Cl | —Cl | —H | —H | —H | —H | —F | —H | 125-128 | 2 Hydrochloride |

TABLE 60

| Ex. No. | R1 | R2 | R3 | R4 | R5 | R6 | R7 | R8 | R9 | M.p. (°C.) | Salt |
|---|---|---|---|---|---|---|---|---|---|---|---|
| 175 | —H | —Cl | —Cl | —H | —H | —H | —H | —OCH₃ | —H | 160-165 | 2 Hydrochloride |
| 176 | —H | —Cl | —F | —H | —H | —H | —CN | —H | —H | 211-213 | Hydrochloride |
| 177 | —H | —Cl | —Cl | —H | —H | —H | —CN | —H | —H | 126-130 | 2 Hydrochloride |
| 178 | —H | —Cl | —Cl | —H | —H | —H | —H | —CH₃ | —H | 204-207 | 2 Hydrochloride |
| 179 | —H | —Cl | —Cl | —H | —H | —H | —CF₃ | —H | —H | 100-105 | 2 Hydrochloride |
| 180 | —H | —Cl | —Cl | —H | —H | —OCH₃ | —H | —H | —H | 190-195 | 2 Hydrochloride |
| 181 | —H | —Cl | —Cl | —H | —H | —H | —H | —CN | —H | 135-138 | 2 Hydrochloride |
| 182 | —H | —Cl | —F | —H | —H | —H | —Cl | —H | —H | 163-165 | Fumarate |
| 183 | —H | —Cl | —F | —H | —H | —H | —Cl | —H | —H | 190-191 | 2-Hydrochloride |
| 184 | —H | —H | —F | —H | —H | —H | —Cl | —H | —H | 95-97 | Fumarate |
| 185 | —H | —CH3 | —F | —H | —H | —H | —Cl | —H | —H | 156-157 | Fumarate |
| 186 | —H | —Cl | —F | —H | —H | —H | —Br | —H | —H | 159-160 | Fumarate |
| 187 | —H | —H | —F | —H | —H | —H | —H | —H | —H | 226-228 | 2 Hydrochloride |
| 188 | —H | —H | —Cl | —Cl | —H | —H | —H | —H | —H | 135-138 | 2 Hydrochloride |
| 189 | —H | —H | —Cl | —Cl | —H | —H | —Cl | —H | —H | 123-125 | 2 Hydrochloride |
| 190 | —H | —H | —F | —Cl | —H | —H | -3-FURYL | —H | —H | 157-160 | 2 Hydrochloride |
| 191 | —H | —H | —F | —Cl | —H | —H | -2-THIENYL | —H | —H | 152-155 | 2 Hydrochloride |
| 192 | —H | —H | —F | —Cl | —H | —H | —F | —H | —H | 115-120 | 2 Hydrochloride |

TABLE 61

| Ex. No. | R1 | R2 | R3 | R4 | R5 | R6 | R7 | R8 | R9 | M.p. (°C.) | Salt |
|---|---|---|---|---|---|---|---|---|---|---|---|
| 193 | —H | —Cl | —F | —H | —H | —H | 4-methoxyphenyl | —H | —H | 143-145 | 2 Hydrochloride |
| 194 | —H | —Cl | —F | —H | —H | —H | 4-cyanophenyl | —H | —H | 145-146 | 2 Hydrochloride |

TABLE 61-continued

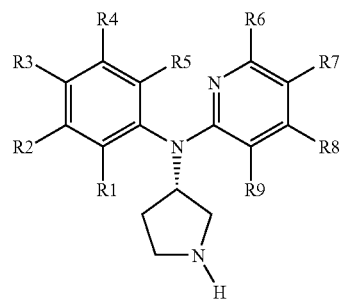

| Ex. No. | R1 | R2 | R3 | R4 | R5 | R6 | R7 | R8 | R9 | M.p. (° C.) | Salt |
|---|---|---|---|---|---|---|---|---|---|---|---|
| 195 | —H | —Cl | —F | —H | —H | —H | 2,3,4-trifluorophenyl | —H | —H | 113-116 | 2 Hydrochloride |
| 196 | —H | —Cl | —F | —H | —H | —H | 2-acetylphenyl | —H | —H | 128-130 | 2 Hydrochloride |
| 197 | —H | —Cl | —F | —H | —H | —H | 3-chlorophenyl | —H | —H | 116-120 | 2 Hydrochloride |
| 198 | —H | —H | —F | —H | —H | —H | 1-methylpyrrolidinyl | —H | —H | 132-135 | 2 Hydrochloride |
| 199 | —H | —Cl | —F | —H | —H | —H | 1-methylpiperidinyl | —H | —H | 142-145 | 3 Hydrochloride |
| 200 | —H | —Cl | —F | —H | —H | —H | 4-methylpiperazinyl | —H | —H | 212-215 | 4 Hydrochloride |
| 201 | —H | —Cl | —F | —H | —H | —H | 4-methyl-1-ethylpiperazinyl | —H | —H | 208-211 | 4 Hydrochloride |
| 202 | —H | —Cl | —F | —H | —H | —H | 4-methyl-1-acetylpiperazinyl | —H | —H | 200-203 | 3 Hydrochloride |

TABLE 62
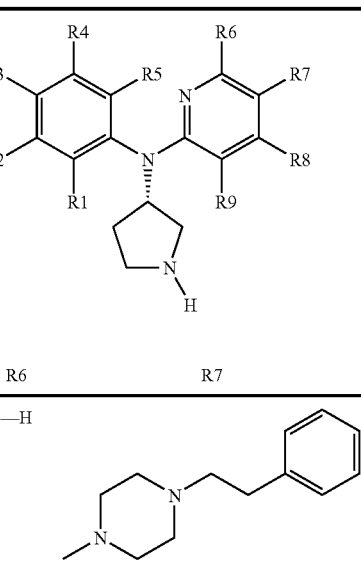
| Ex. No. | R1 | R2 | R3 | R4 | R5 | R6 | R7 | R8 | R9 | M.p. (° C.) | Salt |
|---|---|---|---|---|---|---|---|---|---|---|---|
| 203 | —H | —Cl | —F | —H | —H | —H | 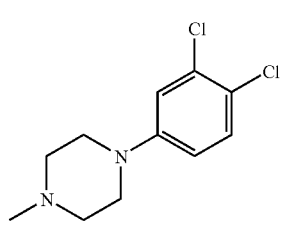 | —H | —H | 160-162 | 4 Hydrochloride |
| 204 | —H | —Cl | —F | —H | —H | —H | 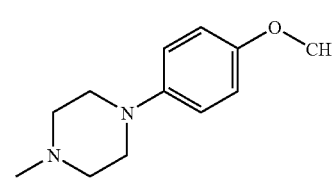 | —H | —H | 167-170 | 2 Hydrochloride |
| 205 | —H | —Cl | —F | —H | —H | —H | 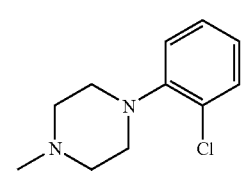 | —H | —H | 200-203 | 3 Hydrochloride |
| 206 | —H | —Cl | —F | —H | —H | —H | 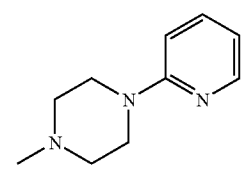 | —H | —H | 243-246 | 3 Hydrochloride |
| 207 | —H | —Cl | —F | —H | —H | —H | 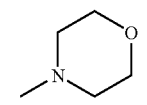 | —H | —H | 145-147 | 4 Hydrochloride |
| 208 | —H | —H | —F | —Cl | —H | —H | 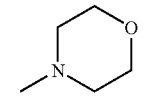 | —H | —H | 143-145 | 3 Hydrochloride |
| 209 | —H | —H | —F | —H | —H | —H | 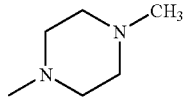 | —H | —H | 131-133 | 3 Hydrochloride |
| 210 | —H | —H | —F | —Cl | —H | —H |  | —H | —H | 184-186 | 3 Hydrochloride |

TABLE 62-continued
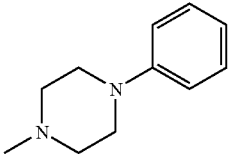
| Ex. No. | R1 | R2 | R3 | R4 | R5 | R6 | R7 | R8 | R9 | M.p. (° C.) | Salt |
|---|---|---|---|---|---|---|---|---|---|---|---|
| 211 | —H | —H | —F | —Cl | —H | —H | 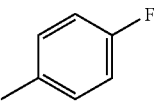 | —H | —H | 160-162 | 3 Hydrochloride |
| 212 | —H | —H | —F | —Cl | —H | —H | 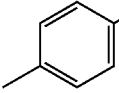 | —H | —H | 133-135 | 2 Hydrochloride |
TABLE 63
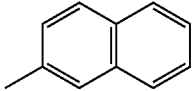
| Ex. No. | R1 | R2 | R3 | R4 | R5 | R6 | R7 | R8 | R9 | M.p. (° C.) | Salt |
|---|---|---|---|---|---|---|---|---|---|---|---|
| 213 | —H | —Cl | —F | —H | —H | —H | (4-methylbenzyl) | —H | —H | 128-131 | 2 Hydrochloride |
| 214 | —H | —Cl | —F | —H | —H | —H | (naphthalenyl) | —H | —H | 164-166 | 2 Hydrochloride |

TABLE 64

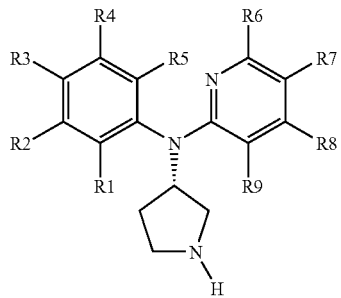

| Ex. No. | R1 | R2 | R3 | R4 | R5 | R6 | R7 | R8 | R9 | M.p. (° C.) | Salt |
|---|---|---|---|---|---|---|---|---|---|---|---|
| 215 | —H | —Cl | —F | —H | —H | 1,4-piperazinyl-N-CH₃ | —H | —H | —H | 181-183 | 4 Hydrochloride |

TABLE 65

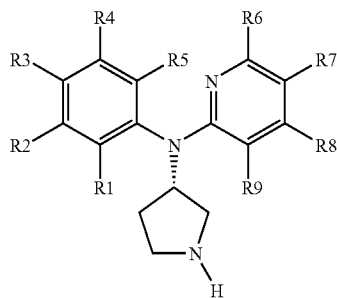

| Ex. No. | R1 | R2 | R3 | R4 | R5 | R6 | R7 | R8 | R9 | NMR | Salt |
|---|---|---|---|---|---|---|---|---|---|---|---|
| 216 | —H | —Cl | —F | —H | —H | —H | —H | —H | —H | 1H-NMR (DMSO-d6) δppm 1.59-1.82 (1 H, m), 2.11-2.35 (1 H, m), 2.85-3.28 (3 H, m), 3.50-3.71 (1 H, m), 5.01-5.21 (1 H, m), 6.25-6.46 (1 H, m), 6.82-6.92 (1 H, m), 7.33-7.50 (1 H, m), 7.55-7.70 (2 H, m), 7.74 (1 H, dd, J = 2.4 Hz, and 6.7 Hz), 8.11-8.21 (1 H, m), 9.20-9.75 (2 H, m) | 2 Hydrochloride |
| 217 | —H | —H | —H | —H | —H | —CH₃ | —H | —H | —H | 1H-NMR (DMSO-d6) δppm 1.60-1.79 (1 H, m), 2.13-2.30 (1 H, m), 2.50 (1 H, s), 2.86-3.02 (1 H, m), 3.05-3.20 (2 H, m), 3.59-3.64 (1 H, m), 5.29-5.45 (1 H, m), 5.80-6.00 (1 H, m), 6.68 (1 H, d, J = 7.2 Hz) 7.32 (1 H, d, J = 7.2 Hz), 7.41-7.51 (2 H, m), 7.53-7.61 (2 H, m), 9.49 (2 H, brs) | Hydrochloride |
| 218 | —H | —H | —H | —H | —H | H | —CH₃ | —H | —H | 1H-NMR (DMSO-d6) δppm 1.61-1.79 (1 H, m), 2.19 (3 H, s), 2.23-2.39 (1 H, m), 2.85-3.20 (3 H, m), 3.59-3.74 (1 H, m), 5.05-5.22 (1 H, m), 6.20-6.40 (1 H, m), 7.32-7.41 (2 H, m), 7.46-7.62 (4 H, m), 7.94-7.99 (1 H, m), 9.30-9.65 (2 H, br) | 2 Hydrochloride |
| 219 | —H | —H | —H | —H | —H | —H | —CH₃ | —H | —H | 1H-NMR (DMSO-d6) δppm 1.60-1.80 (1 H, m), 2.19 (3 H, s), 2.24-2.48 (1 H, m), 2.81-3.00 (1 H, m), 3.02-3.19 (2 H, m), 3.58-3.64 (1 H, m), 6.30 (1 H, d, J = 8.8 Hz), 7.32-7.42 (2 H, m), 7.49-7.68 (4 H, m), 7.93-8.01 (1 H, m), 9.50 (2 H, brs) | 2 Hydrochloride |
| 220 | —H | —Cl | —F | —H | —H | —CH₃ | —H | —H | —H | 1H-NMR (DMSO-d6) δppm 1.52-1.76 (1 H, m), 1.92-2.18 (1 H, m), 2.32 (3 H, s), 2.90-3.22 (3 H, m), 3.50-3.72 (1 H, m), 5.05-5.25 (1 H, m), 5.72-5.90 (1 H, m), 6.35-6.70 (3 H, m), 7.11-7.75 (3 H, m) | Fumarate |
| 221 | —H | —CF₃ | —F | —H | —H | —H | —H | —H | —H | 1H-NMR (DMSO-d6) δppm 1.65-1.83 (1 H, m), 2.16-2.31 (1 H, m), 3.00-3.31 (3 H, m), 3.52-3.67 (1 H, m), 5.03-5.16 (1 H, m), 6.25 (1 H, d, J = 8.5 Hz), 6.80-6.85 (1 H, m), 7.52-7.59 (1 H, m), 7.67-7.81 (1 H, m), 7.84 (1 H, d, J = 6.5 Hz), 8.19-8.22 (1 H, m), 9.07 (1 H, br), 9.34 (1 H, br). | 2 Hydrochloride |

TABLE 66

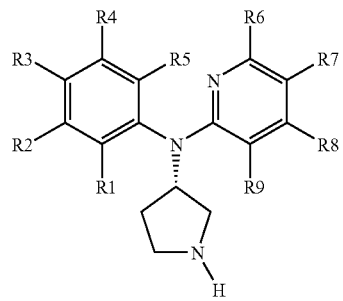

| Ex. No. | R1 | R2 | R3 | R4 | R5 | R6 | R7 | R8 | R9 | NMR | Salt |
|---|---|---|---|---|---|---|---|---|---|---|---|
| 222 | —H | —Cl | —F | —Cl | —H | —H | —H | —CF$_3$ | —H | H-NMR (DMSO-d6) δppm 1.7-1.8 (1 H, m), 2.1-2.3 (1 H, m), 3.0-3.2 (2 H, m), 3.2-3.3 (1 H, m), 3.5-3.7 (1 H, m), 5.1-5.2 (1 H, m), 6.24 (1 H, s), 7.03 (1 H, d, J = 5.3 Hz), 7.4-7.5 (1 H, m), 7.63 (1 H, dd, J = 9.0 Hz, J = 9.0 Hz), 7.7-7.8 (1 H, m), 8.47 (1 H, d, J = 5.3 Hz), 9.21 (1 H, brs), 9.53 (1 H, brs) | 2 Hydrochloride |
| 223 | —H | —Cl | —F | —H | —H | —OCH$_3$ | —H | —H | —H | H-NMR (DMSO-d6) δppm 1.6-1.7 (1 H, m), 2.1-2.2 (1 H, m), 2.9-3.1 (1 H, m), 3.1-3.2 (2 H, m), 3.6-3.8 (1 H, m), 3.85 (3 H, s), 5.1-5.2 (1 H, m), 5.52 (1 H, d, J = 8.0 Hz), 6.12 (1 H, d, J = 7.8 Hz), 7.3-7.4 (2 H, m), 7.5-7.7 (2 H, m), 9.25 (1 H, brs) | 2 Hydrochloride |
| 224 | —H | —CH$_3$ | —F | —H | —H | —H | —H | —H | —Cl | H-NMR (CDCl3) δppm 2.1-2.4 (2 H, m), 2.23 (3 H, s), 3.2-3.3 (1 H, m), 3.4-3.6 (2 H, m), 3.6-3.8 (1 H, m), 4.7-4.9 (1 H, m), 6.7-7.1 (4 H, m), 7.57 (1 H, d, J = 7.1 Hz), 8.52 (1 H, d, J = 3.9 Hz), 9.53 (1 H, brs), 10.10 (1 H, brs) | 2 Hydrochloride |
| 225 | —H | —CH$_3$ | —F | —H | —H | —H | —H | —H | —H | H-NMR (CDCl3) δppm 1.8-2.0 (1 H, m), 2.35 (3 H, s), 2.5-2.7 (1 H, m), 3.1-3.4 (2 H, m), 3.4-3.6 (1 H, m), 4.1-4.3 (1 H, m), 5.3-5.5 (1 H, m), 6.47 (1 H, d, J = 8.9 Hz), 7.05 (1 H, s), 7.2-7.4 (3 H, m), 7.78 (1 H, dd, J = 8.9 Hz, J = 7.6 Hz), 8.25 (1 H, d, J = 4.7 Hz), 9.51 (1 H, brs), 10.39 (1 H, brs) | 2 Hydrochloride |
| 226 | —H | —H | —F | —H | —H | —H | —CH$_3$ | —H | —H | H-NMR (CDCl3) δppm 1.8-2.0 (1 H, m), 2.31 (3 H, s), 2.35 (3 H, s), 2.6-2.7 (1 H, m), 3.1-3.3 (1 H, m), 3.3-3.4 (1 H, m), 3.4-3.6 (1 H, m), 4.1-4.3 (1 H, m), 5.3-5.5 (1 H, m), 6.42 (1 H, d, J = 9.3 Hz), 7.1-7.4 (3 H, m), 7.61 (1 H, d, J = 9.3 Hz), 8.04 (1 H, s), 9.51 (1 H, brs), 10.47 (1 H, brs) | 2 Hydrochloride |
| 227 | —H | —CH$_3$ | —F | —H | —H | —CH$_3$ | —H | —H | —H | H-NMR (CDCl3) δppm 1.8-2.0 (1 H, m), 2.36 (3 H, s), 2.4-2.5 (1 H, m), 2.92 (3 H, s), 3.2-3.4 (2 H, m), 3.4-3.6 (1 H, m), 4.1-4.3 (1 H, m), 6.0-6.1 (1 H, m), 6.20 (1 H, d, J = 8.9 Hz), 6.73 (1 H, d, J = 7.1 Hz), 7.1-7.3 (3 H, m), 7.5-7.7 (1 H, m), 9.29 (1 H, brs), 10.98 (1 H, brs) | 2 Hydrochloride |

TABLE 67

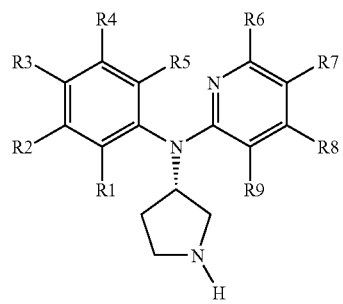

| Ex. No. | R1 | R2 | R3 | R4 | R5 | R6 | R7 | R8 | R9 | NMR | Salt |
|---|---|---|---|---|---|---|---|---|---|---|---|
| 228 | —H | —CH$_3$ | —F | —H | —H | —OCH$_3$ | —H | —H | —H | H-NMR (CDCl3) δppm 1.9-2.1 (1 H, m), 2.26 (3 H, s), 2.2-2.4 (1 H, m), 3.2-3.5 (3 H, m), 3.8-3.9 (1 H, m), 3.90 (3 H, s), 5.0-5.2 (1 H, m), 5.58 (1 H, d, J = 8.1 Hz), | 2 Hydrochloride |

TABLE 67-continued

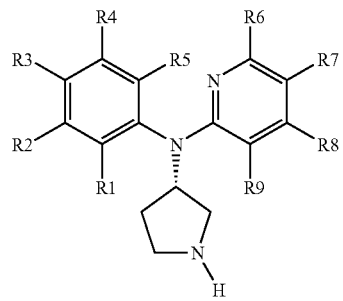

| Ex. No. | R1 | R2 | R3 | R4 | R5 | R6 | R7 | R8 | R9 | NMR | Salt |
|---|---|---|---|---|---|---|---|---|---|---|---|
| | | | | | | | | | | 6.08 (1 H, d, J = 8.0 Hz) 6.9-7.1 (3 H, m), 7.22 (1 H, dd, J = 8.0 Hz, J = 8.1 Hz), 9.74 (1 H, brs), 10.18 (1 H, brs) | |
| 229 | —H | —CH$_3$ | —F | —H | —H | —H | —H | —CH$_3$ | —H | H-NMR (CDCl3) δppm 1.9-2.0 (1 H, m), 2.31 (3 H, s), 2.37 (3 H, s), 2.6-2.7 (1 H, m), 3.1-3.3 (1 H, m), 3.3-3.4 (1 H, m), 3.4-3.6 (1 H, m), 4.1-4.3 (1 H, m), 5.4-5.6 (1 H, m), 6.18 (1 H, s), 6.84 (1 H, d, J = 6.3 Hz), 7.2-7.4 (3 H, m), 8.11 (1 H, d, J = 6.3 Hz), 9.55 (1 H, brs), 10.64 (1 H, brs) | 2 Hydrochloride |
| 230 | —H | —CH$_3$ | —F | —H | —H | —H | —H | —H | —CH$_3$ | H-NMR (CDCl3) δppm 1.96 (3 H, s), 2.0-2.1 (1 H, m), 2.27 (3 H, s), 2.4-2.6 (1 H, m), 3.4-3.7 (3 H, m), 3.8-4.0 (1 H, m), 5.3-5.5 (1 H, m), 7.0-7.3 (3 H, m), 7.3-7.5 (1 H, m), 7.89 (1 H, d, J = 7.0 Hz), 8.50 (1 H, d, J = 5.1 Hz), 9.77 (1 H, brs), 10.39 (1 H, brs) | 2 Hydrochloride |
| 231 | —H | —Cl | —F | —H | —H | —Cl | —H | —Cl | | 1H-NMR (CDCl3) δppm 1.65-1.81 (1 H, m), 1.99-2.09 (1 H, m), 2.81-3.11 (4 H, m), 4.50-4.61 (1 H, m), 6.80-6.87 (1 H, m), 7.00 (1 H, dd, J = 2.8, 6.4 Hz), 7.05 (1 H, t, d, J = 8.7 Hz), 7.61 (1 H, d, J = 2.3 Hz), 8.26 (1 H, d, J = 2.3 Hz). | |
| 232 | —H | —Cl | —F | —H | —H | —CN | —H | —H | —H | 1H-NMR (CDCl3) δppm 1.63-1.77 (1 H, m), 2.01-2.15 (1 H, m), 2.78-2.96 (3 H, m), 3.28-3.35 (1 H, m), 5.02-5.16 (1 H, m), 6.03 (1 H, d, J = 9.0 Hz), 7.02-7.10 (1 H, m), 7.24-7.32 (2 H, m), 7.44 (1 H, dd, J = 2.3, 9.0 Hz), 8.46 (1 H, d, J = 2.3 Hz). | |
| 233 | —H | —Cl | —F | —H | —H | —CN | —H | —H | —H | 1H-NMR (CDCl3) δppm 1.82-1.95 (1 H, m), 2.19-2.25 (1 H, m), 3.11-3.29 (3 H, m), 3.62-3.70 (1 H, m), 5.01-5.11 (1 H, m), 6.27 (1 H, d, J = 8.8 Hz), 7.06 (1 H, d, J = 7.3 Hz), 7.10-7.15 (1 H, m), 7.23-7.31 (2 H, m), 7.39 (1 H, dd J = 7.3, 8.8 Hz). | |

TABLE 68

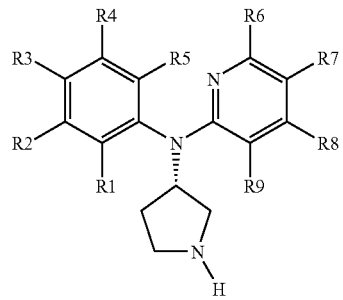

| Ex. No. | R1 | R2 | R3 | R4 | R5 | R6 | R7 | R8 | R9 | NMR | Salt |
|---|---|---|---|---|---|---|---|---|---|---|---|
| 234 | —H | —Cl | —Cl | —H | —H | —H | —H | —Cl | —H | 1H-NMR (DMSO-d6) δppm 1.68-1.82 (1 H, m), 2.11-2.24 (1 H, m), 3.01-3.14 (2 H, m), 3.15-3.29 (1 H, m), 3.48-3.65 (1 H, m), 4.98-5.10 (1 H, m), 6.21 (1 H, s), 6.88 (1 H, d, J = 5.4 Hz), 7.35-7.40 (1 H, m), 7.76 (1 H, d, J = 1.7 Hz), 7.82 (1 H, d, J = 8.4 Hz), 8.21 (1 H, d, J = 5.4 Hz), 9.19 (1 H, brs), 9.55 (1 H, brs). | 2 Hydrochloride |

TABLE 68-continued

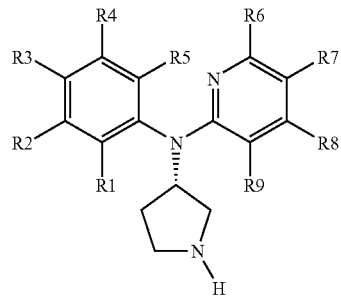

| Ex. No. | R1 | R2 | R3 | R4 | R5 | R6 | R7 | R8 | R9 | NMR | Salt |
|---|---|---|---|---|---|---|---|---|---|---|---|
| 235 | —H | —Cl | —F | —H | —H | —H | —H | —H | —Cl | 1H-NMR (CDCl3) δppm 1.74 (1 H, brs), 2.30 (1 H, brs), 3.34 (1 H, brs), 3.55 (2 H, brs), 3.73 (1 H, brs), 4.79 (1 H, brs), 6.90-7.13 (4 H, m), 7.60 (1 H, d, J = 7.7 Hz), 8.58 (1 H, s), 9.48 (1 H, brs), 10.38 (1 H, brs) | Hydrochloride |
| 236 | —H | —Cl | —F | —H | —H | —H | -3-PYRIDYL | —H | —H | 1H-NMR (DMSO-d6) δppm 1.65-1.90 (1 H, m), 2.13-2.31 (1 H, m), 2.99-3.28 (3 H, m), 3.58-3.72 (1 H, m), 5.13-5.28 (1 H, m), 6.26 (1 H, d, J = 9.0 Hz), 7.45 (1 H, ddd, J = 2.6, 4.3, 8.6 Hz), 7.65 (1 H, t, J = 9.0 Hz), 7.76 (1 H, dd, J = 2.5, 6.7 Hz), 8.02 (1 H, dd, J = 2.5, 9.0 Hz), 8.11 (1 H, dd, J = 5.7, 8.1 Hz), 8.78-8.87 (3 H, m), 9.25 (1 H, s), 9.60 (1 H, brs), 9.85 (1 H, brs). | 2 Hydrochloride |

TABLE 69

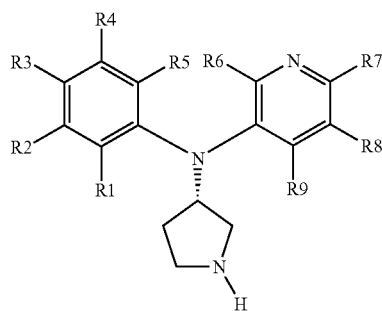

| Ex. No. | R1 | R2 | R3 | R4 | R5 | R6 | R7 | R8 | R9 | M.p. (° C.) | Salt |
|---|---|---|---|---|---|---|---|---|---|---|---|
| 237 | —H | —Cl | —F | —H | —H | —H | —H | —H | —H | 194.0-195.0 | 2Methanesulfonate |
| 238 | —H | —Cl | —F | —H | —H | —H | —C6H5 | —H | —H | 158-161 | 2 Hydrochloride |
| 239 | —H | —Cl | —F | —H | —H | —H | —F | —H | —H | 75-80 | 2 Hydrochloride |
| 240 | —H | —Cl | —F | —H | —H | —H | —F | —H | —H | 121-123 | Fumarate |
| 241 | —H | —Cl | —Cl | —H | —H | —H | —CN | —H | —H | 150-155 | 2 Hydrochloride |
| 242 | —H | —Cl | —Cl | —H | —H | —H | —H | —H | —H | 108-110 | Hydrochloride |
| 243 | —H | —H | —F | —H | —H | —H | —H | —H | —H | 232-234 | 2 Hydrochloride |
| 244 | —H | —Cl | —F | —H | —H | —H | —Cl | —H | —H | 136-137 | Fumarate |
| 245 | —H | —Cl | —F | —H | —H | —H | —H | -4-PYRIDYL | —H | 200-205 | 3 Hydrochloride |

TABLE 70

[Structure: diaryl amine with pyrrolidine substituent on N; phenyl ring with R1-R5, pyridine ring with R6-R9]

| Ex. No. | R1 | R2 | R3 | R4 | R5 | R6 | R7 | R8 | R9 | M.p. (°C.) | Salt |
|---|---|---|---|---|---|---|---|---|---|---|---|
| 246 | —H | —Cl | —F | —H | —H | —H | —H | 4-methylpiperazin-1-yl | —H | 252-257 | 4 Hydrochloride |
| 247 | —H | —H | —F | —Cl | —H | —H | 4-methylpiperazin-1-yl | —H | —H | 223-225 | 3 Hydrochloride |
| 248 | —H | —H | —F | —Cl | —H | —H | morpholin-4-yl | —H | —H | 155-157 | 2 Hydrochloride |

TABLE 71

[Structure: same scaffold]

| Ex. No. | R1 | R2 | R3 | R4 | R5 | R6 | R7 | R8 | R9 | NMR | Salt |
|---|---|---|---|---|---|---|---|---|---|---|---|
| 249 | —H | —H | —H | —H | —H | —H | —H | —H | —H | 1H-NMR (DMSO-d6) δppm 1.50-1.70 (1 H, m), 2.10-2.31 (1 H, m), 2.75-2.90 (1 H, m), 3.00-3.22 (2 H, m), 3.51-3.68 (1 H, m), 4.60-4.80 (1 H, m), 6.47 (2 H, s), 7.01-7.10 (2 H, m), 7.13-7.30 (3 H, m), 7.32-7.45 (2 H, m), 8.07 (1 H, d, J = 2.7 Hz), 8.13 (1 H, dd, J = 1.4 Hz and 4.5 Hz) | Fumarate |
| 250 | —H | —Cl | —F | —H | —H | —H | —H | —H | —H | 1H-NMR (DMSO-d6) δppm 1.51-1.74 (1 H, m), 2.13-2.35 (1 H, m), 2.80-2.99 (1 H, m), 3.01-3.20 (2 H, m), 3.52-3.72 (1 H, m), 4.75-4.94 (1 H, m), 7.39-7.48 (1 H, m), 7.59-7.69 (2 H, m), 7.71-7.81 (2 H, m), 8.19-8.29 (2 H, m) | 2 Hydrochloride |
| 251 | —H | —F | —H | —H | —H | —H | —H | —H | —H | 1H-NMR (DMSO-d6) δppm 1.62-1.81 (1 H, m), 2.20-2.37 (1 H, m), 2.88-3.24 (3 H, m), 3.56-3.72 (1 H, m), 5.10-5.27 (1 H, m), 6.27 (1 H, d, J = 8.6 Hz), 6.82-6.92 (1 H, m), 7.37 (2 H, d, J = 7.1 Hz), 7.49-7.72 (4 H, m with d at δ7.58, J = 7.6 Hz), 8.15 (1 H, dd, | 2 Hydrochloride |

TABLE 71-continued

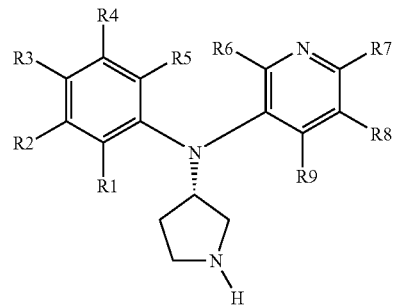

| Ex. No. | R1 | R2 | R3 | R4 | R5 | R6 | R7 | R8 | R9 | NMR | Salt |
|---|---|---|---|---|---|---|---|---|---|---|---|
| 252 | —H | —H | —H | —H | —H | —H | —F | —H | —H | J = 1.2 Hz and 5.6 Hz), 9.30-9.80 (2 H, m) 1H-NMR (DMSO-d6) δppm 1.50-1.71 (1 H, m), 2.05-2.28 (1 H, m), 2.75-2.92 (1 H, m), 3.00-3.24 (2 H, m), 3.45-3.62 (1 H, m), 4.52-4.78 (1 H, m), 6.86-6.98 (2 H, m), 7.01-7.11 (1 H, m), 7.15 (1 H, dd, J = 3.4 Hz and 7.2 Hz), 7.28-7.39 (2 H, m), 7.48-7.62 (1 H, m), 7.84-7.93 (1 H, m), 9.20-9.80 (2 H, m) | Hydro-chloride |
| 253 | —H | —CH$_3$ | —F | —H | —H | —H | —H | —H | —H | 1H-NMR (DMSO-d6) δppm 1.5-1.7 (1 H, m), 2.0-2.2 (1 H, m), 2.27 (3 H, s), 2.36 (6 H, s), 2.8-3.0 (1 H, m), 3.0-3.3 (2 H, m), 3.6-3.7 (1 H, m), 4.7-4.9 (1 H, m), 7.2-7.4 (3 H, m), 7.55 (1 H, d, J = 8.9 Hz), 7.75 (1 H, d, J = 8.9 Hz), 8.14 (1 H, s), 8.22 (1 H, d, J = 5.1 Hz), 8.83 (2 H, brs) | 2 Methane-sulfonate |
| 254 | —H | —Cl | —F | —H | —H | —H | —OCH$_3$ | —H | —H | 1H-NMR (DMSO-d6) δppm 1.5-1.7 (1 H, m), 2.1-2.2 (1 H, m), 2.7-2.9 (1 H, m), 3.0-3.2 (2 H, m), 3.5-3.6 (1 H, m), 3.86 (3 H, s), 4.6-4.7 (1 H, m), 6.46 (2 H, s), 6.5-6.7 (1 H, m), 6.85 (1 H, d, J = 9.1 Hz), 6.90 (1 H, d, J = 8.7 Hz), 7.21 (1 H, dd, J = 9.1 Hz, J = 9.1 Hz), 7.56 (1 H, d, J = 8.7 Hz), 8.03 (1 H, s) | Fumarate |

TABLE 72

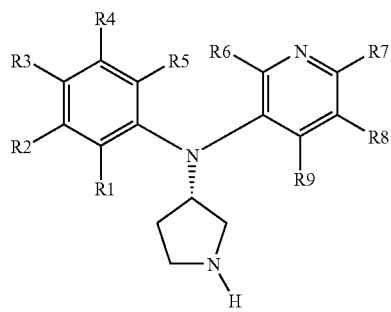

| Ex. No. | R1 | R2 | R3 | R4 | R5 | R6 | R7 | R8 | R9 | NMR | Salt |
|---|---|---|---|---|---|---|---|---|---|---|---|
| 255 | —H | —F | —F | —H | —H | —H | —H | —H | —H | H-NMR (DMSO-d6) δppm 1.6-1.8 (1 H, m), 2.2-2.3 (1 H, m), 2.9-3.0 (1 H, m), 3.0-3.2 (2 H, m), 3.6-3.8 (1H, m), 4.8-4.9 (1 H, m), 7.23 (1 H, d, J = 8.7 Hz), 7.5-7.8 (4 H, m), 8.21 (1 H, s), 8.36 (1 H, d, J = 5.1 Hz), 9.49 (1 H, brs), 9.55 (1 H, brs) | 2 Hydro-chloride |
| 256 | —H | —Cl | —Cl | —H | —H | —H | —H | —H | —H | H-NMR (DMSO-d6) δppm 1.6-1.8 (1 H, m), 2.2-2.3 (1 H, m), 2.9-3.0 (1 H, m), 3.1-3.2 (2 H, m), 3.6-3.8 (1H, m), 4.8-4.9 (1 H, m), 7.26 (1 H, d, J = 8.6 Hz), 7.6-7.8 (4 H, m), 8.32 (1 H, s), 8.34 | 2 Hydro-chloride |

TABLE 72-continued

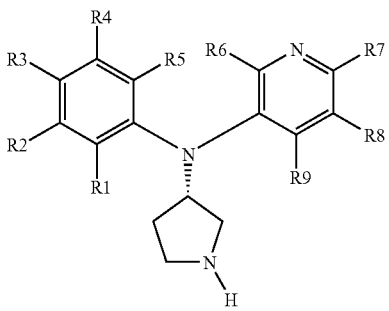

| Ex. No. | R1 | R2 | R3 | R4 | R5 | R6 | R7 | R8 | R9 | NMR | Salt |
|---|---|---|---|---|---|---|---|---|---|---|---|
| | | | | | | | | | | (1 H, d, J = 4.6 Hz), 9.38 (1 H, brs), 9.50 (1 H, brs) | |
| 257 | —H | —CF$_3$ | —F | —H | —H | —H | —H | —H | —H | 1H-NMR (DMSO-d6) δppm 1.52-1.72 (1 H, m), 2.19-2.35 (1 H, m), 2.84-3.01 (1 H, m), 3.05-3.21 (2 H, m), 3.59-3.73 (1 H, m), 4.81-4.94 (1 H, m), 7.61 (1 H, dd, J = 2.0 Hz, 8.5 Hz), 7.71-7.76 (3 H, m), 7.82 (1 H, d, J = 7.0 Hz), 8.26-8.29 (2 H, m), 9.40 (1 H, br), 9.50 (1 H, br). | 2 Hydro-chloride |
| 258 | —H | —Cl | —H | —H | —H | —H | —H | —H | —H | H-NMR (DMSO-d6) δppm 1.6-1.8 (1 H, m), 2.2-2.3 (1 H, m), 2.8-2.9 (1 H, m), 3.0-3.2 (2 H, m), 3.5-3.7 (1 H, m), 4.8-5.0 (1 H, m), 7.29 (1 H, d, J = 7.8 Hz), 7.47 (1 H, s), 7.5-7.7 (3 H, m), 7.76 (1 H, d, J = 8.9 Hz), 8.21 (1 H, s), 8.29 (1 H, d, J = 5.3 Hz), 9.5-9.8 (2 H, br) | 2 Hydro-chloride |
| 259 | —H | —Cl | —F | —H | —H | —H | —H | —Br | —H | H-NMR (DMSO-d6) δppm 1.5-1.7 (1 H, m), 2.1-2.3 (1 H, m), 2.8-3.0 (1 H, m), 3.0-3.2 (2 H, m), 3.5-3.7 (1 H, m), 4.7-4.9 (1 H, m), 7.2-7.4 (1 H, m), 7.50 (1 H, s), 7.56 (1 H, dd, J = 9.0 Hz, J = 9.0 Hz), 7.6-7.7 (1 H, m), 7.97 (1 H, s), 8.23 (1 H, s), 9.41 (1 H, brs), 9.51 (1 H, brs) | 2 Hydro-chloride |

TABLE 73

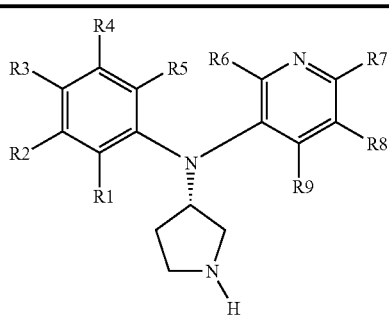

| Ex. No. | R1 | R2 | R3 | R4 | R5 | R6 | R7 | R8 | R9 | NMR | Salt |
|---|---|---|---|---|---|---|---|---|---|---|---|
| 260 | —H | —Cl | —F | —H | —H | —H | —H | —COC$_6$H$_5$ | —H | H-NMR (DMSO-d6) δppm 1.6-1.8 (1 H, m), 2.2-2.4 (1 H, m), 2.9-3.0 (1 H, m), 3.1-3.2 (2 H, m), 3.5-3.7 (1 H, m), 4.8-5.0 (1 H, m), 7.3-7.4 (1 H, m), 7.5-7.9 (8 H, m), 8.37 (1 H, s), 8.39 (1 H, s), 9.4-9.7 (2 H, br) | 2 Hydro-chloride |
| 261 | —H | —Cl | —F | —H | —H | —H | —H | —C$_6$H$_5$ | —H | H-NMR (DMSO-d6) δppm 1.6-1.8 (1 H, m), 2.2-2.4 (1 H, m), 2.9-3.0 (1 H, m), 3.1-3.2 (2 H, m), 3.6-3.8 (1 H, m), 4.9-5.1 (1 H, m), 7.4-7.5 (1 H, m), 7.5-7.6 (3 H, m), 7.62 (1 H, dd, J = 8.9 Hz, J = 8.9 Hz), 7.7-7.8 (1 H, m), 7.79 (2 H, d, J = 8.3 Hz), 7.87 (1 H, s), 8.00 (1 H, s), 8.57 (1 H, s), 9.46 (1 H, brs), 9.58 (1 H, brs) | 2 Hydro-chloride |

TABLE 73-continued

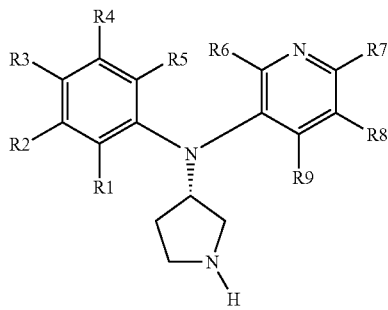

| Ex. No. | R1 | R2 | R3 | R4 | R5 | R6 | R7 | R8 | R9 | NMR | Salt |
|---|---|---|---|---|---|---|---|---|---|---|---|
| 262 | —H | —Cl | —F | —H | —H | —H | —H | —SCH$_3$ | —H | H-NMR (DMSO-d6) δppm 1.5-1.7 (1 H, m), 2.1-2.3 (1 H, m), 2.55 (3 H, s), 2.8-3.0 (1 H, m), 3.0-3.2 (2 H, m), 3.5-3.7 (1 H, m), 4.7-4.9 (1 H, m), 7.2-7.3 (1 H, m), 7.33 (1 H, s), 7.5-7.6 (2 H, m), 7.81 (1 H, s), 8.10 (1 H, s), 9.22 (1 H, brs), 9.36 (1 H, brs) | 2 Hydrochloride |
| 263 | —H | —Cl | —F | —H | —H | —H | —H | —SC$_6$H$_5$ | —H | H-NMR (DMSO-d6) δppm 1.5-1.7 (1 H, m), 2.1-2.3 (1 H, m), 2.8-2.9 (1 H, m), 3.0-3.2 (2 H, m), 3.5-3.7 (1 H, m), 4.7-4.9 (1 H, m), 6.77 (1 H, s), 7.2-7.3 (1 H, m), 7.40 (5 H, m), 7.4-7.6 (2 H, m), 8.01 (1 H, s), 8.08 (1 H, s), 9.38 (1 H, brs), 9.46 (1 H, brs) | 2 Hydrochloride |
| 264 | —H | —Cl | —F | —H | —H | —H | —Cl | —Cl | —H | H-NMR (DMSO-d6) δppm 1.5-1.7 (1 H, m), 2.1-2.3 (1 H, m), 2.8-2.9 (1 H, m), 3.0-3.2 (2 H, m), 3.5-3.7 (1 H, m), 4.7-4.9 (1 H, m), 7.2-7.4 (1 H, m), 7.44 (1 H, s), 7.54 (1 H, dd, J = 9.0 Hz, J = 9.0 Hz), 7.6-7.7 (1 H, m), 7.75 (1 H, s), 9.36 (2 H, brs) | 2 Hydrochloride |

TABLE 74

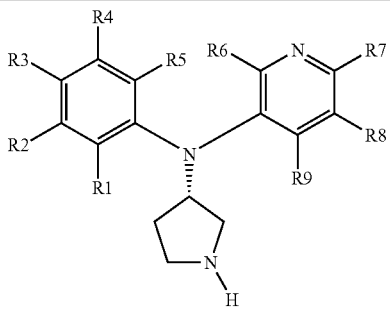

| Ex. No. | R1 | R2 | R3 | R4 | R5 | R6 | R7 | R8 | R9 | NMR | Salt |
|---|---|---|---|---|---|---|---|---|---|---|---|
| 265 | —H | —Cl | —F | —H | —H | —H | —H | —C$_2$H$_5$ | —H | H-NMR (DMSO-d6) δppm 1.16 (3 H, t, J = 7.0 Hz), 1.5-1.7 (1 H, m), 2.2-2.3 (1 H, m), 2.69 (2 H, q, J = 7.0 Hz), 2.8-2.9 (1 H, m), 3.0-3.2 (2 H, m), 3.5-3.7 (1 H, m), 4.8-5.0 (1 H, m), 7.2-7.3 (1 H, m), 7.59 (1 H, s), 7.6-7.7 (2 H, m), 7.95 (1 H, s), 8.19 (1 H, s), 9.42 (1 H, brs), 9.55 (1 H, brs) | 2 Hydrochloride |
| 266 | —H | —Cl | —F | —H | —H | —H | —H | —Cl | —H | H-NMR (DMSO-d6) δppm 1.5-1.7 (1 H, m), 2.1-2.3 (1 H, m), 2.8-2.9 (1 H, m), 3.0-3.2 (2 H, m), 3.5-3.7 (1 H, m), 4.7-4.9 (1 H, m), 7.2-7.3 (1 H, m), 7.33 (1 H, s), 7.55 (1 H, dd, J = 9.0 Hz, J = 9.0 Hz), 7.6-7.7 (1 H, m), 7.92 (1 H, s), 8.13 (1 H, s), 9.44 (1 H, brs), 9.53 (1 H, brs) | 2 Hydrochloride |

TABLE 74-continued

[Structure: substituted phenyl-N(pyrrolidin-3-yl)-pyridinyl amine with R1-R9 substituents]

| Ex. No. | R1 | R2 | R3 | R4 | R5 | R6 | R7 | R8 | R9 | NMR | Salt |
|---|---|---|---|---|---|---|---|---|---|---|---|
| 267 | —H | —Cl | —F | —H | —H | —H | —H | —CN | —H | H-NMR (DMSO-d6) δppm 1.5-1.7 (1 H, m), 2.1-2.3 (1 H, m), 2.44 (6 H, s), 2.8-3.0 (1 H, m), 3.1-3.2 (2 H, m), 3.6-3.8 (1 H, m), 4.7-4.9 (1 H, m), 7.2-7.3 (1 H, m), 7.5-7.7 (2 H, m), 7.67 (1 H, s), 8.17 (1 H, s), 8.45 (1 H, s), 8.79 (1 H, brs), 8.84 (1 H, brs) | 2 Methane-sulfonate |
| 268 | —H | —Cl | —F | —H | —H | —H | —CN | —H | —H | 1H-NMR (DMSO-d6) δppm 1.60-1.78 (1 H, m), 2.18-2.32 (1 H, m), 2.83-2.99 (1 H, m), 3.05-3.19 (2 H, m), 3.55-3.70 (1 H, m), 4.75-4.87 (1 H, m), 7.05 (1 H, dd, J = 3.0, 8.9 Hz), 7.32-7.43 (1 H, m), 7.64 (1 H, t, J = 9.0 Hz), 7.74 (1 H, dd, J = 2.5, 6.7 Hz), 7.78 (1 H, d, J = 8.9 Hz), 8.03 (1 H, d, J = 2.9 Hz), 9.25 (1 H, brs), 9.38 (1 H, brs). | 2 Hydro-chloride |
| 269 | —H | —Cl | —F | —H | —H | —H | —CN | —H | —H | 1H-NMR (CDCl3) δppm 1.67-1.81 (1 H, m), 2.10-2.25 (1 H, m), 2.83-2.89 (1 H, m), 2.90-3.00 (2 H, m), 3.27-3.34 (1 H, m), 4.35-4.52 (1 H, m), 6.86 (1 H, dd, J = 3.0, 5.4 Hz), 7.05-7.10 (1 H, m), 7.23-7.28 (1 H, m), 7.30 (1 H, d, J = 8.8 Hz), 7.44 (1 H, d, J = 8.8 Hz), 8.00 (1 H, d, J = 3.0 Hz). | |

TABLE 75

[Structure: substituted phenyl-N(pyrrolidin-3-yl)-pyridinyl amine with R1-R9 substituents]

| Ex. No. | R1 | R2 | R3 | R4 | R5 | R6 | R7 | R8 | R9 | NMR | Salt |
|---|---|---|---|---|---|---|---|---|---|---|---|
| 270 | —H | —Cl | —Cl | —H | —H | —H | —CN | —H | —H | 1H-NMR (CDCl3) δppm 1.70-1.82 (1 H, m), 2.11-2.25 (1 H, m), 2.83-2.90 (1 H, m), 2.94-3.00 (2 H, m), 3.26-3.33 (1 H, m), 4.35-4.50 (1 H, m), 6.90 (1 H, dd, J = 3.0, 8.8 Hz), 7.04 (1 H, dd, J = 2.4, 8.5 Hz), 7.28 (1 H, d, J = 2.8 Hz), 7.45 (1 H, d, J = 8.8 Hz), 7.59 (1 H, d, J = 8.5 Hz), 8.03 (1 H, d, J = 2.8 Hz). | |
| 271 | —H | —H | —Cl | —F | —H | —H | —H | —H | —H | H-NMR (DMSO-d6) δppm 1.6-1.8 (1 H, m), 2.2-2.3 (1 H, m), 2.36 (6 H, s), 2.9-3.0 (1 H, m), 3.1-3.3 (2 H, m), 3.6-3.8 (1 H, m), 4.8-4.9 (1 H, m), 7.09 (1 H, | 2 Methane sulfonate |

TABLE 75-continued
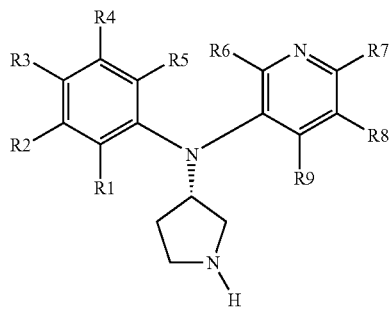
| Ex. No. | R1 | R2 | R3 | R4 | R5 | R6 | R7 | R8 | R9 | NMR | Salt |
|---|---|---|---|---|---|---|---|---|---|---|---|
| | | | | | | | | | | d, J = 8.5 Hz), 7.4-7.5 (1 H, m), 7.7-7.9 (3 H, m), 8.30 (1 H, s), 8.36 (1 H, d, J = 6.1 Hz), 8.76 (1 H, brs), 8.84 (1 H, brs) | |
TABLE 76
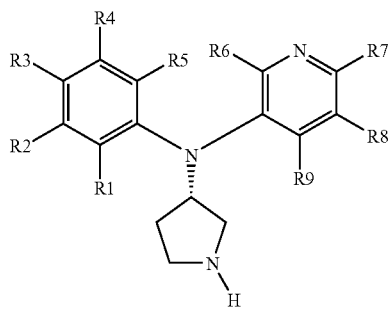
| Ex. No. | R1 | R2 | R3 | R4 | R5 | R6 | R7 | R8 | R9 | NMR |
|---|---|---|---|---|---|---|---|---|---|---|
| 272 | —H | —Cl | —F | —H | —H | —H | —H | 4-cyanophenyl | —H | 1H-NMR (CDCl3) δppm 1.67-1.81 (1 H, m), 2.08-2.19 (1 H, m), 2.87-3.00 (3 H, m), 3.24-3.31 (1 H, m), 4.40-4.48 (1 H, m), 6.95-7.05 (1 H, m), 7.16-7.24 (3 H, m), 7.61 (2 H, d, J = 8.3 Hz), 7.74 (2 H, d, J = 8.3 Hz), 8.12 (1 H, d, J = 2.6 Hz), 8.43 (1 H, d, J = 1.5 Hz). |
TABLE 77
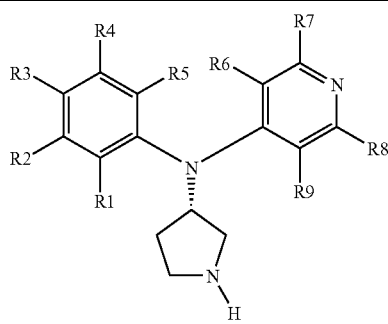
| Ex. No. | R1 | R2 | R3 | R4 | R5 | R6 | R7 | R8 | R9 | M.p. (° C.) | Salt |
|---|---|---|---|---|---|---|---|---|---|---|---|
| 273 | —H | —Cl | —Cl | —H | —H | —H | —H | —H | —H | 229-231 | 2 Hydrochloride |

TABLE 78

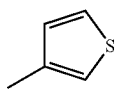

| Ex. No. | R1 | R2 | R3 | R4 | R5 | R6 | R7 | R8 | R9 | NMR | Salt |
|---|---|---|---|---|---|---|---|---|---|---|---|
| 274 | —H | —H | —H | —H | —H | —H | —H | —H | —H | 1H-NMR (DMSO-d6) δppm 1.52-1.71 (1 H, m), 2.21-2.39 (1 H, m), 2.40-2.99 (1 H, m), 3.00-3.25 (2 H, m), 3.61-3.78 (1 H, m), 4.98-5.12 (1 H, m), 6.55-7.10 (2 H, m), 7.35-7.45 (2 H, m), 7.53-7.71 (3 H, m), 8.22-8.38 (2 H, m), 9.80 (2 H, brs), 14.45 (1 H, brs) | Hydro-chloride |
| 275 | —H | —Cl | —F | —H | —H | —H | —H | —H | —H | 1H-NMR (DMSO-d6) δppm 1.56-1.76 (1 H, m), 2.20-2.38 (1 H, m), 2.89-3.02 (1 H, m), 3.03-3.20 (2 H, m), 3.60-3.75 (1 H, m), 4.94-5.11 (1 H, m), 6.70-7.15 (2 H, m), 7.41-7.53 (1 H, m), 7.66-7.76 (1 H, m), 7.85 (1 H, dd, J = 2.5 Hz and 6.9 Hz), 8.33 (2 H, d, J = 7.0 Hz), 9.44-9.80 (2 H, m) | 2 Hydro chloride |
| 276 | —H | —Cl | —F | —H | —H | —H | —CH$_3$ | —H | —H | H-NMR (DMSO-d6) δppm 1.6-1.8 (1 H, m), 2.2-2.4 (1 H, m), 2.50 (3 H, s), 2.8-3.0 (1 H, m), 3.1-3.2 (2 H, m), 3.6-3.8 (1 H, m), 4.9-5.1 (1 H, m), 6.4-7.0 (2 H, m), 7.4-7.5 (1 H, m), 7.69 (1 H, dd, J = 9.0 Hz, J = 9.0 Hz), 7.8-7.9 (1 H, m), 8.20 (1 H, d, J = 5.5 Hz), 9.54 (1 H, brs), 9.70 (1 H, brs) | 2 Hydro chloride |

TABLE 79

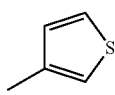

| Ex. No. | R1 | R2 | R3 | R4 | R5 | R6 | M.p. (° C.) | Salt |
|---|---|---|---|---|---|---|---|---|
| 277 | —H | —H | —H | —H | —H | 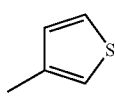 | 124.7-126.7 | Fumarate |
| 278 | —H | —Cl | —F | —H | —H | 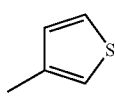 | 135.0-136.0 | Fumarate |
| 279 | —H | —F | —H | —H | —H | 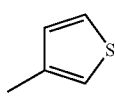 | 139.0-141.0 | Fumarate |

TABLE 80

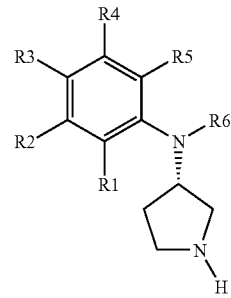

| Ex. No. | R1 | R2 | R3 | R4 | R5 | R6 | NMR | Salt |
|---|---|---|---|---|---|---|---|---|
| 280 | —H | —H | —F | —H | —H | | 1H-NMR (DMSO-d6) δppm 0.99-1.50 (2 H, m), 1.51-2.20 (4 H, m), 2.80-3.65 (7 H, m), 3.60-3.99 (2 H, m), 4.10-4.81 (1 H, m), 7.01-7.99 (4 H, m), 9.15-9.90 (2 H, m) | Hydrochloride |

TABLE 81

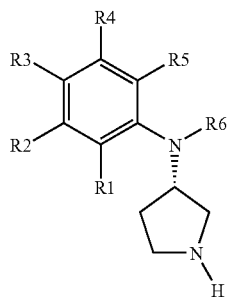

| Ex. No. | R1 | R2 | R3 | R4 | R5 | R6 | NMR | Salt |
|---|---|---|---|---|---|---|---|---|
| 281 | —H | —Cl | —F | —H | —H | 3-methylpyrrole | 1H-NMR (DMSO-d6) δppm 1.68-1.83 (1 H, m), 2.05-2.22 (1 H, m), 2.75-3.20 (3 H, m), 3.41-3.59 (1 H, m), 4.51-4.72 (1 H, m), 5.80-5.90 (1 H, m), 6.57-6.65 (1 H, m), 6.69-6.79 (2 H, m), 6.80-6.88 (1 H, m), 7.09-7.19 (1 H, m), 9.10-9.50 (2 H, m), 11.05 (1 H, brs) | 2 Hydro chloride |
| 282 | —H | —Cl | —F | —H | —H | 5-methyl-2-pyridone | 1H-NMR (DMSO-d6) δppm 1.6-1.8 (1 H, m), 2.1-2.2 (1 H, m), 2.8-3.0 (1 H, m), 3.1-3.3 (2 H, m), 3.4-3.6 (1 H, m), 4.6-4.7 (1 H, m), 6.56 (1 H, d, J = 9.6 Hz), 6.7-6.8 (1 H, m), 6.94 (1 H, d, J = 9.2 Hz), 7.25 (1 H, dd, J = 9.2 Hz, J = 9.0 Hz), 7.43 (1 H, d, J = 9.6 Hz), 7.58 (1 H, s), 8.90 (2 H, brs) | 2 Hydro bromide |
| 283 | —H | —Cl | —F | —H | —H | 1-benzyl-5-methyl-2-pyridone | 1H-NMR (DMSO-d6) δppm 1.6-1.8 (1 H, m), 2.1-2.2 (1 H, m), 2.8-3.0 (1 H, m), 3.0-3.2 (2 H, m), 3.4-3.6 (1 H, m), 4.5-4.7 (1 H, m), 5.04 (1 H, d, J = 14.5 Hz), 5.12 (1 H, d, J = 14.5 Hz), 6.48 (2 H, s), 6.49 (1 H, d, J = 9.5 Hz), 6.6-6.7 (1 H, m), 6.8-6.9 (1 H, m), 7.1-7.5 (7 H, m), 7.94 (1 H, s) | Fumarate |

TABLE 81-continued

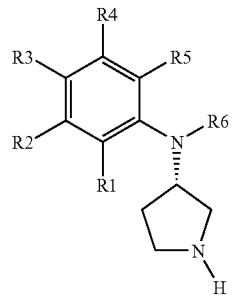

| Ex. No. | R1 | R2 | R3 | R4 | R5 | R6 | NMR | Salt |
|---|---|---|---|---|---|---|---|---|
| 284 | —H | —Cl | —F | —H | —H | ![5-methyl-1-methylpyridin-2(1H)-one] | 1H-NMR (DMSO-d6) δppm 1.6-1.8 (1 H, m), 2.1-2.2 (1 H, m), 2.8-3.0 (1 H, m), 3.0-3.2 (2 H, m), 3.42 (3 H, s), 3.4-3.6 (1 H, m), 4.5-4.7 (1 H, m), 6.46 (1 H, d, J = 9.5 Hz), 6.6-6.7 (1 H, m), 6.8-6.9 (1 H, m), 7.22 (1 H, dd, J = 9.1 Hz, J = 9.1 Hz), 7.30 (1 H, d, J = 9.5 Hz), 7.87 (1 H, s), 9.42 (1 H, brs), 9.49 (1 H, brs) | 2 Hydro chloride |
| 285 | —H | —Cl | —F | —H | —H | ![3-methylindole] | 1H-NMR (CDCl3) δppm 1.65-2.0 (2 H, m), 2.05-2.25 (1 H, m), 2.7-3.05 (3 H, m), 3.1-3.3 (1 H, m), 4.4-4.55 (1 H, m), 6.4-6.55 (1 H, m), 6.65-6.75 (1 H, m), 6.86 (1 H, dd, J = 9, 9 Hz), 7.0-7.1 (2 H, m), 7.1-7.45 (4 H, m), 8.51 (1 H, br). | |

TABLE 82

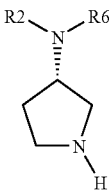

| Ex. No. | R2 | R6 | NMR | Salt |
|---|---|---|---|---|
| 286 | ![indane-5-yl] | ![pyridin-3-yl] | 1H-NMR (DMSO-d6) δppm 1.56-1.76 (1 H, m), 2.01-2.17 (2 H, m), 2.21-2.35 (1 H, m), 2.76-3.01 (5 H, m), 3.05-3.25 (2 H, m), 3.59-3.74 (1 H, m), 4.79-4.91 (1 H, m), 7.07 (1 H, dd, J = 1.5 Hz, 7.5 Hz), 7.20 (1 H, s), 7.42-7.53 (2 H, m), 7.70-7.76 (1 H, m), 8.06 (1 H, d, J = 3.0 Hz), 8.19 (1 H, d, J = 5.0 Hz), 9.46 (1 H, br), 9.52 (1 H, br). | 2 Hydro chloride |
| 287 | ![indane-5-yl] | ![pyridin-2-yl] | 1H-NMR (DMSO-d6) δppm 1.62-1.81 (1 H, m), 1.99-2.15 (2 H, m), 2.20-2.37 (1 H, m), 2.84-3.21 (7 H, m), 3.57-3.73 (1 H, m), 5.10-5.26 (1 H, m), 6.38 (1 H, d, J = 8.5 Hz), 6.90 (1 H, dd, J = 6.5 Hz, 6.5 Hz), 7.11 (1 H, dd, J = 1.5 Hz, 8.0 Hz), 7.24 (1 H, s), 7.44 (1 H, d, J = 8.0 Hz), 7.68 (1 H, dd, J = 7.5 Hz, 7.5 Hz), 8.12 (1 H, dd, J = 1.5 Hz, 5.5 Hz), 9.42 (1 H, br), 9.51 (1 H, br). | 2 Hydro chloride |

TABLE 82-continued

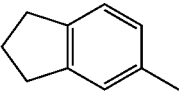

| Ex. No. | R2 | R6 | NMR | Salt |
|---|---|---|---|---|
| 288 |  | 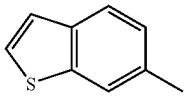 | 1H-NMR (DMSO-d6) δppm 1.64-1.85 (1 H, m), 1.99-2.25 (3 H, m), 2.85-3.28 (7 H, m), 3.47-3.63 (1 H, m), 5.02-5.15 (1 H, m), 7.09 (1 H, dd, J = 2.0 Hz, 8.0 Hz), 7.22 (1 H, s), 7.38-7.43 (2 H, m), 7.88 (1 H, d, J = 2.5 Hz), 8.19-8.21 (1 H, m), 9.26 (1 H, br), 9.54 (1 H, br). | 2 Hydro chloride |
| 289 |  | 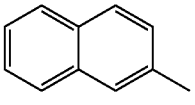 | 1H-NMR (DMSO-d6) δppm 1.66-1.71 (1 H, m), 2.15-2.25 (1 H, m), 2.82-2.91 (1 H, m), 3.01-3.14 (2 H, m), 3.54-3.62 (1 H, m), 4.70-4.85 (1 H, m), 6.47 (2 H, s), 7.09 (1 H, dd, J = 1.9 Hz and 8.5 Hz), 7.12-7.16 (1 H, m), 7.20-7.26 (1 H, m), 7.45 (1 H, d, J = 5.4 Hz), 7.77 (1 H, d, J = 5.4 Hz), 7.85-7.88 (1 H, m), 7.91 (1 H, d, J = 8.5 Hz), 8.04-8.09 (2 H, m) | Fumarate |
| 290 |  | 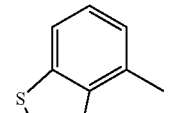 | 1H-NMR (DMSO-d6) δppm: 1.55-1.8 (1 H, m), 2.1-2.35 (1 H, m), 2.75-4.5 (7 H, m), 4.65-4.9 (1 H, m), 6.46 (2 H, s), 7.09 (1 H, dd, J = 2.5, 9 Hz), 7.2-7.35 (2 H, m), 7.35-7.55 (2 H, m), 7.60 (1 H, d, J = 2 Hz), 7.75-7.95 (3 H, m), 8.1-8.25 (2 H, m). | Fumarate |
| 291 |  | 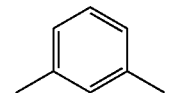 | 1H-NMR (DMSO-d6) δppm: 1.45-1.7 (1 H, m), 2.1-2.3 (1 H, m), 2.6-4.3 (7 H, m), 4.75-4.95 (1 H, m), 6.48 (2 H, s), 6.85-6.95 (1 H, m), 7.1-7.25 (2 H, m), 7.25-7.4 (1 H, m), 7.51 (1 H, dd, J = 7.5, 7.5 Hz), 7.78 (1 H, d, J = 5.5 Hz), 7.85-8.0 (2 H, m), 8.10 (1 H, d, J = 8 Hz). | Fumarate |
| 292 |  | 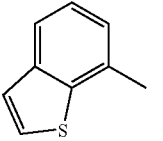 | 1H-NMR (DMSO-d6) δppm: 1.4-1.7 (1 H, m), 2.0-2.3 (1 H, m), 2.6-4.65 (7 H, m), 4.85-5.0 (1 H, m), 6.49 (2 H, s), 6.8-6.9 (1 H, m), 7.12 (1 H, dd, J = 4.5, 8.5), 7.45-7.7 (4 H, m), 7.77 (1 H, d, J = 8 Hz), 7.84 (1 H, d, J = 3 Hz), 7.91 (1 H, dd, J = 1, 4.5 Hz), 7.99 -8.1 (2 H, m). | Fumarate |

TABLE 83

| Ex. No. | R2 | R6 | NMR | Salt |
|---|---|---|---|---|
| 293 | | | 1H-NMR (DMSO-d6) δppm: 1.55-1.75 (1 H, m), 2.15-2.3 (1 H, m), 2.55-4.55 (7 H, m), 4.75-4.9 (1 H, m), 6.48 (2 H, s), 6.95-7.05 (1 H, m), 7.1-7.25 (1 H, m), 7.38 (1 H, d, J = 7.5 Hz), 7.45-7.6 (2 H, m), 7.75 (1 H, d, J = 5.5 Hz), 7.85-8.05 (3 H, m). | Fumarate |

TABLE 83-continued

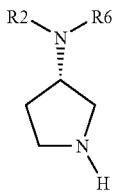

| Ex. No. | R2 | R6 | NMR | Salt |
|---|---|---|---|---|
| 294 | benzothiophene-5-yl | pyridine-3-yl-methyl | 1H-NMR (DMSO-d6) δppm 1.59-1.69 (1 H, m), 2.21-2.49 (1 H, m), 2.82-3.24 (3 H, m), 3.61-3.75 (1 H, m), 4.84-5.02 (1 H, m), 7.90 (1 H, d, J = 2.0 Hz), 7.92 (1 H, d, J = 5.5 Hz), 8.14 (1 H, d, J = 2.8 Hz), 8.19 (1 H, d, J = 5.5 Hz), 8.24 (1 H, d, J = 8.5 Hz) | 2 Hydro chloride |
| 295 | benzofuran-5-yl | pyridine-3-yl-methyl | 1H-NMR (CDCl3) δppm: 1.7-1.9 (2 H, m), 2.16 (1 H, dt, J = 7.5, 7.5 Hz), 2.85-3.0 (3 H, m), 3.21 (1 H, dd, J = 6.5, 11.5 Hz), 4.45 (1 H, tt, J = 6.5, 6.5 Hz), 6.77 (1 H, dd, J = 1, 2 Hz), 6.8-6.9 (1 H, m), 7.0-7.1 (2 H, m), 7.38 (1 H, d, J = 2 Hz), 7.55 (1 H, d, J = 8.5 Hz), 7.68 (1 H, d, J = 2 Hz), 7.99 (1 H, dd, J = 1.5, 4.5 Hz), 8.04 (1 H, d, J = 3 Hz). | |
| 296 | 1-methylindol-5-yl | pyridine-3-yl-methyl | 1H-NMR (CDCl3) δppm: 1.75-1.95 (1 H, m), 2.05-2.4 (2 H, m), 2.88 (2 H, t, J = 7.5 Hz), 2.98 (1 H, dd, J = 5.5, 11.5 Hz), 3.17 (1 H, dd, J = 6.5, 12 Hz), 3.83 (3 H, s), 4.35-4.5 (1 H, m), 6.48 (1 H, dd, J = 0.5, 3 Hz), 6.75-6.85 (1 H, m), 6.9-7.05 (2 H, m), 7.11 (1 H, d, J = 3 Hz), 7.3-7.45 (2 H, m), 7.92 (1 H, dd, J = 1.5, 4.5 Hz), 8.03 (1 H, d, J = 3 Hz). | |
| 297 | quinolin-5-yl | phenyl-X | 1H-NMR (DMSO-d6) δppm: 1.3-1.65 (1 H, m), 2.0-2.25 (1 H, m), 2.6-5.65 (8 H, m), 6.46 (2 H, s), 6.54 (2 H, d, J = 8 Hz), 6.71 (1 H, dd, J = 7.5, 7.5 Hz), 7.12 (2 H, dd, J = 7.5, 8.5 Hz), 7.52 (1 H, dd, J = 4, 8.5 Hz), 7.59 (1 H, dd, J = 1, 7.5 Hz), 7.87 (1 H, dd, J = 7.5, 8.5 Hz), 8.09 (1 H, d, J = 8.5 Hz), 8.15-8.25 (1 H, m), 8.93 (1 H, dd, J = 1.5, 4 Hz). | Fumarate |
| 298 | benzothiophen-3-yl | pyridine-3-yl-methyl | 1H-NMR (DMSO-d6) δppm: 1.55-1.75 (1 H, m), 2.15-2.35 (1 H, m), 2.6-5.75 (8 H, m), 6.50 (2 H, s), 6.95-7.05 (1 H, m), 7.1-7.2 (1 H, m), 7.3-7.5 (3 H, m), 7.9-8.0 (3 H, m), 8.0-8.1 (1 H, m). | Fumarate |
| 299 | benzothiophen-5-yl-methyl | benzothiophen-5-yl-methyl | 1H-NMR (DMSO-d6) δppm: 1.65-1.85 (1 H, m), 2.15-2.35 (1 H, m), 2.85-3.05 (1 H, m), 3.05-3.3 (2 H, m), 3.5-3.7 (1 H, m), 4.7-4.9 (1 H, m), 6.9-7.05 (2 H, m), 7.38 (2 H, d, J = 5.5 Hz), 7.55 (2 H, d, J = 1.5 Hz), 7.76 (2 H, d, J = 5.5 Hz), 7.91 (2 H, d, J = 8.5 Hz), 9.28 (1 H, br), 9.50 (1 H, br). | Hydro chloride |
| 300 | benzothiophen-6-yl-methyl | benzothiophen-6-yl-methyl | 1H-NMR (DMSO-d6) δppm: 1.65-1.85 (1 H, m), 2.15-2.35 (1 H, m), 2.8-3.05 (1 H, m), 3.05-3.25 (2 H, m), 3.35-3.8 (1 H, m), 4.75-4.9 (1 H, m), 6.9-7.0 (2 H, m), 7.39 (2 H, d, J = 5.5 Hz), 7.64 (2 H, d, J = 5.5 Hz), 7.70 (2 H, s), 7.79 (2 H, d, J = 8.5 Hz), 9.24 (1 H, br), 9.43 (1 H, br). | Hydro chloride |

TABLE 84

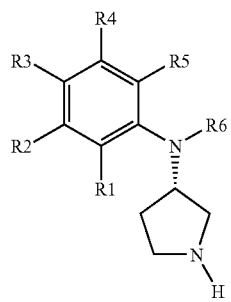

| Ex. No. | R1 | R2 | R3 | R4 | R5 | R6 | M.p. (° C.) | Salt |
|---|---|---|---|---|---|---|---|---|
| 301 | —H | —Cl | —F | —H | —H | —cyclo-C$_6$H$_{11}$ | 194.9-196.1 (dec.) | Hydrochloride |
| 302 | —H | —Cl | —F | —H | —H | —CH$_2$-cyclo-C$_6$H$_{11}$ | 158.5-161.0 | Hydrochloride |

TABLE 85

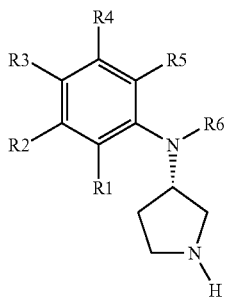

| Ex. No. | R1 | R2 | R3 | R4 | R5 | R6 | NMR | Salt |
|---|---|---|---|---|---|---|---|---|
| 303 | —H | —Cl | —F | —H | —H | —cyclo-C$_6$H$_{11}$ | 1H-NMR (DMSO-d6) δppm 0.80-1.09 (3 H, m), 1.15-1.38 (2 H, m), 1.42-1.58 (2 H, m), 1.60-1.87 (5 H, m), 1.88-2.05 (1 H, m), 2.81-3.12 (3 H, m), 3.12-3.29 (1 H, m), 4.09-4.25 (1 H, m), 7.00-7.10 (1 H, m), 7.20 (1 H, dd, J = 2.6 Hz and 6.7 Hz), 7.24-7.34 (1 H, m), | Fumarate |
| 304 | —H | —H | —F | —H | —H | —cyclo-C$_6$H$_{11}$ | 1H-NMR (DMSO-d6) δppm 0.59-1.55 (8 H, m), 1.58-2.43 (5 H, m), 2.81-4.11 (4 H, m), 4.40-5.22 (1 H, m), 7.00-8.20 (4 H, m), 9.25-10.45 (2 H, m) | Hydrochloride |
| 305 | —H | —Cl | —F | —H | —H | —(CH$_2$)$_3$SCH$_3$ | 1H-NMR (DMSO-d6) δppm 1.52-1.70 (2 H, m), 1.80-2.18 (5 H, m with s at δ2.07), 2.40-2.51 (2 H, m), 2.84-3.49 (6 H, m), 4.29-4.49 (1 H, m), 6.85-6.95 (1 H, m), 7.05-7.35 (2 H, m), 9.30-9.79 (2 H, m) | Hydrochloride |
| 306 | —H | —Cl | —F | —H | —H | —cyclo-C$_5$H$_9$ | 1H-NMR (DMSO-d6) δppm 1.15-1.88 (9 H, m), 1.95-2.18 (1 H, m), 2.71-3.49 (4 H, m), 3.60-3.85 (1 H, m), 4.35-4.55 (1 H, m), 7.05-7.55 (3 H, m), 9.01-9.45 (2 H, m) | Hydrochloride |
| 307 | —H | —Cl | —F | —H | —H | —(CH$_2$)$_3$NHCH$_3$ | 1H-NMR (DMSO-d6) δppm 1.5-3.5 (14 H, m), 3.7-3.9 (1 H, m), 4.1-4.6 (2 H, m), 5-5.75 (1 H, brs), 6.8-7.1 (1 H, m), 7.1-7.3 (2 H, m), 8.7-9.7 (2 H, m) | 3 Hydro chloride |
| 308 | —H | —Cl | —F | —H | —H | —(CH$_2$)$_3$N(CH$_3$)$_2$ | 1H-NMR (DMSO-d6) δppm 1.7-2.3 (3 H, m), 2.70 (3 H, s), 2.72 (3 H, s), 2.9-3.4 (8 H, m), 4.38 (1 H, m), 6.8-7.0 (1 H, m), 7.1-7.2 (1 H, m), 7.28 (1 H, t, J = 9.1 Hz), 9.2-9.4 (1 H, brs), 9.6-9.8 (1 H, brs), 10.3-10.6 (1 H, brs) | 3 Hydro chloride |

TABLE 86

| Ex. No. | R1 | R2 | R3 | R4 | R5 | R6 | NMR | Salt |
|---|---|---|---|---|---|---|---|---|
| 309 | —H | —Cl | —F | —H | —H | —(CH$_2$)$_2$OC$_6$H$_5$ | 1H-NMR (DMSO-d6) δ ppm: 1.85-2.1 (1H, m), 2.1-2.3 (1H, m), 2.95-3.25 (2H, m), 3.25-3.55 (2H, m), 3.67 (2H, t, J = 5.5 Hz), 3.85-4.1 (3H, m), 4.4-4.6 (2H, m), 6.8-7.0 (4H, m), 7.1-7.2 (1H, m), 7.2-7.35 (3H, m), 9.43 (1H, br), 9.60 (1H, br). | 2 Hydro chloride |
| 310 | —H | —Cl | —F | —H | —H | butoxy-pyridine | 1H-NMR (DMSO-d6) δ ppm: 1.8-1.95 (3H, m), 2.05-2.15 (1H, m), 2.6-3.95 (11H, m), 4.07 (2H, t, J = 6 Hz), 4.35-4.45 (1H, m), 6.57 (4H, s), 6.9-6.95 (1H, m), 7.12 (1H, dd, J = 3, 6.5 Hz), 7.26 (1H, dd, J = 9, 9 Hz), 7.32 (1H, dd, J = 4.5, 8.5 Hz), 7.38 (1H, dd, J = 1.5, 8.5 Hz), 8.17 (1H, dd, J = 3.5, 3.5 Hz), 8.31 (1H, d, J = 3 Hz). | 2 Fumarate |
| 311 | —H | —Cl | —F | —H | —H | pentyloxy-pyridine | 1H-NMR (DMSO-d6) δppm: 1.45-1.55 (2H, m), 1.65-1.8 (2H, m), 1.8-1.95 (1H, m), 2.05-2.15 (1H, m), 2.6-4.05 (11H, m), 4.25 (2H, t, J = 6.5 Hz), 4.3-4.4 (1H, m), 6.55 (4H, s), 6.77 (1H, d, J = 8.5 Hz), 6.8-6.9 (1H, m), 6.9-7.0 (1H, m), 7.03 (1H, dd, J = 3, 6.5 Hz), 7.22 (1H, dd, J = 9, 9 Hz), 7.65-7.7 (1H, m), 8.1-8.15 (1H, m). | 2 Fumarate |

TABLE 87

| Ex. No. | R1 | R2 | R3 | R4 | R5 | MS (M + 1) |
|---|---|---|---|---|---|---|
| 312 | —H | —H | —OC$_2$H$_5$ | —H | —H | 283 |
| 313 | —CH$_3$ | —H | —H | —H | —H | 253 |
| 314 | —H | —H | —CF$_3$ | —H | —H | 307 |
| 315 | —H | —H | —CN | —H | —H | 264 |
| 316 | —H | —NO$_2$ | —H | —H | —H | 284 |
| 317 | —H | —H | —NO$_2$ | —H | —H | 284 |
| 318 | —H | —H | —N(CH$_3$)$_2$ | —H | —H | 282 |
| 319 | —H | —CH$_3$ | —H | —H | —H | 253 |
| 320 | —OCH$_3$ | —H | —H | —H | —H | 269 |
| 321 | —H | —OCH$_3$ | —H | —H | —H | 269 |
| 322 | —H | —OC$_2$H$_5$ | —H | —H | —H | 283 |
| 323 | —H | —OCF$_3$ | —H | —H | —H | 323 |
| 324 | —H | —SCH$_3$ | —H | —H | —H | 285 |
| 325 | —H | —N(CH$_3$)$_2$ | —H | —H | —H | 282 |

TABLE 87-continued

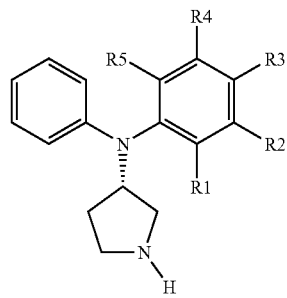

| Ex. No. | R1 | R2 | R3 | R4 | R5 | MS (M + 1) |
|---|---|---|---|---|---|---|
| 326 | —CN | —H | —H | —H | —H | 264 |
| 327 | —H | —H | —SCH₃ | —H | —H | 285 |
| 328 | —H | —CF₃ | —H | —H | —H | 307 |
| 329 | —CH₃ | —F | —H | —H | —H | 271 |
| 330 | —H | —CF₃ | —H | —H | —H | 341 |
| 331 | —H | —H | —CH₃ | —H | —H | 253 |
| 332 | —H | —Cl | —H | —Cl | —H | 307 |
| 333 | —H | —H | —COC₆H₅ | —H | —H | 343 |
| 334 | —H | —H | —CH(CH₃)₂ | —H | —H | 281 |
| 335 | —H | —H | —OC₆H₅ | —H | —H | 331 |
| 336 | —H | —H | —OC₆H₁₃ | —H | —H | 339 |
| 337 | —H | —H | —C₂H₅ | —H | —H | 267 |
| 338 | —H | —H | —OCH₂C₆H₅ | —H | —H | 345 |
| 339 | —H | —CF₃ | —F | —H | —H | 325 |
| 340 | —H | —CF₃ | —H | —CF₃ | —H | 375 |
| 341 | —H | —H | —OCH₃ | —H | —H | 269 |
| 342 | —CH₃ | —CH₃ | —H | —H | —H | 267 |
| 343 | —C₂H₅ | —H | —H | —H | —H | 267 |
| 344 | —H | —F | —H | —H | —OCH₃ | 287 |
| 345 | —H | —H | —COCH₃ | —H | —H | 281 |
| 346 | —H | —COCH₃ | —H | —H | —H | 281 |
| 347 | —CH₃ | —H | —Cl | —H | —H | 287 |
| 348 | —H | —Cl | —Cl | —H | —H | 307 |

TABLE 88

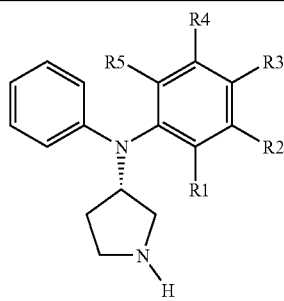

| Ex.No. | R1 | R2 | R3 | R4 | R5 | MS (M + 1) |
|---|---|---|---|---|---|---|
| 349 | —H | —F | —F | —H | —H | 275 |
| 350 | —H | —F | —H | —F | —H | 275 |
| 351 | —H | —H | —CF₃ | —F | —H | 325 |
| 352 | —H | —CF₃ | —H | —F | —H | 325 |
| 353 | —H | —CF₃ | —CH₃ | —H | —H | 321 |
| 354 | —H | —SCF₃ | —H | —H | —H | 339 |
| 355 | —H | —CF₃ | —OCH₃ | —H | —H | 337 |
| 356 | —H | —CH₃ | —N(CH₃)₂ | —CH₃ | —H | 310 |
| 357 | —H | —CH(CH₃)₂ | —H | —H | —H | 281 |
| 358 | —H | —H | —SC₂H₅ | —H | —H | 299 |
| 359 | —H | —H | —N(C₂H₅)₂ | —H | —H | 310 |
| 360 | —H | —OCH(CH₃)₂ | —H | —H | —H | 297 |
| 361 | —H | —F | —H | —Cl | —H | 291 |
| 362 | —H | —CH₃ | —H | —CH₃ | —H |  |
| 363 | —H | —F | —CH₃ | —H | —H | 271 |
| 364 | —H | —F | —Cl | —H | —H | 291 |
| 365 | —H | —C₆H₅ | —H | —H | —H | 315 |
| 366 | —H | —F | —H | —H | —H | 257 |

TABLE 88-continued

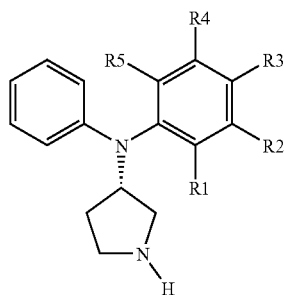

| Ex.No. | R1 | R2 | R3 | R4 | R5 | MS (M + 1) |
|---|---|---|---|---|---|---|
| 367 | —H | —Cl | —CH$_3$ | —H | —H | 287 |
| 368 | —H | —F | —F | —F | —H | 293 |
| 369 | —H | —F | —H | —H | —CH$_3$ | 271 |
| 370 | —F | —H | —H | —CH$_3$ | —H | 271 |
| 371 | —H | —F | —OCH$_3$ | —H | —H | 287 |
| 372 | —H | —CH$_3$ | —Cl | —H | —H | 287 |
| 373 | —H | —H | —C$_3$H$_7$ | —H | —H | 281 |
| 374 | —OCH$_3$ | —H | —H | —CH$_3$ | —H | 283 |
| 375 | —CH$_3$ | —Cl | —H | —H | —H | 287 |
| 376 | —H | —H | —CH$_2$C$_6$H$_5$ | —H | —H | 329 |
| 377 | —H | —Cl | —H | —H | —OCH$_3$ | 303 |
| 378 | —CH$_3$ | —F | —CH$_3$ | —H | —H | 285 |
| 379 | —H | —CH$_2$CH$_2$CN | —H | —H | —H | 292 |
| 380 | —H | —H | —CH$_2$CH$_2$CN | —H | —H | 292 |
| 381 | —H | —Cl | —H | —H | —CH$_3$ | 287 |
| 382 | —H | —OCHF$_2$ | —H | —H | —H | 305 |
| 383 | —H | —C$_2$H$_5$ | —H | —H | —H | 267 |
| 384 | —H | —F | —OCH$_3$ | —F | —H | 305 |
| 385 | —CH$_3$ | —H | —CH$_3$ | —H | —H | 267 |

TABLE 89

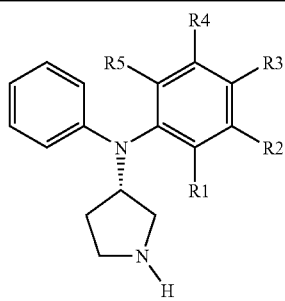

| Ex.No. | R1 | R2 | R3 | R4 | R5 | MS (M + 1) |
|---|---|---|---|---|---|---|
| 386 | —H | —F | —F | —OCH$_3$ | —H | 305 |
| 387 | —H | —Cl | —H | —H | —H | 273 |
| 388 | —CH$_3$ | —H | —H | —CH$_3$ | —H | 267 |
| 389 | —H | —CH$_3$ | —CH$_3$ | —H | —H | 267 |
| 390 | —H | —OCH$_3$ | —OCH$_3$ | —OCH$_3$ | —H | 329 |
| 391 | —H | —CN | —F | —H | —H | 282 |
| 392 | —CH(CH$_3$)$_2$ | —H | —H | —CH$_3$ | —H | 295 |
| 393 | —H | —H | —COC$_2$H$_5$ | —H | —H | 295 |
| 394 | —H | —H | —CF$_3$ | —H | —F | 325 |
| 395 | —F | —H | —CF$_3$ | —F | —H | 343 |
| 396 | —H | —CO$_2$C$_2$H$_5$ | —Cl | —H | —H | 345 |
| 397 | —CH$_2$C$_6$H$_5$ | —H | —H | —H | —H | 329 |
| 398 | —H | —CH$_3$ | —OCH$_3$ | —H | —H | 283 |
| 399 | —H | —H | —C$_6$H$_5$ | —H | —H | 315 |
| 400 | —H | —Cl | —CN | —H | —H | 298 |
| 401 | —H | —CH$_3$ | —F | —CH$_3$ | —H | 285 |
| 402 | —H | —H | —OCF$_2$CHF$_2$ | —H | —H | 355 |
| 403 | —H | —H | —OH | —H | —H | 255 |

TABLE 90
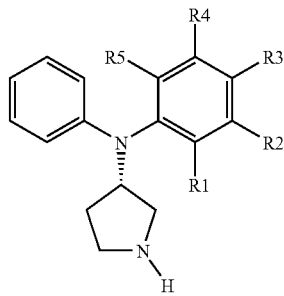
| Ex.No. | R1 | R2 | R3 | R4 | R5 | MS (M + 1) |
|---|---|---|---|---|---|---|
| 404 | —H | —H | 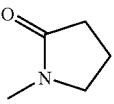 | —H | —H | 322 |
| 405 | —H | 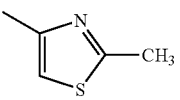 | —H | —H | —H | 336 |
| 406 | —H | —H | 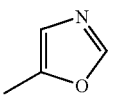 | —H | —H | 306 |
| 407 | —H | —H | 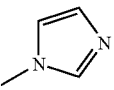 | —H | —H | 305 |
| 408 | —H | —H | 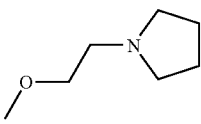 | —H | —H | 352 |
| 409 | —H | —H | 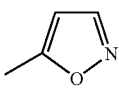 | —H | —H | 306 |
| 410 | —H | —H | 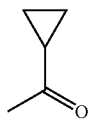 | —H | —H | 307 |
| 411 | —H | 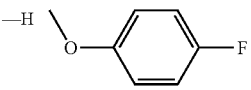 | —H | —H | —H | 349 |

TABLE 91

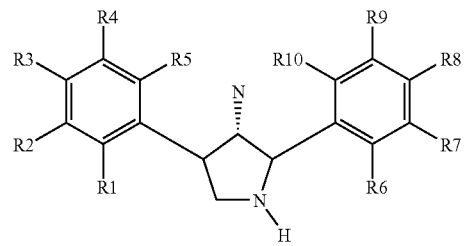

| Ex. No. | R1 | R2 | R3 | R4 | R5 | R6 | R7 | R8 | R9 | R10 | MS (M + 1) |
|---|---|---|---|---|---|---|---|---|---|---|---|
| 412 | —H | —Cl | —F | —H | —H | —H | —H | —OC$_2$H$_5$ | —H | —H | 335 |
| 413 | —H | —Cl | —F | —H | —H | —CH$_3$ | —H | —H | —H | —H | 305 |
| 414 | —H | —Cl | —F | —H | —H | —H | —H | —CF$_3$ | —H | —H | 359 |
| 415 | —H | —Cl | —F | —H | —H | —H | —H | —CN | —H | —H | 316 |
| 416 | —H | —Cl | —F | —H | —H | —H | —H | —N(CH$_3$)$_2$ | —H | —H | 334 |
| 417 | —H | —Cl | —F | —H | —H | —H | —CH$_3$ | —H | —H | —H | 305 |
| 418 | —H | —Cl | —F | —H | —H | —H | —CO$_2$C$_2$H$_5$ | —H | —H | —H | 363 |
| 419 | —H | —Cl | —F | —H | —H | —OCH$_3$ | —H | —H | —H | —H | 321 |
| 420 | —H | —Cl | —F | —H | —H | —H | —OCH$_3$ | —H | —H | —H | 321 |
| 421 | —H | —Cl | —F | —H | —H | —H | —OC$_2$H$_5$ | —H | —H | —H | 335 |
| 422 | —H | —Cl | —F | —H | —H | —H | —OCF$_3$ | —H | —H | —H | 375 |
| 423 | —H | —Cl | —F | —H | —H | —H | —SCH$_3$ | —H | —H | —H | 337 |
| 424 | —H | —CH$_3$ | —F | —H | —H | —H | —H | —OC$_2$H$_5$ | —H | —H | 315 |
| 425 | —H | —CH$_3$ | —F | —H | —H | —CH$_3$ | —H | —H | —H | —H | 285 |
| 426 | —H | —CH$_3$ | —F | —H | —H | —H | —H | —CF$_3$ | —H | —H | 339 |
| 427 | —H | —CH$_3$ | —F | —H | —H | —H | —H | —CN | —H | —H | 296 |
| 428 | —H | —CH$_3$ | —F | —H | —H | —H | —NO$_2$ | —N(CH$_3$)$_2$ | —H | —H | 316 |
| 429 | —H | —CH$_3$ | —F | —H | —H | —H | —H | —N(CH$_3$)$_2$ | —H | —H | 316 |
| 430 | —H | —CH$_3$ | —F | —H | —H | —H | —H | —H | —H | —H | 314 |
| 431 | —H | —CH$_3$ | —F | —H | —H | —H | —CH$_3$ | —H | —H | —H | 285 |
| 432 | —H | —CH$_3$ | —F | —H | —H | —OCH$_3$ | —H | —H | —H | —H | 301 |
| 433 | —H | —CH$_3$ | —F | —H | —H | —H | —OCH$_3$ | —H | —H | —H | 301 |
| 434 | —H | —CH$_3$ | —F | —H | —H | —H | —OC$_2$H$_5$ | —H | —H | —H | 315 |
| 435 | —H | —CH$_3$ | —F | —H | —H | —H | —OCF$_3$ | —OC$_2$H$_5$ | —H | —H | 355 |
| 436 | —H | —CH$_3$ | —F | —H | —H | —H | —SCH$_3$ | —F | —H | —H | 317 |
| 437 | —H | —H | —F | —H | —H | —H | —H | —F | —H | —H | 301 |
| 438 | —CH$_3$ | —H | —H | —H | —H | —H | —H | —CN | —H | —H | 271 |
| 439 | —H | —H | —CF$_3$ | —H | —H | —H | —H | —F | —H | —H | 325 |
| 440 | —H | —H | —F | —H | —H | —H | —H | —F | —H | —H | 282 |
| 441 | —H | —NO$_2$ | —H | —H | —H | —H | —H | —F | —H | —H | 302 |
| 442 | —H | —H | —NO$_2$ | —H | —H | —H | —H | —F | —H | —H | 302 |
| 443 | —H | —H | —N(CH$_3$)$_2$ | —H | —H | —H | —H | —F | —H | —H | 300 |
| 444 | —H | —CH$_3$ | —H | —H | —H | —H | —H | —F | —H | —H | 271 |
| 445 | —OCH$_3$ | —H | —H | —H | —H | —H | —H | —F | —H | —H | 287 |
| 446 | —H | —OCH$_3$ | —H | —H | —H | —H | —H | —F | —H | —H | 287 |

TABLE 92

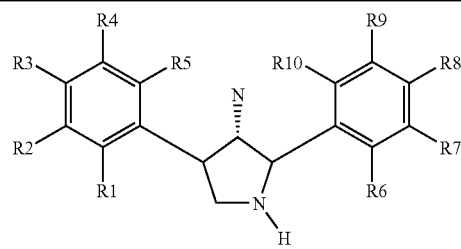

| Ex. No. | R1 | R2 | R3 | R4 | R5 | R6 | R7 | R8 | R9 | R10 | MS (M + 1) |
|---|---|---|---|---|---|---|---|---|---|---|---|
| 447 | —H | —OC$_2$H$_5$ | —H | —H | —H | —H | —H | —F | —H | —H | 301 |
| 448 | —H | —OCF$_3$ | —H | —H | —H | —H | —H | —F | —H | —H | 341 |
| 449 | —H | —SCH$_3$ | —H | —H | —H | —H | —H | —F | —H | —H | 303 |
| 450 | —H | —N(CH$_3$)$_2$ | —H | —H | —H | —H | —Cl | —F | —H | —H | 334 |
| 451 | —H | —Cl | —F | —H | —H | —CN | —H | —H | —H | —H | 316 |
| 452 | —H | —Cl | —F | —H | —H | —H | —H | —SCH$_3$ | —H | —H | 337 |
| 453 | —H | —N(CH$_3$)$_2$ | —H | —H | —H | —H | —CH$_3$ | —F | —H | —H | 314 |
| 454 | —H | —CH$_3$ | —F | —H | —H | —H | —H | —SCH$_3$ | —H | —H | 317 |
| 455 | —H | —N(CH$_3$)$_2$ | —H | —H | —H | —H | —H | —F | —H | —H | 300 |
| 456 | —H | —H | —F | —H | —H | —H | —H | —SCH$_3$ | —H | —H | 303 |

TABLE 93
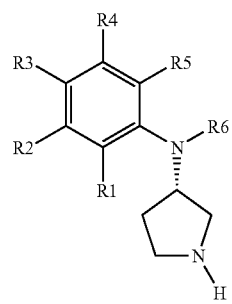
| Ex.No. | R1 | R2 | R3 | R4 | R5 | R6 | MS (M + 1) |
|---|---|---|---|---|---|---|---|
| 457 | —H | —H | —H | —H | —H | 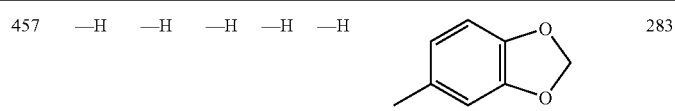 | 283 |
| 458 | —H | —H | —H | —H | —H | 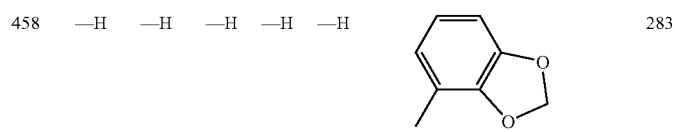 | 283 |
| 459 | —H | —H | —H | —H | —H | 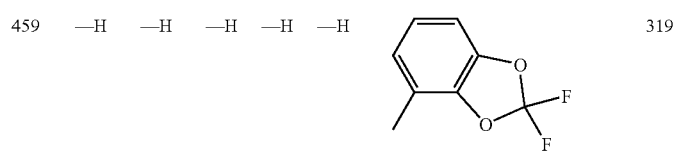 | 319 |
| 460 | —H | —Cl | —F | —H | —H | 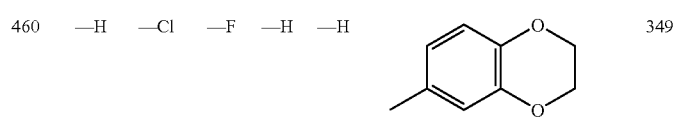 | 349 |
| 461 | —H | —H | —H | —H | —H | 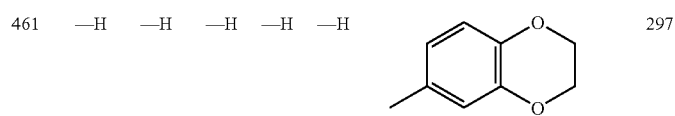 | 297 |
| 462 | —H | —CH₃ | —F | —H | —H | 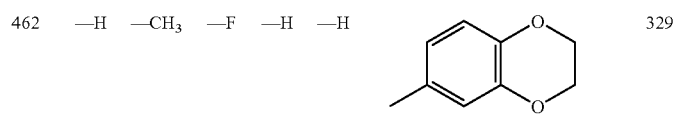 | 329 |
| 463 | —H | —H | —F | —H | —H | 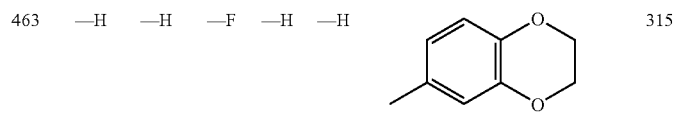 | 315 |
| 464 | —H | —H | —H | —H | —H | 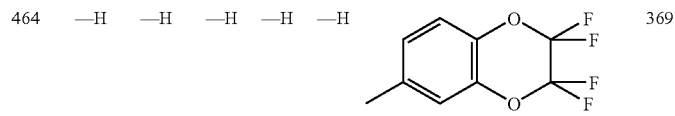 | 369 |
| 465 | —H | —H | —H | —H | —H | 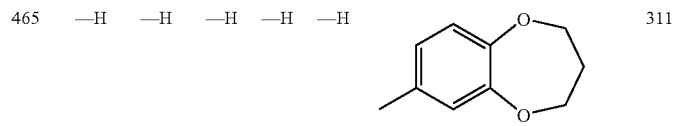 | 311 |

TABLE 93-continued

| Ex.No. | R1 | R2 | R3 | R4 | R5 | R6 | MS (M + 1) |
|---|---|---|---|---|---|---|---|
| 466 | —H | —H | —H | —H | —H | 6-methyl-2,2,4,4-tetrafluoro-4H-benzo[1,3]dioxine | 369 |
| 467 | —H | —H | —H | —H | —H | 5-methyl-indan-1-one | 293 |

TABLE 94

| Ex.No. | R1 | R2 | R3 | R4 | R5 | R6 | MS (M + 1) |
|---|---|---|---|---|---|---|---|
| 468 | —H | —H | —H | —H | —H | 1-methylnaphthalene | 289 |
| 469 | —H | —H | —H | —H | —H | 2-methylnaphthalene | 289 |
| 470 | —H | —H | —H | —H | —H | 6-methyl-2-methoxynaphthalene | 319 |
| 471 | —H | —H | —H | —H | —H | 4-fluoro-1-methylnaphthalene | 307 |

TABLE 94-continued
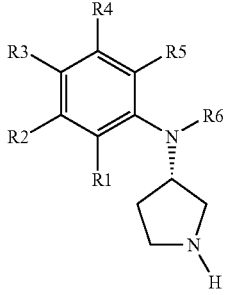
| Ex.No. | R1 | R2 | R3 | R4 | R5 | R6 | MS (M + 1) |
|---|---|---|---|---|---|---|---|
| 472 | —H | —H | —H | —H | —H | 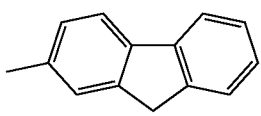 | 327 |
| 473 | —H | —H | —H | —H | —H | 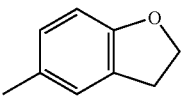 | 281 |
| 474 | —H | —H | —H | —H | —H | 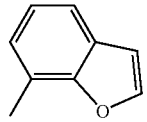 | 279 |
| 475 | —H | —Cl | —F | —H | —H | 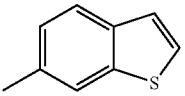 | 347 |
| 476 | —H | —H | —H | —H | —H | 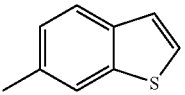 | 295 |
| 477 | —H | —CH₃ | —F | —H | —H | 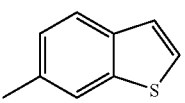 | 327 |
| 478 | —H | —H | —F | —H | —H | 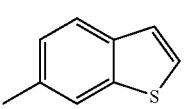 | 313 |

TABLE 95
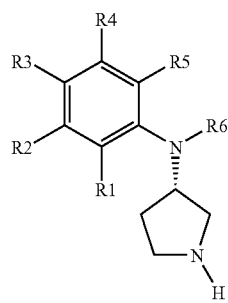
| Ex.No. | R1 | R2 | R3 | R4 | R5 | R6 | MS (M + 1) |
|---|---|---|---|---|---|---|---|
| 479 | —H | —H | —H | —H | —H | 7-methylbenzo[b]thiophene | 295 |
| 480 | —H | —Cl | —F | —H | —H | 3-methylthiophene | 297 |
| 481 | —H | —Cl | —F | —H | —H | 5-methyl-2-(2-methylthiazol-4-yl)thiophene | 394 |
| 482 | —H | —H | —H | —H | —H | 5-methyl-2-phenylthiophene | 321 |
| 483 | —H | —H | —H | —H | —H | 2-methylthiazole | 246 |
| 484 | —H | —Cl | —F | —H | —H | 2-methylthiazole | 298 |
| 485 | —H | —CH₃ | —F | —H | —H | 2-methylthiazole | 278 |
| 486 | —H | —H | —H | —H | —H | 1,4-dimethylpyrazole | 243 |
| 487 | —H | —H | —F | —H | —H | 1,4-dimethylpyrazole | 261 |

TABLE 96
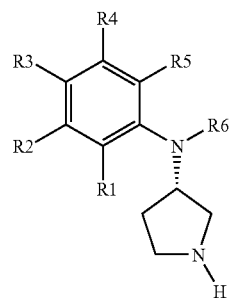
| Ex.No. | R1 | R2 | R3 | R4 | R5 | R6 | MS (M + 1) |
|---|---|---|---|---|---|---|---|
| 488 | —H | —H | —H | —H | —H | 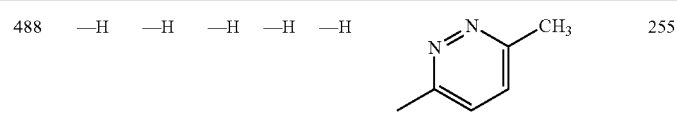 | 255 |
| 489 | —H | —Cl | —F | —H | —H | 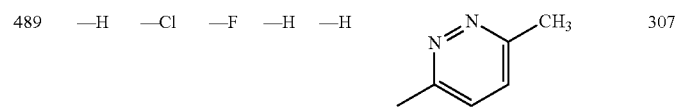 | 307 |
| 490 | —H | —CH₃ | —F | —H | —H | 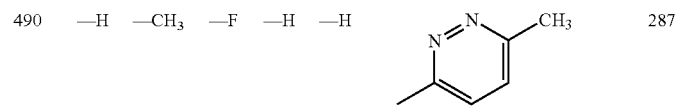 | 287 |
| 491 | —H | —H | —F | —H | —H | 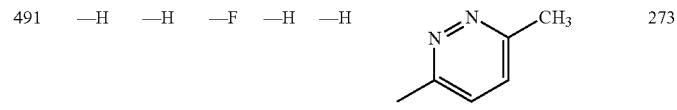 | 273 |
| 492 | —H | —CH₃ | —F | —H | —H | 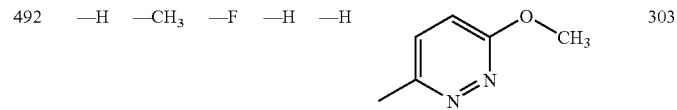 | 303 |
| 493 | —H | —H | —H | —H | —H | 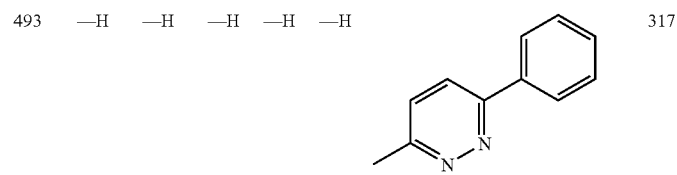 | 317 |
| 494 | —H | —Cl | —F | —H | —H | 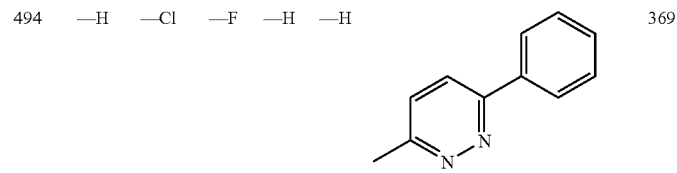 | 369 |
| 495 | —H | —CH₃ | —F | —H | —H | 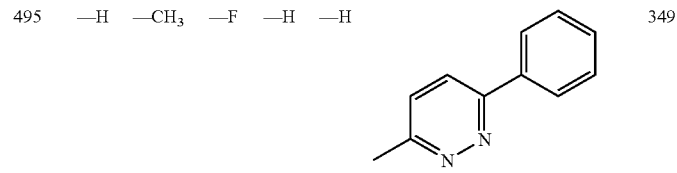 | 349 |

TABLE 97
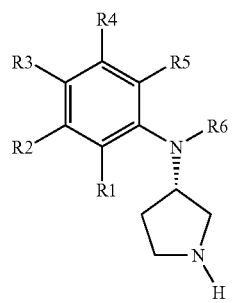
| Ex.No. | R1 | R2 | R3 | R4 | R5 | R6 | MS (M + 1) |
|---|---|---|---|---|---|---|---|
| 496 | —H | —H | —H | —H | —H | 2-methylpyrimidin-yl | 241 |
| 497 | —H | —Cl | —F | —H | —H | 2-methylpyrimidin-yl | 293 |
| 498 | —H | —CH₃ | —F | —H | —H | 2-methylpyrimidin-yl | 273 |
| 499 | —H | —H | —H | —H | —H | 5-ethyl-2-methylpyrimidin-yl | 269 |
| 500 | —H | —H | —F | —H | —H | 5-ethyl-2-methylpyrimidin-yl | 287 |
| 501 | —H | —CH₃ | —F | —H | —H | 5-ethyl-2-methylpyrimidin-yl | 301 |
| 502 | —H | —Cl | —F | —H | —H | 5-ethyl-2-methylpyrimidin-yl | 321 |
| 503 | —H | —H | —H | —H | —H | 2-methyl-5-propylpyrimidin-yl | 283 |
| 504 | —H | —Cl | —F | —H | —H | 2-methyl-5-propylpyrimidin-yl | 335 |
| 505 | —H | —H | —F | —H | —H | 2-methyl-5-propylpyrimidin-yl | 301 |

TABLE 97-continued

| Ex.No. | R1 | R2 | R3 | R4 | R5 | R6 | MS (M + 1) |
|---|---|---|---|---|---|---|---|
| 506 | —H | —CH₃ | —F | —H | —H | 2-methyl-5-propyl-pyrimidinyl | 315 |

TABLE 98

| Ex.No. | R1 | R2 | R3 | R4 | R5 | R6 | MS (M + 1) |
|---|---|---|---|---|---|---|---|
| 507 | —H | —H | —H | —H | —H | 2,4,6-trimethylpyrimidin-5-yl | 269 |
| 508 | —H | —Cl | —F | —H | —H | 2,4,6-trimethylpyrimidin-5-yl | 321 |
| 509 | —H | —CH₃ | —F | —H | —H | 2,4,6-trimethylpyrimidin-5-yl | 301 |
| 510 | —H | —H | —F | —H | —H | 2,4,6-trimethylpyrimidin-5-yl | 287 |

TABLE 98-continued
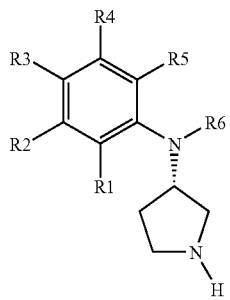
| Ex.No. | R1 | R2 | R3 | R4 | R5 | R6 | MS (M + 1) |
|---|---|---|---|---|---|---|---|
| 511 | —H | —Cl | —F | —H | —H | 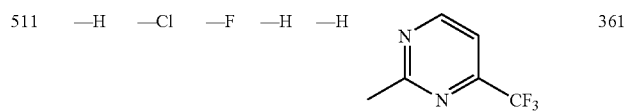 | 361 |
| 512 | —H | —CH₃ | —F | —H | —H | 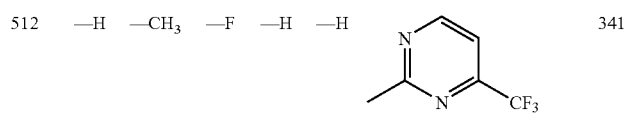 | 341 |
| 513 | —H | —H | —F | —H | —H | 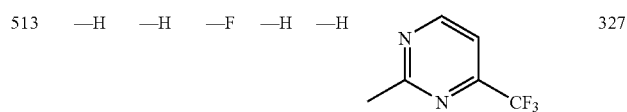 | 327 |
| 514 | —H | —H | —H | —H | —H | 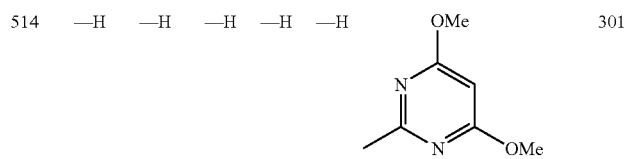 | 301 |
| 515 | —H | —Cl | —F | —H | —H | 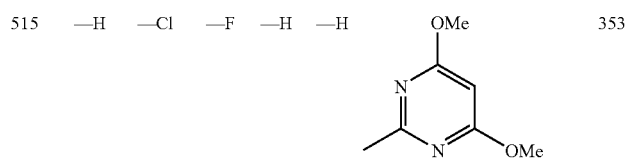 | 353 |
| 516 | —H | —CH₃ | —F | —H | —H | 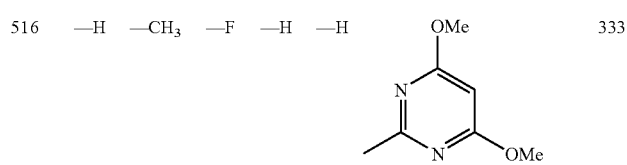 | 333 |

TABLE 99
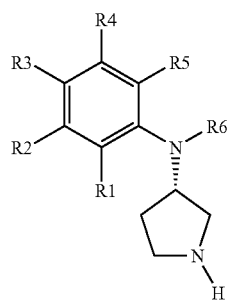
| Ex.No. | R1 | R2 | R3 | R4 | R5 | R6 | MS (M + 1) |
|---|---|---|---|---|---|---|---|
| 517 | —H | —H | —F | —H | —H | 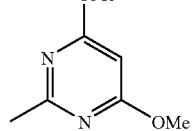 | 319 |
| 518 | —H | —H | —H | —H | —H | 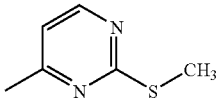 | 287 |
| 519 | —H | —Cl | —F | —H | —H | 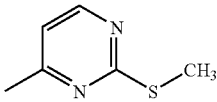 | 339 |
| 520 | —H | —CH₃ | —F | —H | —H | 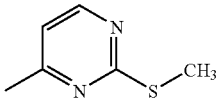 | 319 |
| 521 | —H | —H | —F | —H | —H | 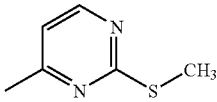 | 305 |
| 522 | —H | —Cl | —F | —H | —H | 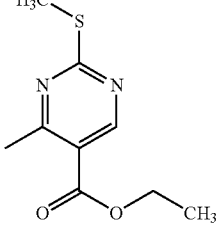 | 411 |
| 523 | —H | —CH₃ | —F | —H | —H | 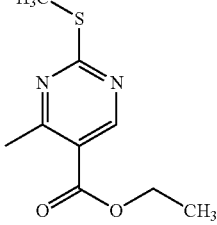 | 391 |

TABLE 100
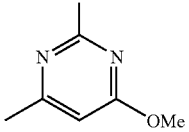
| Ex.No. | R1 | R2 | R3 | R4 | R5 | R6 | MS (M + 1) |
|---|---|---|---|---|---|---|---|
| 524 | —H | —Cl | —F | —H | —H | 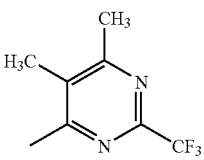 | 353 |
| 525 | —H | —H | —H | —H | —H | 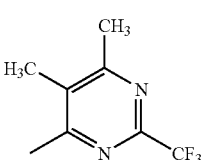 | 337 |
| 526 | —H | —CH₃ | —F | —H | —H | 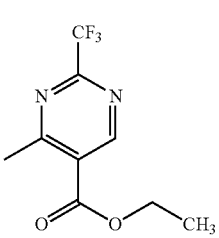 | 369 |
| 527 | —H | —H | —F | —H | —H | 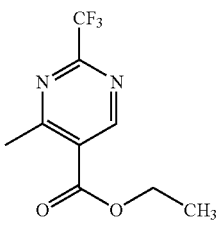 | 399 |
| 528 | —H | —CH₃ | —F | —H | —H | 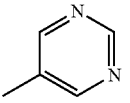 | 413 |
| 529 | —H | —H | —H | —H | —H | 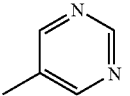 | 241 |
| 530 | —H | —CH₃ | —F | —H | —H | 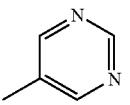 | 273 |
| 531 | —H | —H | —F | —H | —H | 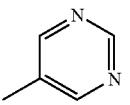 | 259 |

TABLE 100-continued
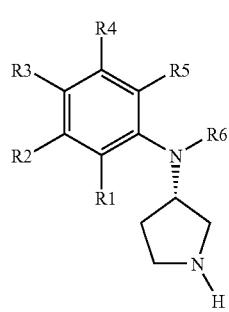
| Ex.No. | R1 | R2 | R3 | R4 | R5 | R6 | MS (M + 1) |
|---|---|---|---|---|---|---|---|
| 532 | —H | —Cl | —F | —H | —H | 5-methylpyrimidin-yl | 293 |
TABLE 101
| Ex. No. | R1 | R2 | R3 | R4 | R5 | R6 | MS (M + 1) |
|---|---|---|---|---|---|---|---|
| 533 | —H | —H | —H | —H | —H | 3-methylpyrazin-yl | 241 |
| 534 | —H | —Cl | —F | —H | —H | 3-methylpyrazin-yl | 293 |
| 535 | —H | —CH₃ | —F | —H | —H | 3-methylpyrazin-yl | 273 |
| 536 | —H | —H | —F | —H | —H | 3-methylpyrazin-yl | 259 |
| 537 | —H | —H | —H | —H | —H | 3,5,6-trimethylpyrazin-yl | 269 |

TABLE 101-continued
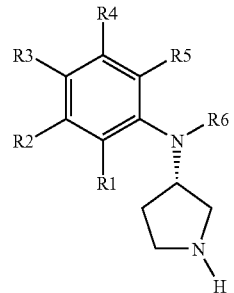
| Ex. No. | R1 | R2 | R3 | R4 | R5 | R6 | MS (M + 1) |
|---|---|---|---|---|---|---|---|
| 538 | —H | —Cl | —F | —H | —H | 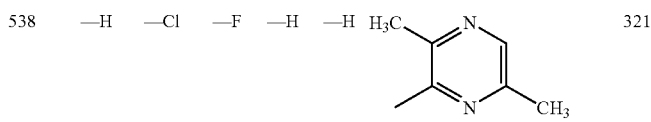 | 321 |
| 539 | —H | —CH₃ | —F | —H | —H | 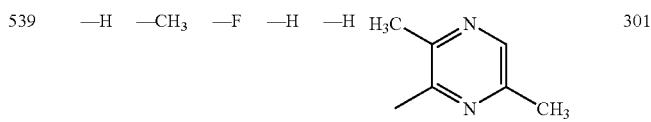 | 301 |
| 540 | —H | —H | —F | —H | —H | 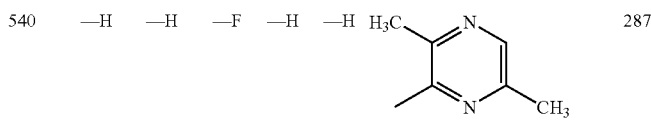 | 287 |
| 541 | —H | —H | —H | —H | —H | 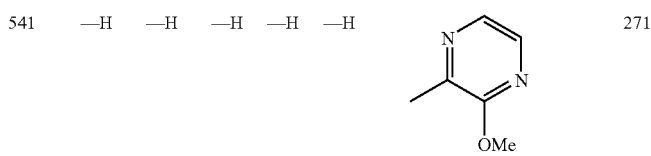 | 271 |
| 542 | —H | —Cl | —F | —H | —H | 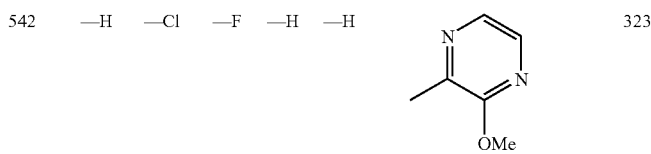 | 323 |
| 543 | —H | —CH₃ | —F | —H | —H | 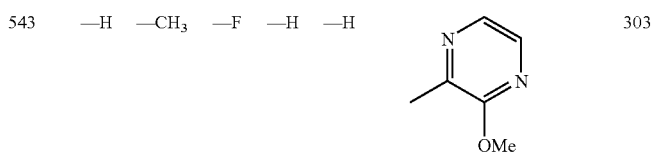 | 303 |

TABLE 102
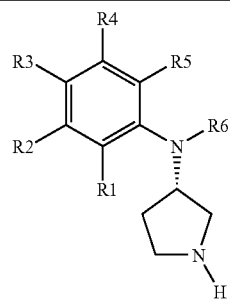
| Ex. No. | R1 | R2 | R4 | R4 | R5 | R6 | MS (M + 1) |
|---|---|---|---|---|---|---|---|
| 544 | —H | —H | —F | —H | —H | 3-methyl-2-methoxypyrazinyl | 289 |
| 545 | —H | —H | —H | —H | —H | 1-acetyl-5-methylindolin-yl | 322 |
| 546 | —H | —H | —H | —H | —H | 2-methylbenzothiazolyl | 296 |
| 547 | —H | —Cl | —F | —H | —H | 2-methylbenzothiazolyl | 348 |
| 548 | —H | —CH₃ | —F | —H | —H | 2-methylbenzothiazolyl | 328 |
| 549 | —H | —H | —F | —H | —H | 2-methylbenzothiazolyl | 314 |
| 550 | —H | —H | —H | —H | —H | 2-methyl-5-methoxybenzothiazolyl | 326 |
| 551 | —H | —Cl | —F | —H | —H | 2-methyl-5-methoxybenzothiazolyl | 378 |
| 552 | —H | —CH₃ | —F | —H | —H | 2-methyl-5-methoxybenzothiazolyl | 358 |

TABLE 102-continued
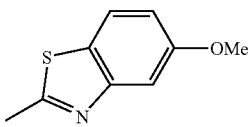
| Ex. No. | R1 | R2 | R4 | R4 | R5 | R6 | MS (M + 1) |
|---|---|---|---|---|---|---|---|
| 553 | —H | —H | —F | —H | —H | 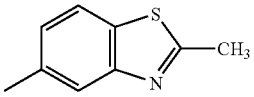 | 344 |
| 554 | —H | —H | —H | —H | —H | 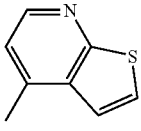 | 310 |
TABLE 103
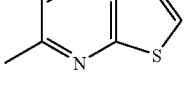
| Ex. No. | R1 | R2 | R3 | R4 | R5 | R6 | MS (M + 1) |
|---|---|---|---|---|---|---|---|
| 555 | —H | —H | —H | —H | —H | 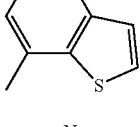 | 296 |
| 556 | —H | —H | —H | —H | —H | 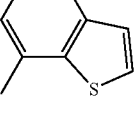 | 296 |
| 557 | —H | —H | —H | —H | —H |  | 296 |
| 558 | —H | —Cl | —F | —H | —H |  | 348 |

TABLE 103-continued
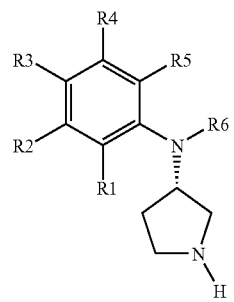
| Ex. No. | R1 | R2 | R3 | R4 | R5 | R6 | MS (M + 1) |
|---|---|---|---|---|---|---|---|
| 559 | —H | —CH₃ | —F | —H | —H | 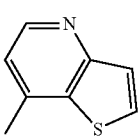 | 328 |
| 560 | —H | —H | —F | —H | —H | 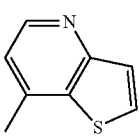 | 314 |
| 561 | —H | —H | —H | —H | —H | 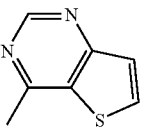 | 297 |
| 562 | —H | —Cl | —F | —H | —H | 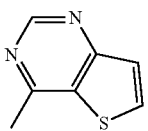 | 349 |
| 563 | —H | —CH₃ | —F | —H | —H | 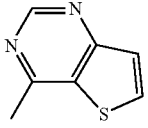 | 329 |
| 564 | —H | —H | —F | —H | —H | 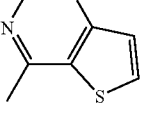 | 315 |
| 565 | —H | —H | —H | —H | —H | 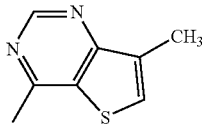 | 311 |

TABLE 104

| Ex. No. | R1 | R2 | R3 | R4 | R5 | R6 | MS (M + 1) |
|---|---|---|---|---|---|---|---|
| 566 | —H | —Cl | —F | —H | —H | 4,7-dimethylthieno[3,2-d]pyrimidine | 363 |
| 567 | —H | —CH₃ | —F | —H | —H | 4,7-dimethylthieno[3,2-d]pyrimidine | 343 |
| 568 | —H | —H | —F | —H | —H | 4,7-dimethylthieno[3,2-d]pyrimidine | 329 |
| 569 | —H | —H | —F | —H | —H | 4-methylthieno[3,2-d]pyrimidine | 315 |
| 570 | —H | —Cl | —F | —H | —H | 4,5-dimethylthieno[2,3-d]pyrimidine | 363 |
| 571 | —H | —CH₃ | —F | —H | —H | 4,5-dimethylthieno[2,3-d]pyrimidine | 343 |
| 572 | —H | —H | —F | —H | —H | 4,5-dimethylthieno[2,3-d]pyrimidine | 329 |

TABLE 104-continued

[Structure: phenyl ring with substituents R1-R5, connected via N(R6) to a pyrrolidine ring]

| Ex. No. | R1 | R2 | R3 | R4 | R5 | R6 | MS (M + 1) |
|---|---|---|---|---|---|---|---|
| 573 | —H | —H | —H | —H | —H | 4-methyl-5-methyl-6-phenyl-thieno[2,3-d]pyrimidinyl | 387 |
| 574 | —H | —Cl | —F | —H | —H | 4-methyl-5-methyl-6-phenyl-thieno[2,3-d]pyrimidinyl | 439 |

TABLE 105

[Structure: phenyl ring with substituents R1-R5, connected via N(R6) to a pyrrolidine ring]

| Ex. No. | R1 | R2 | R3 | R4 | R5 | R6 | MS (M + 1) |
|---|---|---|---|---|---|---|---|
| 575 | —H | —CH₃ | —F | —H | —H | 4-methyl-5-methyl-6-phenyl-thieno[2,3-d]pyrimidinyl | 419 |

TABLE 105-continued

| Ex. No. | R1 | R2 | R3 | R4 | R5 | R6 | MS (M + 1) |
|---|---|---|---|---|---|---|---|
| 576 | —H | —H | —H | —H | —H | 4-chloro-3,6-dimethyl-1-methyl-pyrazolo[3,4-b]pyridine | 322 |
| 577 | —H | —Cl | —F | —H | —H | 4-chloro-3,6-dimethyl-1-methyl-pyrazolo[3,4-b]pyridine | 374 |
| 578 | —H | —CH₃ | —F | —H | —H | 4-chloro-3,6-dimethyl-1-methyl-pyrazolo[3,4-b]pyridine | 354 |
| 579 | —H | —H | —F | —H | —H | 4-chloro-3,6-dimethyl-1-methyl-pyrazolo[3,4-b]pyridine | 340 |
| 580 | —H | —H | —H | —H | —H | 1-methylisoquinoline | 290 |
| 581 | —H | —Cl | —F | —H | —H | 1-methylisoquinoline | 342 |
| 582 | —H | —CH₃ | —F | —H | —H | 1-methyl-2,6-naphthyridine | 322 |

TABLE 105-continued
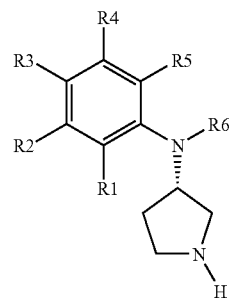
| Ex. No. | R1 | R2 | R3 | R4 | R5 | R6 | MS (M + 1) |
|---|---|---|---|---|---|---|---|
| 583 | —H | —H | —F | —H | —H | 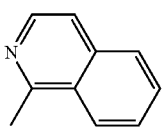 | 308 |
TABLE 106
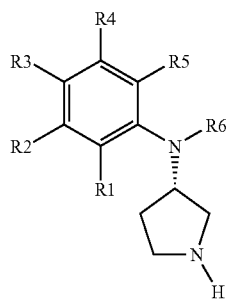
| Ex. No. | R1 | R2 | R3 | R4 | R5 | R6 | MS (M + 1) |
|---|---|---|---|---|---|---|---|
| 584 | —H | —H | —H | —H | —H | 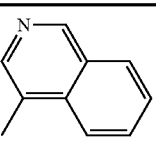 | 290 |
| 585 | —H | —H | —F | —H | —H | 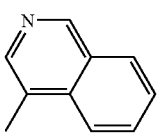 | 308 |
| 586 | —H | —Cl | —F | —H | —H | 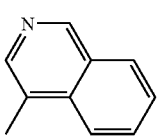 | 342 |
| 587 | —H | —H | —H | —H | —H | 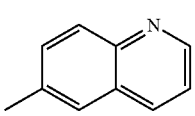 | 290 |
| 588 | —H | —H | —H | —H | —H | 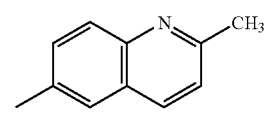 | 304 |

TABLE 106-continued

| Ex. No. | R1 | R2 | R3 | R4 | R5 | R6 | MS (M + 1) |
|---|---|---|---|---|---|---|---|
| 589 | —H | —H | —H | —H | —H | 4-methyl-7-yl-3,4-dihydro-2H-benzo[b][1,4]oxazine | 310 |
| 590 | —H | —H | —H | —H | —H | 8-OMe-4-methyl-6-yl-benzo[b][1,4]oxazin-3(4H)-one | 354 |
| 591 | —H | —H | —H | —H | —H | quinoxalin-2-ylmethyl | 291 |
| 592 | —H | —Cl | —F | —H | —H | quinoxalin-2-ylmethyl | 343 |
| 593 | —H | —CH₃ | —F | —H | —H | quinoxalin-2-ylmethyl | 323 |
| 594 | —H | —H | —H | —H | —H | quinoxalin-6-ylmethyl | 291 |

TABLE 107

| Ex. No. | R1 | R2 | R3 | R4 | R5 | R6 | MS (M + 1) |
|---|---|---|---|---|---|---|---|
| 595 | —H | —H | —H | —H | —H | 4-methyl-2-phenylquinazolinyl | 367 |
| 596 | —H | —Cl | —F | —H | —H | 4-methyl-2-phenylquinazolinyl | 419 |
| 597 | —H | —CH₃ | —F | —H | —H | 4-methyl-2-phenylquinazolinyl | 399 |
| 598 | —H | —H | —F | —H | —H | 4-methyl-2-phenylquinazolinyl | 385 |

TABLE 108

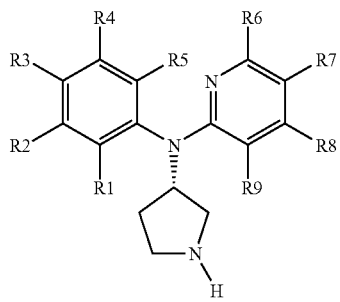

| Ex. No. | R1 | R2 | R3 | R4 | R5 | R6 | R7 | R8 | R9 | MS (M + 1) |
|---|---|---|---|---|---|---|---|---|---|---|
| 599 | —H | —Cl | —F | —H | —H | —H | —NO$_2$ | —H | —H | 337 |
| 600 | —H | —Cl | —F | —H | —H | —H | —CO$_2$CH$_3$ | —H | —H | 350 |
| 601 | —H | —Cl | —F | —H | —H | —H | —H | —H | —CF$_3$ | 360 |
| 602 | —H | —Cl | —F | —H | —H | —H | —Cl | —H | —H | 326 |
| 603 | —H | —Cl | —F | —H | —H | —H | —H | —H | —Cl | 326 |
| 604 | —H | —Cl | —F | —H | —H | —OCH$_3$ | —H | —H | —H | 326 |
| 605 | —H | —Cl | —F | —H | —H | —H | —H | —H | —H | 322 |
| 606 | —H | —Cl | —F | —H | —H | —H | —CH$_3$ | —H | —H | 306 |
| 607 | —H | —Cl | —F | —H | —H | —H | —H | —CH$_3$ | —H | 306 |
| 608 | —H | —Cl | —F | —H | —H | —H | —H | —CF$_3$ | —H | 360 |
| 609 | —H | —Cl | —F | —H | —H | —CH$_3$ | —H | —H | —H | 306 |
| 610 | —H | —Cl | —F | —H | —H | —H | —CF$_3$ | —H | —H | 360 |
| 611 | —H | —H | —H | —H | —H | —H | —NO$_2$ | —H | —H | 285 |
| 612 | —H | —H | —H | —H | —H | —H | —CO$_2$CH$_3$ | —H | —H | 298 |
| 613 | —H | —H | —H | —H | —H | —H | —H | —H | —CF$_3$ | 308 |
| 614 | —H | —H | —H | —H | —H | —H | —Cl | —H | —H | 274 |
| 615 | —H | —H | —H | —H | —H | —H | —H | —H | —Cl | 274 |
| 616 | —H | —H | —H | —H | —H | —H | —H | —H | —H | 240 |
| 617 | —H | —H | —H | —H | —H | —H | —CH$_3$ | —H | —H | 254 |
| 618 | —H | —H | —H | —H | —H | —H | —H | —CH$_3$ | —H | 254 |
| 619 | —H | —H | —H | —H | —H | —H | —H | —CF$_3$ | —H | 308 |
| 620 | —H | —H | —H | —H | —H | —CH$_3$ | —H | —H | —H | 254 |
| 621 | —H | —H | —H | —H | —H | —OCH$_3$ | —H | —H | —H | 270 |
| 622 | —H | —H | —H | —H | —H | —H | —H | —H | —CH$_3$ | 254 |
| 623 | —H | —H | —H | —H | —H | —H | —CF$_3$ | —H | —H | 308 |
| 624 | —H | —CH$_3$ | —F | —H | —H | —H | —NO$_2$ | —H | —H | 317 |
| 625 | —H | —CH$_3$ | —F | —H | —H | —H | —CO$_2$CH$_3$ | —H | —H | 330 |
| 626 | —H | —CH$_3$ | —F | —H | —H | —H | —H | —H | —CF$_3$ | 340 |
| 627 | —H | —CH$_3$ | —F | —H | —H | —H | —H | —H | —NO$_2$ | 317 |
| 628 | —H | —CH$_3$ | —F | —H | —H | —H | —Cl | —H | —H | 306 |
| 629 | —H | —CH$_3$ | —F | —H | —H | —H | —H | —H | —Cl | 306 |
| 630 | —H | —CH$_3$ | —F | —H | —H | —H | —H | —H | —H | 272 |
| 631 | —H | —CH$_3$ | —F | —H | —H | —H | —CH$_3$ | —H | —H | 286 |
| 632 | —H | —CH$_3$ | —F | —H | —H | —H | —H | —CH$_3$ | —H | 286 |
| 633 | —H | —CH$_3$ | —F | —H | —H | —H | —H | —CF$_3$ | —H | 340 |
| 634 | —H | —CH$_3$ | —F | —H | —H | —CH$_3$ | —H | —H | —H | 286 |
| 635 | —H | —CH$_3$ | —F | —H | —H | —OCH$_3$ | —H | —H | —H | 302 |

TABLE 109

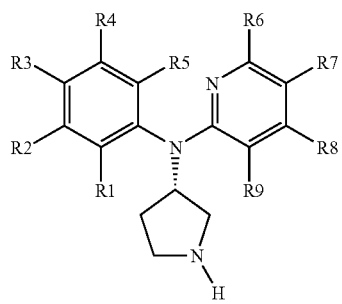

| Ex. No. | R1 | R2 | R3 | R4 | R5 | R6 | R7 | R8 | R9 | MS (M + 1) |
|---|---|---|---|---|---|---|---|---|---|---|
| 636 | —H | —CH$_3$ | —F | —H | —H | —H | —H | —H | —CH$_3$ | 286 |
| 637 | —H | —CH$_3$ | —F | —H | —H | —H | —CF$_3$ | —H | —H | 340 |
| 638 | —H | —H | —F | —H | —H | —H | —NO$_2$ | —H | —H | 303 |
| 639 | —H | —H | —F | —H | —H | —H | —CO$_2$CH$_3$ | —H | —H | 316 |

TABLE 109-continued

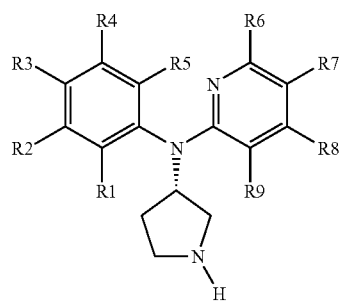

| Ex. No. | R1 | R2 | R3 | R4 | R5 | R6 | R7 | R8 | R9 | MS (M + 1) |
|---|---|---|---|---|---|---|---|---|---|---|
| 640 | —H | —H | —F | —H | —H | —H | —H | —H | —CF$_3$ | 326 |
| 641 | —H | —H | —F | —H | —H | —H | —Cl | —H | —H | 292 |
| 642 | —H | —H | —F | —H | —H | —H | —H | —Cl | —H | 292 |
| 643 | —H | —H | —F | —H | —H | —H | —H | —H | —H | 258 |
| 644 | —H | —H | —F | —H | —H | —H | —CH$_3$ | —H | —H | 272 |
| 645 | —H | —H | —F | —H | —H | —H | —H | —CH$_3$ | —H | 272 |
| 646 | —H | —H | —F | —H | —H | —H | —H | —CF$_3$ | —H | 326 |
| 647 | —H | —H | —F | —H | —H | —CH$_3$ | —H | —H | —H | 272 |
| 648 | —H | —H | —F | —H | —H | —OCH$_3$ | —H | —H | —H | 288 |
| 649 | —H | —H | —F | —H | —H | —H | —CF$_3$ | —H | —H | 326 |
| 650 | —H | —Cl | —F | —H | —H | —CH$_3$ | —H | —CF$_3$ | —H | 374 |
| 651 | —H | —Cl | —F | —H | —H | —H | —H | —NO$_2$ | —H | 337 |
| 652 | —H | —Cl | —F | —H | —H | —H | —H | —OCH$_3$ | —H | 322 |
| 653 | —H | —Cl | —F | —H | —H | —H | —H | —C$_2$H$_5$ | —H | 320 |
| 654 | —H | —H | —H | —H | —H | —CH$_3$ | —H | —CF$_3$ | —H | 322 |
| 655 | —H | —H | —H | —H | —H | —H | —H | —NO$_2$ | —H | 285 |
| 656 | —H | —H | —H | —H | —H | —H | —H | —OCH$_3$ | —H | 270 |
| 657 | —H | —H | —H | —H | —H | —H | —H | —C$_2$H$_5$ | —H | 268 |
| 658 | —H | —CH$_3$ | —F | —H | —H | —CH$_3$ | —H | —CF$_3$ | —H | 354 |
| 659 | —H | —CH$_3$ | —F | —H | —H | —H | —H | —NO$_2$ | —H | 317 |
| 660 | —H | —CH$_3$ | —F | —H | —H | —H | —H | —OCH$_3$ | —H | 302 |
| 661 | —H | —CH$_3$ | —F | —H | —H | —H | —H | —C$_2$H$_5$ | —H | 300 |
| 662 | —H | —H | —F | —H | —H | —CH$_3$ | —H | —CF$_3$ | —H | 340 |
| 663 | —H | —H | —F | —H | —H | —H | —H | —NO$_2$ | —H | 303 |
| 664 | —H | —H | —F | —H | —H | —H | —H | —OCH$_3$ | —H | 288 |
| 665 | —H | —H | —F | —H | —H | —H | —H | —C$_2$H$_5$ | —H | 286 |

TABLE 110

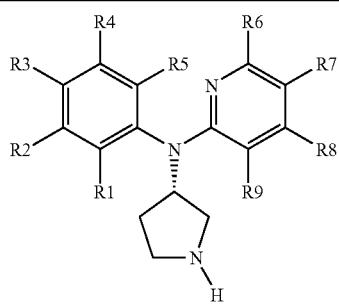

| Ex. No. | R1 | R2 | R3 | R4 | R5 | R6 | R7 | R8 | R9 | MS (M + 1) |
|---|---|---|---|---|---|---|---|---|---|---|
| 666 | —H | —H | —H | —H | —H | —H | —H |  | —H | 309 |

TABLE 111

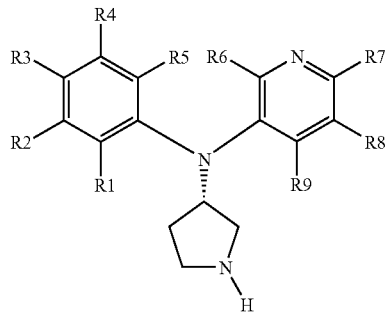

| Ex. No. | R1 | R2 | R3 | R4 | R5 | R6 | R7 | R8 | R9 | MS (M + 1) |
|---|---|---|---|---|---|---|---|---|---|---|
| 667 | —H | —Cl | —F | —H | —H | —H | —H | —H | —H | 292 |
| 668 | —H | —H | —H | —H | —H | —H | —H | —H | —H | 240 |
| 669 | —H | —H | —H | —H | —H | —H | —NO₂ | —H | —H | 285 |
| 670 | —H | —H | —H | —H | —H | —CH₃ | —CH₃ | —H | —H | 268 |
| 671 | —H | —CH₃ | —F | —H | —H | —H | —H | —H | —H | 272 |
| 672 | —H | —CH₃ | —F | —H | —H | —H | —NO₂ | —H | —H | 317 |
| 673 | —H | —H | —F | —H | —H | —H | —H | —H | —H | 258 |
| 674 | —H | —H | —F | —H | —H | —H | —NO₂ | —H | —H | 303 |
| 675 | —H | —H | —F | —H | —H | —CH₃ | —CH₃ | —H | —H | 286 |
| 676 | —H | —Cl | —F | —H | —H | —H | —CH₃ | —H | —H | 306 |
| 677 | —H | —Cl | —F | —H | —H | —H | —OCH₃ | —H | —H | 322 |
| 678 | —H | —Cl | —F | —H | —H | —H | —H | —OCH₃ | —H | 322 |
| 679 | —H | —H | —H | —H | —H | —H | —CH₃ | —H | —H | 254 |
| 680 | —H | —H | —H | —H | —H | —H | —H | —OCH₃ | —H | 270 |
| 681 | —H | —CH₃ | —F | —H | —H | —H | —CH₃ | —H | —H | 286 |
| 682 | —H | —CH₃ | —F | —H | —H | —H | —H | —OCH₃ | —H | 302 |
| 683 | —H | —H | —F | —H | —H | —H | —CH₃ | —H | —H | 272 |
| 684 | —H | —H | —F | —H | —H | —H | —H | —OCH₃ | —H | 288 |
| 685 | —H | —H | —OC₂H₅ | —H | —H | —H | —H | —H | —H | 284 |
| 686 | —CH₃ | —H | —H | —H | —H | —H | —H | —H | —H | 254 |
| 687 | —H | —H | —CF₃ | —H | —H | —H | —H | —H | —H | 308 |
| 688 | —H | —H | —CN | —H | —H | —H | —H | —H | —H | 265 |
| 689 | —H | —NO₂ | —H | —H | —H | —H | —H | —H | —H | 285 |
| 690 | —H | —H | —NO₂ | —H | —H | —H | —H | —H | —H | 285 |
| 691 | —H | —H | —N(CH₃)₂ | —H | —H | —H | —H | —H | —H | 283 |
| 692 | —H | —CF₃ | —H | —H | —H | —H | —H | —H | —H | 308 |
| 693 | —CH₃ | —H | —F | —H | —H | —H | —H | —H | —H | 272 |
| 694 | —H | —CF₃ | —Cl | —H | —H | —H | —H | —H | —H | 342 |
| 695 | —H | —H | —CH₃ | —H | —H | —H | —H | —H | —H | 254 |
| 696 | —H | —H | —C(CH₃)₃ | —H | —H | —H | —H | —H | —H | 296 |
| 697 | —H | —Cl | —H | —Cl | —H | —H | —H | —H | —H | 308 |
| 698 | —H | —H | —SCH₃ | —H | —H | —H | —H | —H | —H | 286 |
| 699 | —H | —H | —COC₆H₅ | —H | —H | —H | —H | —H | —H | 344 |
| 700 | —H | —H | —CH(CH₃)₂ | —H | —H | —H | —H | —H | —H | 282 |
| 701 | —H | —H | —OC₆H₅ | —H | —H | —H | —H | —H | —H | 332 |
| 702 | —H | —H | —OC₆H₁₃ | —H | —H | —H | —H | —H | —H | 340 |
| 703 | —H | —H | —C₆H₁₃ | —H | —H | —H | —H | —H | —H | 324 |
| 704 | —H | —H | —C₂H₅ | —H | —H | —H | —H | —H | —H | 268 |

TABLE 112

| Ex. No. | R1 | R2 | R3 | R4 | R5 | R6 | R7 | R8 | R9 | MS (M + 1) |
|---|---|---|---|---|---|---|---|---|---|---|
| 705 | —H | —H | —OCH$_2$C$_6$H$_5$ | —H | —H | —H | —H | —H | —H | 346 |
| 706 | —H | —CF$_3$ | —F | —H | —H | —H | —H | —H | —H | 326 |
| 707 | —H | —CF$_3$ | —H | —H | —CF$_3$ | —H | —H | —H | —H | 376 |
| 708 | —H | —OCH$_3$ | —H | —H | —OCH$_3$ | —H | —H | —H | —H | 300 |
| 709 | —Cl | —H | —H | —H | —H | —H | —H | —H | —H | 274 |
| 710 | —H | —H | —OCH$_3$ | —H | —H | —H | —H | —H | —H | 270 |
| 711 | —CH$_3$ | —CH$_3$ | —H | —H | —H | —H | —H | —H | —H | 268 |
| 712 | —C$_2$H$_5$ | —H | —H | —H | —H | —H | —H | —H | —H | 268 |
| 713 | —H | —F | —H | —H | —OCH$_3$ | —H | —H | —H | —H | 288 |
| 714 | —H | —COCH$_3$ | —H | —H | —H | —H | —H | —H | —H | 282 |
| 715 | —H | —COCH$_3$ | —H | —H | —H | —H | —H | —H | —H | 282 |
| 716 | —CH$_3$ | —H | —Cl | —H | —H | —H | —H | —H | —H | 288 |
| 717 | —H | —Cl | —Cl | —H | —H | —H | —H | —H | —H | 308 |
| 718 | —H | —F | —F | —H | —H | —H | —H | —H | —H | 276 |
| 719 | —H | —F | —H | —F | —H | —H | —H | —H | —H | 276 |
| 720 | —H | —H | —CF$_3$ | —F | —H | —H | —H | —H | —H | 326 |
| 721 | —H | —CF$_3$ | —H | —F | —H | —H | —H | —H | —H | 326 |
| 722 | —H | —CF$_3$ | —CH$_3$ | —H | —H | —H | —H | —H | —H | 322 |
| 723 | —H | —SCF$_3$ | —H | —H | —H | —H | —H | —H | —H | 340 |
| 724 | —H | —CF$_3$ | —OCH$_3$ | —H | —H | —H | —H | —H | —H | 338 |
| 725 | —H | —CH$_3$ | —N(CH$_3$)$_2$ | —CH$_3$ | —H | —H | —H | —H | —H | 311 |
| 726 | —H | —CH(CH$_3$)$_2$ | —H | —H | —H | —H | —H | —H | —H | 282 |
| 727 | —H | —H | —SC$_2$H$_5$ | —H | —H | —H | —H | —H | —H | 300 |
| 728 | —H | —H | —N(C$_2$H$_5$)$_2$ | —H | —H | —H | —H | —H | —H | 311 |
| 729 | —H | —OCH(CH$_3$)$_2$ | —H | —H | —H | —H | —H | —H | —H | 298 |
| 730 | —H | —H | —OCHF$_2$ | —H | —H | —H | —H | —H | —H | 306 |
| 731 | —H | —F | —H | —Cl | —H | —H | —H | —H | —H | 292 |
| 732 | —H | —CH$_3$ | —OCH$_3$ | —CH$_3$ | —H | —H | —H | —H | —H | 298 |
| 733 | —H | —CH$_3$ | —H | —CH$_3$ | —H | —H | —H | —H | —H | 268 |
| 734 | —H | —F | —CH$_3$ | —H | —H | —H | —H | —H | —H | 272 |
| 735 | —H | —F | —Cl | —H | —H | —H | —H | —H | —H | 292 |
| 736 | —H | —C$_6$H$_5$ | —H | —H | —H | —H | —H | —H | —H | 316 |
| 737 | —H | —F | —H | —H | —H | —H | —H | —H | —H | 258 |
| 738 | —H | —Cl | —CH$_3$ | —H | —H | —H | —H | —H | —H | 288 |
| 739 | —H | —F | —F | —F | —H | —H | —H | —H | —H | 294 |
| 740 | —H | —F | —H | —H | —CH$_3$ | —H | —H | —H | —H | 272 |
| 741 | —F | —H | —H | —CH$_3$ | —H | —H | —H | —H | —H | 272 |
| 742 | —H | —F | —OCH$_3$ | —H | —H | —H | —H | —H | —H | 288 |

TABLE 113

| Ex. No. | R1 | R2 | R3 | R4 | R5 | R6 | R7 | R8 | R9 | MS (M + 1) |
|---|---|---|---|---|---|---|---|---|---|---|
| 743 | —H | —CH$_3$ | —Cl | —H | —H | —H | —H | —H | —H | 288 |
| 744 | —H | —H | —C$_3$H$_7$ | —H | —H | —H | —H | —H | —H | 282 |

TABLE 113-continued

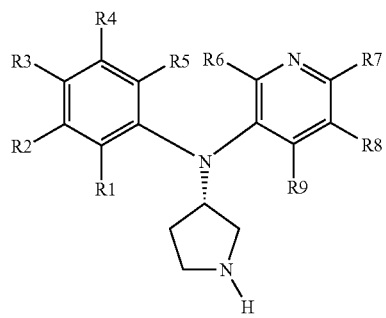

| Ex. No. | R1 | R2 | R3 | R4 | R5 | R6 | R7 | R8 | R9 | MS (M + 1) |
|---|---|---|---|---|---|---|---|---|---|---|
| 745 | —OCH₃ | —H | —H | —CH₃ | —H | —H | —H | —H | —H | 284 |
| 746 | —CH₃ | —Cl | —H | —H | —H | —H | —H | —H | —H | 288 |
| 747 | —H | —H | —CH₂C₆H₅ | —H | —H | —H | —H | —H | —H | 330 |
| 748 | —H | —Cl | —H | —H | —OCH₃ | —H | —H | —H | —H | 304 |
| 749 | —CH₃ | —F | —CH₃ | —H | —H | —H | —H | —H | —H | 286 |
| 750 | —H | —CH₂CH₂CN | —H | —H | —H | —H | —H | —H | —H | 293 |
| 751 | —H | —H | —CH₂CH₂CN | —H | —H | —H | —H | —H | —H | 293 |
| 752 | —H | —Cl | —H | —H | —CH₃ | —H | —H | —H | —H | 288 |
| 753 | —H | —OCHF₂ | —H | —H | —H | —H | —H | —H | —H | 306 |
| 754 | —H | —C₂H₅ | —H | —H | —H | —H | —H | —H | —H | 268 |
| 755 | —H | —F | —OCH₃ | —F | —H | —H | —H | —H | —H | 306 |
| 756 | —H | —F | —F | —H | —OCH₃ | —H | —H | —H | —H | 306 |
| 757 | —CH₃ | —H | —CH₃ | —H | —H | —H | —H | —H | —H | 268 |
| 758 | —H | —F | —F | —OCH₃ | —H | —H | —H | —H | —H | 306 |
| 759 | —H | —OCH₃ | —OCH₃ | —H | —H | —H | —H | —H | —H | 300 |
| 760 | —H | —Cl | —H | —H | —H | —H | —H | —H | —H | 274 |
| 761 | —CH₃ | —H | —H | —CH₃ | —H | —H | —H | —H | —H | 268 |
| 762 | —H | —CH₃ | —CH₃ | —H | —H | —H | —H | —H | —H | 268 |
| 763 | —H | —CN | —F | —H | —H | —H | —H | —H | —H | 283 |
| 764 | —CH(CH₃)₂ | —H | —H | —CH₃ | —H | —H | —H | —H | —H | 296 |
| 765 | —H | —NO₂ | —F | —H | —H | —H | —H | —H | —H | 303 |
| 766 | —CH₂C₆H₅ | —H | —H | —H | —H | —H | —H | —H | —H | 330 |
| 767 | —H | —CH₃ | —OCH₃ | —H | —H | —H | —H | —H | —H | 284 |
| 768 | —H | —H | —C₆H₅ | —H | —H | —H | —H | —H | —H | 316 |
| 769 | —H | —Cl | —CN | —H | —H | —H | —H | —H | —H | 299 |
| 770 | —H | —CH₃ | —F | —CH₃ | —H | —H | —H | —H | —H | 286 |
| 771 | —H | —H | —OCF₂CHF₂ | —H | —H | —H | —H | —H | —H | 356 |
| 772 | —H | —H | —OH | —H | —H | —H | —H | —H | —H | 256 |

TABLE 114

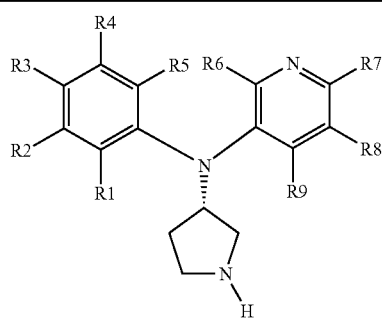

| Ex. No. | R1 | R2 | R3 | R4 | R5 | R6 | R7 | R8 | R9 | MS (M + 1) |
|---|---|---|---|---|---|---|---|---|---|---|
| 773 | —H | 2-methylthiazol-4-yl (H₃C–thiazole) | —H | —H | —H | —H | —H | —H | —H | 337 |
| 774 | —H | —H | 5-methyloxazol-yl | —H | —H | —H | —H | —H | —H | 307 |

TABLE 114-continued

| Ex. No. | R1 | R2 | R3 | R4 | R5 | R6 | R7 | R8 | R9 | MS (M + 1) |
|---|---|---|---|---|---|---|---|---|---|---|
| 775 | —H | —H | (2-methoxyethyl)pyrrolidin-1-yl | —H | —H | —H | —H | —H | —H | 353 |
| 776 | —H | —H | cyclopropyl ketone | —H | —H | —H | —H | —H | —H | 308 |
| 777 | —H | 4-fluoro-methoxyphenyl | —H | —H | —H | —H | —H | —H | —H | 350 |

TABLE 115

| Ex. No. | R1 | MS (M + 1) |
|---|---|---|
| 778 | 6-methylbenzothiophen-yl | 296 |
| 779 | 6-methyl-2,3-dihydrobenzo[1,4]dioxin-yl | 298 |
| 780 | 1-methylnaphthyl | 290 |
| 781 | 2-methyl-5-methylbenzothiazol-yl | 311 |

TABLE 115-continued

| Ex. No. | R1 | MS (M + 1) |
|---|---|---|
| 782 | 6-methylnaphthyl | 290 |
| 783 | 5-methylbenzo[1,3]dioxol-yl | 284 |
| 784 | 5-methyl-indan-1-one-yl | 294 |

TABLE 115-continued

| Ex. No. | R1 | MS (M + 1) |
|---|---|---|
| 785 | (7-methyl-3,4-dihydro-2H-benzo[b][1,4]dioxepine) | 312 |
| 786 | (6-methylquinoline) | 291 |
| 787 | (6-methylquinoxaline) | 292 |
| 788 | (4,7-dimethyl-3,4-dihydro-2H-benzo[b][1,4]oxazine) | 311 |

TABLE 116

| Ex. No. | R1 | MS (M + 1) |
|---|---|---|
| 789 | (4-methylbenzo[d][1,3]dioxole) | 284 |
| 790 | (5-methyl-2,3-dihydrobenzofuran) | 282 |
| 791 | (2,6-dimethylquinoline) | 305 |
| 792 | (2,2,4,4-tetrafluoro-6-methyl-4H-benzo[d][1,3]dioxine) | 370 |
| 793 | (2,2,3,3-tetrafluoro-6-methyl-2,3-dihydrobenzo[b][1,4]dioxine) | 370 |
| 794 | (2-methoxy-6-methylnaphthalene) | 320 |
| 795 | (2,2-difluoro-4-methylbenzo[d][1,3]dioxole) | 320 |
| 796 | (1-acetyl-5-methylindoline) | 323 |
| 797 | (5-fluoro-8-methylnaphthalene) | 308 |
| 798 | (2-methyl-9H-fluorene) | 328 |

TABLE 116-continued
| Ex. No. | R1 | MS (M + 1) |
|---|---|---|
| 799 | 7-methylbenzofuran | 280 |
TABLE 117
| Ex. No. | R1 | MS (M + 1) |
|---|---|---|
| 800 | 5-methyl-1H-indole | 279 |
| 801 | 6-methoxy-1,7-dimethyl-3,4-dihydroquinolin-2(1H)-one | 353 |
| 802 | 8-methoxy-4,6-dimethyl-2H-benzo[b][1,4]oxazin-3(4H)-one | 355 |
| 803 | 2-methyl-4-(pyrrolidin-1-yl)pyridine | 310 |
| 804 | 6-methylthieno[2,3-b]pyridine | 297 |
| 805 | 4-methylthieno[3,2-b]pyridine | 297 |
TABLE 118
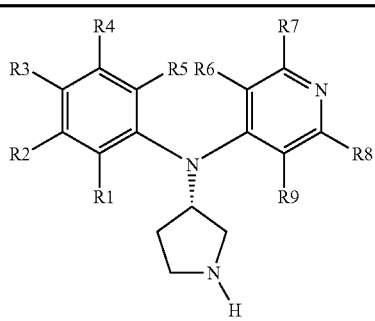
| Ex. No. | R1 | R2 | R3 | R4 | R5 | R6 | R7 | R8 | R9 | MS (M + 1) |
|---|---|---|---|---|---|---|---|---|---|---|
| 806 | —H | —Cl | —F | —H | —H | —H | —H | —CH$_3$ | —H | 306 |
| 807 | —H | —Cl | —F | —H | —H | —H | -2-PYRIDYL | -2-PYRIDYL | —H | 446 |
| 808 | —H | —H | —H | —H | —H | —H | —H | —CH$_3$ | —H | 254 |

TABLE 118-continued

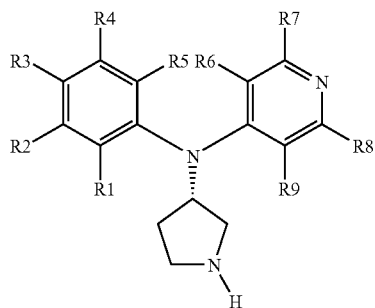

| Ex. No. | R1 | R2 | R3 | R4 | R5 | R6 | R7 | R8 | R9 | MS (M + 1) |
|---|---|---|---|---|---|---|---|---|---|---|
| 809 | —H | —H | —H | —H | —H | —H | —H | —H | —CH$_3$ | 254 |
| 810 | —H | —H | —H | —H | —H | —H | -2-PYRIDYL | -2-PYRIDYL | —H | 394 |
| 811 | —H | —CH$_3$ | —F | —H | —H | —H | —H | —CH$_3$ | —H | 286 |
| 812 | —H | —CH$_3$ | —F | —H | —H | —H | -2-PYRIDYL | -2-PYRIDYL | —H | 426 |
| 813 | —H | —H | —F | —H | —H | —H | -2-PYRIDYL | -2-PYRIDYL | —H | 412 |

TABLE 119

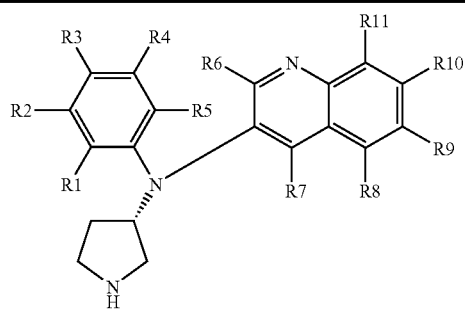

| Ex. No. | R1 | R2 | R3 | R4 | R5 | R6 | R7 | R8 | R9 | R10 | R11 | MS (M + 1) |
|---|---|---|---|---|---|---|---|---|---|---|---|---|
| 814 | —H | —Cl | —F | —H | —H | —H | —H | —H | —H | —H | —H | 342 |
| 815 | —H | —H | —H | —H | —H | —H | —H | —H | —H | —H | —H | 290 |
| 816 | —H | —CH$_3$ | —F | —H | —H | —H | —H | —H | —H | —H | —H | 322 |
| 817 | —H | —H | —F | —H | —H | —H | —H | —H | —H | —H | —H | 308 |

TABLE 120

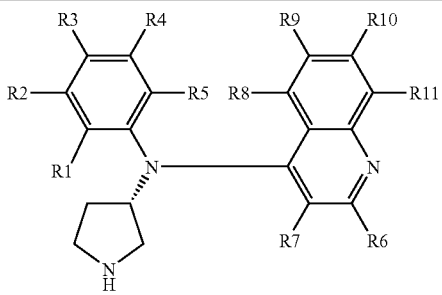

| Ex. No. | R1 | R2 | R3 | R4 | R5 | R6 | R7 | R8 | R9 | R10 | R11 | MS (M + 1) |
|---|---|---|---|---|---|---|---|---|---|---|---|---|
| 818 | —H | —Cl | —F | —H | —H | —CH$_3$ | —H | —H | —H | —H | —H | 356 |
| 819 | —H | —Cl | —F | —H | —H | —H | —H | —H | —H | —H | —H | 342 |
| 820 | —H | —Cl | —F | —H | —H | —H | —H | —H | —H | —CF$_3$ | —H | 410 |
| 821 | —H | —Cl | —F | —H | —H | —C$_6$H$_5$ | —H | —H | —H | —H | —H | 418 |
| 822 | —H | —Cl | —F | —H | —H | —H | —H | —H | —H | —Cl | —H | 376 |
| 823 | —H | —Cl | —F | —H | —H | —CF$_3$ | —H | —H | —H | —H | —H | 410 |
| 824 | —H | —Cl | —F | —H | —H | —H | —H | —H | —H | —H | —CF$_3$ | 410 |
| 825 | —H | —H | —H | —H | —H | —CH$_3$ | —H | —H | —H | —H | —H | 304 |
| 826 | —H | —H | —H | —H | —H | —H | —H | —H | —H | —H | —H | 290 |

TABLE 120-continued

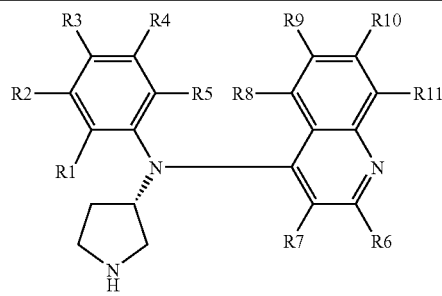

| Ex. No. | R1 | R2 | R3 | R4 | R5 | R6 | R7 | R8 | R9 | R10 | R11 | MS (M + 1) |
|---|---|---|---|---|---|---|---|---|---|---|---|---|
| 827 | —H | —H | —H | —H | —H | —H | —H | —H | —H | —CF₃ | —H | 358 |
| 828 | —H | —H | —H | —H | —H | —C₆H₅ | —H | —H | —H | —H | —H | 366 |
| 829 | —H | —H | —H | —H | —H | —H | —H | —H | —H | —Cl | —H | 324 |
| 830 | —H | —H | —H | —H | —H | —CF₃ | —H | —H | —H | —H | —H | 358 |
| 831 | —H | —H | —H | —H | —H | —H | —H | —H | —H | —H | —CF₃ | 358 |
| 832 | —H | —CH₃ | —F | —H | —H | —CH₃ | —H | —H | —H | —H | —H | 336 |
| 833 | —H | —CH₃ | —F | —H | —H | —H | —H | —H | —H | —H | —H | 322 |
| 834 | —H | —CH₃ | —F | —H | —H | —H | —H | —H | —H | —CF₃ | —H | 390 |
| 835 | —H | —CH₃ | —F | —H | —H | —C₆H₅ | —H | —H | —H | —H | —H | 398 |
| 836 | —H | —CH₃ | —F | —H | —H | —H | —H | —H | —H | —Cl | —H | 356 |
| 837 | —H | —CH₃ | —F | —H | —H | —CF₃ | —H | —H | —H | —H | —H | 390 |
| 838 | —H | —CH₃ | —F | —H | —H | —H | —H | —H | —H | —H | —CF₃ | 390 |
| 839 | —H | —H | —F | —H | —H | —CH₃ | —H | —H | —H | —H | —H | 322 |
| 840 | —H | —H | —F | —H | —H | —H | —H | —H | —H | —H | —H | 308 |
| 841 | —H | —H | —F | —H | —H | —H | —H | —H | —H | —CF₃ | —H | 376 |
| 842 | —H | —H | —F | —H | —H | —C₆H₅ | —H | —H | —H | —H | —H | 384 |
| 843 | —H | —H | —F | —H | —H | —H | —H | —H | —H | —Cl | —H | 342 |
| 844 | —H | —H | —F | —H | —H | —CF₃ | —H | —H | —H | —H | —H | 376 |
| 845 | —H | —H | —F | —H | —H | —H | —H | —H | —H | —H | —CF₃ | 376 |
| 846 | —H | —Cl | —F | —H | —H | —H | —H | —H | —CF₃ | —H | —H | 410 |
| 847 | —H | —H | —H | —H | —H | —H | —H | —H | —F | —H | —F | 326 |
| 848 | —H | —H | —H | —H | —H | —H | —H | —H | —CF₃ | —H | —H | 358 |
| 849 | —H | —CH₃ | —F | —H | —H | —H | —H | —H | —H | —H | —F | 358 |
| 850 | —H | —CH₃ | —F | —H | —H | —H | —H | —H | —CF₃ | —H | —H | 390 |
| 851 | —H | —H | —F | —H | —H | —H | —H | —H | —H | —H | —F | 344 |
| 852 | —H | —H | —F | —H | —H | —H | —H | —H | —CF₃ | —H | —H | 376 |
| 853 | —H | —H | —H | —H | —H | —OCH₃ | —H | —H | —H | —H | —H | 320 |

TABLE 121

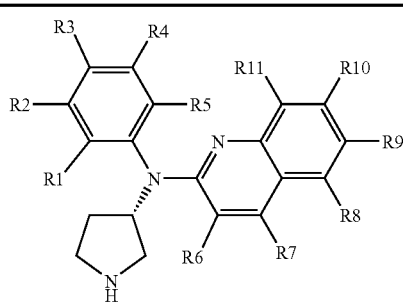

| Ex. No. | R1 | R2 | R3 | R4 | R5 | R6 | R7 | R8 | R9 | R10 | R11 | MS (M + 1) |
|---|---|---|---|---|---|---|---|---|---|---|---|---|
| 854 | —H | —H | —F | —Cl | —H | —H | —H | —H | —H | —H | —H | 342 |
| 855 | —H | —H | —F | —Cl | —H | —CH₃ | —H | —H | —H | —H | —H | 356 |
| 856 | —H | —H | —F | —Cl | —H | —OCH₃ | —H | —H | —H | —H | —H | 372 |
| 857 | —H | —H | —F | —Cl | —H | —H | —CH₃ | —H | —H | —H | —H | 356 |
| 858 | —H | —H | —F | —Cl | —H | —H | —H | —NO₂ | —H | —H | —F | 405 |
| 859 | —H | —H | —F | —Cl | —H | —CH₂C₆H₅ | —H | —H | —H | —H | —H | 432 |
| 860 | —H | —H | —F | —Cl | —H | —H | —H | —H | —OCH₃ | —H | —H | 372 |
| 861 | —H | —H | —F | —Cl | —H | —H | —OCH₃ | —H | —H | —H | —H | 372 |
| 862 | —H | —H | —F | —Cl | —H | —H | —H | —H | —H | —OCH₃ | —H | 372 |
| 863 | —H | —H | —H | —H | —H | —H | —H | —H | —H | —H | —H | 290 |
| 864 | —H | —H | —H | —H | —H | —CH₃ | —H | —H | —H | —H | —H | 304 |
| 865 | —H | —H | —H | —H | —H | —OCH₃ | —H | —H | —H | —H | —H | 320 |
| 866 | —H | —H | —H | —H | —H | —H | —CH₃ | —H | —H | —H | —H | 304 |
| 867 | —H | —H | —H | —H | —H | —H | —H | —NO₂ | —H | —H | —F | 353 |

TABLE 121-continued

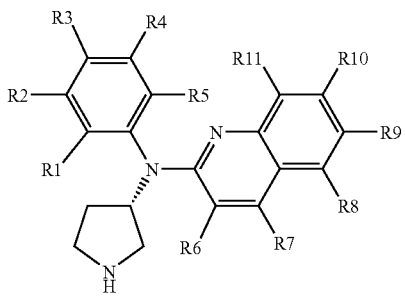

| Ex. No. | R1 | R2 | R3 | R4 | R5 | R6 | R7 | R8 | R9 | R10 | R11 | MS (M + 1) |
|---|---|---|---|---|---|---|---|---|---|---|---|---|
| 868 | —H | —H | —H | —H | —H | —CH₂C₆H₅ | —H | —H | —H | —H | —H | 380 |
| 869 | —H | —H | —H | —H | —H | —H | —H | —H | —OCH₃ | —H | —H | 320 |
| 870 | —H | —H | —H | —H | —H | —H | —OCH₃ | —H | —H | —H | —H | 320 |
| 871 | —H | —H | —H | —H | —H | —H | —H | —H | —H | —OCH₃ | —H | 320 |
| 872 | —H | —H | —F | —CH₃ | —H | —H | —H | —H | —H | —H | —H | 322 |
| 873 | —H | —H | —F | —CH₃ | —H | —CH₃ | —H | —H | —H | —H | —H | 336 |
| 874 | —H | —H | —F | —CH₃ | —H | —OCH₃ | —H | —H | —H | —H | —H | 352 |
| 875 | —H | —H | —F | —CH₃ | —H | —H | —CH₃ | —H | —H | —H | —H | 336 |
| 876 | —H | —H | —F | —CH₃ | —H | —H | —H | —NO₂ | —H | —H | —F | 385 |
| 877 | —H | —H | —F | —CH₃ | —H | —H | —H | —H | —OCH₃ | —H | —H | 352 |
| 878 | —H | —H | —F | —CH₃ | —H | —H | —H | —H | —H | —OCH₃ | —H | 352 |
| 879 | —H | —H | —F | —H | —H | —H | —H | —H | —H | —H | —H | 308 |
| 880 | —H | —H | —F | —H | —H | —CH₃ | —H | —H | —H | —H | —H | 322 |
| 881 | —H | —H | —F | —H | —H | —OCH₃ | —H | —H | —H | —H | —H | 338 |
| 882 | —H | —H | —F | —H | —H | —H | —CH₃ | —H | —H | —H | —H | 322 |
| 883 | —H | —H | —F | —H | —H | —H | —H | —NO₂ | —H | —H | —F | 371 |
| 884 | —H | —H | —F | —H | —H | —H | —H | —OCH₃ | —H | —H | —H | 338 |
| 885 | —H | —H | —F | —H | —H | —H | —OCH₃ | —H | —H | —H | —H | 338 |
| 886 | —H | —H | —F | —H | —H | —H | —H | —H | —H | —OCH₃ | —H | 338 |
| 887 | —H | —H | —H | —H | —H | —H | —OC₂H₅ | —H | —H | —H | —H | 334 |

TABLE 122

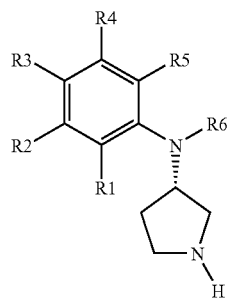

| Ex. No. | R1 | R2 | R3 | R4 | R5 | R6 | MS (M + 1) |
|---|---|---|---|---|---|---|---|
| 888 | —H | —H | —F | —H | —H | | 297 |
| 889 | —H | —H | —F | —Cl | —H | —CH₂C≡CH | 253 |
| 890 | —H | —H | —F | —Cl | —H | (7-ethyl-1,1,4,4-tetramethyl-tetralinyl) | 415 |

TABLE 122-continued

| Ex. No. | R1 | R2 | R3 | R4 | R5 | R6 | MS (M + 1) |
|---|---|---|---|---|---|---|---|
| 891 | —H | —H | —F | —Cl | —H | 2-ethylimidazo[1,2-a]pyridinyl | 345 |
| 892 | —H | —H | —F | —Cl | —H | 2-chloro-5-ethylthiazolyl | 346 |

TABLE 123

| Ex. No. | R1 | R2 | R3 | R4 | R5 | R6 | NMR | Salt |
|---|---|---|---|---|---|---|---|---|
| 893 | —H | —H | —F | —Cl | —H | 5-fluoro-3-methylpyridinyl | $^1$H-NMR (DMSO-$d_6$) δppm: 1.55-1.75 (1H, m), 2.2-2.35 (1H, m), 2.38 (6H, s), 2.85-3.0 (1H, m), 3.1-3.2 (2H, m), 3.6-3.75 (1H, m), 4.17 (1H, br), 4.77 (1H, tt, J = 7.7, 7.7 Hz), 7.21 (1H, dt, J = 4.0, 7.1 Hz), 7.25-7.35 (1H, m), 7.55-7.65 (2H, m), 7.86 (1H, bs), 8.14 (1H, d, J = 2.3 Hz), 8.76 (2H, br). | 2Methanesulfonate |
| 894 | —H | —H | —F | —Cl | —H | 5-fluoro-3-methylpyridinyl | $^1$H-NMR (DMSO-$d_6$) δppm: 1.55-1.75 (1H, m), 2.15-2.3 (1H, m), 2.8-3.0 (1H, m), 3.05-3.2 (2H, m), 3.61 (1H, dd, J = 7.1, 11.8), 4.74 (1H, tt, J = 7.5, 7.5 Hz), 7.10 (1H, ddd, J = 2.4, 2.4, 12.0 Hz), 7.25-7.35 (1H, m), 7.45-7.65 (2H, m), 7.82 (1H, s), 8.05 (1H, d, J = 2.2 Hz), 9.1-9.55 (2H, m). | Hydrochloride |
| 895 | —H | —H | —F | —CH$_3$ | —H | 5-fluoro-3-methylpyridinyl | $^1$H-NMR (DMSO-$d_6$) δppm: 1.55-1.75 (1H, m), 2.15-2.35 (4H, m), 2.75-2.95 (1H, m), 3.0-3.2 (2H, m), 3.55-3.7 (1H, m), 4.76 (1H, tt, J = 7.6, 7.6 Hz), 5.38 (1H, br), 7.05-7.25 (2H, m), 7.25-7.4 (2H, m), 7.75 (1H, dd, J = 1.2, 2.3 Hz), 8.07 (1H, d, J = 1.8 Hz), 9.43 (2H, br). | 2Hydrochloride |

TABLE 123-continued

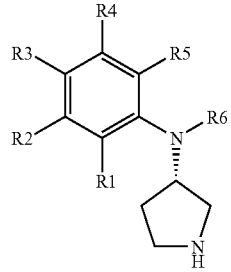

| Ex. No. | R1 | R2 | R3 | R4 | R5 | R6 | NMR | Salt |
|---|---|---|---|---|---|---|---|---|
| 896 | —H | —H | —F | —Cl | —H | | $^1$H-NMR (DMSO-d$_6$) δppm: 1.55-1.75 (1H, m), 2.15-2.3 (1H, m), 2.8-3.0 (1H, m), 3.0-3.2 (2H, m), 3.55-3.7 (1H, m), 4.75 (1H, tt, J = 7.6, 7.6 Hz), 5.04 (1H, br), 6.9-7.05 (1H, m), 7.3-7.5 (2H, m), 7.62 (1H, dd, J = 9.0, 9.0 Hz), 7.71 (1H, dd, J = 2.4, 6.7 Hz), 7.95-8.15 (2H, m), 9.40 (2H, br). | 2Hydrochloride |

TABLE 124

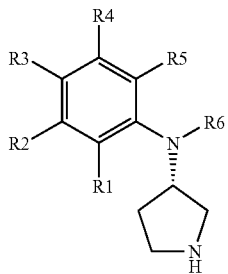

| Ex. No. | R1 | R2 | R3 | R4 | R5 | R6 | NMR | Salt |
|---|---|---|---|---|---|---|---|---|
| 897 | —H | —H | —F | —Cl | —H | | $^1$H-NMR (DMSO-d$_6$) δppm: 1.5-1.7 (1H, m), 2.15-2.3 (1H, m), 2.8-2.95 (1H, m), 3.0-3.2 (2H, m), 3.5-3.65 (1H, m), 4.39 (1H, br), 4.70 (1H, tt, J = 7.8, 7.8 Hz), 6.68 (1H, d, J = 11.3 Hz), 7.35-7.45 (1H, m), 7.46 (1H, s), 7.61 (1H, dd, J = 9.0, 9.0 Hz), 7.71 (1H, dd, J = 2.6, 6.8 Hz), 7.95-8.05 (1H, m), 9.27 (2H, br). | 2Hydrochloride |
| 898 | —H | —H | —F | —Cl | —H | | $^1$H-NMR (DMSO-d$_6$) δppm: 1.55-1.75 (1H, m), 2.05-2.3 (1H, m), 2.8-3.0 (1H, m), 3.05-3.3 (2H, m), 3.5-3.7 (1H, m), 4.78 (1H, tt, J = 7.3, 7.3 Hz), 6.8-6.9 (1H, m), 7.1-7.2 (2H, m), 7.34 (1H, dd, J = 9.0, 9.0 Hz), 7.44 (1H, d, J = 2.1 Hz), 7.97 (1H, s), 8.08 (1H, d, J = 8.7 Hz), 9.29 (1H, br), 9.44 (1H, br). | Hydrochloride |
| 899 | —H | —H | —F | —H | —H | | $^1$H-NMR (DMSO-d$_6$) δppm: 1.55-1.75 (1H, m), 2.1-2.25 (1H, m), 2.85-3.05 (1H, m), 3.1-3.25 (2H, m), 3.6-3.75 (1H, m), 3.8-5.0 (1H, m), 5.28 (1H, tt, J = 8.2, 8.2 Hz), 6.06 (1H, d, J = 8.9 Hz), 7.22 (1H, d, J = 5.9 Hz), 7.35-7.5 (5H, m), 7.85 (1H, d, J = 8.9 Hz), 9.34 (2H, br). | 2Hydrochloride |
| 900 | —H | —H | —H | —H | —H | | $^1$H-NMR (DMSO-d$_6$) δppm: 1.55-1.8 (1H, m), 2.2-2.35 (1H, m), 2.8-2.95 (1H, m), 3.0-3.25 (2H, m), 3.6-3.75 (1H, m), 4.10 (1H, br), 4.75-4.9 (1H, m), 6.68 (1H, dd, J = 2.1, 8.9 Hz), 7.15-7.3 (2H, m), 7.3-7.45 (1H, m), 7.45-7.6 (3H, m), 7.93 (1H, d, J = 8.9 Hz), 8.87 (1H, s), 9.26 (1H, br), 9.38 (1H, br). | 2Hydrochloride |

TABLE 125

| Ex. No. | R1 | R2 | R3 | R4 | R5 | R6 | NMR | Salt |
|---|---|---|---|---|---|---|---|---|
| 901 | —H | —H | —F | —H | —H | 6-methyl-benzo[d]isothiazol-3-yl | ¹H-NMR (DMSO-d₆) δppm: 1.6-1.75 (1H, m), 2.2-2.35 (1H, m), 2.8-2.95 (1H, m), 3.05-3.25 (2H, m), 3.6-3.75 (1H, m), 4.47 (1H, br), 4.80 (1H, tt, J = 7.6, 7.6 Hz), 6.66 (1H, dd, J = 2.2, 8.9 Hz), 7.25-7.4 (4H, m), 7.48 (1H, d, J = 1.8 Hz), 7.92 (1H, d, J = 9.0 Hz), 8.85 (1H, s), 9.34 (1H, br), 9.45 (1H, br). | 2Hydrochloride |
| 902 | —H | —H | —H | —H | —H | 4-chloro-6-methyl-benzo[b]thiophen-3-yl | ¹H-NMR (DMSO-d₆) δppm: 1.6-1.75 (1H, m), 2.15-2.3 (1H, m), 2.90 (1H, dd, J = 8.0, 11.6 Hz), 3.05-3.2 (2H, m), 3.62 (1H, dd, J = 6.9, 11.6 Hz), 4.7-4.85 (1H, m), 6.92 (1H, d, J = 1.8 Hz), 7.04 (2H, d, J = 7.7 Hz), 7.17 (1H, dd, J = 7.3, 7.3 Hz), 7.35-7.45 (3H, m), 7.63 (1H, d, J = 1.3 Hz), 7.76 (1H, d, J = 5.5 Hz), 9.23 (2H, br). | Hydrochloride |
| 903 | —H | —H | —H | —H | —H | 2,6-dimethyl-benzo[b]thiophen-3-yl | ¹H-NMR (DMSO-d₆) δppm: 1.6-1.75 (1H, m), 2.1-2.25 (1H, m), 2.55 (3H, d, J = 0.9 Hz), 2.8-2.95 (1H, m), 3.0-3.25 (2H, m), 3.5-3.65 (1H, m), 4.72 (1H, tt, J = 7.3, 7.3 Hz), 6.80 (2H, d, J = 7.7 Hz), 6.85-7.0 (2H, m), 7.10 (1H, s), 7.2-7.3 (2H, m), 7.63 (1H, d, J = 1.9 Hz), 7.69 (1H, d, J = 8.5 Hz), 9.17 (1H, br), 9.34 (1H, br). | Hydrochloride |
| 904 | —H | —H | —F | —H | —H | 2,6-dimethyl-benzo[b]thiophen-3-yl | ¹H-NMR (DMSO-d₆) δppm: 1.6-1.75 (1H, m), 2.1-2.25 (1H, m), 2.53 (3H, d, J = 0.7 Hz), 2.8-2.95 (1H, m), 3.0-3.25 (2H, m), 3.5-3.65 (1H, m), 4.69 (1H, tt, J = 7.1, 7.1 Hz), 6.86 (1H, dd, J = 2.1, 8.5 Hz), 6.9-7.05 (2H, m), 7.05 (1H, s), 7.1-7.2 (2H, m), 7.54 (1H, d, J = 1.9 Hz), 7.62 (1H, d, J = 8.6 Hz), 9.30 (1H, br), 9.45 (1H, br). | Hydrochloride |

TABLE 126

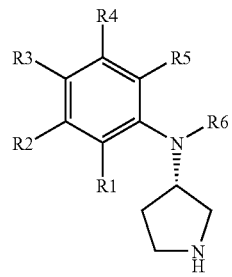

| Ex. No. | R1 | R2 | R3 | R4 | R5 | R6 | NMR | Salt |
|---|---|---|---|---|---|---|---|---|
| 905 | —H | —H | —CH₃ | —F | —H | ![](CH3-dihydroquinolinone with 6-methyl) | ¹H-NMR (DMSO-d₆) δppm: 1.58-1.71 (1H, m), 2.12 (3H, s), 2.19-2.23 (1H, m), 2.55 (2H, dd, J = 7.0, 8.0 Hz, with DMSO-d₆), 2.78-2.89 (1H, m), 2.86 (2H, dd, J = 7.0, 8.0 Hz), 3.08-3.22 (2H, m), 3.27 (3H, s), 3.48-3.62 (1H, m, with H2O), 4.59-4.69 (1H, m), 6.44 (1H, dd, J = 2.3, 8.3 Hz), 6.52 (1H, dd, J = 2.3, 12.8 Hz), 7.02-7.16 (4H, m), 9.34 (2H, br). | Hydrochloride |
| 906 | —H | —H | —CH₃ | —F | —H | ![](CH3-quinolinone with 6-methyl) | ¹H-NMR (DMSO-d₆) δppm: 1.59-1.72 (1H, m), 2.13 (3H, d, J = 0.86 Hz), 2.17-2.27 (1H, m), 2.82-2.91 (1H, m), 3.09-3.20 (2H, m), 3.61-3.63 (1H, m, with H2O), 3.63 (3H, s), 4.66-4.73 (1H, m), 6.47 (1H, dd, J = 2.3, 8.5 Hz), 6.58 (1H, dd, J = 2.3, 12.6 Hz), 6.65 (1H, d, J = 9.5 Hz), 7.11 (1H, dd, J = 8.5, 8.9 Hz), 7.36 (1H, dd, J = 2.5, 8.9 Hz), 7.56-7.60 (2H, m), 7.89 (1H, d, J = 9.5 Hz), 9.33 (1H, br), 9.41 (1H, br). | Hydrochloride |
| 907 | —H | —H | —F | —CH₃ | —H | ![](CH3-dihydroquinolinone with 6-methyl) | ¹H-NMR (DMSO-d₆) δppm: 1.59-1.72 (1H, m), 2.09-2.19 (1H, m), 2.19 (3H, d, J = 1.4 Hz), 2.48-2.51 (2H, m, with DMSO-d6), 2.78-2.90 (1H, m), 2.81 (2H, dd, J = 6.8, 8.0 Hz), 3.09-3.19 (2H, m), 3.22 (3H, s), 3.40-3.54 (1H, m, with H2O), 4.56-4.66 (1H, m), 6.75-6.80 (1H, m), 6.83-6.85 (2H, m), 6.90 (1H, dd, J = 2.6, 6.8 Hz), 7.02-7.11 (2H, m), 9.29 (1H, br), 9.40 (1H, br). | Hydrochloride |
| 908 | —H | —H | —F | —CH₃ | —H | ![](CH3-quinolinone with 6-methyl) | ¹H-NMR (DMSO-d₆) δppm: 1.62-1.75 (1H, m), 2.14-2.26 (1H, m), 2.20 (3H, d, J = 1.6 Hz), 2.85-2.95 (1H, m), 3.11-3.43 (2H, m), 3.53-3.69 (1H, m, with H2O), 3.59 (3H, s), 4.64-4.73 (1H, m), 6.61 (1H, d, J = 9.4 Hz), 6.82-6.87 (1H, m), 6.95 (1H, dd, J = 2.6, 6.8 Hz), 7.11 (1H, dd, J = 9.0, 9.1 Hz), 7.16 (1H, dd, J = 2.6, 9.1 Hz), 7.38 (1H, d, J = 2.6 Hz), 7.48 (1H, d, J = 9.1 Hz), 7.86 (1H, d, J = 9.4 Hz), 9.35 (1H, br), 9.48 (1H, br). | Hydrochloride |

TABLE 127

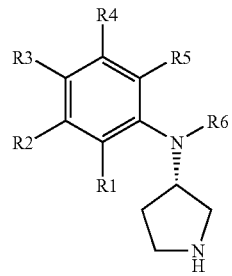

| Ex. No. | R1 | R2 | R3 | R4 | R5 | R6 | NMR | Salt |
|---|---|---|---|---|---|---|---|---|
| 909 | —H | —H | —F | —CH₃ | —H | 6-methyl-3,4-dihydroquinolin-2(1H)-one | ¹H-NMR (DMSO-d₆) δppm: 1.58-1.71 (1H, m), 2.08-2.17 (1H, m), 2.17 (3H, d, J = 1.5 Hz), 2.42 (2H, dd, J = 6.9, 8.0 Hz), 2.81-2.89 (1H, m), 2.83 (2H, dd, J = 6.9, 8.0 Hz), 3.08-3.14 (2H, m), 3.16-3.56 (1H, m, with H2O), 4.52-4.61 (1H, m), 6.63-6.69 (1H, m), 6.79 (1H, dd, J = 2.6, 6.9 Hz), 6.84-6.86 (3H, m), 7.02 (1H, dd, J = 9.1, 9.1 Hz), 9.17 (1H, br), 9.29 (1H, br), 10.07 (1H, s). | Hydrochloride |
| 910 | —H | —H | —F | —CH₃ | —H | 2,6-dimethyl-3,4-dihydroisoquinolin-1(2H)-one | ¹H-NMR (DMSO-d₆) δppm: 1.56-1.69 (1H, m), 2.16-2.65 (1H, m), 2.63 (3H, d, J = 1.5 Hz), 2.78-2.89 (1H, m), 2.83 (2H, dd, J = 6.5, 6.5 Hz), 2.96 (3H, s), 3.07-3.19 (2H, m), 3.37-3.45 (2H, m, with H2O), 3.56-3.66 (1H, m), 4.71-4.80 (1H, m), 6.41 (1H, d, J = 2.4 Hz), 6.47 (1H, dd, J = 2.4, 8.7 Hz), 7.07-7.12 (1H, m), 7.20 (1H, dd, J = 2.4, 7.0 Hz), 7.29 (1H, dd, J = 8.9, 9.2 Hz), 7.64 (1H, d, J = 8.7 Hz), 9.11 (1H, br), 9.19 (1H, br). | Hydrochloride |
| 911 | —H | —H | —F | —Cl | —H | 1,6-dimethyl-3,4-dihydroquinolin-2(1H)-one | ¹H-NMR (DMSO-d₆) δppm: 1.58-1.71 (1H, m), 2.15-2.22 (1H, m), 2.55 (2H, dd, J = 6.4, 8.3 Hz), 2.81-2.89 (1H, m), 2.86 (2H, dd, J = 6.4, 8.3 Hz), 3.12-3.17 (2H, m), 3.26 (3H, s), 3.55 (1H, dd, J = 6.9, 11.7 Hz), 4.60-4.70 (1H, m), 6.69 (1H, ddd, J = 3.0, 3.9, 9.1 Hz), 6.93 (1H, dd, J = 3.0, 6.3 Hz), 7.03-7.06 (2H, m), 7.15 (1H, d, J = 9.3 Hz), 7.27 (1H, dd, J = 9.1, 9.1 Hz), 9.17 (2H, br). | Hydrochloride |
| 912 | —H | —H | —F | —Cl | —H | 1,6-dimethylquinolin-2(1H)-one | ¹H-NMR (DMSO-d₆) δppm: 1.62-1.72 (1H, m), 2.17-2.27 (1H, m), 2.83-2.94 (1H, m), 3.12-3.19 (1H, m), 3.54-3.60 (1H, m), 3.63 (3H, s), 4.67-4.77 (1H, m), 6.66 (1H, d, J = 9.5 Hz), 6.74 (1H, ddd, J = 3.1, 3.8, 9.1 Hz), 6.99 (1H, dd, J = 3.1, 6.3 Hz), 7.29 (1H, dd, J = 9.1, 9.1 Hz), 7.37 (1H, dd, J = 2.6, 8.9 Hz), 7.56-7.60 (2H, m), 7.88 (1H, d, J = 9.5 Hz), 9.13 (1H, br), 9.21 (1H, br). | Hydrochloride |

TABLE 128

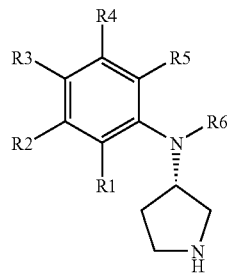

| Ex. No. | R1 | R2 | R3 | R4 | R5 | R6 | NMR | Salt |
|---|---|---|---|---|---|---|---|---|
| 913 | —H | —Cl | —F | —H | —H | 6-methylquinolin-3-yl | ¹H-NMR (DMSO-d₆) δppm; 1.65-1.82 (1H, m), 2.19-2.40 (1H, m), 2.90-3.10 (1H, m), 3.10-3.20 (2H, m), 3.65-3.80 (1H, m), 4.80-4.90 (1H, m), 7.30-7.45 (2H, m), 7.52 (1H, d, J = 2.5 Hz), 7.55-7.69 (2H, m), 7.88 (1H, dd, J = 8.4, 5.1 Hz), 8.15 (1H, d, J = 9.4 Hz), 8.83 (1H, d, J = 8.4 Hz), 8.94 (1H, d, J = 4.1 Hz), 9.45 (1H, bs), 9.62 (1H, bs) | 2Hydrochloride |
| 914 | —H | —H | —F | —Cl | —H | 6-methyl-3,4-dihydroquinolin-2(1H)-one | ¹H-NMR (DMSO-d₆) δppm: 1.56-1.70 (1H, m), 2.12-2.22 (1H, m), 2.46 (2H, dd, J = 7.1, 8.0 Hz), 2.80-2.90 (1H, m), 2.88 (2H, dd, J = 7.1, 8.0 Hz), 3.09-3.16 (2H, m), 3.50-3.60 (1H, m), 4.58-4.68 (1H, m), 6.61 (1H, ddd, J = 3.4, 3.5, 9.1 Hz), 6.86 (1H, dd, J = 2.9, 6.3 Hz), 6.91-7.00 (3H, m), 7.23 (1H, dd, J = 9.1, 9.1 Hz), 8.80 (2H, br), 10.19 (1H, s) | 2Trifluoroacetate |
| 915 | —H | —H | —F | —H | —H | 6-methyl-3,4-dihydroquinolin-2(1H)-one | ¹H-NMR (DMSO-d₆) δppm: 1.59-1.66 (1H, m), 2.10-2.20 (1H, m), 2.43 (2H, dd, J = 7.0, 8.1 Hz), 2.84 (2H, dd, J = 7.0, 8.1 Hz), 2.84-2.92 (1H, m), 3.11-3.21 (2H, m), 3.47-3.55 (1H, m), 4.54-4.64 (1H, m), 6.79-6.89 (5H, m), 7.09 (2H, dd, J = 8.8, 8.9 Hz), 8.71 (2H, br), 10.10 (1H, s). | 2Trifluoroacetate |

TABLE 129

| Ex. No. | R1 | R2 | R3 | R4 | R5 | R6 | NMR | Salt |
|---|---|---|---|---|---|---|---|---|
| 916 | —H | —H | —F | —H | —H | 1-methyl-6-yl-3,4-dihydroquinolin-2(1H)-one | ¹H-NMR (DMSO-d₆) δppm: 1.60-1.71 (1H, m), 2.12-2.22 (1H, m), 2.49-2.54 (2H, m, with DMSO-d₆), 2.82 (2H, dd, J = 7.4, 8.0), 2.84-2.91 (1H, m), 3.12-3.16 (2H, m), 3.23 (3H, s), 3.45-3.55 (1H, m), 4.56-4.65 (1H, m), 6.87-6.95 (4H, m), 7.06 (1H, d, J = 9.4 Hz), 7.14 (2H, dd, J = 8.8, 8.9 Hz), 8.67 (2H, br). | Hydrochloride |
| 917 | —H | —H | —F | —H | —H | 7-methyl-3,4-dihydroquinolin-2(1H)-one | ¹H-NMR (DMSO-d₆) δppm: 1.58-1.73 (1H, m), 2.10-2.31 (1H, m), 2.41 (2H, dd, J = 7.0, 8.0 Hz), 2.80 (2H, dd, J = 7.0, 8.0 Hz), 2.82-3.14 (1H, m), 3.14 (2H, br), 3.46-3.56 (1H, m), 4.54-4.62 (1H, m), 6.31 (1H, d, J = 2.2 Hz), 6.47 (1H, dd, J = 2.2, 8.1 Hz), 7.01-7.10 (3H, m), 7.21 (2H, dd, J = 8.7, 8.8 Hz), 8.83 (2H, br), 9.88 (1H, s). | Hydrochloride |
| 918 | —H | —F | —CH₃ | —H | —H | 6-methyl-3,4-dihydroquinolin-2(1H)-one | ¹H-NMR (DMSO-d₆) δppm: 1.60-1.70 (1H, m), 2.10 (3H, s), 2.13-2.21 (1H, m), 2.43-2.48 (2H, m), 2.79-2.90 (1H, m), 2.87 (2H, dd, J = 7.1, 8.0 Hz), 3.11 (2H, br), 3.48-3.55 (1H, m), 4.56-4.66 (1H, m), 6.37 (1H, dd, J = 2.4, 8.4 Hz), 6.44 (1H, dd, J = 2.4, 13.0 Hz), 6.90-7.08 (4H, m), 9.22 (1H, br), 9.32 (1H, br), 10.19 (1H, s). | Hydrochloride |

TABLE 130

| Ex. No. | R1 | R2 | R3 | R4 | R5 | R6 | NMR | Salt |
|---|---|---|---|---|---|---|---|---|
| 919 | —H | —CH$_3$ | —F | —H | —H | 1-methyl-5-methyl-3,4-dihydroquinolin-2(1H)-one | $^1$H-NMR (DMSO-d$_6$) δppm: 1.53-1.65 (1H, m), 2.14-2.21 (1H, m), 2.14 (3H, d, J = 1.6 Hz), 2.44-2.49 (2H, m, with DMSO-d6), 2.63-2.69 (2H, m), 2.85 (1H, dd, J = 7.8, 11.6 Hz), 3.13-3.17 (2H, m), 3.28 (3H, s), 3.59 (1H, dd, J = 6.9, 11.6 Hz), 4.57-4.67 (1H, m), 6.33-6.39 (1H, m), 6.51 (1H, dd, J = 3.1, 6.4 Hz), 6.91-6.97 (2H, m), 7.15 (1H, d, J = 8.1 Hz), 7.38 (1H, t, J = 8.1 Hz), 9.03 (2H, br). | Hydrochloride |
| 920 | —H | —Cl | —F | —H | —H | 2-methoxy-6-methylquinoline | $^1$H-NMR (DMSO-d$_6$) δppm: 1.58-1.71 (1H, m), 2.15-2.25 (1H, m), 2.82-2.92 (1H, m), 3.11-3.16 (2H, m), 3.37 (3H, s, with H2O), 3.54-3.60 (1H, m), 4.65-4.74 (1H, m), 6.54 (1H, d, J = 9.6 Hz), 6.64-6.69 (1H, m), 6.93 (1H, dd, J = 2.9, 6.3 Hz), 7.22-7.30 (2H, m), 7.37 (1H, d, J = 8.7 Hz), 7.53 (1H, d, J = 2.2 Hz), 7.88 (1H, d, J = 9.6 Hz), 9.04 (1H, br), 9.13 (1H, br), 11.86 (1H, s). | 2Hydrochloride |

TABLE 131

| Ex. No. | R1 | R2 | R3 | R4 | R5 | R6 | NMR | Salt |
|---|---|---|---|---|---|---|---|---|
| 921 | —H | —H | —F | —Cl | —H | 4-methyltetrahydro-2H-pyran | $^1$H-NMR (DMSO-d$_6$) δppm: 1.18-1.35 (2H, m), 1.66-1.90 (3H, m), 1.95-2.12 (1H, m), 2.88-3.46 (7H, m), 3.83 (2H, dd, J = 3.2, 11.1 Hz), 4.18-4.36 (1H, brs), 7.11-7.30 (1H, m), 7.30-7.50 (2H, m), 9.25-9.65 (2H, br). | Hydrochloride |
| 922 | —H | —H | —F | —Cl | —H | 4-ethyltetrahydro-2H-pyran | $^1$H-NMR (DMSO-d$_6$) δppm: 1.08-1.29 (2H, m), 1.45-1.70 (3H, m), 1.79-2.14 (2H, m), 2.85-3.40 (8H, m), 3.73-3.85 (2H, m), 4.28-4.46 (1H, m), 6.91-7.08 (1H, m), 7.11-7.35 (2H, m), 9.00-9.85 (2H, m). | Hydrochloride |

TABLE 131-continued

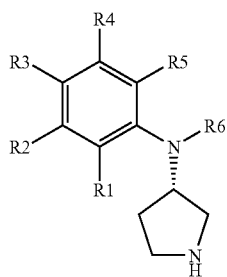

| Ex. No. | R1 | R2 | R3 | R4 | R5 | R6 | NMR | Salt |
|---|---|---|---|---|---|---|---|---|
| 923 | —H | —H | —Cl | —CH₃ | —H | 3-methylpyridine | $^1$H-NMR (DMSO-d$_6$) δppm: 1.57-1.75 (1H, m), 2.19-2.35 (1H, m), 2.37 (3H, s), 2.83-2.96 (1H, m), 3.00-3.19 (2H, m), 3.58-3.74 (1H, m), 4.80-4.95 (1H, m), 7.22 (1H, dd, J = 8.4, 2.4 Hz), 7.40 (1H, d, J = 2.4 Hz), 7.55-7.66 (2H, m), 7.77 (1H, dd, J = 8.9, 5.3 Hz), 8.17 (1H, J = 2.7 Hz), 8.24 (1H, d, J = 5.3 Hz), 9.62 (2H, br). | 2Hydrochloride |
| 924 | —H | —H | —F | —Cl | —H | 4-ethyl-1-phenylpiperidine | $^1$H-NMR (DMSO-d$_6$) δppm: 1.76-1.93 (6H, m), 2.07-2.09 (1H, m), 2.94 (1H, br), 3.10 (1H, br), 3.13 (2H, s), 3.34-3.71 (6H, m, with H2O), 4.36-4.42 (1H, m), 7.02-7.07 (1H, m), 7.24-7.51 (5H, m), 7.77 (2H, br), 9.06 (1H, br), 9.40 (1H, br). | Hydrochloride |

TABLE 132

| Ex. No. | R1 | R2 | R3 | R4 | R5 | R6 | m.p.(°C.) | Salt |
|---|---|---|---|---|---|---|---|---|
| 925 | —H | —H | —F | —H | —H | 3-fluoro-5-methylpyridine | 195.5-198.5 | 2Hydrochloride |
| 926 | —H | —H | —Cl | —Cl | —H | 2-chloro-6-methylpyrazine | 102-105 | Hydrochloride |
| 927 | —H | —H | —Cl | —Cl | —H | 3,4-dimethylpyridine | 119-122 | 2Hydrochloride |
| 928 | —H | —H | —Cl | —Cl | —H | 2-chloro-5-methylpyridine | 123-124 | 2Hydrochloride |

TABLE 132-continued
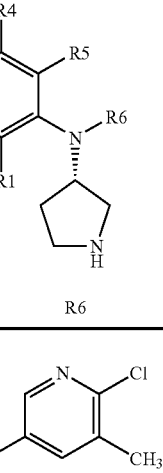
| Ex. No. | R1 | R2 | R3 | R4 | R5 | R6 | m.p.(°C.) | Salt |
|---|---|---|---|---|---|---|---|---|
| 929 | —H | —H | —Cl | —Cl | —H | 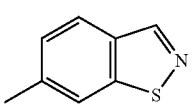 | 191-193 | Hydrochloride |
| 930 | —H | —H | —F | —Cl | —H | 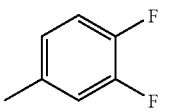 | 150-156 | 2Hydrochloride |
| 931 | —H | —F | —F | —H | —H | 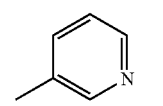 | 153-155 | Fumarate |
| 932 | —H | —Cl | —H | —Cl | —H | 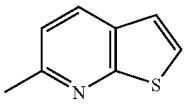 | 174.7-176.7 | 2Hydrochloride |
| 933 | —H | —H | —H | —H | —H | 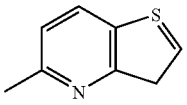 | 227-228.5 | 2Hydrochloride |
| 934 | —H | —H | —H | —H | —H | 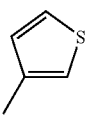 | 241.5-243.5 | 2Hydrochloride |
TABLE 133
| Ex. No. | R1 | R2 | R3 | R4 | R5 | R6 | m.p.(°C.) | Salt |
|---|---|---|---|---|---|---|---|---|
| 935 | —H | —H | —F | —H | —H | | 133-135 | Fumarate |

TABLE 133-continued
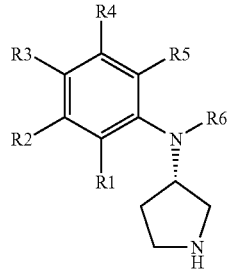
| Ex. No. | R1 | R2 | R3 | R4 | R5 | R6 | m.p.(°C.) | Salt |
|---|---|---|---|---|---|---|---|---|
| 936 | —H | —Cl | —Cl | —H | —H | 3-thienyl | 134-136 | Fumarate |
| 937 | —H | —F | —F | —H | —H | 3-thienyl | 138-141 | Fumarate |
| 938 | —H | —H | —Cl | —CH₃ | —H | 3-thienyl | 110.3-111.9 | Fumarate |
| 939 | —H | —Cl | —H | —Cl | —H | 3-thienyl | 179.2-181.1 | Fumarate |
| 940 | —H | —H | —F | —Cl | —H | 3-chloro-6-methylbenzo[b]thiophene | 203.5-206 | Hydrochloride |
| 941 | —H | —H | —H | —H | —H | 3,6-dimethylbenzo[b]thiophene | 141-144 | Fumarate |
| 942 | —H | —H | —H | —H | —H | 3,5-dimethylbenzo[b]thiophene | 135-161 | Fumarate |
| 943 | —H | —H | —H | —H | —H | 3-chloro-6-methylbenzo[b]thiophene | 155-156 | Hydrochloride |

TABLE 134

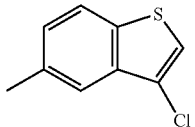

| Ex. No. | R1 | R2 | R3 | R4 | R5 | R6 | m.p.(°C.) | Salt |
|---|---|---|---|---|---|---|---|---|
| 944 | —H | —H | —H | —H | —H | 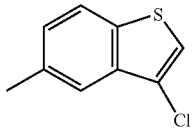 | 160-180 | Hydrochloride |
| 945 | —H | —H | —F | —H | —H | 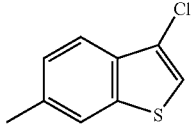 | 155.5-164.5 | Hydrochloride |
| 946 | —H | —H | —F | —H | —H | 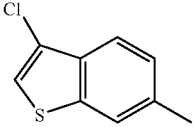 | 161-167.5 | Hydrochloride |

TABLE 135

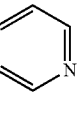

| Ex. No. | R1 | R6 | NMR | Salt |
|---|---|---|---|---|
| 947 | 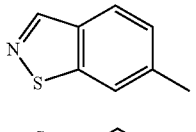 | 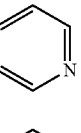 | $^1$H-NMR (DMSO-$d_6$)δppm: 1.6-1.8 (1H, m), 2.25-2.4 (1H, m), 2.85-3.0 (1H, m), 3.0-3.2 (2H, m), 3.25-4.45 (2H, m), 4.9-5.0 (1H, m), 7.45 (1H, dd, J = 1.8, 8.5 Hz), 7.58 (1H, dd, J = 2.3, 8.8 Hz), 7.72 (1H, dd, J = 5.3, 8.8 Hz), 7.98 (1H, d, J = 8.5 Hz), 8.08 (1H, s), 8.16 (1H, d, J = 1.6 Hz), 8.22 (1H, d, J = 2.8 Hz), 8.25 (1H, d, J = 5.0 Hz), 9.45 (1H, br), 9.58 (1H, br). | 2Hydrochloride |
| 948 | 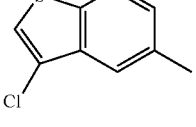 | 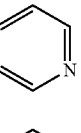 | $^1$H-NMR (DMSO-$d_6$)δppm: 1.6-1.8 (1H, m), 2.25-2.4 (1H, m), 2.85-3.25 (3H, m), 3.6-3.8 (1H, m), 4.97 (1H, tt, J = 7.7, 7.7 Hz), 7.32 (1H, dd, J = 1.7, 8.6 Hz), 7.65-7.8 (2H, m), 8.16 (1H, s), 8.3-8.4 (3H, m), 9.17 (1H, d, J = 0.7 Hz), 9.3-9.8 (2H, m). | 2Hydrochloride |
| 949 | 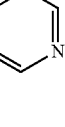 | 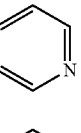 | $^1$H-NMR (DMSO-$d_6$)δppm: 1.55-1.75 (1H, m), 2.25-2.4 (1H, m), 2.7-5.3 (1H, br), 2.85-3.0 (1H, m), 3.05-3.25 (2H, m), 3.65-3.8 (1H, m), 4.95 (1H, tt, J = 7.7, 7.7 Hz), 7.45 (1H, dd, J = 1.9, 8.6 Hz), 7.55-7.6 (1H, m), 7.74 (1H, dd, J = 5.3, 8.8 Hz), 7.81 (1H, d, J = 1.8 Hz), 8.09 (1H, s), 8.19 (1H, d, J = 2.8 Hz), 8.23 (1H, d, J = 5.2 Hz), 8.33 (1H, d, J = 8.6 Hz), 9.44 (1, br), 9.62 (1H, br). | 2Hydrochloride |

TABLE 135-continued

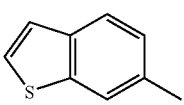

| Ex. No. | R1 | R6 | NMR | Salt |
|---|---|---|---|---|
| 950 | 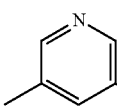 | 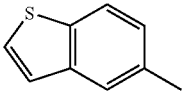 | ¹H-NMR (DMSO-$d_6$)δppm: 1.55-1.75 (1H, m), 2.2-2.35 (1H, m), 2.8-3.0 (1H, m), 3.0-3.25 (2H, m), 3.55-3.75 (1H, m), 4.35-5.5 (2H, m), 7.20 (1H, d, J = 12.2 Hz), 7.28 (1H, dd, J = 1.8, 8.5 Hz), 7.55 (1H, d, J = 5.4 Hz), 7.7-7.8 (1H, m), 7.91 (1H, d, J = 5.4 Hz), 8.0-8.1 (2H, m), 8.10 (1H, d, J = 2.2 Hz), 9.32 (1H, br), 9.47 (1H, br). | 2Hydrochloride |
| 951 | 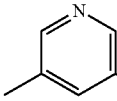 | 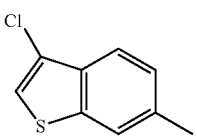 | ¹H-NMR (DMSO-$d_6$)δppm: 1.55-1.8 (1H, m), 2.2-2.35 (1H, m), 2.8-3.0 (1H, m), 3.0-3.2 (2H, m), 3.6-3.75 (1H, m), 4.3-5.0 (2H, m), 7.1-7.25 (1H, m), 7.27 (1H, dd, J = 2.0, 8.5 Hz), 7.51 (1H, d, J = 5.5 Hz), 7.76 (1H, d, J = 1.1 Hz), 7.87 (1H, d, J = 1.9 Hz), 7.91 (1H, d, J = 5.4 Hz), 8.08 (1H, d, J = 2.2 Hz), 8.20 (1H, d, J = 8.5 Hz), 9.27 (1H, br), 9.43 (1H, br). | 2Hydrochloride |
| 952 | 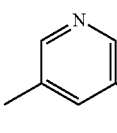 | 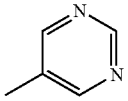 | ¹H-NMR (DMSO-$d_6$)δppm: 1.6-1.75 (1H, m), 2.2-2.35 (1H, m), 2.85-3.0 (1H, m), 3.0-3.2 (2H, m), 3.6-3.75 (1H, m), 4.32 (1H, br), 4.85 (1H, tt, J = 7.7, 7.7 Hz), 7.19 (1H, ddd, J = 2.4, 2.4, 12.0 Hz), 7.37 (1H, dd, J = 1.9, 8.5 Hz), 7.8-7.85 (1H, m), 7.92 (1H, d, J = 8.5 Hz), 8.02 (1H, s), 8.05-8.15 (2H, m), 9.21 (1H, br), 9.33 (1H, br). | 2Hydrochloride |

TABLE 136

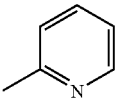

| Ex. No. | R1 | R2 | R3 | R4 | R5 | R6 | m.p.(°C.) | Salt |
|---|---|---|---|---|---|---|---|---|
| 953 | —H | —H | —Cl | —Cl | —H | 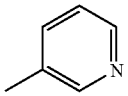 | 96-98 | 2Hydrochloride |
| 954 | —H | —H | —Cl | —Cl | —H | 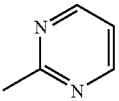 | 126-129 | 2Hydrochloride |
| 955 | —H | —H | —Cl | —Cl | —H |  | 139-143 | 2Hydrochloride |
| 956 | —H | —H | —Cl | —Cl | —H |  | 117-120 | 2Hydrochloride |

TABLE 136-continued

| Ex. No. | R1 | R2 | R3 | R4 | R5 | R6 | m.p.(°C.) | Salt |
|---|---|---|---|---|---|---|---|---|
| 957 | —H | —H | —Cl | —Cl | —H | 2-chloro-5-methylpyrimidin-yl | 155-159 | Hydrochloride |
| 958 | —H | —H | —F | —Cl | —H | 2-chloro-5-methylpyridin-yl | 101-103 | Hydrochloride |
| 959 | —H | —H | —F | —Cl | —H | 2-chloro-5-methylpyrimidin-yl | 157-160 | Hydrochloride |
| 960 | —H | —H | —Cl | —Cl | —H | 4-fluoro-2-methylpyridin-yl | 151-153 | 2Hydrochloride |
| 961 | —H | —H | —Cl | —Cl | —H | 5-fluoro-2-methylpyridin-yl | 96-98 | Hydrochloride |
| 962 | —H | —H | —F | —Cl | —H | methylpyrazinyl | 119-123 | 2Hydrochloride |
| 963 | —H | —H | —Cl | —Cl | —H | methylpyrazinyl | 120-124 | 2Hydrochloride |

TABLE 137

| Ex. No. | R1 | R2 | R3 | R4 | R5 | R6 | NMR | Salt |
|---|---|---|---|---|---|---|---|---|
| 964 | —H | —Cl | —F | —H | —H | —(CH$_2$)$_2$OCH(C$_6$H$_5$)$_2$ | $^1$H-NMR (CDCl$_3$)δppm; 1.99-2.18 (2H, m), 3.13-3.34 (2H, m), 3.38-3.3.47 (7H, m), 4.23-4.35 (1H, m), 5.25 (1H, s), 6.71-6.78 | — |

TABLE 137-continued

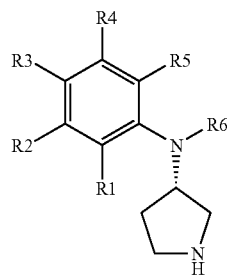

| Ex. No. | R1 | R2 | R3 | R4 | R5 | R6 | NMR | Salt |
|---|---|---|---|---|---|---|---|---|
| | | | | | | | (1H, m), 6.92-7.00 (2H, m), 7.18-7.33 (10H, m) | |
| 965 | —H | —Cl | —F | —H | —H | —CH$_2$CO$_2$C$_2$H$_5$ | $^1$H-NMR (DMSO-d$_6$)δppm; 1.15 (3H, t, J = 7.1 Hz), 2.05-2.36 (2H, m), 3.04-3.22 (1H, m), 3.22-3.72 (4H, m), 3.71-4.50 (3H, m), 5.34 (1H, brs), 7.52-7.69 (2H, m), 7.87-7.98 (1H, m), 9.10-9.70 (2H, m). | Hydrochloride |
| 966 | —H | —Cl | —F | —H | —H | —(CH$_2$)$_2$OH | $^1$H-NMR (CDCl$_3$)δppm; 1.25 (1H, s), 1.80-1.94 (1H, m), 2.04-2.19 (1H, m), 2.97-3.74 (9H, m), 4.05-4.14 (1H, m), 6.76 (1H, ddd, J = 8.9, 3.6, 2.9 Hz), 6.92 (1H, dd, J = 6.2, 2.9 Hz), 7.03 (1H, dd, J = 8.9, 8.8 Hz) | — |
| 967 | —H | —Cl | —F | —H | —H | —CH$_2$C(CH$_3$)$_2$OH | $^1$H-NMR (DMSO-d$_6$)δppm; 1.01 (3H, s), 1.04 (3H, s), 1.88-2.15 (2H, m), 3.03-3.22 (4H, m), 3.22-3.45 (2H, m), 3.45-3.55 (5H, m; including 1H, quint at 4.30), 7.01-7.10 (1H, m), 7.23 (1H, t, J = 9.1 Hz), 7.25-7.32 (1H, m). | Oxalate |
| 968 | —H | —Cl | —F | —H | —H | —(CH$_2$)$_2$OCH$_3$ | $^1$H-NMR (DMSO-d$_6$)δppm; 1.82-2.00 (1H, m), 2.06-2.20 (1H, m), 2.90-3.19 (2H, m), 3.24 (3H, s), 3.26-3.50 (6H, m), 4.44 (1H, quint, J = 8.2 Hz), 6.89 (1H, td, J = 3.3, 9.1 Hz), 7.07 (1H, dd, J = 3.3, 9.1 Hz), 7.25 (1H, t, J = 9.1 Hz), 9.34 (1H, br), 9.52 (1H, br). | Hydrochloride |
| 969 | —H | —Cl | —F | —H | —H | —CH$_2$CO$_2$H | $^1$H-NMR (DMSO-d$_6$)δppm; 2.05-2.34 (2H, m), 2.80-4.40 (5H, m), 5.22 (1H, brs), 7.51-7.71 (2H, m), 7.89 (1H, dd, J = 1.8, 5.3 Hz), 7.15-7.65 (2H, br), 9.85-11.65 (2H, br). | Hydrochloride |
| 970 | —H | —Cl | —F | —H | —H | —CH$_2$CONH$_2$ | | |
| 971 | —H | —Cl | —F | —H | —H | —CH$_2$CONHCH$_3$ | $^1$H-NMR (DMSO-d$_6$)δppm; 2.09-2.31 (2H, m), 2.63 (3H, d, J = 4.6 Hz), 3.05-3.25 (1H, m), 3.25-3.54 (3H, m), 3.54-3.79 (1H, m), 5.27 (1H, brs), 7.50-7.70 (2H, m), 7.80-7.97 (1H, m), 8.92 (1H, brs), 9.36-9.85 (2H, m), 9.80-11.10 (1H, br). | Hydrochloride |

TABLE 138

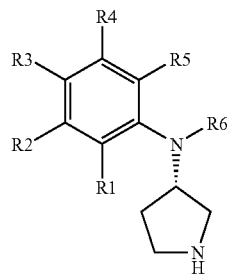

| Ex. No. | R1 | R2 | R3 | R4 | R5 | R6 | NMR | Salt |
|---|---|---|---|---|---|---|---|---|
| 972 | —H | —Cl | —F | —H | —H | —CH$_2$CON(CH$_3$)$_2$ | $^1$H-NMR (DMSO-d$_6$)δppm; 2.07-2.40 (2H, m), 2.89 (3H, s), 2.90 (3H, s), 3.02-3.24 (1H, m), 3.24-3.83 (4H, m), 5.63 (1H, brs), 7.53-7.69 (2H, m), 7.83-7.93 (1H, m), 9.32-9.75 (2H, m), 9.82-10.50 (1H, m). | Hydrochloride |

TABLE 138-continued

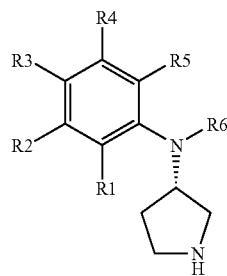

| Ex. No. | R1 | R2 | R3 | R4 | R5 | R6 | NMR | Salt |
|---|---|---|---|---|---|---|---|---|
| 973 | —H | —Cl | —F | —H | —H | —CH$_2$CH=CH$_2$ | $^1$H-NMR (DMSO-d$_6$)δppm; 1.76-1.95 (1H, m), 2.10-2.25 (1H, m), 2.85-3.02 (1H, m), 3.02-3.19 (1H, m), 3.25-3.50 (2H, m), 3.89 (2H, brs), 4.59 (1H, quint, J = 7.8 Hz), 5.05-5.20 (2H, m), 5.76-5.94 (1H, m), 6.69-6.82 (1H, m), 6.88-6.97 (1H, m), 7.23 (1H, t, J = 9.2 Hz), 8.90-9.95 (2H, br). | Hydrochloride |
| 974 | —H | —Cl | —F | —H | —H | —(CH$_2$)$_3$OH | $^1$H-NMR (DMSO-d$_6$)δppm; 1.49-2.79 (2H, m), 1.81-2.04 (2H, m), 2.05-2.20 (1H, m), 2.82-3.20 (2H, m), 3.20-3.50 (6H, m), 4.33-4.52 (1H, m), 6.84-7.04 (1H, m), 7.04-7.21 (1H, m), 7.22-7.35 (1H, m), 9.15-9.75 (2H, m). | Hydrochloride |
| 975 | —H | —Cl | —F | —H | —H | —(CH$_2$)$_2$C(CH$_3$)$_2$OH | | |
| 976 | —H | —Cl | —F | —H | —H | —(CH$_2$)$_3$OCH$_3$ | $^1$H-NMR (DMSO-d$_6$)δppm; 1.55-1.72 (2H, m), 1.80-1.99 (1H, m), 2.04-2.20 (1H, m), 2.93 (1H, dd, J = 9.4, 11.6 Hz), 3.05-3.50 (10H, m), 4.40 (1H, quint, J = 7.9 Hz), 5.25-8.20 (6H, m; including 6.80-6.90 (1H, m), 7.00-7.10 (1H, m), and 7.26 (1H, t, J = 9.1 Hz). | Oxalate |

TABLE 139

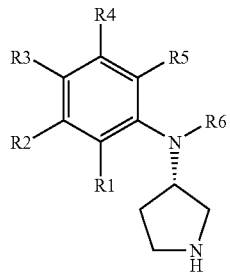

| Ex. No. | R1 | R2 | R3 | R4 | R5 | R6 | NMR | Salt |
|---|---|---|---|---|---|---|---|---|
| 977 | —H | —Cl | —F | —H | —H | (2-methylbenzoxazol-5-yl) | $^1$H-NMR (CDCl$_3$)δppm; 1.58-1.71 (1H, m), 2.03-2.18 (2H, m), 2.79 (1H, dd, J = 11.2, 4.3 Hz), 2.91 (1H, ddd, J = 11.2, 8.2, 6.2 Hz), 3.03-3.15 (2H, m), 4.25-4.35 (1H, m), 6.88-6.92 (1H, m), 6.97-7.15 (3H, m), 7.25 (1H, dd, J = 8.7, 8.7 Hz), 7.49 (1H, ddd, J = 8.7, 4.2, 2.6 Hz), 7.66 (1H, dd, J = 6.5, 2.6 Hz) | — |
| 978 | —H | —Cl | —F | —H | —H | (5-methyl-2,3-dihydrobenzofuran-6-yl) | $^1$H-NMR (CDCl$_3$)δppm; 1.59 (1H, s), 1.66-1.81 (1H, m), 2.00-2.16 (1H, m), 2.83-2.93 (3H, m), 3.12 (1H, dd, J = 11.5, 6.6 Hz), 3.22 (1H, t, J = 8.7 Hz), 4.20-4.31 (1H, m), 4.62 (1H, t, J = 8.7 Hz), 6.44 (1H, ddd, J = 9.1, 3.6, 3.0 Hz), 6.62 (1H, dd, J = 6.2, 3.0 Hz), 6.75-6.85 (2H, m), 6.86-6.94 (2H, m) | |
| 979 | —H | —Cl | —F | —H | —H | (1,5-dimethylindol-6-yl) | | |

TABLE 139-continued

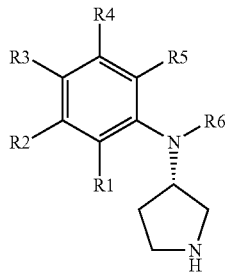

| Ex. No. | R1 | R2 | R3 | R4 | R5 | R6 | NMR | Salt |
|---|---|---|---|---|---|---|---|---|
| 980 | —H | —Cl | —F | —H | —H | ![biphenyl-methyl] | ¹H-NMR (CDCl₃)δppm; 1.64-1.84 (2H, m), 2.07-2.19 (1H, m), 2.87-3.02 (3H, m), 3.21 (1H, dd, J = 11.5, 6.7 Hz), 4.34-4.44 (1H, m), 6.81 (1H, ddd, J = 8.9, 4.1, 2.8 Hz), 6.90-6.95 (2H, m), 7.00 (1H, dd, J = 6.5, 2.8 Hz), 7.07 (1H, dd, J = 8.9, 8.7 Hz), 7.30-7.34 (1H, m), 7.39-7.45 (2H, m), 7.49-7.61 (4H, m) | Oxalate |
| 981 | —H | —Cl | —F | —H | —H | ![bis(4-chlorophenyl)-propoxymethyl] | ¹H-NMR (CDCl₃)δppm; 1.66-1.82 (1H, m), 1.98-2.12 (1H, m), 2.83-3.20 (5H, m), 3.40-3.52 (4H, m), 4.02-4.15 (1H, m), 5.23 (1H, s), 6.67 (1H, ddd, J = 8.9, 3.6, 3.0 Hz), 6.89 (1H, dd, J = 6.2, 3.0 Hz), 6.96 (1H, dd, J = 8.9, 8.8 Hz), 7.16-7.21 (4H, m), 7.25-7.32 (4H, m) | — |
| 982 | —H | —Cl | —F | —H | —H | ![bis(4-fluorophenyl)-propoxymethyl] | ¹H-NMR (CDCl₃)δppm; 1.67-1.82 (1H, m), 1.98-2.13 (1H, m), 2.83-3.20 (4H, m), 3.24 (1H, br), 3.40-3.52 (4H, m), 4.03-4.15 (1H, m), 5.26 (1H, s), 6.67 (1H, ddd, J = 9.0, 3.6, 3.0 Hz), 6.89 (1H, dd, J = 6.2, 3.0 Hz), 6.91-7.05 (5H, m), 7.20-7.29 (4H, m) | — |

TABLE 140

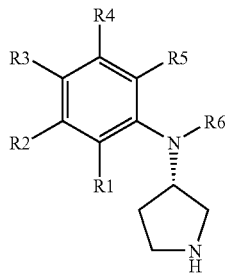

| Ex. No. | R1 | R2 | R3 | R4 | R5 | R6 | NMR | Salt |
|---|---|---|---|---|---|---|---|---|
| 983 | —H | —Cl | —F | —H | —H | ![(4-phenoxyphenyl)methyl] | ¹H-NMR (CDCl₃)δppm; 1.68-1.82 (2H, m), 2.03-2.17 (1H, m), 2.83-2.95 (3H, m), 3.16 (1H, dd, J = 11.6, 6.7 Hz), 4.25-4.35 (1H, m), 6.58 (1H, ddd, J = 9.0, 3.9, 2.9 Hz), 6.78 (1H, dd, J = 6.3, 2.9 Hz), 6.94-7.06 (7H, m), 7.09-7.16 (1H, m), 7.32-7.40 (2H, m) | Oxalate |

TABLE 140-continued

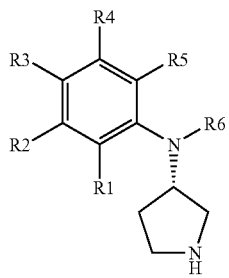

| Ex. No. | R1 | R2 | R3 | R4 | R5 | R6 | NMR | Salt |
|---|---|---|---|---|---|---|---|---|
| 984 | —H | —Cl | —F | —H | —H | ![structure with tolyl-O-phenyl-Cl] | ¹H-NMR (CDCl₃)δppm; 1.67-1.90 (2H, m), 2.04-2.18 (1H, m), 2.80-3.01 (3H, m), 3.05-3.30 (1H, m), 4.20-4.44 (1H, m), 6.58-6.69 (1H, m), 6.78-6.82 (1H, m), 6.84-7.00 (7H, m), 7.27-7.34 (2H, m) | — |
| 985 | —H | —Cl | —F | —H | —H | ![structure with tolyl-O-phenyl-F] | ¹H-NMR (CDCl₃)δppm; 1.66-1.80 (2H, m), 2.02-2.17 (1H, m), 2.80-2.95 (3H, m), 3.03-3.26 (1H, m), 4.24-4.37 (1H, m), 6.54-6.62 (1H, m), 6.74-6.81 (1H, m), 6.83-7.10 (9H, m) | — |

TABLE 141

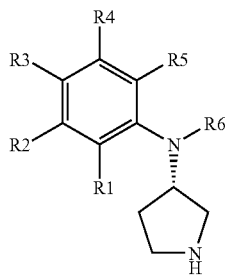

| Ex. No. | R1 | R2 | R3 | R4 | R5 | R6 | NMR | Salt |
|---|---|---|---|---|---|---|---|---|
| 986 | —H | —Cl | —F | —H | —H | ![4'-fluoro-4-methylbiphenyl] | ¹H-NMR (CDCl₃)δppm; 1.70-1.84 (2H, m), 2.06-2.20 (1H, m), 2.86-2.98 (3H, m), 3.18-3.26 (1H, m), 4.33-4.45 (1H, m), 6.78-6.85 (1H, m), 6.87-6.94 (2H, m), 6.98-7.02 (1H, m), 7.04-7.16 (3H, m), 7.43-7.55 (4H, m) | — |
| 987 | —H | —Cl | —F | —H | —H | ![4'-chloro-4-methylbiphenyl] | ¹H-NMR (CDCl₃)δppm; 1.68 (1H, s), 1.69-1.83 (1H, m), 2.04-2.20 (1H, m), 2.75-2.97 (3H, m), 3.22 (1H, dd, J = 11.5, 6.8 Hz), 4.34-4.45 (1H, m), 6.84 (1H, ddd, J = 8.8, 4.1, 2.7 Hz), 6.85-6.92 (2H, m), 7.03 (1H, dd, J = 6.5, 2.7 Hz), 7.10 (1H, dd, J = 8.8, 8.7 Hz), 7.34-7.41 (2H, m), 7.43-7.52 (4H, m) | — |
| 988 | —H | —Cl | —F | —H | —H | ![5-methylbenzoxazole] | | 2Trifluoroacetate |
| 989 | —H | —Cl | —F | —H | —H | ![6-methylbenzothiazole] | ¹H-NMR (CDCl₃)δppm; 1.85-2.1 (1H, m), 2.15-2.35 (1H, m), 2.35-2.95 (1H, m), 3.14 (1H, br), 3.33 (2H, br), 3.59 (1H, br), 4.55-4.8 (1H, m), 6.8-6.95 (1H, m), 7.01 (1H, dd, J = 2.7, 6.3 Hz), 7.05-7.2 (2H, m), 7.55 (1H, d, J = 2.0 Hz), 8.06 (1H, d, J = 8.8 Hz), 8.97 (1H, s), 9.86 (2H, br). | 2Trifluoroacetate |

TABLE 141-continued

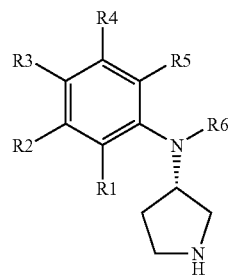

| Ex. No. | R1 | R2 | R3 | R4 | R5 | R6 | NMR | Salt |
|---|---|---|---|---|---|---|---|---|
| 990 | —H | —Cl | —F | —H | —H | (6-methyl-1-methyl-indazol-3-yl) | $^1$H-NMR (DMSO-$d_6$)δppm; 1.6-1.8 (1H, m), 2.15-2.3 (1H, m), 2.85-3.0 (1H, m), 3.05-3.25 (2H, m), 3.55-3.7 (1H, m), 4.03 (3H, s), 4.76 (1H, tt, J = 7.2, 7.2 Hz), 5.28 (1H, br), 6.8-6.9 (1H, br), 6.8-6.9 (1H, m), 7.08 (1H, dd, J = 2.9, 6.4 Hz), 7.32 (1H, dd, J = 9.0, 9.0 Hz), 7.44 (1H, s), 7.71 (1H, d, J = 8.6 Hz), 8.01 (1H, s), 9.36 (1H, br), 9.52 (1H, br). | 2Hydrochloride |

TABLE 142

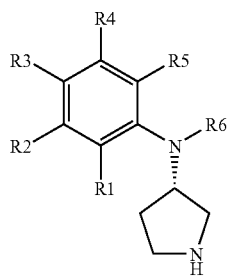

| Ex. No. | R1 | R2 | R3 | R4 | R5 | R6 | NMR | Salt |
|---|---|---|---|---|---|---|---|---|
| 991 | —H | —Cl | —F | —H | —H | (1-methyl-5-methyl-indazol-3-yl) | $^1$H-NMR (DMSO-$d_6$)δppm; 1.5-1.75 (1H, m), 2.1-2.3 (1H, m), 2.75-2.95 (1H, m), 2.95-3.25 (2H, m), 3.45-3.65 (1H, m), 3.65-4.35 (4H, m), 4.72 (1H, tt, J = 7.2, 7.2 Hz), 6.59 (1H, ddd, J = 3.5, 3.5, 9.1 Hz), 6.79 (1H, dd, J = 3.0, 6.3 Hz), 7.1-7.25 (2H, m), 7.67 (1H, d, J = 1.5 Hz), 7.75 (1H, d, J = 8.8 Hz), 8.08 (1H, d, J = 0.4 Hz), 9.31 (1H, br), 9.42 (1H, br). | Hydrochloride |
| 992 | —H | —Cl | —F | —H | —H | (5-methyl-benzimidazol-2-yl) | | |
| 993 | —H | —Cl | —F | —H | —H | (3-methyl-benzofuran-2-yl) | | |
| 994 | —H | —Cl | —F | —H | —H | (3-methyl-benzothiophen-2-yl) | $^1$H-NMR (CDCl$_3$)δppm; 1.85-2.05 (1H, m), 2.2-2.35 (1H, m), 3.1-3.25 (1H, m), 3.25-3.4 (2H, m), 3.55-3.7 (1H, m), 4.79 (1H, tt, J = 6.8, 6.8 Hz), 6.60 (1H, ddd, J = 3.4, 3.4, 9.0 Hz), 6.76 (1H, dd, J = 3.0, 6.0 Hz), 6.95 (1H, dd, J = 8.8, 8.8 Hz), 7.25-7.45 (4H, m), 7.85 (1H, dd, J = 1.2, 7.6 Hz), 9.07 (1H, br), 9.24 (1H, br), 10.44 (1H, br). | 2Trifluoroacetate |

TABLE 142-continued

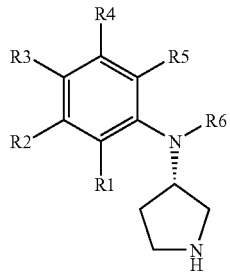

| Ex. No. | R1 | R2 | R3 | R4 | R5 | R6 | NMR | Salt |
|---|---|---|---|---|---|---|---|---|
| 995 | —H | —Cl | —F | —H | —H | (3-methylthiophen-4-yl, via S, CH₃) | $^1$H-NMR (CDCl$_3$)δppm; 1.8-2.05 (4H, m), 2.15-2.35 (1H, m), 3.0-3.2 (1H, m), 3.25-3.45 (2H, m), 3.5-3.7 (1H, m), 4.64 (1H, tt, J = 6.8, 6.8 Hz), 6.46 (1H, ddd, J = 3.4, 3.4, 9.1 Hz), 6.60 (1H, dd, J = 3.0, 6.1 Hz), 6.96 (1H, dd, J = 8.8, 8.8 Hz), 7.05-7.15 (2H, m), 8.85-9.65 (2H, m), 10.42 (1H, br). | 2Trifluoroacetate |

TABLE 143

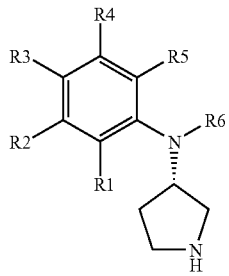

| Ex. No. | R1 | R2 | R3 | R4 | R5 | R6 | NMR | Salt |
|---|---|---|---|---|---|---|---|---|
| 996 | —H | —Cl | —F | —H | —H | 2-methylthiophene | | |
| 997 | —H | —Cl | —F | —H | —H | 2,5-dimethylthiophene | $^1$H-NMR (CDCl$_3$)δppm; 2.05-2.2 (1H, m), 2.2-2.35 (1H, m), 2.44 (3H, d, J = 1.0 Hz), 3.15-3.45 (3H, m), 3.5-3.7 (1H, m), 4.59 (1H, tt, J = 6.6, 6.6 Hz), 6.55-6.65 (2H, m), 6.69 (1H, ddd, J = 3.4, 9.0 Hz), 6.84 (1H, dd, J = 3.0, 6.1 Hz), 7.00 (1H, dd, J = 8.7, 8.7 Hz), 9.14 (2H, br), 9.52 (1H, br). | 2Trifluoroacetate |
| 998 | —H | —Cl | —F | —H | —H | 4-methylthiophen-2-yl | $^1$H-NMR (DMSO-d$_6$)δppm; 1.6-1.75 (1H, m), 2.05-2.2 (1H, m), 2.39 (3H, d, J = 0.7 Hz), 2.86 (1H, dd, J = 7.4, 11.5 Hz), 2.95-3.15 (2H, m), 3.50 (1H, dd, J = 7.0, 11.5 Hz), 3.65-6.1 (4H, m), 6.46 (2H, s), 6.50 (1H, s), 6.7-6.85 (1H, m), 6.9-7.0 (2H, m), 7.27 (1H, dd, J = 9.1, 9.1 Hz). | Fumarate |
| 999 | —H | —Cl | —F | —H | —H | 1-methoxy-3-methyl-5-fluoropyridinium | | 2Trifluoroacetate |

TABLE 144

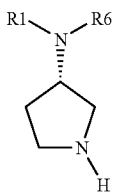

| Ex. No. | R1 | R6 | NMR | Salt |
|---|---|---|---|---|
| 1000 | 2-naphthyl | 3-thienyl | ¹H-NMR (DMSO-d₆)δppm; 1.7-1.85 (1H, m), 2.15-2.3 (1H, m), 2.9-3.2 (3H, m), 3.63 (1H, dd, J = 7.0, 11.5 Hz), 4.73 (1H, tt, J = 7.3, 7.3 Hz), 6.47 (2H, s), 6.82 (1H, dd, J = 1.4, 5.1 Hz), 6.95 (1H, dd, J = 2.4, 9.0 Hz), 7.26 (1H, dd, J = 1.4, 3.1 Hz), 7.25-7.35 (2H, m), 7.35-7.45 (1H, m), 7.59 (1H, dd, J = 3.1, 5.1 Hz), 7.7-7.8 (3H, m), 10.3 (3H, br). | Fumarate |
| 1001 | benzothiophen-6-yl | 3-thienyl | ¹H-NMR (DMSO-d₆)δppm; 1.6-1.9 (1H, m), 2.0-2.35 (1H, m), 2.65-5.55 (8H, m), 6.48 (2H, s), 6.68 (1H, dd, J = 1.4, 5.1 Hz), 6.92 (1H, dd, J = 2.1, 8.6 Hz), 7.04 (1H, dd, J = 1.4, 3.0 Hz), 7.35 (1H, d, J = 5.5 Hz), 7.50 (1H, dd, J = 3.1, 5.1 Hz), 7.55-7.65 (2H, m), 7.75 (1H, d, J = 8.6 Hz). | Fumarate |
| 1002 | benzothiophen-5-yl | 3-thienyl | ¹H-NMR (DMSO-d₆)δppm; 1.55-1.9 (1H, m), 2.0-2.25 (1H, m), 2.3-5.45 (8H, m), 6.48 (2H, s), 6.59 (1H, dd, J = 1.4, 5.1 Hz), 6.92 (1H, dd, J = 1.4, 3.0 Hz), 6.99 (1H, dd, J = 2.2, 8.7 Hz), 7.38 (1H, d, J = 5.4 Hz), 7.45 (1H, dd, J = 3.1, 5.1 Hz), 7.54 (1H, d, J = 2.1 Hz), 7.75 (1H, d, J = 5.4 Hz), 7.91 (1H, d, J = 8.6 Hz). | Fumarate |

TABLE 145

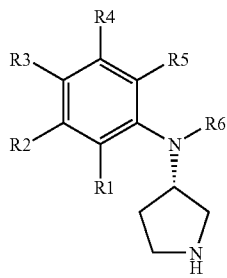

| Ex. No. | R1 | R2 | R3 | R4 | R5 | R6 | MS(M + 1) |
|---|---|---|---|---|---|---|---|
| 1003 | —H | —Cl | —F | —H | —H | —(CH₂)₂CO₂CH₃ | |
| 1004 | —H | —Cl | —F | —H | —H | —(CH₂)₂CO₂C₂H₅ | |
| 1005 | —H | —Cl | —F | —H | —H | —(CH₂)₂CO₂CH₂C₆H₅ | |
| 1006 | —H | —Cl | —F | —H | —H | —(CH₂)₂CON(CH₃)₂ | 314 |
| 1007 | —H | —Cl | —F | —H | —H | —(CH₂)₂COCH₃ | |
| 1008 | —H | —Cl | —F | —H | —H | —(CH₂)₂COC₂H₅ | |
| 1009 | —H | —Cl | —F | —H | —H | —(CH₂)₂COC₆H₅ | |
| 1010 | —H | —Cl | —F | —H | —H | —(CH₂)₂CH(OH)CH₃ | |
| 1011 | —H | —Cl | —F | —H | —H | —(CH₂)₂CH(OH)C₂H₅ | |
| 1012 | —H | —Cl | —F | —H | —H | —(CH₂)₂CH(OH)C₆H₅ | |
| 1013 | —H | —Cl | —F | —H | —H | —(CH₂)₂CH(OH)(CH₃)₂ | |
| 1014 | —H | —Cl | —F | —H | —H | —(CH₂)₃SC₆H₅ | 365 |
| 1015 | —H | —Cl | —F | —H | —H | —(CH₂)₃S(CH₂)₂N(C₂H₅)₂ | |
| 1016 | —H | —Cl | —F | —H | —H | —(CH₂)₃S(CH₂)₂CH₃ | 331 |
| 1017 | —H | —Cl | —F | —H | —H | —(CH₂)₃SCH₂C₆H₅ | 379 |
| 1018 | —H | —Cl | —F | —H | —H | —(CH₂)₃S(CH₂)₂C₆H₅ | 393 |
| 1019 | —H | —Cl | —F | —H | —H | —(CH₂)₃S(CH₂)₂NH₂ | |
| 1020 | —H | —Cl | —F | —H | —H | —(CH₂)₃SC₂H₅ | |
| 1021 | —H | —Cl | —F | —H | —H | —(CH₂)₃S(CH₂)₂OH | 333 |
| 1022 | —H | —Cl | —F | —H | —H | —(CH₂)₃S(CH₂)₂CO₂CH₃ | 375 |
| 1023 | —H | —Cl | —F | —H | —H | —(CH₂)₃SCH₂CO₂CH₃ | 361 |
| 1024 | —H | —Cl | —F | —H | —H | —(CH₂)₃S-cyclo-C₅H₉ | 357 |
| 1025 | —H | —Cl | —F | —H | —H | —(CH₂)₃S-cyclo-C₆H₁₁ | 371 |
| 1026 | —H | —Cl | —F | —H | —H | —(CH₂)₃S(CH₂)₃C₆H₅ | 407 |
| 1027 | —H | —Cl | —F | —H | —H | —(CH₂)₃S(CH₂)₂OC₆H₅ | 409 |

TABLE 146
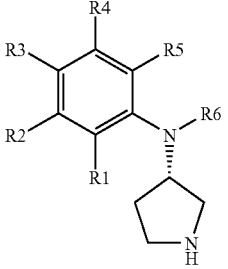
| Ex. No. | R1 | R2 | R3 | R4 | R5 | R6 | MS(M + 1) |
|---|---|---|---|---|---|---|---|
| 1028 | —H | —Cl | —F | —H | —H | 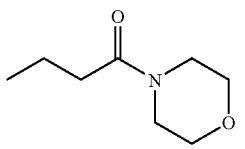 | |
| 1029 | —H | —Cl | —F | —H | —H | 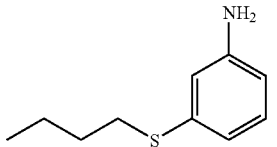 | 380 |
| 1030 | —H | —Cl | —F | —H | —H | 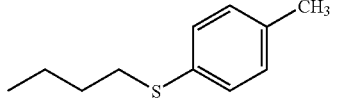 | 379 |
| 1031 | —H | —Cl | —F | —H | —H | 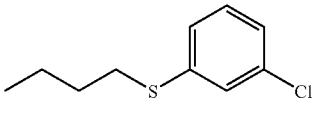 | 399 |
| 1032 | —H | —Cl | —F | —H | —H | 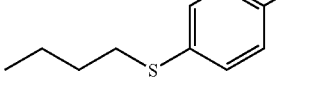 | |
| 1033 | —H | —Cl | —F | —H | —H | 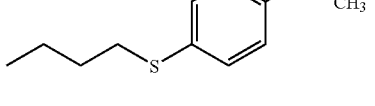 | |
| 1034 | —H | —Cl | —F | —H | —H | 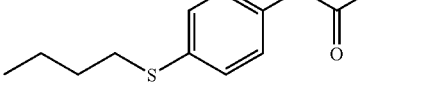 | 422 |
| 1035 | —H | —Cl | —F | —H | —H | 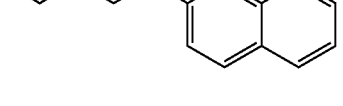 | |
| 1036 | —H | —Cl | —F | —H | —H | 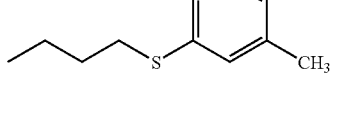 | |

TABLE 146-continued
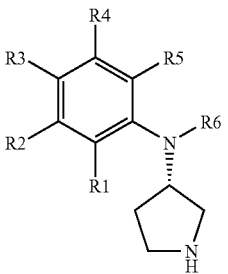
| Ex. No. | R1 | R2 | R3 | R4 | R5 | R6 | MS(M + 1) |
|---|---|---|---|---|---|---|---|
| 1037 | —H | —Cl | —F | —H | —H | | 395 |
TABLE 147
| Ex. No. | R1 | R2 | R3 | R4 | R5 | R6 | MS (M + 1) |
|---|---|---|---|---|---|---|---|
| 1038 | —H | —Cl | —F | —H | —H | | |
| 1039 | —H | —Cl | —F | —H | —H | | 366 |
| 1040 | —H | —Cl | —F | —H | —H | | 366 |
| 1041 | —H | —Cl | —F | —H | —H | | 395 |
| 1042 | —H | —Cl | —F | —H | —H | | 367 |

TABLE 147-continued

| Ex. No. | R1 | R2 | R3 | R4 | R5 | R6 | MS (M + 1) |
|---|---|---|---|---|---|---|---|
| 1043 | —H | —Cl | —F | —H | —H | (butyl-S-1,3,4-thiadiazole-2-yl, 5-methyl) | 387 |
| 1044 | —H | —Cl | —F | —H | —H | (butyl-S-1-methyl-imidazol-2-yl) | 369 |
| 1045 | —H | —Cl | —F | —H | —H | (butyl-S-1H-benzimidazol-2-yl) | 405 |
| 1046 | —H | —Cl | —F | —H | —H | (butyl-S-benzothiazol-2-yl) | 422 |
| 1047 | —H | —Cl | —F | —H | —H | (butyl-S-1-phenyl-tetrazol-5-yl) | 433 |

TABLE 148

| Ex. No. | R1 | R2 | R3 | R4 | R5 | R6 | MS (M + 1) |
|---|---|---|---|---|---|---|---|
| 1048 | —H | —Cl | —F | —H | —H | (butyl-S-benzoxazol-2-yl) | 406 |

TABLE 148-continued

| Ex. No. | R1 | R2 | R3 | R4 | R5 | R6 | MS (M + 1) |
|---|---|---|---|---|---|---|---|
| 1049 | —H | —Cl | —F | —H | —H | | |
| 1050 | —H | —Cl | —F | —H | —H | | 369 |
| 1051 | —H | —Cl | —F | —H | —H | | |
| 1052 | —H | —Cl | —F | —H | —H | | 369 |
| 1053 | —H | —Cl | —F | —H | —H | | |
| 1054 | —H | —Cl | —F | —H | —H | | 386 |
| 1055 | —H | —Cl | —F | —H | —H | | |
| 1056 | —H | —Cl | —F | —H | —H | | 371 |
| 1057 | —H | —Cl | —F | —H | —H | | 409 |

TABLE 149

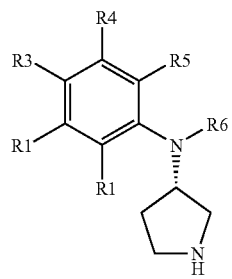

| Ex. No. | R1 | R2 | R3 | R4 | R5 | R6 | MS (M + 1) |
|---|---|---|---|---|---|---|---|
| 1058 | —H | —Cl | —F | —H | —H | butyl-S-CH2-(4-Cl-phenyl) | 413 |
| 1059 | —H | —Cl | —F | —H | —H | butyl-S-CH2-(3-CH3-phenyl) | 393 |
| 1060 | —H | —Cl | —F | —H | —H | butyl-S-CH2-(2-pyridyl) | |
| 1061 | —H | —Cl | —F | —H | —H | butyl-S-CH2-(4-CO2Et-phenyl) | |

TABLE 150

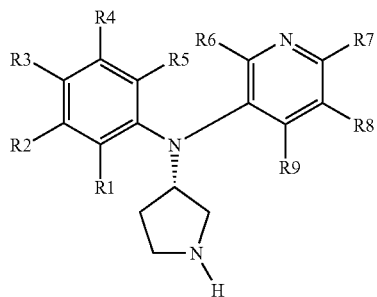

| Ex. No. | R1 | R2 | R3 | R4 | R5 | R6 | R7 | R8 | R9 | MS (M + 1) |
|---|---|---|---|---|---|---|---|---|---|---|
| 1062 | —H | —H | —CF3 | —H | —H | —H | —H | —F | —H | 326 |
| 1063 | —H | —H | —N(CH3)2 | —H | —H | —H | —H | —F | —H | 301 |
| 1064 | —H | —OCH3 | —H | —H | —H | —H | —H | —F | —H | 288 |
| 1065 | —H | —OC2H5 | —H | —H | —H | —H | —H | —F | —H | 302 |
| 1066 | —H | —SCH3 | —H | —H | —H | —H | —H | —F | —H | 304 |
| 1067 | —H | —CF3 | —Cl | —H | —H | —H | —H | —F | —H | 360 |
| 1068 | —H | —H | —CH3 | —H | —H | —H | —H | —F | —H | 272 |
| 1069 | —Cl | —Cl | —H | —H | —H | —H | —H | —F | —H | |
| 1070 | —H | —H | —SCH3 | —H | —H | —H | —H | —F | —H | 304 |
| 1071 | —H | —H | —CH(CH3)2 | —H | —H | —H | —H | —F | —H | 300 |
| 1072 | —H | —H | —OC6H5 | —H | —H | —H | —H | —F | —H | 350 |
| 1073 | —H | —H | —C2H5 | —H | —H | —H | —H | —F | —H | 286 |
| 1074 | —H | —CF3 | —F | —H | —H | —H | —H | —F | —H | 344 |
| 1075 | —F | —CF3 | —H | —H | —H | —H | —H | —F | —H | |
| 1076 | —Cl | —H | —H | —H | —H | —H | —H | —F | —H | 292 |
| 1077 | —H | —H | —OCH3 | —H | —H | —H | —H | —F | —H | 288 |
| 1078 | —CH3 | —CH3 | —H | —H | —H | —H | —H | —F | —H | 286 |
| 1079 | —C2H5 | —H | —H | —H | —H | —H | —H | —F | —H | 286 |

TABLE 150-continued

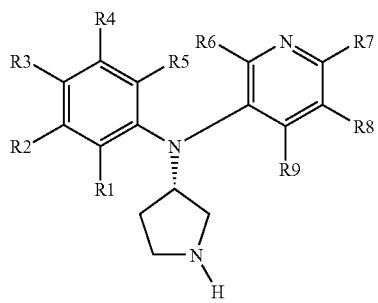

| Ex. No. | R1 | R2 | R3 | R4 | R5 | R6 | R7 | R8 | R9 | MS (M + 1) |
|---|---|---|---|---|---|---|---|---|---|---|
| 1080 | —H | —Cl | —Cl | —H | —H | —H | —H | —F | —H | 326 |
| 1081 | —H | —F | —F | —H | —H | —H | —H | —F | —H | 294 |
| 1082 | —H | —F | —H | —F | —H | —H | —H | —F | —H | 294 |
| 1083 | —H | —H | —CF$_3$ | —F | —H | —H | —H | —F | —H | 344 |
| 1084 | —CF$_3$ | —F | —H | —H | —H | —H | —H | —F | —H | |
| 1085 | —F | —H | —CF$_3$ | —H | —H | —H | —H | —F | —H | 344 |
| 1086 | —H | —CF$_3$ | —H | —F | —H | —H | —H | —F | —H | 344 |
| 1087 | —H | —CF$_3$ | —CH$_3$ | —H | —H | —H | —H | —F | —H | 340 |
| 1088 | —H | —CF$_3$ | —OCH$_3$ | —H | —H | —H | —H | —F | —H | 356 |
| 1089 | —H | —CH$_3$ | —N(CH$_3$)$_2$ | —CH$_3$ | —H | —H | —H | —F | —H | 329 |
| 1090 | —H | —CH(CH$_3$)$_2$ | —H | —H | —H | —H | —H | —F | —H | 300 |
| 1091 | —H | —F | —Br | —H | —H | —H | —H | —F | —H | |
| 1092 | —H | —F | —H | —Cl | —H | —H | —H | —F | —H | 310 |
| 1093 | —H | —CH$_3$ | —OCH$_3$ | —CH$_3$ | —H | —H | —H | —F | —H | 316 |
| 1094 | —H | —CH$_3$ | —H | —CH$_3$ | —H | —H | —H | —F | —H | 286 |

TABLE 151

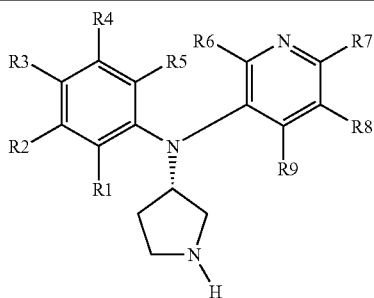

| Ex. No. | R1 | R2 | R3 | R4 | R5 | R6 | R7 | R8 | R9 | MS (M + 1) |
|---|---|---|---|---|---|---|---|---|---|---|
| 1095 | —H | —F | —CH$_3$ | —H | —H | —H | —H | —F | —H | 290 |
| 1096 | —H | —F | —Cl | —H | —H | —H | —H | —F | —H | 310 |
| 1097 | —H | —F | —F | —H | —F | —H | —H | —F | —H | |
| 1098 | —F | —H | —F | —H | —H | —H | —H | —F | —H | |
| 1099 | —H | —F | —H | —H | —F | —H | —H | —F | —H | 294 |
| 1100 | —H | —F | —H | —H | —H | —H | —H | —F | —H | 276 |
| 1101 | —H | —Cl | —CH$_3$ | —H | —H | —H | —H | —F | —H | 306 |
| 1102 | —H | —F | —F | —F | —H | —H | —H | —F | —H | 312 |
| 1103 | —F | —F | —H | —H | —H | —H | —H | —F | —H | 294 |
| 1104 | —H | —F | —OCH$_3$ | —H | —H | —H | —H | —F | —H | 306 |
| 1105 | —H | —CH$_3$ | —Cl | —H | —H | —H | —H | —F | —H | 306 |
| 1106 | —H | —H | —C$_3$H$_7$ | —H | —H | —H | —H | —F | —H | 300 |
| 1107 | —H | —C$_2$H$_5$ | —H | —H | —H | —H | —H | —F | —H | |
| 1108 | —H | —OCH$_3$ | —OCH$_3$ | —H | —H | —H | —H | —F | —H | 318 |
| 1109 | —H | —Cl | —H | —H | —H | —H | —H | —F | —H | 292 |
| 1110 | —H | —CH$_3$ | —CH$_3$ | —H | —H | —H | —H | —F | —H | 286 |
| 1111 | —H | —CH$_3$ | —OCH$_3$ | —H | —H | —H | —H | —F | —H | 302 |
| 1112 | —H | —CH$_3$ | —F | —CH$_3$ | —H | —H | —H | —F | —H | 304 |
| 1113 | —H | —H | —Cl | —H | —H | —H | —H | —F | —H | 292 |
| 1114 | —H | —H | —H | —H | —H | —H | —H | —F | —H | 258 |
| 1115 | —H | —H | —F | —H | —H | —H | —H | —F | —H | 276 |

TABLE 151-continued
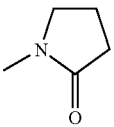
| Ex. No. | R1 | R2 | R3 | R4 | R5 | R6 | R7 | R8 | R9 | MS (M + 1) |
|---|---|---|---|---|---|---|---|---|---|---|
| 1116 | —H | —H | 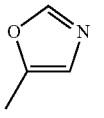 | —H | —H | —H | —H | —F | —H | 341 |
| 1117 | —H | —H | 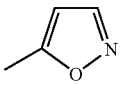 | —H | —H | —H | —H | —F | —H | 325 |
| 1118 | —H | 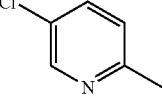 | —H | —H | —H | —H | —H | —F | —H | |
TABLE 152
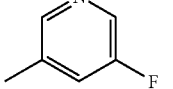
| Ex. No. | R1 | R6 | MS (M + 1) |
|---|---|---|---|
| 1119 | 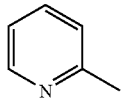 | 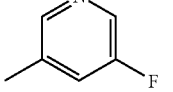 | 293 |
| 1120 | 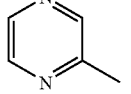 | 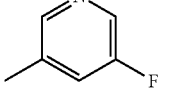 | 259 |
| 1121 | 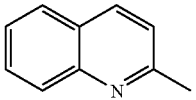 | 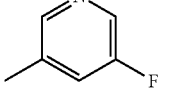 | 260 |
| 1122 | 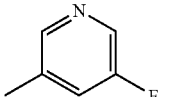 | 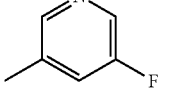 | 309 |

TABLE 152-continued
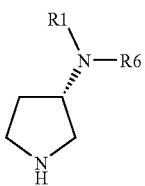
| Ex. No. | R1 | R6 | MS (M + 1) |
|---|---|---|---|
| 1123 | isoquinolin-4-yl | 5-fluoropyridin-3-yl | 309 |
| 1124 | benzoxazol-2-yl | 5-fluoropyridin-3-yl | |
| 1125 | pyrimidin-5-yl | 5-fluoropyridin-3-yl | 260 |
| 1126 | 2-methylquinolin-4-yl | 5-fluoropyridin-3-yl | 323 |
| 1127 | quinolin-3-yl | 5-fluoropyridin-3-yl | 309 |
| 1128 | isoquinolin-4-yl | 5-fluoropyridin-3-yl | |

TABLE 153
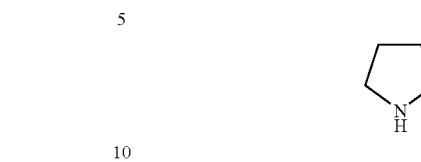
| Ex. No. | R1 | R6 | MS (M + 1) |
|---|---|---|---|
| 1129 | 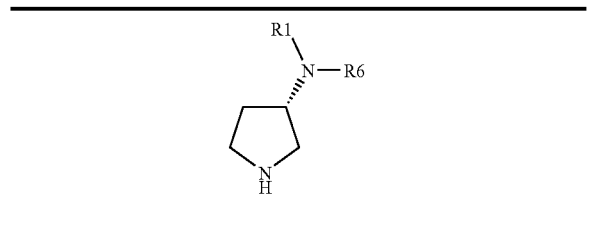 | | 314 |
| 1130 | 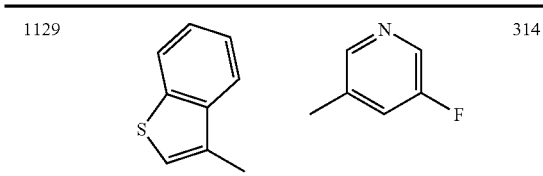 | | 309 |
| 1131 | 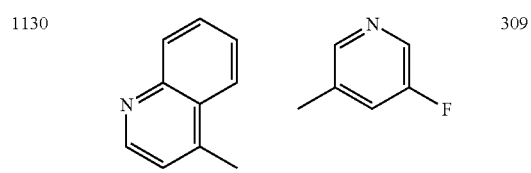 | | 310 |
| 1132 | 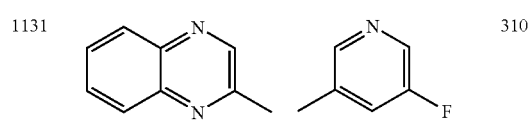 | | 288 |
| 1133 | 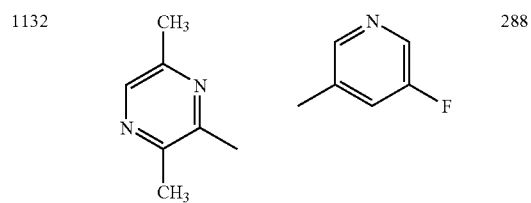 | | |
| 1134 | 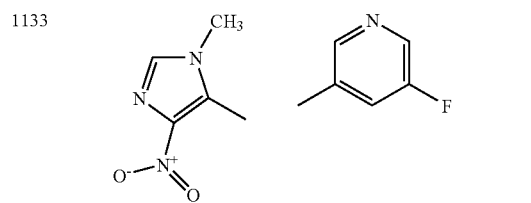 | | |
| 1135 | 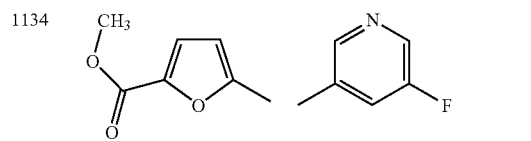 | | 320 |
TABLE 153-continued
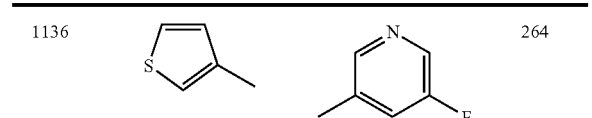
| Ex. No. | R1 | R6 | MS (M + 1) |
|---|---|---|---|
| 1136 |  | | 264 |
| 1137 | 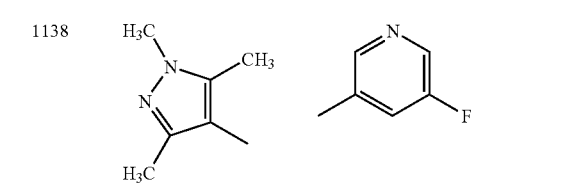 | | 265 |
| 1138 | 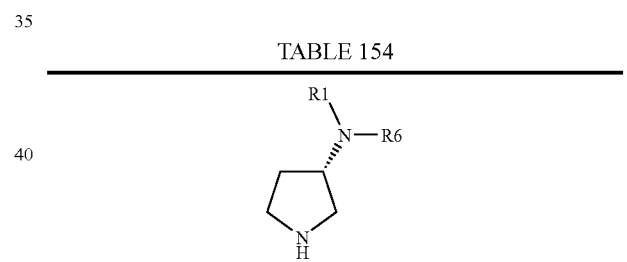 | | |
TABLE 154
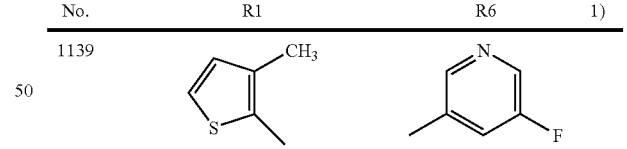
| Ex. No. | R1 | R6 | MS (M + 1) |
|---|---|---|---|
| 1139 | 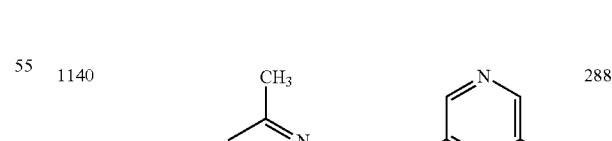 | | |
| 1140 | 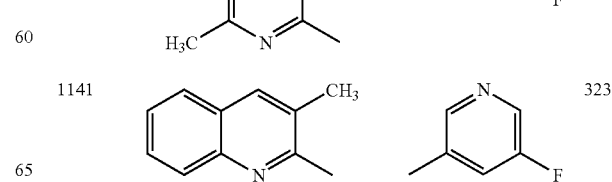 | | 288 |
| 1141 | | | 323 |

TABLE 154-continued

| Ex. No. | R1 | R6 | MS (M+1) |
|---|---|---|---|
| 1142 | 2-(trifluoromethyl)quinolin-4-yl | 5-fluoropyridin-3-yl | 377 |
| 1143 | thieno[3,2-b]pyridin-7-yl | 5-fluoropyridin-3-yl | 315 |
| 1144 | 2,4-dimethylquinolinyl | 5-fluoropyridin-3-yl | 323 |
| 1145 | 2-methylquinolin-6-yl acetate | 5-fluoropyridin-3-yl | — |
| 1146 | 7-methoxy-2-methylquinolinyl | 5-fluoropyridin-3-yl | 339 |
| 1147 | 4-methyl-6-(trifluoromethyl)quinolinyl | 5-fluoropyridin-3-yl | 377 |
| 1148 | 3-methoxy-6-methylpyridazinyl | 5-fluoropyridin-3-yl | — |

TABLE 155

| Ex. No. | R1 | R6 | MS (M+1) |
|---|---|---|---|
| 1149 | 1,4-dimethyl-1H-imidazol-2-yl | 5-fluoropyridin-3-yl | — |
| 1150 | 6-methylbenzo[b]thiophen-2-yl | 5-fluoropyridin-3-yl | 314 |
| 1151 | 2,3-dihydrobenzo[b][1,4]dioxin-6-yl | 5-fluoropyridin-3-yl | 316 |
| 1152 | 5-methylnaphthalen-1-yl | 5-fluoropyridin-3-yl | 308 |
| 1153 | 2,5-dimethylbenzo[d]thiazol-2-yl | 5-fluoropyridin-3-yl | 329 |
| 1154 | 6-methylnaphthalen-2-yl | 5-fluoropyridin-3-yl | 308 |
| 1155 | 6-methylbenzo[d][1,3]dioxol-5-yl | 5-fluoropyridin-3-yl | 302 |
| 1156 | 7-methyl-3,4-dihydro-2H-benzo[b][1,4]dioxepin-6-yl | 5-fluoropyridin-3-yl | 330 |

TABLE 155-continued

| Ex. No. | R1 | R6 | MS (M + 1) |
|---|---|---|---|
| 1157 | 6-methylquinoline | 5-fluoro-3-pyridyl | 309 |
| 1158 | 6-methylquinoxaline | 5-fluoro-3-pyridyl | 310 |

TABLE 156

| Ex. No. | R1 | R6 | MS (M + 1) |
|---|---|---|---|
| 1159 | 4-methyl-7-methyl-3,4-dihydro-2H-benzo[b][1,4]oxazine | 5-fluoro-3-pyridyl | 329 |
| 1160 | 4-methylbenzo[d][1,3]dioxole | 5-fluoro-3-pyridyl | 302 |
| 1161 | 6-methyl-2,3-dihydrobenzofuran | 5-fluoro-3-pyridyl | 300 |
| 1162 | 2,6-dimethylquinoline | 5-fluoro-3-pyridyl | 323 |
| 1163 | 6-methoxy-2-methylnaphthalene | 5-fluoro-3-pyridyl | 338 |

TABLE 156-continued

| Ex. No. | R1 | R6 | MS (M + 1) |
|---|---|---|---|
| 1164 | 1-acetyl-5-methylindoline | 5-fluoro-3-pyridyl | 341 |
| 1165 | 5-fluoro-1-methylnaphthalene | 5-fluoro-3-pyridyl | 326 |
| 1166 | 7-methyl-9H-fluorene | 5-fluoro-3-pyridyl | 346 |
| 1167 | 7-methylbenzo[b]thiophene | 5-fluoro-3-pyridyl | 314 |
| 1168 | 7-methylbenzofuran | 5-fluoro-3-pyridyl | 298 |

TABLE 157

| Ex. No. | R1 | R6 | MS (M + 1) |
|---|---|---|---|
| 1169 | 2-methylthieno[2,3-b]pyridine | 5-fluoro-3-pyridyl | 315 |

TABLE 157-continued
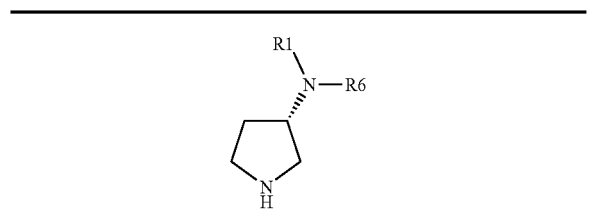
| Ex. No. | R1 | R6 | MS (M + 1) |
|---|---|---|---|
| 1170 | 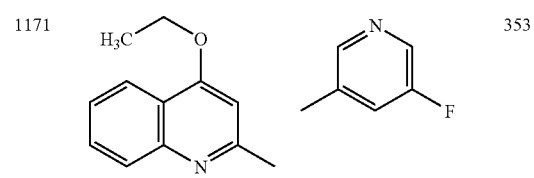 | | 339 |
| 1171 | | | 353 |
| 1172 | 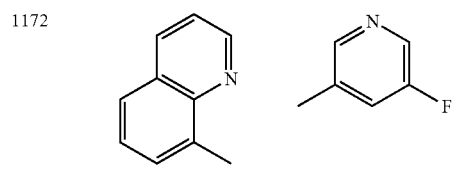 | | |
| 1173 | | | 298 |
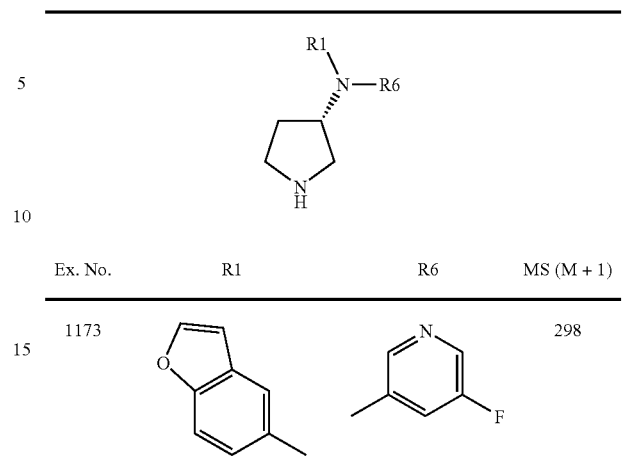
TABLE 158
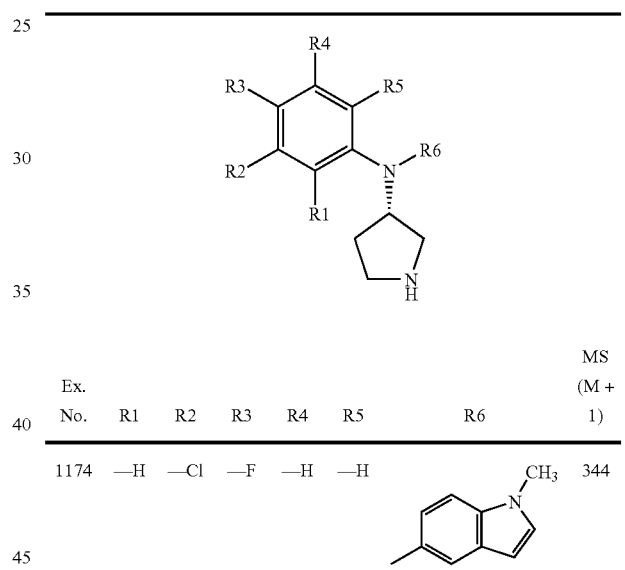
| Ex. No. | R1 | R2 | R3 | R4 | R5 | R6 | MS (M + 1) |
|---|---|---|---|---|---|---|---|
| 1174 | —H | —Cl | —F | —H | —H | | 344 |
| 1175 | —H | —Cl | —F | —H | —H | | 332 |
| 1176 | —H | —Cl | —F | —H | —H | 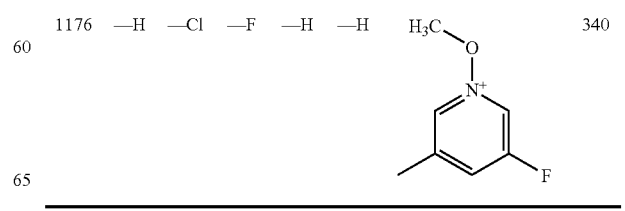 | 340 |
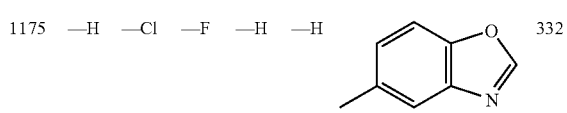

TABLE 159

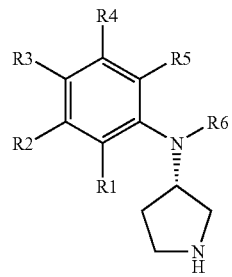

| Ex. No. | R1 | R2 | R3 | R4 | R5 | R6 | NMR | salt |
|---|---|---|---|---|---|---|---|---|
| 1177 | —H | —H | —F | —Cl | —H | 5-methyl-1-methyl-indazol-3-yl | $^1$H-NMR (DMSO-$d_6$) δ ppm: 1.55-1.75 (1 H, m), 2.1-2.25 (1 H, m), 2.8-2.95 (1 H, m), 3.0-3.25 (2 H, m), 3.5-3.65 (1 H, m), 4.19 (3H, s), 4.64 (1 H, tt, J = 7.3, 7.3 Hz), 5.01 (1 H, br), 6.60 (1 H, ddd, J = 3.5, 3.5, 9.1 Hz), 6.81 (1 H, dd, J = 3.0, 6.3 Hz), 6.96 (1 H, dd, J = 2.0, 9.0 Hz), 7.22 (1 H, dd, J = 9.1, 9.1 Hz), 7.61 (1 H, d, J = 1.5 Hz), 7.68 (1 H, d, J = 9.0 Hz), 8.39 (1 H, s), 9.28 (1 H, br), 9.39 (1 H, br). | 2 Hydrochloride |
| 1178 | —H | —H | —F | —Cl | —H | 6-methyl-2-methyl-indazol-3-yl | $^1$H-NMR (DMSO-$d_6$) δ ppm: 1.6-1.75 (1 H, m), 2.1-2.3 (1 H, m), 2.8-3.0 (1 H, m), 3.05-3.25 (2 H, m), 3.5-3.65 (1 H, m), 4.18 (3 H, s), 4.72 (1 H, tt J = 7.3, 7.3 Hz), 5.88 (1 H, br), 6.67 (1 H, dd, J = 1.9, 8.9 Hz), 6.8-6.9 (1 H, m), 7.07 (1 H, dd, J = 2.9, 6.4 Hz), 7.25-7.4 (2 H, m), 7.73 (1 H, dd, J = 0.3, 8.9 Hz), 8.42 (1 H, s), 9.43 (1 H, br), 9.56 (1 H, br). | 2 Hydrochloride |
| 1179 | —H | —H | —H | —H | —H | 5-methyl-1-methyl-indazol-3-yl | $^1$H-NMR (DMSO-$d_6$) δ ppm: 1.6-1.8 (1 H, 3 m), 2.1-2.25 (1 H, m), 2.8-2.95 (1 H, m), 3.0-3.25 (2 H, m), 3.5-3.65 (1 H, m), 4.0-4.5 (4 H, m), 4.70 (1 H, tt, J = 7.3, 7.3 Hz), 6.70 (2 H, d, J = 7.9 Hz), 6.80 (1 H, dd, J = 7.3, 7.3 Hz), 6.92 (1 H, dd, J = 2.0, 9.0 Hz), 7.1-7.25 (2 H, m), 7.55 (1 H, d, J = 1.4 Hz), 7.64 (1 H, d, J = 9.0 Hz), 8.36 (1 H, s), 9.30 1H, br), 9.47 (1 H, br). | 2 Hydrochloride |
| 1180 | —H | —H | —H | —H | —H | 6-methyl-2-methyl-indazol-3-yl | $^1$H-NMR (DMSO-$d_6$) δ ppm: 1.6-1.8 (1 H, m), 2.1-2.25 (1 H, m), 2.8-3.0 (1 H, m), 3.0-3.25 (2 H, m), 3.5-3.65 (1 H, m), 4.15 (3 H, s), 4.22 (1 H, br), 4.73 (1 H, tt, J = 7.3, 7.3 Hz), 6.60 (1 H, dd, J = 1.8, 8.9 Hz), 6.91 (2 H, d, J = 7.6 Hz), 7.02 (1 H, dd, J = 7.3, 7.3 Hz), 7.22 (1 H, s), 7.25-7.4 (2 H, m), 7.66 (1 H, d, J = 8.9 Hz), 8.37 (1 H, s), 9.26 (1 H, br), 9.42 (1 H, br). | 2 Hydrochloride |

Pharmacological Test 1
Evaluation of Inhibitory Activity of Test Compound on Serotonin (5-HT) Uptake into Rat Brain Synaptosome Male Wistar rats were decapitated and the brains were removed and the frontal cortices were dissected. The separated frontal cortices were homogenized in 20 volumes as weight of 0.32 M sucrose solution by a Potter-type homogenizer. The homogenate was centrifuged at 1000 g at 4° C. for 10 minutes, and the supernatant was then centrifuged at 20000 g at 4° C. for 20 minutes. The pellet was resuspended in incubation buffer (20 mM HEPES buffer (pH 7.4)) containing 10 mM glucose, 145 mM sodium chloride, 4.5 mM potassium chloride, 1.2 mM magnesium chloride, and 1.5 mM calcium chloride) and used as crude synaptosome fractions.

The uptake reaction mixture was suspended in a final volume of 200 μl containing pargyline (final concentration of 10 μM) and sodium ascorbate (final concentration of 0.2 mg/ml) in each well of 96-well-round-bottom-plate.

Solvent, unlabeled 5-HT, and serial diluted test compounds were added in each well, and synaptosome fraction of ¹/₁₀ volume of the final volume were added. After a 10 min pre-incubation at 37° C., the uptake was initiated by the addition of tritium-labeled 5-HT solution (final concentration of 8 nM) at 37° C. The uptake was stopped after 10 minutes by filtration under vacuum through a 96-well glass fiber filter plate. After washing the filter with cold physiological saline and drying up, Microscint-O (Perkin-Elmer) was added, and remained radioactivity on the filter was measured.

The total uptake activity with only solvent was determined as 100%, and the nonspecific uptake activity with unlabeled 5-HT (final concentration of 10 μM) was determined as 0%. The 50% inhibitory concentrations were calculated based on the concentrations of the test compounds and their inhibitory activities. Table 160 shows the results.

TABLE 160

| Test Compound | 50% inhibittory concentration (nM) |
|---|---|
| Compound of Example 5 | 1.6 |
| Compound of Example 7 | 3.0 |
| Compound of Example 19 | 0.7 |
| Compound of Example 40 | 0.8 |
| Compound of Example 73 | 0.6 |
| Compound of Example 90 | 1.2 |
| Compound of Example 114 | 0.8 |
| Compound of Example 131 | 0.6 |
| Compound of Example 145 | 0.6 |
| Compound of Example 149 | 1.2 |
| Compound of Example 151 | 0.8 |
| Compound of Example 154 | 0.8 |
| Compound of Example 268 | 0.8 |
| Compound of Example 278 | 2.2 |
| Compound of Example 306 | 1.4 |
| Compound of Example 894 | 2.6 |
| Compound of Example 895 | 3.0 |
| Compound of Example 896 | 2.5 |
| Compound of Example 899 | 0.7 |
| Compound of Example 900 | 1.5 |
| Compound of Example 901 | 0.7 |
| Compound of Example 903 | 1.2 |
| Compound of Example 912 | 1.0 |
| Compound of Example 913 | 0.8 |
| Compound of Example 917 | 0.7 |
| Compound of Example 930 | 0.8 |
| Compound of Example 934 | 1.8 |
| Compound of Example 961 | 2.8 |
| Compound of Example 963 | 1.0 |
| Compound of Example 967 | 0.9 |
| Compound of Example 989 | 0.6 |

Pharmacological Test 2

Evaluation of Inhibitory Activity of Test Compound on Norepinephrine (NE) Uptake into Rat Brain Synaptosome Male Wistar rats were decapitated and the brains were removed and the hippocampi were dissected. The separated hippocampi were homogenaized in 20 volumes as weight of 0.32 M sucrose solution by a Potter-type homogenizer. The homogenate was centrifuged at 1000 g at 4° C. for 10 minutes, and the supernatant was then centrifuged at 20000 g at 4° C. for 20 minutes. The pellet was resuspended in incubation buffer (20 mM HEPES buffer (pH 7.4)) containing 10 mM glucose, 145 mM sodium chloride, 4.5 mM potassium chloride, 1.2 mM magnesium chloride, and 1.5 mM calcium chloride) and used as crude synaptosome fraction.

The uptake reaction mixture was suspended in final volume of 200 µl containing pargyline (final concentration of 10 µM) and sodium ascorbate (final concentration of 0.2 mg/ml) in each well of 96-well-round-bottom-plate.

Solvent, unlabeled NE, and serial diluted test compounds were added to each well, and synaptosome fraction of ¹⁄₁₀ volume of the final volume were added. After 10 minutes preincubation at 37° C., the uptake was initiated by the addition of tritium-labeled NE solution (final concentration of 12 nM) at 37° C. The uptake was stopped after 10 minutes by filtration under vacuum through a 96-well glass fiber filter plate. After washing the filter with coldphysiological saline and drying up, Microscint-0 (Perkin-Elmer) was added, and remained radioactivity on the filter was measured.

The total uptake activity with only solvent was determined as 100%, and the nonspecific uptake activity with unlabeled NE (final concentration of 10 µM) was determined as 0%. The 50% inhibitory concentrations were calculated based on the concentrations of the test compounds and their inhibitory activities. Table 161 shows the results.

TABLE 161

| Test Compound | 50% inhibitory concentration (nM) |
|---|---|
| Compound of Example 1 | 0.6 |
| Compound of Example 7 | 0.4 |
| Compound of Example 20 | 0.8 |
| Compound of Example 22 | 2.2 |
| Compound of Example 44 | 0.4 |
| Compound of Example 90 | 0.7 |
| Compound of Example 98 | 0.3 |
| Compound of Example 114 | 0.4 |
| Compound of Example 116 | 0.1 |
| Compound of Example 131 | 0.2 |
| Compound of Example 154 | 0.2 |
| Compound of Example 188 | 0.1 |
| Compound of Example 223 | 0.2 |
| Compound of Example 242 | 0.2 |
| Compound of Example 244 | 0.5 |
| Compound of Example 256 | 0.1 |
| Compound of Example 278 | 0.3 |
| Compound of Example 289 | 0.1 |
| Compound of Example 306 | 0.8 |
| Compound of Example 894 | 0.3 |
| Compound of Example 895 | 0.5 |
| Compound of Example 896 | 0.9 |
| Compound of Example 900 | 0.6 |
| Compound of Example 903 | 0.7 |
| Compound of Example 913 | 0.8 |
| Compound of Example 922 | 0.5 |
| Compound of Example 930 | 1.0 |
| Compound of Example 951 | 0.5 |
| Compound of Example 961 | 0.7 |
| Compound of Example 963 | 0.8 |
| Compound of Example 967 | 0.1 |
| Compound of Example 989 | 0.3 |
| Compound of Example 990 | 0.8 |
| Compound of Example 1000 | 0.4 |
| Compound of Example 1001 | 0.1 |
| Compound of Example 1002 | 0.1 |

Pharmacological Test 3

Evaluation of Inhibitory Activity of Test Compound on Dopamine (DA) into Rat Brain Synaptosome Male Wistar ratswere decapitated and the brains were removed and the striata were dissected. The separated striata were homogenized in 20 volumes as weight of 0.32 M sucrose solution by a Potter-type homogenizer. The homogenate was centrifuged at 1000 g at 4° C. for 10 minutes, and the supernatant was then centrifuged at 20000 g at 4° C. for 20 minutes. The pellet was resuspended in incubation buffer (20 mM HEPES buffer (pH 7.4)) containing 10 mM glucose, 145 mM sodium chloride, 4.5 mM potassium chloride, 1.2 mM magnesium chloride, and 1.5 mM calcium chloride) and used as crude synaptosome fraction.

The uptake reaction mixture was suspended in a final volume of 200 µl containing pargyline (final concentration of 10 µM) and sodium ascorbate (final concentration of 0.2 mg/ml) in each well of 96-well-round-bottom-plate.

Solvent, unlabeled DA, and serial diluted test compounds were added in each well, and synaptosome fraction of ¹⁄₁₀ volume of the final volume were added. After 10-min preincubation at 37° C., the uptake was initiated by the addition of tritium labeled DA solution (final concentration of 2 nM) at 37° C. The uptake was stopped after 10 minutes by filtration under vacuum through a 96-well glass fiber filter plate. After washing the filter with cold physiological saline and drying up, Microscint-0 (Perkin-Elmer) was added and remained radioactivity on the filter was measured.

The uptake activity with only solvent was determined as 100%, and the nonspecific uptake activity with unlabeled DA (final concentration of 10 µM) was determined as 0%. The 50% inhibitory concentrations were calculated based on the concentrations of the test compounds and their inhibitory activities. Table 162 shows the results.

TABLE 162

| Test Compound | 50% inhibitory concentration (nM) |
|---|---|
| Compound of Example 7 | 45.0 |
| Compound of Example 44 | 8.7 |
| Compound of Example 46 | 9.3 |
| Compound of Example 73 | 9.0 |
| Compound of Example 90 | 4.8 |
| Compound of Example 114 | 32.5 |
| Compound of Example 116 | 8.9 |
| Compound of Example 154 | 9.2 |
| Compound of Example 200 | 3.8 |
| Compound of Example 201 | 4.3 |
| Compound of Example 268 | 6.5 |
| Compound of Example 270 | 8.2 |
| Compound of Example 272 | 30.0 |
| Compound of Example 273 | 32.9 |
| Compound of Example 278 | 34.7 |
| Compound of Example 289 | 30.6 |
| Compound of Example 294 | 24.0 |
| Compound of Example 299 | 48.6 |
| Compound of Example 300 | 9.6 |
| Compound of Example 894 | 9.4 |
| Compound of Example 895 | 38.0 |
| Compound of Example 912 | 30.2 |
| Compound of Example 913 | 6.5 |
| Compound of Example 930 | 6.8 |
| Compound of Example 951 | 29.8 |
| Compound of Example 961 | 9.6 |
| Compound of Example 963 | 47.1 |
| Compound of Example 967 | 25.4 |
| Compound of Example 989 | 5.8 |
| Compound of Example 990 | 26.0 |
| Compound of Example 1001 | 16.4 |
| Compound of Example 1002 | 32.9 |

Pharmacological Test 4

Forced-Swimming Test

Forced-swimming test was conducted based on the method of Porsolt, R. D., et al. (Porsolt, R. D., et al., Behavioural despair in mice: A primary screening test for antidepressants. Arch. Int. Pharmacodyn., 229, pp 327-336 (1977) with a modification.

The test compound was suspended in a 5% gum arabic/physiological saline solution (w/v) and then orally administered to male ICR mice (provided by Clea Japan Inc., 5 to 6 weeks old). One hour after administration, the mice were dropped into a tank containing 9.5 cm water maintained at 21 to 25° C. Then, the mice were forced to swim for 6 minutes. During the last four minutes of the test, the period of time the mice were not moving was measured (i.e., immobility time). The analysis and measurement of the immobility time was conducted using a SCANET MV-20 AQ system (product name of Melquest Co., Ltd.).

In this test, the test compound treated animal exhibited reduction of immobility time. Therefore it is clear that the test compound is effective as an antidepressant.

The invention claimed is:

1. A pyrrolidine compound of General Formula (1)

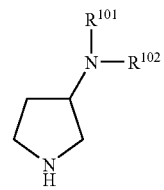

or a salt thereof,
wherein $R^{101}$ and $R^{102}$ are each independently the following group (1):
(1) a phenyl group,
   and the group (1) may have one or more substituents selected from the following (1-1) to (1-36) on the aromatic ring:
(1-1) halogen atoms,
(1-2) lower alkylthio groups optionally substituted with one or more halogen atoms,
(1-3) lower alkyl groups optionally substituted with one or more halogen atoms,
(1-4) lower alkoxy groups optionally substituted with one or more halogen atoms,
(1-5) nitro group,
(1-6) lower alkoxycarbonyl groups,
(1-7) amino groups optionally substituted with one or two lower alkyl groups,
(1-8) lower alkylsulfonyl groups,
(1-9) cyano group,
(1-10) carboxy group,
(1-11) hydroxy group,
(1-12) thienyl groups,
(1-13) oxazolyl groups,
(1-14) naphthyl groups,
(1-15) benzoyl group,
(1-16) phenoxy groups optionally substituted with one to three halogen atoms on the phenyl ring,
(1-17) phenyl lower alkoxy groups,
(1-18) lower alkanoyl groups,
(1-19) phenyl groups optionally substituted on the phenyl ring with one to five substituents selected from the group consisting of halogen atoms, lower alkoxy groups, cyano group, lower alkanoyl groups and lower alkyl groups,
(1-20) phenyl lower alkyl groups,
(1-21) cyano lower alkyl groups,
(1-22) 5 to 7-membered saturated heterocyclic group-substituted sulfonyl groups, the heterocyclic group containing on the heterocyclic ring one or two heteroatoms selected from the group consisting of nitrogen, oxygen and sulfur,
(1-23) thiazolyl groups optionally substituted with one or two lower alkyl groups on the thiazole ring,
(1-24) imidazolyl groups,
(1-25) amino lower alkyl groups optionally substituted with one or two lower alkyl groups on the amino group,
(1-26) pyrrolidinyl lower alkoxy groups,
(1-27) isoxazolyl groups,
(1-28) cycloalkylcarbonyl groups,
(1-29) naphthyloxy groups,
(1-30) pyridyl groups,
(1-31) furyl groups,
(1-32) phenylthio group, (1-33) oxo group,
(1-34) 5 to 7-membered saturated heterocyclic groups containing one or two heteroatoms selected from the group consisting of nitrogen, oxygen and sulfur, the heterocyclic group optionally being substituted with one to three substituents selected from the group consisting of oxo group; lower alkyl groups; lower alkanoyl groups; phenyl lower alkyl groups; phenyl groups optionally substituted on the phenyl ring with one to three members selected from the group consisting of halogen atoms and lower alkoxy groups; and pyridyl groups,
(1-35) oxido group and
(1-36) lower alkoxido groups,
with the proviso that $R^{101}$ and $R^{102}$ are not simultaneously unsubstituted phenyl.

2. A pyrrolidine compound of General Formula (1) or a salt thereof according to claim 1, wherein
$R^{101}$ is
(1) a phenyl group,
and may have on the aromatic ring one to three substituents selected from the groups (1-1) to (1-36).

3. A pyrrolidine compound of General Formula (1) or a salt thereof according to claim 2, wherein
$R^{101}$ is
(1) a phenyl group
and may have on the aromatic ring one to three substituents selected from the group consisting of (1-1) halogen atoms and (1-3) lower alkyl groups optionally substituted with one to three halogen atoms.

4. A pyrrolidine compound of General Formula (1) or a salt thereof according to claim 3, wherein
$R^{102}$ is
(1) a phenyl group,
and the group (1), may have on the aromatic ring one to three substituents selected from the groups (1-1) to (1-36).

5. A pyrrolidine compound of General Formula (1) or a salt thereof according to claim 4, wherein
$R^{101}$ is
a monohalophenyl group, a dihalophenyl group or a phenyl group substituted with one halogen atom and one lower alkyl group,
$R^{101}$ is
(1) a phenyl group,
and the group (1)
may have on the aromatic ring one or two substituents selected from the group consisting of (1-1) halogen atoms, (1-3) lower alkyl groups optionally substituted with one or more halogen atoms, and (1-9) cyano group.

6. A pyrrolidine compound of General Formula (1) or a salt thereof according to claim 5 selected from the group consisting of:
(4-chlorophenyl)phenyl-(S)-pyrrolidin-3-ylamine,
(4-fluorophenyl)phenyl-(S)-pyrrolidin-3-ylamine,
(3,4-difluorophenyl)phenyl-(S)-pyrrolidin-3-ylamine,
bis-(4-fluorophenyl)-(S)-pyrrolidin-3-ylamine,
(3,4-difluorophenyl)-(4-fluorophenyl)-(S)-pyrrolidin-3-ylamine,
(3-chloro-4-fluorophenyl)-(S)-pyrrolidin-3-yl-p-tolylamine,
4-[(S)-(4-fluoro-3-methylphenyl)pyrrolidin-3-ylamino]-benzonitrile, and
bis-(3-fluorophenyl)-(S)-pyrrolidin-3-ylamine.

7. A pharmaceutical composition comprising a pyrrolidine compound of General Formula (1) or a salt thereof according to claim 1 as an active ingredient and a pharmaceutically acceptable carrier.

8. A method of treating disorders caused by reduced neurotransmission of serotonin, norepinephrine or dopamine, comprising administering a therapeutically effective amount of a pyrrolidine compound of General Formula (1) or a salt thereof according to claim 1 to a human or an animal in need thereof wherein the disorder is depression.

9. A process for producing a pyrrolidine compound of General Formula (1):

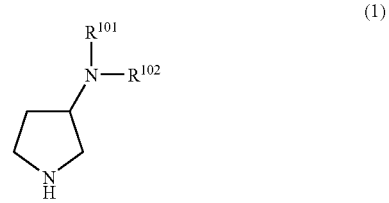

(1)

or a salt thereof, wherein $R^{101}$ and $R^{102}$ are defined above in claim 1,
the process comprising
(1) subjecting a compound of General Formula (2)

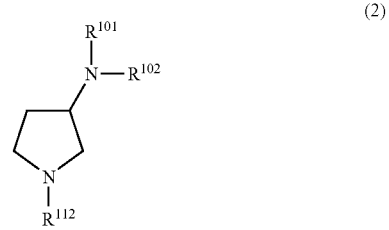

(2)

wherein $R^{101}$ and $R^{102}$ are as defined above in claim 1, and $R^{112}$ is an amino-protecting group to an elimination reaction to remove the amino protecting group.

* * * * *